United States Patent
Matsuno et al.

(10) Patent No.: US 6,207,667 B1
(45) Date of Patent: Mar. 27, 2001

(54) 1,3 DIAZINES WITH PLATELET-DERIVED GROWTH FACTOR RECEPTOR INHIBITORY ACTIVITY

(75) Inventors: Kenji Matsuno, Shizuoka; Michio Ichimura, Mishima; Yuji Nomoto, Shizuoka; Shigeki Fujiwara, Mishima; Shinichi Ide, Numadzu; Eiji Tsukuda, Odawara; Junko Irie; Shoji Oda, both of Shizuoka, all of (JP)

(73) Assignee: Kyowa Hakko Kogyo Co., Ltd., Tokyo (JP)

( * ) Notice: Subject to any disclaimer, the term of this patent is extended or adjusted under 35 U.S.C. 154(b) by 0 days.

(21) Appl. No.: 09/481,544

(22) Filed: Jan. 12, 2000

Related U.S. Application Data

(60) Division of application No. 09/088,199, filed on Jun. 1, 1998, which is a continuation-in-part of application No. PCT/JP97/03510, filed on Oct. 1, 1997.

(51) Int. Cl.[7] .................... A61K 31/535; A61K 31/495; C07D 403/02
(52) U.S. Cl. .................. 514/252.13; 546/167; 546/169; 546/170; 546/171
(58) Field of Search .................... 546/167, 169, 546/170, 171; 514/249, 252.13

(56) References Cited

FOREIGN PATENT DOCUMENTS

| | | |
|---|---|---|
| 58-172379 | 10/1983 | (JP) . |
| 60-120872 | 6/1985 | (JP) . |
| 2-167277 | 6/1990 | (JP) . |
| 6-247942 | 9/1994 | (JP) . |

OTHER PUBLICATIONS

Campbell et al., J. Med. Chem., 1988, 31 pp. 1031–1035, 1988.*
Chem. Abs: 1988, 1988: 186530 Agarwal et al., Caplus, 1988.*

* cited by examiner

*Primary Examiner*—Mukund J. Shah
*Assistant Examiner*—Pavanaram K Sripada
(74) *Attorney, Agent, or Firm*—Fitzpatrick, Cella, Harper & Scinto

(57) ABSTRACT

1,3 Diazines according to formula (I):

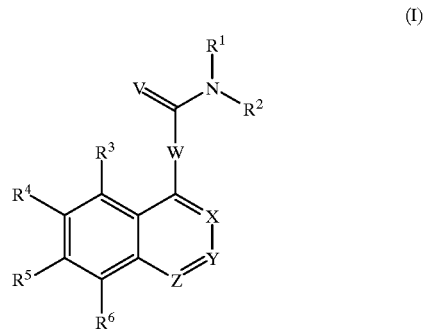

and pharmaceutically acceptable salts thereof inhibit phosphorylation of platelet-derived growth factor receptor and thereby hinder abnormal cell growth and cell wandering. The compounds may be used to treat or prevent cell-proliferative disorders such as arteriosclerosis, vascular reobstruction, cancer and glomerulosclerosis.

9 Claims, No Drawings

1,3 DIAZINES WITH PLATELET-DERIVED GROWTH FACTOR RECEPTOR INHIBITORY ACTIVITY

CROSS REFERENCE TO THE RELATED APPLICATION

This application is a division of application Ser. No. 09/088,199, filed Jun. 1, 1998, which in turn is a continuation-in-part of application PCT/JP97/03510, filed Oct. 1, 1997.

TECHNICAL FIELD

The present invention relates to nitrogen-containing heterocyclic compounds and pharmaceutically acceptable salts thereof which have inhibitory activity on phosphorylation of platelet-derived growth factor (PDGF) receptor and are useful for the treatment of cell-proliferative diseases such as arteriosclerosis, vascular reobstruction, cancer and glomerulosclerosis.

BACKGROUND ART

PDGF is known to act as an aggravating factor for cell-proliferative diseases such as arteriosclerosis, vascular reobstruction after percutaneous coronary angioplasty and bypass operation, cancer, glomerulonephritis, glomerulosclerosis, psoriasis and articular rheumatism [Cell, 46, 155–169 (1986); Science, 253, 1129–1132 (1991); Nippon Rinsho (Japanese J. of Clinical Medicine), 50, 3038–3045 (1992); Nephrol Dial Transplant, 10, 787–795 (1995); Kidney International, 43 (Suppl. 39), S86–S89 (1993); Journal of Rheumatology, 21, 1507–1511 (1994); Scandinavian Journal of Immunology, 27, 285–294 (1988), etc.].

As for quinazoline derivatives which are useful as drugs, N,N-dimethyl-4-(6,7-dimethoxy-4-quinazolinyl)-1-piperazine carboxamide is described as a bronchodilator in South African Patent No. 67 06512 (1968). Dimethoxyquinazoline derivatives are described as inhibitors of phosphorylation of epidermal growth factor (EGF) receptor in Japanese Published Unexamined Patent Application No. 208911/93 and WO 96/09294. Quinoline derivatives having benzodiazepine receptor agonist activity are described in Pharmacology Biochemistry and Behavior, 53, 87–97 (1996) and European Journal of Medicinal Chemistry, 31, 417–425 (1996), and quinoline derivatives which are useful as anti-parasite agents are described in Indian Journal of Chemistry, 26B, 550–555 (1987).

Inhibitors of phosphorylation of PDGF receptor so far known include bismono- and bicyclic aryl compounds and heteroaryl compounds (WO 92/20642), quinoxaline derivatives [Cancer Research, 54, 6106–6114 (1994)], pyrimidine derivatives (Japanese Published Unexamined Patent Application No. 87834/94) and dimethoxyquinoline derivatives [Abstracts of the 116th Annual Meeting of the Pharmaceutical Society of Japan (Kanazawa) (1996), 2, p. 275, 29(C2) 15-2].

DISCLOSURE OF THE INVENTION

An object of the present invention is to provide nitrogen-containing heterocyclic compounds and pharmaceutically acceptable salts thereof which inhibit phosphorylation of PDGF receptor to hinder abnormal cell growth and cell wandering and thus are useful for the prevention or treatment of cell-proliferative diseases such as arteriosclerosis, vascular reobstruction, cancer and glomerulosclerosis.

The present invention relates to nitrogen-containing heterocyclic compounds represented by general formula (I):

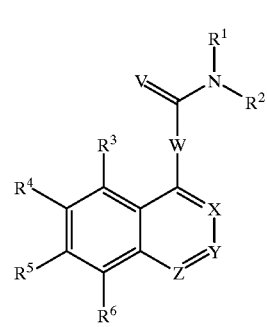

(I)

{wherein V represents an oxygen atom or a sulfur atom;
W represents 1,4-piperazinediyl or 1,4-homopiperazinediyl in which carbons on the ring may be substituted by 1–4-alkyl groups which may be the same or different;
$R^1$ represents a hydrogen atom, a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group;
$R^2$ represents a substituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, a substituted or unsubstituted heteroarylalkyl group, $-COR^{10}$ (wherein $R^{10}$ has the same significance as $R^1$) or $-SO_2R^{11}$ (wherein $R^{11}$ represents a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group);
$R^3$, $R^4$, $R^5$ and $R^6$, which may be the same or different, each represents a hydrogen atom, a halogen atom, a substituted or unsubstituted alkyl group, a nitro group, a cyano group, $-OR^{12}$ [wherein $R^{12}$ has the same significance as $R^{10}$, or represents $-COR^{13}$ (wherein $R^{13}$ has the same significance as $R^{10}$) or $-SO_2R^{14}$ (wherein $R^{14}$ has the same significance as $R^{11}$)], $-NR^{15}R^{16}$ {wherein $R^{15}$ has the same significance as $R^{10}$, and $R^{16}$ has the same significance as $R^{10}$, or represents $-SO_2R^{17}$ (wherein $R^{17}$ has the same significance as $R^{11}$) or

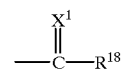

[wherein $X^1$ represents an oxygen atom or a sulfur atom; and $R^{18}$ has the same significance as $R^{10}$, or represents —$OR^{19}$ (wherein $R^{19}$ has the same significance as $R^{11}$) or —$NR^{20}R^{21}$ (wherein $R^{20}$ has the same significance as $R^{10}$ and $R^{21}$ has the same significance as $R^{10}$, or $R^{20}$ and $R^{21}$ are combined together with the adjoining nitrogen atom to represent a substituted or unsubstituted nitrogen-containing alicyclic heterocyclic group)]; or $R^{15}$ and $R^{16}$ are combined together with the adjoining nitrogen atom to represent a substituted or unsubstituted nitrogen-containing heterocyclic group},

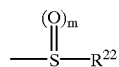

[wherein m represents an integer of 0–2; and when m is 0, $R^{22}$ has the same significance as $R^{10}$; when m is 1, $R^{22}$ has the same significance as $R^{11}$; and when m is 2, $R^{22}$ has the same significance as $R^{11}$, or represents —$OR^{23}$ (wherein $R^{23}$ has the same significance as $R^{10}$) or —$NR^{24}R^{25}$ (wherein $R^{24}$ and $R^{25}$, which may be the same or different, each has the same significance as $R^{10}$, or $R^{24}$ and $R^{25}$ are combined together with the adjoining nitrogen atom to represent a substituted or unsubstituted nitrogen-containing alicyclic heterocyclic group)] or —$COR^{26}$ [wherein $R^{26}$ has the same significance as $R^{10}$, or represents —$OR^{27}$ (wherein $R^{27}$ has the same significance as $R^{10}$) or —$NR^{28}R^{29}$ (wherein $R^{28}$ and $R^{29}$, which may be the same or different, each has the same significance as $R^{10}$, or $R^{28}$ and $R^{29}$ are combined together with the adjoining nitrogen atom to represent a substituted or unsubstituted nitrogen-containing alicyclic heterocyclic group)]; or any adjoining two of $R^3$, $R^4$, $R^5$ and $R^6$ are combined together to represent methylenedioxy or ethylenedioxy; or any adjoining two of $R^3$, $R^4$, $R^5$ and $R^6$ are combined together with the two adjoining carbon atoms to form a substituted or unsubstituted phenyl ring; or $R^3$ and $R^4$, $R^4$ and $R^5$, or $R^5$ and $R^6$ are combined together with the two adjoining carbon atoms to represent

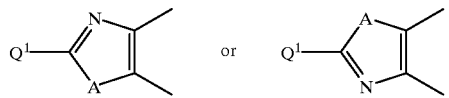

[wherein A represents an oxygen atom, a sulfur atom or —$NR^{30}$— (wherein $R^{30}$ has the same significance as $R^{10}$); and $Q^1$ has the same significance as $R^{10}$, or represents —$NR^{31}R^{32}$ (wherein $R^{31}$ and $R^{32}$, which may be the same or different, each has the same significance as $R^{10}$, or $R^{31}$ and $R^{32}$ are combined together with the adjoining nitrogen atom to represent a substituted or unsubstituted nitrogen-containing alicyclic heterocyclic group) or —$SR^{33}$ (wherein $R^{33}$ has the same significance as $R^{10}$)], or

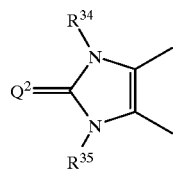

(wherein $R^{34}$ and $R^{35}$, which may be the same or different, each has the same significance as $R^{10}$; and $Q^2$ represents an oxygen atom, a sulfur atom or =N—CN), or (wherein $R^{36}$ has the same significance as $R^{10}$);

Z represents a nitrogen atom or C—$R^7$ [wherein $R^7$ has the same significance as $R^{10}$, or represents a halogen atom, —$OR^{37}$ (wherein $R^{37}$ has the same significance as $R^{10}$), —$SR^{38}$ (wherein $R^{38}$ has the same significance as $R^{10}$) or —$NR^{39}R^{40}$ (wherein $R^{39}$ has the same significance as $R^{10}$ and $R^{40}$ has the same significance as $R^{10}$, or $R^{39}$ and $R^{40}$ are combined together with the adjoining nitrogen atom to represent a substituted or unsubstituted nitrogen-containing alicyclic heterocyclic group)];

Y represents a nitrogen atom or C—$R^8$ (wherein $R^8$ has the same significance as $R^7$); and X represents a nitrogen atom or C—$R^9$ [wherein $R^9$ represents a hydrogen atom or —$COOR^{41}$ (wherein $R^{41}$ has the same significance as $R^{18}$)].

provided that at least one of X, Y and Z represents a nitrogen atom}, and pharmaceutically acceptable salts thereof.

Specific examples of the substituents mentioned in the definitions of the groups in Compounds (I) of the present invention are given below. The examples are preferred ones and do not restrict the present invention.

In the definitions of the groups in general formula (I), the alkyl group includes straight-chain or branched alkyl groups having 1–16 carbon atoms, such as methyl, ethyl, propyl, isopropyl, butyl, isobutyl, sec-butyl, tert-butyl, pentyl, isopentyl, neopentyl, hexyl, heptyl, octyl, nonyl, decyl, undecyl, dodecyl and hexadecyl. The alicyclic alkyl group includes those having 3–12 carbon atoms, for example, monocyclic ones such as cyclopropyl, cyclobutyl, cyclopentyl, cyclohexyl, cycloheptyl, cyclooctyl and cyclododecyl and polycyclic ones such as pinanyl, 1,7,7-trimethylbicyclo[2.2.1]heptyl, adamantyl, hexahydro-4,7-methano-1H-indenyl and 4-hexylbicyclo[2.2.2]octyl. The alicyclic heterocyclic group includes tetrahydrofuryl, tetrahydropyranyl, pyrrolidinyl, piperidinyl, piperazinyl, morpholinyl, thiomorpholinyl, etc. The nitrogen-containing alicyclic heterocyclic group formed with the adjoining nitrogen atom includes pyrrolidinyl, peperidino, homopiperidino, piperazinyl, homopiperazinyl, morpholinyl, thiomorpholinyl, etc. The nitrogen-containing heterocyclic group formed with the adjoining nitrogen atom includes pyrrolidinyl, piperidyl, homopiperidyl, piperazinyl, homopiperazinyl, morpholino, thiomorpholino, pyrrolyl, imidazolyl, pyrazolyl, triazolyl, tetrazolyl, indolyl, indazolyl, benzimidazolyl, benzotriazolyl, etc. The alkenyl group includes straight-chain or branched alkenyl groups having 2–16 carbon atoms, such as vinyl, allyl, 1-propenyl, isopropenyl, methacryl, butenyl, crotyl, pentenyl, hexenyl, heptenyl, decenyl, dodecenyl and hexadecenyl. The alkynyl group includes straight-chain or branched alkynyl groups having 2–16 carbon atoms, such as ethynyl, propargyl, butynyl, pentynyl, hexynyl, heptynyl, decynyl, dodecynyl and hexadecynyl. The aryl group includes phenyl, naphthyl, anthryl, pyrenyl, etc. The aralkyl group includes those having 7–15 carbon atoms, such as benzyl, phenethyl, phenylpropyl, phenylbutyl, benzhydryl, trityl, naphthylmethyl, naphthylethyl and phenylcyclopropyl. The heteroaryl group includes pyridyl, pyrimidinyl, pyrazinyl, pyridazinyl, triazinyl, quinolyl, isoquinolyl, quinazolinyl, phthalazinyl, quinoxalinyl, naphthyridinyl, cinnolinyl, thienyl, furyl, pyrrolyl, imidazolyl, pyrazolyl, triazolyl, tetrazolyl, oxazolyl, thiazolyl, thiadiazolyl, benzothienyl, benzofuryl, indolyl, indazolyl, benzimidazolyl, benzotriazolyl, benzoxazolyl, benzothiazolyl, prinyl, etc. The heteroaryl moiety of the heteroarylalkyl group has the same significance as the above heteroaryl group and the alkyl moiety has the same significance as the above alkyl group. The halogen atom includes fluorine, chlorine, bromine and iodine atoms.

The substituted alkyl group, the substituted alkenyl group and the substituted alkynyl group each has 1 to 3 substituents which are the same or different. Examples of the substituents are a nitro group, a cyano group, a hydroxyl group, an oxo group, a halogen atom, an alicyclic alkyl group, an aryl group, an alicyclic heterocyclic group, a carboxyl group, a formyl group, $R^{42}CO$—$E^1$— (wherein $E^1$ represents a single bond or an oxygen atom; and $R^{42}$ represents an alkyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkoxy group, a trifluoromethyl group, a trifluoromethoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, an amino group, an alkylamino group, an alicyclic alkylamino group, an N-alicyclic heterocyclic substituted amino group, an alkenylamino group, an alkynylamino group, a substituted or unsubstituted arylamino group, an aralkylamino group, a heteroarylamino group or a heteroarylalkylamino group), —$NR^{43}R^{44}$ (wherein $R^{43}$ and $R^{44}$, which may be the same or different, each represents a hydrogen atom, an alkyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkanoyl group, an alicyclic alkanoyl group, an alicyclic heterocyclic carbonyl group, an alkenoyl group, an alkynoyl group, a substituted or unsubstituted aroyl group, an aralkylcarbonyl group, a heteroarylcarbonyl group, a heteroarylalkylcarbonyl group, an alkoxycarbonyl group, an alicyclic alkoxycarbonyl group, an O-alicyclic heterocyclic substituted hydroxycarbonyl group, an alkenyloxycarbonyl group, an alkynyloxycarbonyl group, a substituted or unsubstituted aryloxycarbonyl group, an aralkyloxycarbonyl group, a heteroaryloxycarbonyl group, a heteroarylalkoxycarbonyl group, an alkylsulfonyl group, an alicyclic alkylsulfonyl group, an alicyclic heterocyclic sulfonyl group, an alkenylsulfonyl group, an alkynylsulfonyl group, a substituted or unsubstituted arylsulfonyl group, an aralkylsulfonyl group, a heteroarylsulfonyl group or a heteroarylalkylsulfonyl group), a ureido group, a thioureido group, an alkoxycarbonylamino group, an alicyclic alkoxycarbonylamino group, an O-alicyclic heterocyclic substituted hydroxycarbonylamino group, an alkenyloxycarbonylamino group, an alkynyloxycarbonylamino group, a substituted or unsubstituted aryloxycarbonylamino group, an aralkyloxycarbonylamino group, a heteroaryloxycarbonylamino group, a heteroarylalkoxycarbonylamino group, an alkoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, a sulfo group, a trifluoromethylsulfinyl group, an alkylsulfinyl group, an alicyclic alkylsulfinyl group, an alicyclic heterocyclic sulfinyl group, an alkenylsulfinyl group, an alkynylsulfinyl group, a substituted or unsubstituted arylsulfinyl group, an aralkylsulfinyl group, a heteroarylsulfinyl group, a heteroarylalkylsulfinyl group, —$SO_2R^{45}$ (wherein $R^{45}$ represents a trifluoromethyl group, an alkyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, an amino group, an alkylamino group, an alicyclic alkylamino group, an N-alicyclic heterocyclic substituted amino group, an alkenylamino group, an alkynylamino group, a substituted or unsubstituted arylamino group, an aralkylamino group, a heteroarylamino group or a heteroarylalkylamino group), an alkylsulfonyloxy group, an alicyclic alkylsulfonyloxy group, an alicyclic heterocyclic sulfonyloxy group, an alkenylsulfonyloxy group, an alkynylsulfonyloxy group, a substituted or unsubstituted arylsulfonyloxy group, an aralkylsulfonyloxy group, a heteroarylsulfonyloxy group, a heteroarylalkylsulfonyloxy group, a mercapto group and —S—$G^1$—$R^{46}$ (wherein $G^1$ represents a single bond, CO or $SO_2$; and $R^{46}$ represents a trifluoromethyl group, an alkyl group, an alicyclic alkyl group, an alicyclic heterocyclic group, an alkenyl group, an alkynyl group, a substituted or unsubstituted aryl group, an aralkyl group, a heteroaryl group or a heteroarylalkyl group).

The substituted alicyclic alkyl group, the substituted alicyclic heterocyclic group, the substituted nitrogen-containing alicyclic heterocyclic group, the substituted nitrogen-containing heterocyclic group, the substituted aryl group, the substituted aralkyl group, the substituted heteroaryl group, the substituted heteroarylalkyl group and the substituted phenyl ring each has 1 to 3 substituents which are the same or different. Examples of the substituents are a nitro group, a cyano group, a hydroxyl group, a halogen atom, a methylenedioxy group, —$(OCH_2CH_2)nO$— (wherein n represents an integer of 1 to 6), a trimethylene group, a trifluoromethyl group, a difluoromethoxy group, a trifluoromethoxy group, an azido group, a thiocyanato group, a substituted or unsubstituted alkyl group, a substituted or unsubstituted alicyclic alkyl group, an alicyclic heterocyclic group, an alkenyl group, an alkynyl group, a substituted or unsubstituted aryl group, an aralkyl group, a heteroaryl group, a heteroarylalkyl group, a carboxyl group, a formyl group, $R^{47}CO-E^2-$ (wherein $E^2$ represents a single bond or an oxygen atom; and $R^{47}$ represents an alkyl group, a trifluoromethyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, an amino group, an alkylamino group, an alicyclic alkylamino group, a substituted or unsubstituted N-alicyclic heterocyclic substituted amino group, an alkenylamino group, an alkynylamino group, a substituted or unsubstituted arylamino group, an aralkylamino group, a heteroarylamino group or a heteroarylalkylamino group), $-NR^{48}R^{49}$ (wherein $R^{48}$ and $R^{49}$, which may be the same or different, each represents a hydrogen atom, an alkyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkanoyl group, an alicyclic alkanoyl group, an alicyclic heterocyclic carbonyl group, an alkenoyl group, an alkynoyl group, a substituted or unsubstituted aroyl group, an aralkylcarbonyl group, a heteroarylcarbonyl group, a heteroarylalkylcarbonyl group, an alkoxycarbonyl group, an alicyclic alkoxycarbonyl group, an O-alicyclic heterocyclic substituted hydroxycarbonyl group, an alkenyloxycarbonyl group, an alkynyloxycarbonyl group, a substituted or unsubstituted aryloxycarbonyl group, an aralkyloxycarbonyl group, a heteroaryloxycarbonyl group, a heteroarylalkoxycarbonyl group, an alkylsulfonyl group, an alicyclic alkylsulfonyl group, an alicyclic heterocyclic sulfonyl group, an alkenylsulfonyl group, an alkynylsulfonyl group, a substituted or unsubstituted arylsulfonyl group, an aralkylsulfonyl group, a heteroarylsulfonyl group or a heteroarylalkylsulfonyl group), $-CBNR_xR_y$ (wherein B represents an oxygen atom or a sulfur atom; and $R_x$ and $R_y$, which may be the same or different, each represents a hydrogen atom, a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group), an alkoxycarbonylamino group, an alicyclic alkoxycarbonylamino group, an O-alicyclic heterocyclic substituted hydroxycarbonylamino group, an alkenyloxycarbonylamino group, an alkynyloxycarbonylamino group, a substituted or unsubstituted aryloxycarbonylamino group, an aralkyloxycarbonylamino group, a heteroaryloxycarbonylamino group, a heteroarylalkoxycarbonylamino group, an alkoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, a sulfo group, a trifluoromethylsulfinyl group, an alkylsulfinyl group, an alicyclic alkylsulfinyl group, an alicyclic heterocyclic sulfinyl group, an alkenylsulfinyl group, an alkynylsulfinyl group, a substituted or unsubstituted arylsulfinyl group, an aralkylsulfinyl group, a heteroarylsulfinyl group, a heteroarylalkylsulfinyl group, $-SO_2R^{50}$ (wherein $R^{50}$ represents a trifluoromethyl group, an alkyl group, an alicyclic alkyl group, an alicyclic heterocyclic group, an alkenyl group, an alkynyl group, a substituted or unsubstituted aryl group, an aralkyl group, a heteroaryl group, a heteroarylalkyl group, an alkoxy group, an alicyclic alkoxy group, an O-alicyclic heterocyclic substituted hydroxyl group, an alkenyloxy group, an alkynyloxy group, a substituted or unsubstituted aryloxy group, an aralkyloxy group, a heteroaryloxy group, a heteroarylalkoxy group, an amino group, an alkylamino group, an alicyclic alkylamino group, an N-alicyclic heterocyclic substituted amino group, an alkenylamino group, an alkynylamino group, a substituted or unsubstituted arylamino group, an aralkylamino group, a heteroarylamino group or a heteroarylalkylamino group), an alkylsulfonyloxy group, an alicyclic alkylsulfonyloxy group, an alicyclic heterocyclic sulfonyloxy group, an alkenylsulfonyloxy group, an alkynylsulfonyloxy group, a substituted or unsubstituted arylsulfonyloxy group, an aralkylsulfonyloxy group, a heteroarylsulfonyloxy group, a heteroarylalkylsulfonyloxy group, a mercapto group or $-S-G^2-R^{51}$ (wherein $G^2$ represents a single bond, CO or $SO_2$; and $R^{51}$ represents a trifluoromethyl group, an alkyl group, an alicyclic alkyl group, an alicyclic heterocyclic group, an alkenyl group, an alkynyl group, a substituted or unsubstituted aryl group, an aralkyl group, a heteroaryl group or a heteroarylalkyl group), a substituted or unsubstituted arylazo group, and a heteroarylazo group.

In the definitions of the substituents, the alkyl group and the alkyl moiety of the alkoxy group, the alkylamino group, the alkanoyl group, the alkylsulfonyl group, the alkoxycarbonyl group, the alkoxycarbonylamino group, the alkylsulfinyl group and the alkylsulfonyloxy group have the same significance as the above-described alkyl group. The alicyclic alkyl group and the alicyclic alkyl moiety of the alicyclic alkoxy group, the alicyclic alkylamino group, the alicyclic alkanoyl group, the alicyclic alkylsulfonyl group, the alicyclic alkoxycarbonyl group, the alicyclic alkoxycarbonylamino group, the alicyclic alkylsulfinyl group and the alicyclic alkylsulfonyloxy group have the same significance as the above-described alicyclic alkyl group. The alicyclic heterocyclic group and the alicyclic heterocyclic moiety of the O-alicyclic heterocyclic substituted hydroxyl group, the N-alicyclic heterocyclic substituted amino group, the alicyclic heterocyclic carbonyl group, the alicyclic heterocyclic sulfonyl group, the O-alicyclic heterocyclic substituted hydroxycarbonyl group, the O-alicyclic heterocyclic substituted hydroxycarbonylamino group, the alicyclic heterocyclic sulfinyl group and the alicyclic heterocyclic sulfonyloxy group have the same significance as the above-described alicyclic heterocyclic group. The alkenyl group and the alkenyl moiety of the alkenyloxy group, the alkenylamino group, the alkenoyl group, the alkenylsulfonyl group, the alkenyloxycarbonyl group, the alkenyloxycarbonylamino group, the alkenylsulfinyl group and the alkenylsulfonyloxy group have the same significance as the above-described alkenyl group. The alkynyl group and the alkynyl moiety of the alkynyloxy group, the alkynylamino group, the alkynoyl group, the alkynylsulfonyl group, the alkynyloxycarbonyl group, the alkynyloxycarbonylamino group, the alkynylsulfinyl group and the alkynylsulfonyloxy group have the same significance as the above-described alkynyl group. The aryl group and the aryl moiety of the aryloxy group, the arylamino group, the aroyl group, the arylsulfonyl group, the aryloxycarbonyl group, the aryloxycarbonylamino group, the arylsulfinyl group, the arylsulfonyloxy group and the arylazo group have the same significance as the above-described aryl group. The aralkyl group and the aralkyl moiety of the aralkyloxy group, the aralkylamino group, the aralkylcarbonyl group, the aralkylsulfonyl group, the aralkyloxycarbonyl group, the aralkyloxycarbonylamino group, the aralkylsulfinyl group and the aralkylsulfonyloxy group have the same significance as the above-described aralkyl group. The heteroaryl group and the heteroaryl moiety of the heteroaryloxy group, the heteroarylamino group, the heteroarylcarbonyl group, the heteroarylsulfonyl group, the heteroaryloxycarbonyl group, the heteroaryloxycarbonylamino group, the heteroarylsulfinyl group, the heteroarylsulfonyloxy group and the heteroarylazo group have the same significance as the above-described heteroaryl group. The heteroarylalkyl group and the heteroarylalkyl moiety of the heteroarylalkyloxy group, the heteroarylalkylamino group, the heteroarylalkylcarbonyl group, the heteroarylalkylsulfonyl group, the heteroarylalkyloxycarbonyl group, the heteroarylalkyloxycarbonylamino group, the heteroarylalkylsulfinyl group and the heteroarylalkylsulfonyloxy group have the same significance as the above-described heteroarylalkyl group. The halogen atom has the same significance as the above-described halogen atom. Examples of the substituents in the substituted alkyl group and the substituted N-alicyclic heterocyclic substituted amino group are a hydroxyl group, an oxo group and —NR$^{52}$R$^{53}$ (wherein R$^{52}$ and R$^{53}$, which may be the same or different, each represents a hydrogen atom, an alkyl group, an alicyclic alkyl group, an alicyclic heterocyclic group, an alkenyl group, an alkynyl group, an aryl group, an aralkyl group, a heteroaryl group, a heteroarylalkyl group or an alkoxycarbonyl group, or R$^{52}$ and R$^{53}$ are combined together with the adjoining nitrogen atom to represent a nitrogen-containing alicyclic heterocyclic group; and the alkyl group, the alicyclic alkyl group, the alicyclic heterocyclic group, the alkenyl group, the alkynyl group, the aryl group, the aralkyl group, the heteroaryl group, the heteroarylalkyl group, the alkoxycarbonyl group and the nitrogen-containing alicyclic heterocyclic group formed with the adjoining nitrogen atom have the same significances as defined above). Examples of the substituents in the substituted alicyclic alkyl group, the substituted aryl group, the substituted aryloxy group, the substituted arylamino group, the substituted aroyl group, the substituted arylsulfonyl group, the substituted aryloxycarbonyl group, the substituted aryloxycarbonylamino group, the substituted aryloxy group, the substituted arylsulfinyl group, the substituted arylsulfonyloxy group and the substituted arylazo group are an alkyl group, a nitro group, a cyano group, a hydroxyl group, a halogen atom and —NR$^{54}$R$^{55}$ (wherein R$^{54}$ and R$^{55}$, which may be the same or different, each represents a hydrogen atom, an alkyl group, an alicyclic alkyl group, an alicyclic heterocyclic group, an alkenyl group, an alkynyl group, an aryl group, an aralkyl group, a heteroaryl group or a heteroarylalkyl group; and the alkyl group, the alicyclic alkyl group, the alicyclic heterocyclic group, the alkenyl group, the alkynyl group, the aryl group, the aralkyl group, the heteroaryl group and the heteroarylalkyl group have the same significances as defined above), and the alkyl group and the halogen atom have the same significances as defined above.

The pharmaceutically acceptable salts of Compounds (I) include pharmaceutically acceptable acid addition salts, metal salts, ammonium salts, organic amine addition salts, amino acid addition salts, etc. Examples of the pharmaceutically acceptable acid addition salts of Compounds (I) are inorganic acid addition salts such as hydrochloride, sulfate and phosphate, and organic acid addition salts such as acetate, maleate, fumarate, tartrate, citrate and methanesulfonate. Examples of the pharmaceutically acceptable metal salts are alkali metal salts such as sodium salt and potassium salt, alkaline earth metal salts such as magnesium salt and calcium salt, aluminum salt and zinc salt. Examples of the pharmaceutically acceptable ammonium salts are ammonium salt and tetramethylammounium salt. Examples of the pharmaceutically acceptable organic amine addition salts are salts with morpholine and piperidine. Examples of the pharmaceutically acceptable amino acid addition salts are salts with lysine, glycine and phenylalanine.

The processes for preparing Compounds (I) are described below.

Process 1

Compound (I-a), i.e., Compound (I) wherein R$^1$ is hydrogen can be prepared according to the following reaction step.

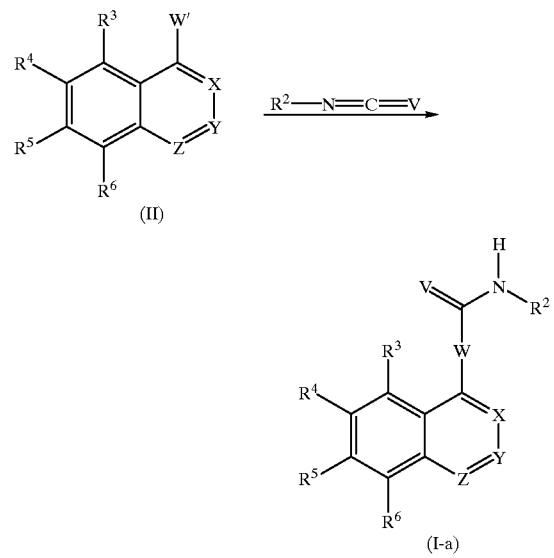

(In the formulae, R$^2$, R$^3$, R$^4$, R$^5$, R$^6$, X, Y, Z, V and W have the same significances as defined above; and W' represents 1-piperazinyl or 1-homopiperazinyl wherein carbons on the ring may be substituted by unsubstituted alkyl groups.)

Compound (I-a) can be obtained by reaction of Compound (II) with isocyanate (R$^2$NCO) obtained according to a known method [e.g., S. R. Sandler, et al., Organic Functional Group Preparations, vol. 1, p. 305, Academic Press Inc. (New York and London) (1968); and R. B. Wagner, et al., Synthetic Organic Chemistry, vol. 3, p. 640, John Wiley (1961)] or isothiocyanate (R$^2$NCS) obtained according to a known method [e.g., S. R. Sandier, et al., Organic Functional Group Preparations, vol. 1, p. 312, Academic Press Inc. (New York and London) (1968); and R. B. Wagner, et al., Synthetic Organic Chemistry, vol. 3, p. 829, John Wiley, (1961)] in an appropriate inert solvent, e.g., a halogenated hydrocarbon such as chloroform or dichloromethane, an aromatic hydrocarbon such as benzene or toluene, an ether solvent such as diethyl ether, tetrahydrofuran (THF) or 1,4-dioxane, a lower alcohol such as methanol, ethanol or isopropanol, an aprotic polar solvent such as dimethylformamide, N-methylpyrrolidone or dimethyl sulfoxide, or a mixture thereof at a temperature between –20° C. and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium tert-butoxide.

The starting Compound (II) can be obtained by the methods described in South African Patent No. 67 06512 (1968), Ind. J. Chem., 26B, 550–555 (1987), Reference Examples of the present application, and the like, and also by the following reaction step.

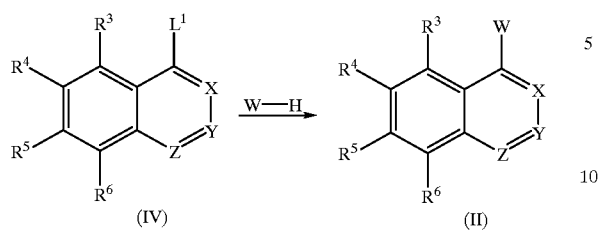

(In the formulae, $L^1$ represents a leaving group; and $R^3$, $R^4$, $R^5$, $R^6$, W, X, Y and Z have the same significances as defined above.)

The leaving group represented by $L^1$ includes halogen, lower alkoxy, lower alkylthio, lower alkylsulfonyloxy, arylsulfonyloxy, etc. The halogen, the lower alkoxy, the lower alkylthio, the lower alkylsulfonyloxy and the arylsulfonyloxy have the same significances as defined above.

Compound (II) can be obtained by reaction of Compound (IV) with Compound W—H in an appropriate inert solvent, e.g., a lower alcohol such as methanol, ethanol or isopropanol, a halogenated hydrocarbon such as chloroform or dichloromethane, an aromatic hydrocarbon such as benzene or toluene, an ether solvent such as diethyl ether, THF or 1,4-dioxane, an aprotic polar solvent such as dimethylformamide, N-methylpyrrolidone or dimethyl sulfoxide, or a mixture thereof at a temperature between room temperature and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium t-butoxide.

In the above process, if the defined groups change under the conditions of the working method or are not appropriate for carrying out the method, the desired compound can be obtained by conducting the reaction using W—H which is protected except for the reaction point, followed by deprotection. Suitable protective groups are, for example, those described in T. W. Greene, Protective Groups in Organic Synthesis, John Wiley & Sons Inc. (1981), etc., such as ethoxycarbonyl, t-butoxycarbonyl, acetyl and benzyl. The protective groups can be introduced and eliminated according to conventional methods used in organic synthetic chemistry [e.g., T. W. Greene, Protective Groups in Organic Synthesis, John Wiley & Sons Inc. (1981)].

The starting Compound (IV) is commercially available, or can be obtained according to the methods described in J. Chem. Soc., 890–899 (1947); J. Chem. Soc., 561–572 (1962); J. Chem. Soc., B, 449–454 (1967); J. Indian Chem. Soc., 36, 787–791 (1959); J. Org. Chem., 17, 1571–1575 (1952); J. Med. Chem., 14, 1060–1066 (1971); French Patent No. 1388756 (1965); J. Am. Chem. Soc., 68, 1204–1208 (1946); Japanese Published Unexamined Patent Application No. 120872/85; J. Med. Chem., 39, 918–928 (1966); and South African Patent No. 67 06512 (1968), the methods described in Reference Examples, or the like.

Process 2

Compound (I) can be prepared according to the following reaction step.

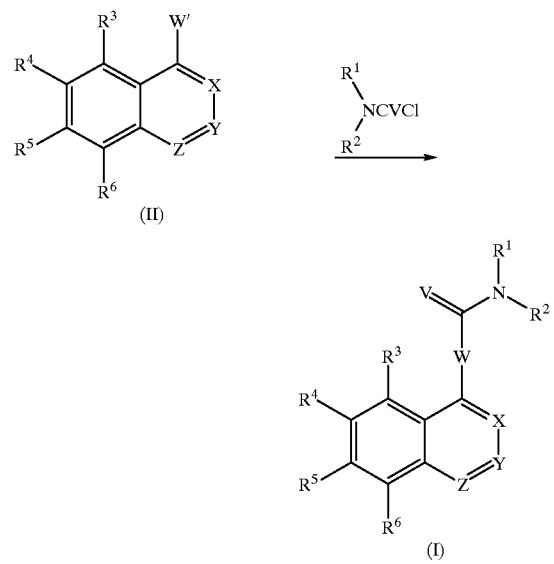

(In the formulae, $R^1$, $R^2$, $R^3$, $R^4$, $R^5$, $R^6$, X, Y, Z, V, W and W' have the same significances as described above.)

Compound (I) can be obtained by reaction of Compound (II) with carbamoyl chloride or thiocarbamoyl chloride obtained according to a known method [e.g., Beilstein, 4, 73 (1922); Beilstein, 4, 75 (1922); Berichte der Deutschen Chemischen Gesellschaft, 12, 1163 (1879); and Berichte der Deutschen Chemischen Gesellschaft, 26, 1681 (1893)] in an appropriate inert solvent, e.g., a halogenated hydrocarbon such as chloroform or dichloromethane, an aromatic hydrocarbon such as benzene or toluene, an ether solvent such as diethyl ether, THF or 1,4-dioxane, a lower alcohol such as methanol, ethanol or isopropanol, an aprotic polar solvent such as dimethylformamide, N-methylpyrrolidone or dimethyl sulfoxide, or a mixture thereof at a temperature between −20° C. and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium tert-butoxide.

Process 3

Compound (I) can also be prepared according to the following reaction step.

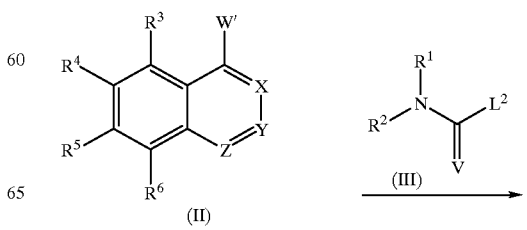

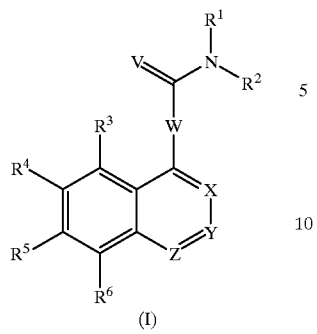

(I)

(In the formulae, $L^2$ represents a leaving group; and $R^1$, $R^2$, $R^3$, $R^4$, $R^5$, $R^6$, X, Y, Z, V, W and W' have the same significances as defined above.)

The leaving group represented by $L^2$ includes lower alkoxy, lower alkylthio, 4-nitrophenyloxy, etc. The lower alkoxy and the lower alkylthio have the same significances as defined above.

Compound (I) can be obtained by reaction of Compound (II) with Compound (III) in an appropriate inert solvent, e.g., a halogenated hydrocarbon such as chloroform or dichloromethane, an aromatic hydrocarbon such as benzene or toluene, an ether solvent such as diethyl ether, THF or 1,4-dioxane, a lower alcohol such as methanol, ethanol or isopropanol, an aprotic polar solvent such as dimethylformamide, N-methylpyrrolidone or dimethyl sulfoxide, or a mixture thereof at a temperature between room temperature and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium tert-butoxide.

The starting Compound (III) can be obtained according to the method described in S. R. Sandler, et al., Organic Functional Group Preparations, vol. 2, p. 223, Academic Press Inc. (New York and London) (1971), or the like.

Process 4

Compound (I) can also be prepared according to the following reaction step.

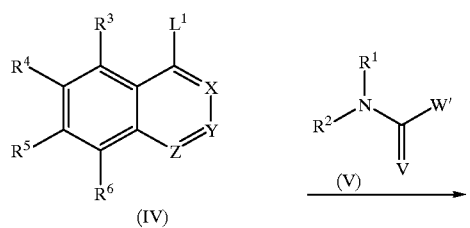

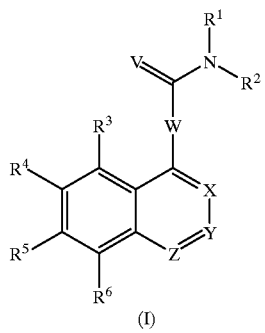

(I)

(In the formulae, $L^1$ represents a leaving group; and $R^1$, $R^2$, $R^3$, $R^4$, $R^5$, $R^6$, X, Y, Z, V, W and W' have the same significances as defined above.)

The leaving group represented by $L^1$ has the same significance as defined above, and the halogen, the lower alkoxy, the lower alkylsulfonyloxy and the lower alkylsulfonyl have the same significances as defined above.

Compound (I) can be obtained by reaction of Compound (IV) with Compound (V) in an appropriate inert solvent, e.g., a halogenated hydrocarbon such as chloroform or dichloromethane, an aromatic hydrocarbon such as benzene or toluene, an ether solvent such as diethyl ether, THF or 1,4-dioxane, a lower alcohol such as methanol, ethanol or isopropanol, an aprotic polar solvent such as dimethylformamide, N-methylpyrrolidone or dimethyl sulfoxide, or a mixture thereof at a temperature between room temperature and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium tert-butoxide.

The starting Compound (V) can be obtained according to the method described in Japanese Published Unexamined Patent Application No. 120872/85, or the like.

Process 5

Compound (I) can also be prepared according to the following reaction step.

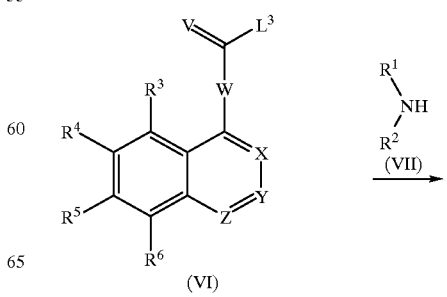

-continued

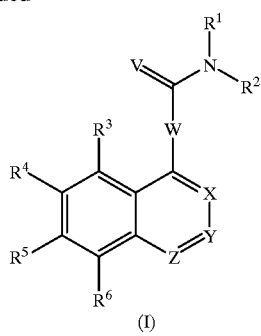

(I)

(In the formulae, $L^3$ represents a leaving group; and $R^1$, $R^2$, $R^3$, $R^4$, $R^5$, $R^6$, V, W, X, Y and Z have the same significances as defined above.)

The leaving group represented by $L^3$ includes halogen, lower alkoxy, lower alkylthio, 4-nitrophenyloxy, etc. The halogen, the lower alkoxy and the lower alkylthio have the same significances as defined above.

Compound (I) can be obtained by reaction of Compound (VI) with Compound (VII) in an appropriate inert solvent, e.g., a halogenated hydrocarbon such as chloroform or dichloromethane, an aromatic hydrocarbon such as benzene or toluene, an ether solvent such as diethyl ether, THF or 1,4-dioxane, a lower alcohol such as methanol, ethanol or isopropanol, an aprotic polar solvent such as dimethylformamide, N-methylpyrrolidone or dimethyl sulfoxide, or a mixture thereof at a temperature between room temperature and the boiling point of the solvent used for 10 minutes to 48 hours. If necessary, the reaction is carried out in the presence of a base, e.g., an organic base such as triethylamine or pyridine, an inorganic base such as potassium carbonate, sodium hydroxide or sodium hydride, or a metal alkoxide such as sodium methoxide or potassium tert-butoxide.

The starting Compound (VI) can be obtained according to the methods described in South African Patent No. 67 06512 (1968), U.S. Pat. No. 3,723,434 (1973), etc., the methods described in Reference Examples, or the like.

In the above process, if the defined groups change under the conditions of the working method or are not appropriate for carrying out the method, the desired compound can be obtained by using the methods for introducing and eliminating protective groups which are conventionally used in organic synthetic chemistry [e.g., T. W. Greene, Protective Groups in Organic Synthesis, John Wiley & Sons Inc. (1981)], etc. Conversion of functional groups contained in the substituents can be carried out by known methods [e.g., R. C. Larock, Comprehensive Organic Transformations (1989)] in addition to the above-described processes, and some of Compounds (I) can be used as intermediates for further synthesizing novel derivatives (I).

The intermediates and the desired compounds in the processes described above can be isolated and purified by purification methods conventionally used in organic synthetic chemistry, for example, neutralization, filtration, extraction, washing, drying, concentration, recrystallization, and various kinds of chromatography. The intermediates may be subjected to the subsequent reaction without purification.

There may be tautomers for some Compounds (I), and the present invention covers all possible isomers including tautomers and mixtures thereof.

In the case where a salt of Compound (I) is desired and it is produced in the form of the desired salt, it can be subjected to purification as such. In the case where Compound (I) is produced in the free state and its salt is desired, Compound (I) is dissolved or suspended in a suitable organic solvent, followed by addition of an acid or a base to form a salt.

Compounds (I) and pharmaceutically acceptable salts thereof may exist in the form of adducts with water or various solvents, which are also within the scope of the present invention.

Examples of Compounds (I) obtained by the above-described processes are shown in Table 1.

TABLE 1-1

| Compd. No. | V | $R^1$ | $R^2$ |
|---|---|---|---|
| 1 | O | H | phenyl |
| 2 | S | H | phenyl |
| 3 | O | H | —CH$_2$—phenyl |
| 4 | O | H | —C(=O)—phenyl |
| 5 | O | H | —S(=O)$_2$—phenyl |
| 6 | S | H | —(CH$_2$)$_2$—phenyl |

TABLE 1-1-continued
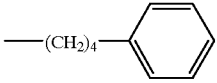
| Compd. No. | V | R[1] | R[2] |
|---|---|---|---|
| 7 | S | H | —(CH$_2$)$_4$—phenyl |
| 8 | O | H | methylnaphthyl |
TABLE 1-2
| Compd. No. | V | R[1] | R[2] |
|---|---|---|---|
| 9 | S | H | methyl-indanyl |
| 10 | S | H | methyl-pyrenyl |
TABLE 1-2-continued
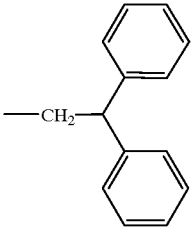
| Compd. No. | V | R[1] | R[2] |
|---|---|---|---|
| 11 | S | H | —CH$_2$—CH(phenyl)$_2$ |
| 12 | O | H | trans-2-phenylcyclopropyl |
| 13 | O | H | methylcyclohexyl |
TABLE 1-3
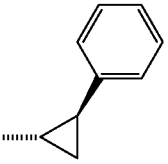
| Compd. No. | V | R[1] | R[2] |
|---|---|---|---|
| 14 | O | H | adamantyl |

TABLE 1-3-continued
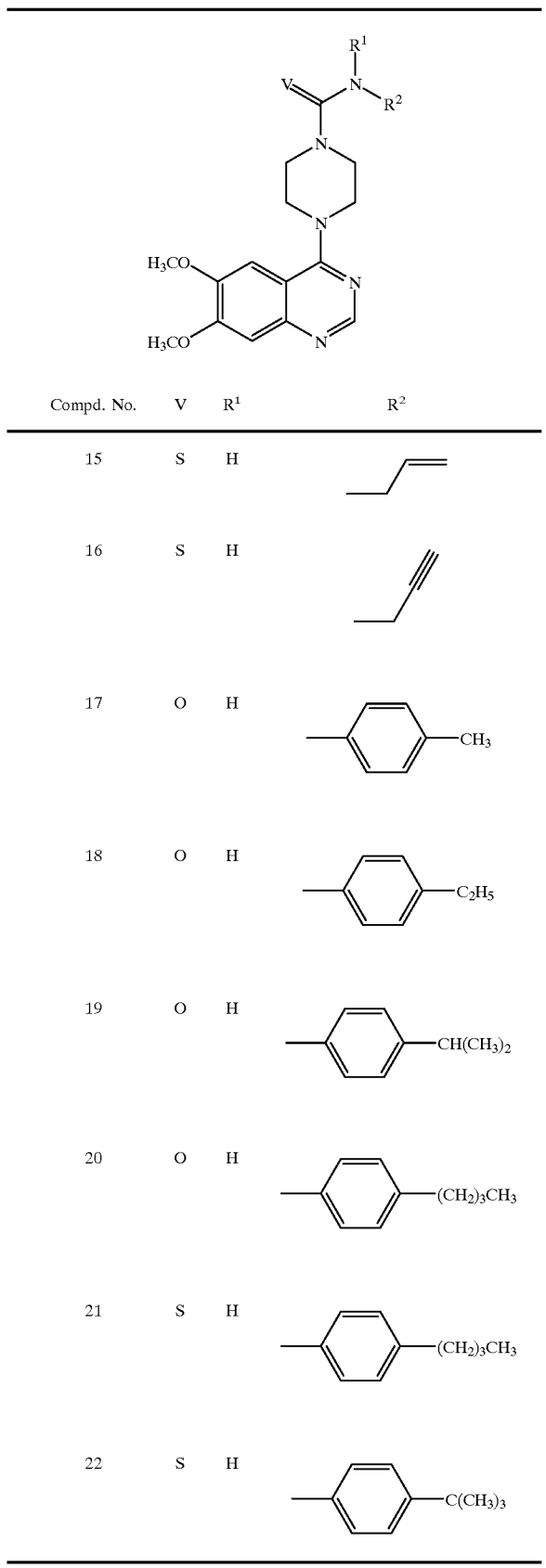
| Compd. No. | V | R¹ | R² |
|---|---|---|---|
| 15 | S | H | —CH₂—CH=CH₂ (allyl) |
| 16 | S | H | —CH₂—C≡CH (propargyl) |
| 17 | O | H | —C₆H₄—CH₃ (p-tolyl) |
| 18 | O | H | —C₆H₄—C₂H₅ |
| 19 | O | H | —C₆H₄—CH(CH₃)₂ |
| 20 | O | H | —C₆H₄—(CH₂)₃CH₃ |
| 21 | S | H | —C₆H₄—(CH₂)₃CH₃ |
| 22 | S | H | —C₆H₄—C(CH₃)₃ |
TABLE 1-4
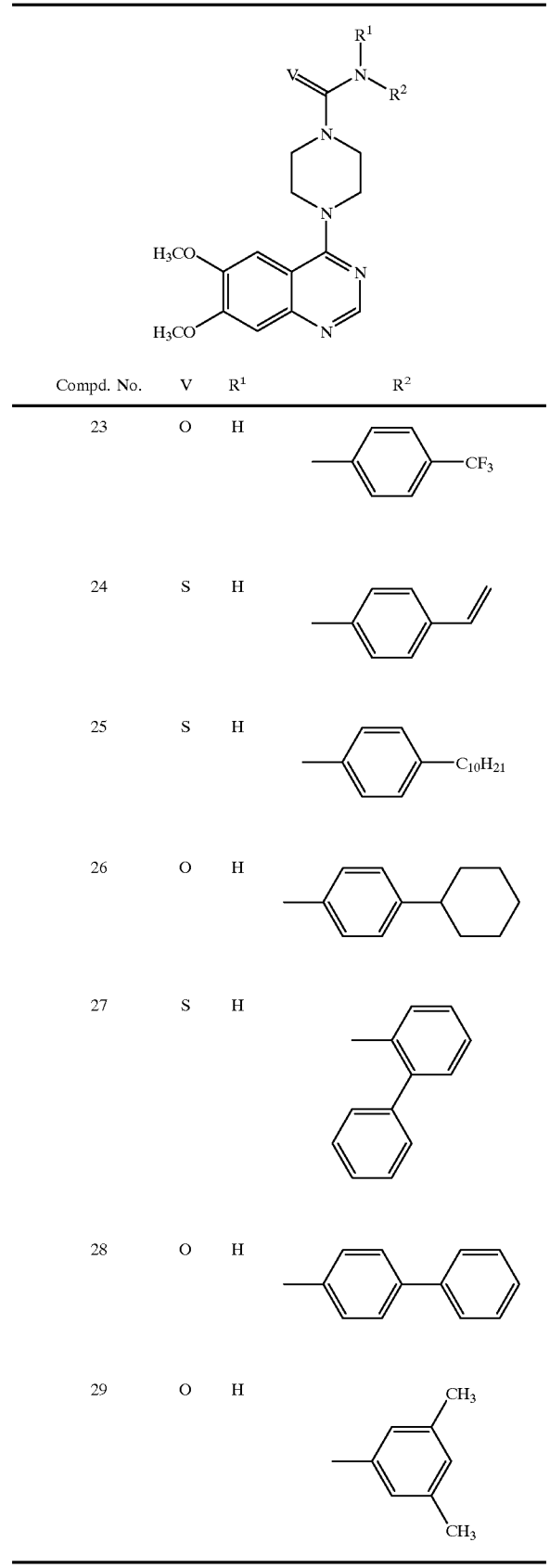
| Compd. No. | V | R¹ | R² |
|---|---|---|---|
| 23 | O | H | —C₆H₄—CF₃ |
| 24 | S | H | —C₆H₄—CH=CH₂ |
| 25 | S | H | —C₆H₄—C₁₀H₂₁ |
| 26 | O | H | —C₆H₄—cyclohexyl |
| 27 | S | H | 2-biphenyl |
| 28 | O | H | 4-biphenyl |
| 29 | O | H | 3,5-dimethylphenyl |

TABLE 1-5

[Structure: piperazine linked to 6,7-dimethoxyquinazoline at position 4; N1 of piperazine bears C(=V)-NR¹R²]

| Compd. No. | V | R¹ | R² |
|---|---|---|---|
| 30 | O | H | 2,4-dimethylphenyl (2,3-dimethylphenyl per image: CH₃ at two positions) |
| 31 | O | H | 2,6-diisopropylphenyl |
| 32 | O | H | 3,5-bis(trifluoromethyl)phenyl |
| 33 | O | H | 3-tert-butyl-5-(prop-1-en-2-yl)phenyl |
| 34 | O | H | 2-fluorophenyl |
| 35 | O | H | 3-fluorophenyl |
| 36 | O | H | 4-fluorophenyl |

TABLE 1-6

[Structure: piperazine linked to 6,7-dimethoxyquinazoline at position 4; N1 of piperazine bears C(=V)-NR¹R²]

| Compd. No. | V | R¹ | R² |
|---|---|---|---|
| 37 | S | H | 4-fluorophenyl |
| 38 | O | H | 2-chlorophenyl |
| 39 | O | H | 3-chlorophenyl |
| 40 | O | H | 4-chlorophenyl |
| 41 | S | H | 4-chlorophenyl |
| 42 | S | H | —CH₂—(4-chlorophenyl) |
| 43 | O | H | 4-(methylsulfonyl)-... 4-chlorophenyl with SO₂CH₃ |

TABLE 1-7
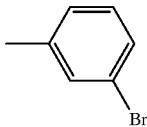
| Compd. No. | V | R¹ | R² |
|---|---|---|---|
| 44 | O | H | 3-bromophenyl |
| 45 | O | H | 4-bromophenyl |
| 46 | O | H | 4-iodophenyl |
| 47 | S | H | 4-iodophenyl |
| 48 | O | H | 4-chloro-2-trifluoromethylphenyl |
| 49 | O | H | 4-chloro-3-trifluoromethylphenyl |
| 50 | O | H | 2,4-difluorophenyl |
TABLE 1-8
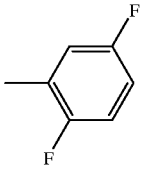
| Compd. No. | V | R¹ | R² |
|---|---|---|---|
| 51 | O | H | 2,5-difluorophenyl |
| 52 | O | H | 2,6-dichlorophenyl |
| 53 | O | H | 2,4-dichlorophenyl |
| 54 | O | H | 3,4-dichlorophenyl |
| 55 | O | H | 3,5-dichlorophenyl |

TABLE 1-9

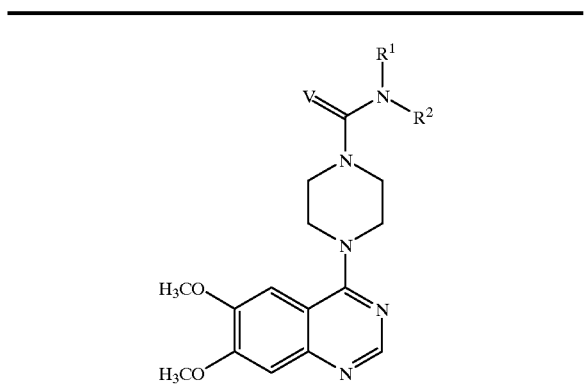

| Compd. No. | V | R¹ | R² |
|---|---|---|---|
| 56 | O | H | –C₆H₄–OCH₃ (4-methoxyphenyl) |
| 57 | O | H | –C₆H₄–OC₂H₅ (4-ethoxyphenyl) |
| 58 | O | H | –C₆H₄–O(CH₂)₃CH₃ (4-butoxyphenyl) |
| 59 | O | H | –C₆H₄–OCF₃ (4-trifluoromethoxyphenyl) |
| 60 | O | H | –C₆H₄–O–C₆H₅ (4-phenoxyphenyl) |
| 61 | S | H | –C₆H₄–O–C₆H₅ (4-phenoxyphenyl) |
| 62 | S | H | –C₆H₄–O–C₆H₄–NO₂ (4-(4-nitrophenoxy)phenyl) |
| 63 | S | H | –C₆H₄–OCH₂–C₆H₅ (4-benzyloxyphenyl) |

TABLE 1-10

| Compd. No. | V | R¹ | R² |
|---|---|---|---|
| 64 | O | H | 2,4-dimethoxyphenyl (with H₃CO substituents) |
| 65 | O | H | 2,5-dimethoxyphenyl |
| 66 | S | H | 3,4-dimethoxyphenyl |
| 67 | S | H | 3,5-dimethoxyphenyl |
| 68 | S | H | 3,4-methylenedioxyphenyl |
| 69 | O | H | –C₆H₄–SCH₃ (4-methylthiophenyl) |
| 70 | S | H | –C₆H₄–S–C₆H₄–NO₂ (4-(4-nitrophenylthio)phenyl) |

TABLE 1-11

[Structure: 6,7-dimethoxyquinazoline substituted at 4-position with piperazine, whose other N bears C(=V)N(R¹)(R²)]

| Compd. No. | V | R¹ | R² |
|---|---|---|---|
| 71 | S | H | -C₆H₄-N(CH₃)₂ (para) |
| 72 | S | H | -C₆H₄-N(C₂H₅)₂ (para) |
| 73 | S | H | -C₆H₄-NH-SO₂-(5-dimethylamino-naphth-1-yl) (para) |
| 74 | S | H | -C₆H₄-N=N-C₆H₄-N(CH₃)₂ (para,para') |
| 75 | O | H | -C₆H₄-NO₂ (ortho) |
| 76 | O | H | -C₆H₄-NO₂ (meta) |
| 77 | O | H | -C₆H₄-NO₂ (para) |

TABLE 1-12

| Compd. No. | V | R¹ | R² |
|---|---|---|---|
| 78 | S | H | 2-nitrophenyl |
| 79 | S | H | 3-nitrophenyl |
| 80 | S | H | 4-nitrophenyl |
| 81 | O | H | 4-fluoro-3-nitrophenyl |
| 82 | O | H | 2-chloro-4-nitrophenyl |
| 83 | O | H | 4-chloro-3-nitrophenyl |
| 84 | O | H | 3-cyanophenyl |

TABLE 1-13

| Compd. No. | V | R¹ | R² |
|---|---|---|---|
| 85 | S | H | 4-cyanophenyl |
| 86 | O | H | 3-acetylphenyl |
| 87 | O | H | 4-acetylphenyl |
| 88 | S | H | 4-benzoylphenyl |
| 89 | O | H | 4-(ethoxycarbonyl)phenyl |
| 90 | O | H | 4-(butoxycarbonyl)phenyl |
| 91 | O | H | 3,5-bis(methoxycarbonyl)phenyl |

TABLE 1-14

| Compd. No. | V | R¹ | R² |
|---|---|---|---|
| 92 | S | H | 4-methylphenyl-C(O)NH-(2-oxotetrahydrofuran-3-yl) |
| 93 | S | H | 4-methylphenyl-SO₂NH₂ |
| 94 | S | H | —CH₂-(2-furyl) |
| 95 | S | H | —C(O)-(2-furyl) |

TABLE 1-14-continued

| Compd. No. | V | R¹ | R² |
|---|---|---|---|
| 96 | O | H | —(CH₂)₂-(2-thienyl) |
| 97 | S | H | 3-pyridyl |
| 98 | S | H | —CH₂-(3-pyridyl) |
| 99 | S | H | 4-methyl-1,4-dihydroxyphthalazinyl |

TABLE 1-15

[Structure: quinazoline with 6,7-dimethoxy substituents, 4-position connected to piperazine, which is connected via C(=V) to N(R¹)(R²)]

| Compd. No. | V | R¹ | R² |
|---|---|---|---|
| 100 | O | H | -C₆H₄-CH₂-N(piperidine) (para) |
| 101 | O | H | -C₆H₄-CH₂-NH-CH₂-C₆H₅ (para) |
| 102 | O | H | -C₆H₄-CH₂-NH-CH₂-(4-pyridyl) (para) |
| 116 | O | phenyl | phenyl |
| 117 | O | H | -C₆H₄-N(morpholine) (para) |
| 118 | O | H | 5-indolyl |
| 119 | O | H | -(CH₂)₂-C₆H₄-Cl (para) |
| 120 | O | H | -(CH₂)₂-C₆H₄-Br (para) |

TABLE 1-16

| Compd. No. | R⁴ | R⁵ | R⁶ | R⁸ | n | Rx |
|---|---|---|---|---|---|---|
| 103 | H | H | H | H | 1 | NO₂ |
| 104 | H | H | H | H | 1 | OPh |
| 105 | OC₂H₅ | OC₂H₅ | H | H | 1 | NO₂ |
| 106 | OC₂H₅ | OC₂H₅ | H | H | 1 | OPh |
| 107 | OCH₃ | OCH₃ | OCH₃ | H | 1 | NO₂ |
| 108 | OCH₃ | OCH₃ | OCH₃ | H | 1 | OPh |
| 109 | NO₂ | NHC₂H₅ | H | H | 1 | OPh |
| 110 | H | H | H | Ph | 1 | NO₂ |
| 111 | OCH₃ | OCH₃ | H | Ph | 1 | NO₂ |
| 112 | OCH₃ | OCH₃ | H | H | 2 | NO₂ |

TABLE 1-17
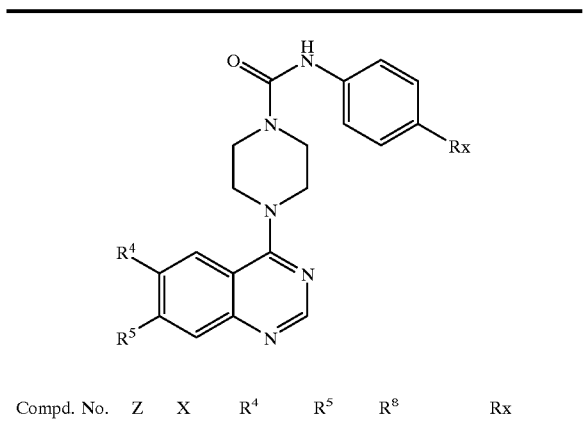
| Compd. No. | Z | X | R⁴ | R⁵ | R⁸ | Rx |
|---|---|---|---|---|---|---|
| 113 | CH | N | OCH₃ | OCH₃ | H | NO₂ |
| 114 | CH | N | OCH₃ | OCH₃ | Cl | NO₂ |
| 115 | N | CH | H | Cl | H | 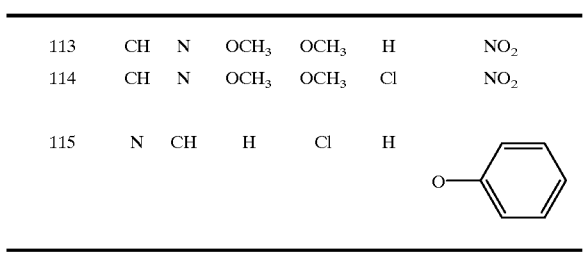 |
TABLE 1-18
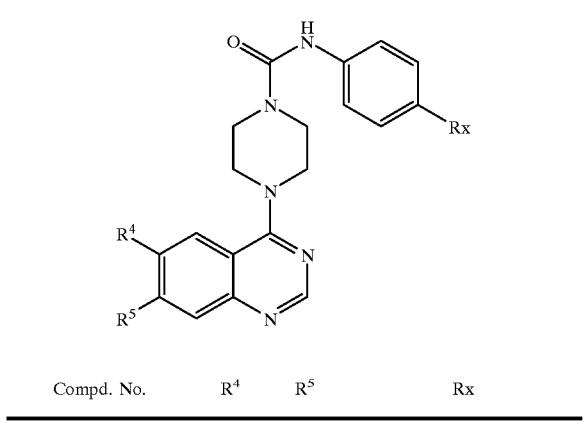
| Compd. No. | R⁴ | R⁵ | Rx |
|---|---|---|---|
| 121 | 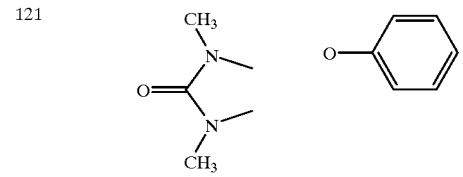 | | 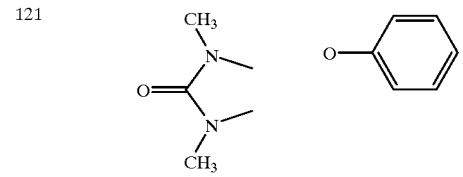 |
| 122 | 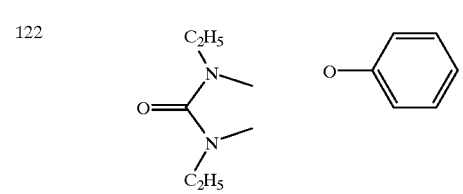 | | 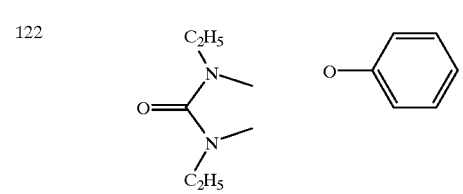 |
TABLE 1-18-continued
| Compd. No. | R⁴ | R⁵ | Rx |
|---|---|---|---|
| 123 | 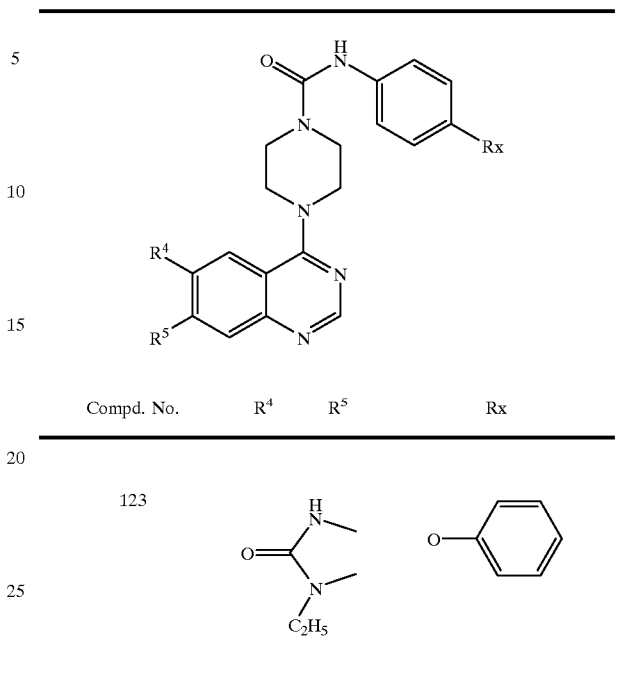 | | |
| 124 | | | |
TABLE 1-19
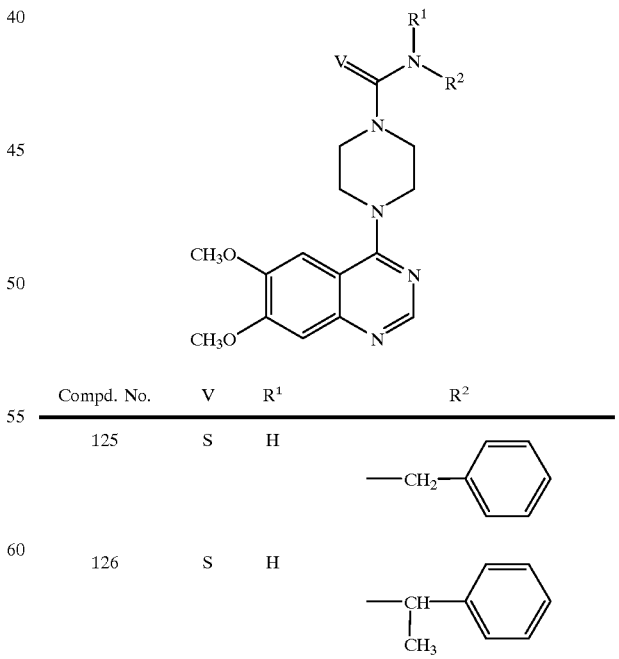
| Compd. No. | V | R¹ | R² |
|---|---|---|---|
| 125 | S | H | —CH₂—C₆H₅ |
| 126 | S | H | —CH(CH₃)—C₆H₅ |

TABLE 1-19-continued
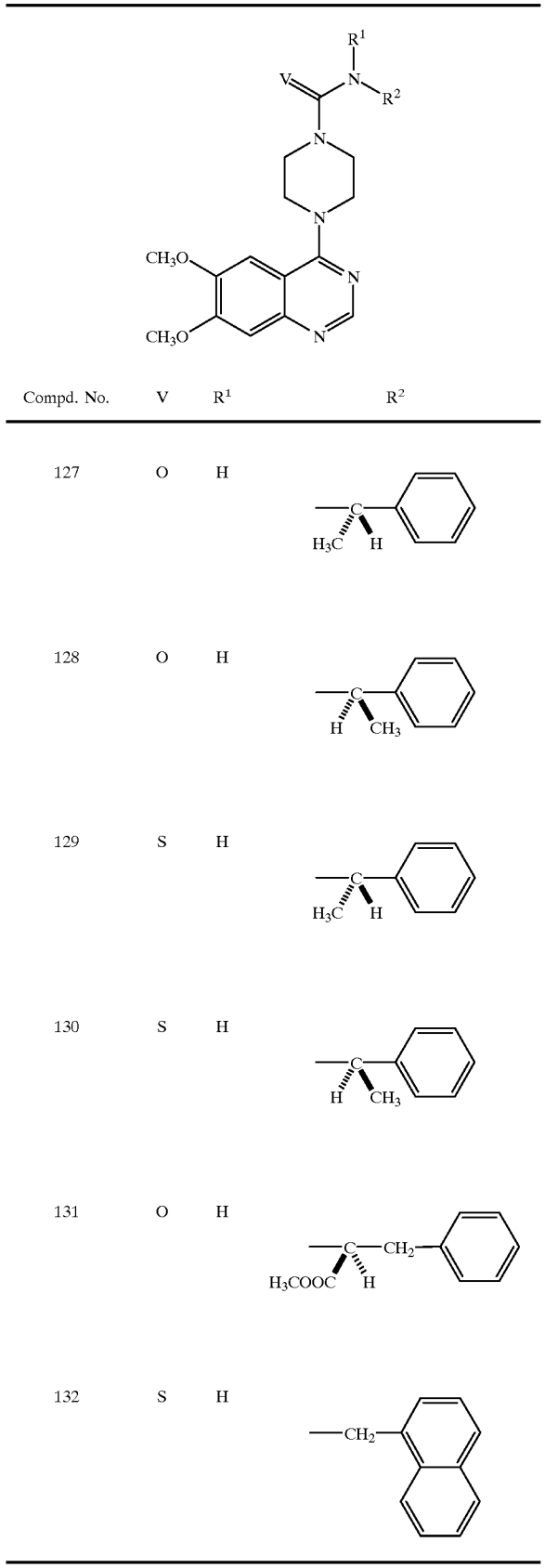
| Compd. No. | V | R¹ | R² |
|---|---|---|---|
| 127 | O | H | (S)-CH(CH₃)-phenyl |
| 128 | O | H | (R)-CH(CH₃)-phenyl |
| 129 | S | H | (S)-CH(CH₃)-phenyl |
| 130 | S | H | (R)-CH(CH₃)-phenyl |
| 131 | O | H | -C(CH₃)(COOCH₃)-CH₂-phenyl |
| 132 | S | H | -CH₂-(1-naphthyl) |
TABLE 1-20
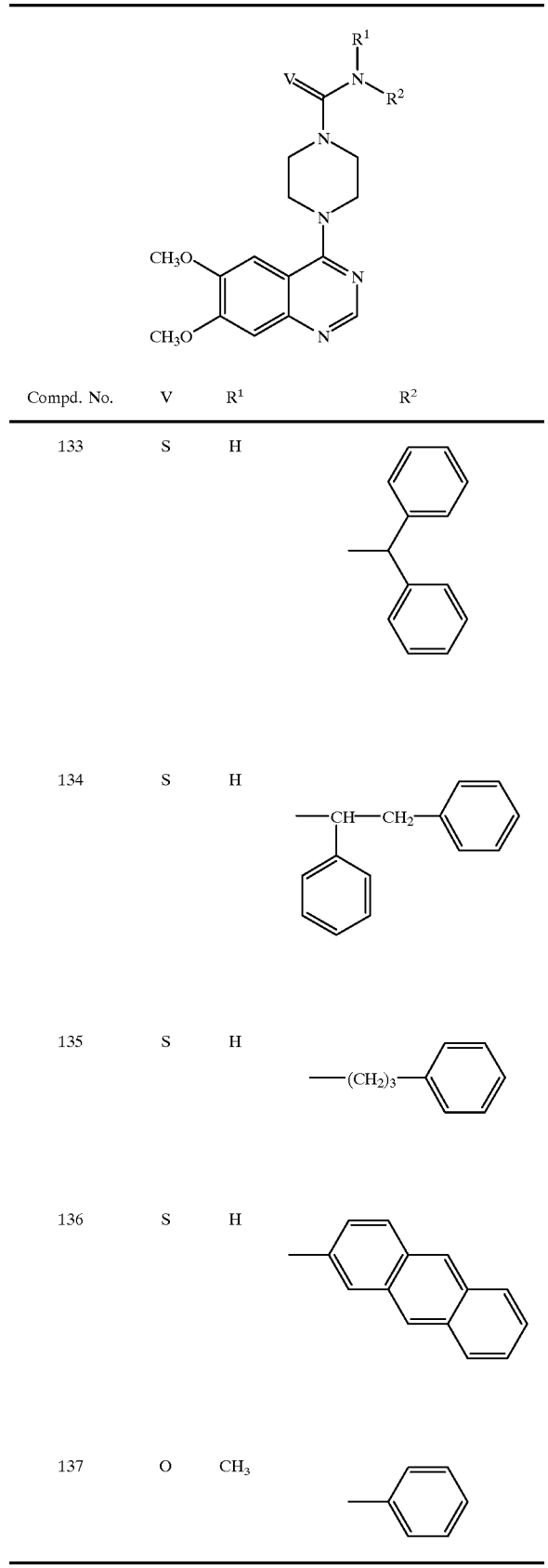
| Compd. No. | V | R¹ | R² |
|---|---|---|---|
| 133 | S | H | -CH(CH₃)(diphenyl) |
| 134 | S | H | -CH(phenyl)-CH₂-phenyl |
| 135 | S | H | -(CH₂)₃-phenyl |
| 136 | S | H | 2-anthracenyl |
| 137 | O | CH₃ | phenyl |

TABLE 1-21

| Compd. No. | V | R¹ | R² |
|---|---|---|---|
| 138 | S | H | —CH₂-cyclohexyl |
| 139 | S | H | dicyclopentadienyl |
| 140 | O | H | tetrahydropyran-2-yl |
| 141 | S | H | —CH₂-tetrahydrofuran-2-yl |
| 142 | S | H | —(CH₂)₂-morpholinyl |
| 143 | S | H | —C(O)—CH=CH—phenyl |

TABLE 1-22

| Compd. No. | V | R¹ | R² |
|---|---|---|---|
| 144 | O | H | 3-methylphenyl |
| 145 | S | H | 3-methylphenyl |
| 146 | S | H | 4-methylphenyl |
| 147 | S | H | —CH₂-(4-methylphenyl) |
| 148 | O | H | 3-ethylphenyl |
| 149 | S | H | 3-ethylphenyl |
| 150 | O | H | 3-isopropylphenyl |
| 151 | S | H | 3-isopropylphenyl |

TABLE 1-23

| Compd. No. | V | R¹ | R² |
|---|---|---|---|
| 152 | S | H | -C₆H₄-CH(CH₃)₂ (para) |
| 153 | O | H | -CH₂-C₆H₄-CH(CH₃)₂ (para) |
| 154 | S | H | -CH₂-C₆H₄-CH(CH₃)₂ (para) |
| 155 | O | H | -C₆H₄-CH₂CH(CH₃)₂ (para) |
| 156 | O | H | -C₆H₄-C(CH₃)₃ (para) |
| 157 | S | H | -CH₂-C₆H₄-C(CH₃)₃ (para) |
| 158 | O | H | -C₆H₄-OCHF₂ (para) |
| 159 | S | H | -C₆H₄-CF₃ (para) |

TABLE 1-24

| Compd. No. | V | R¹ | R² |
|---|---|---|---|
| 160 | O | H | -CH₂-C₆H₄-CF₃ (para) |
| 161 | S | H | -CH₂-C₆H₄-CF₃ (para) |
| 162 | O | H | -C₆H₄-CF₃ (meta) |
| 163 | S | H | -C₆H₄-CF₃ (meta) |
| 164 | O | H | -C₆H₄-CH=CH₂ (para) |
| 165 | O | H | -CH₂-C₆H₄-C(CH₃)=CH₂ (para) |
| 166 | S | H | -CH₂-C₆H₄-C(CH₃)=CH₂ (para) |
| 167 | O | H | -CH₂-C₆H₄-CH=C(CH₃)₂ (para) |

TABLE 1-24-continued
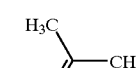
| Compd. No. | V | R¹ | R² |
|---|---|---|---|
| 168 | S | H |  |
TABLE 1-25
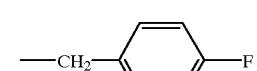
| Compd. No. | V | R¹ | R² |
|---|---|---|---|
| 169 | S | H | 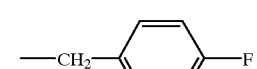 |
| 170 | S | H | 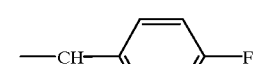 |
| 171 | S | H | 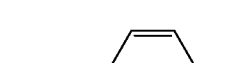 |
TABLE 1-25-continued
| Compd. No. | V | R¹ | R² |
|---|---|---|---|
| 172 | O | H | 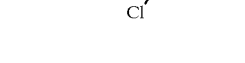 |
| 173 | S | H |  |
| 174 | S | H |  |
| 175 | S | H | 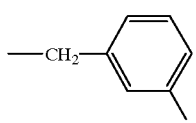 |
| 176 | S | H |  |
| 177 | S | H |  |

TABLE 1-26

Structure: piperazine linked to 6,7-dimethoxyquinazoline with V=C(NR¹R²) group

| Compd. No. | V | R¹ | R² |
|---|---|---|---|
| 178 | O | H | −CH₂−(4-Cl-phenyl) |
| 179 | S | H | −C(=O)−(4-Cl-phenyl) |
| 180 | S | H | −(CH₂)₂−(4-Cl-phenyl) |
| 181 | S | H | 3-Br-phenyl |
| 182 | S | H | 4-Br-phenyl |
| 183 | O | CH₃ | 4-Br-phenyl |
| 184 | O | H | −CH₂−(4-Br-phenyl) |
| 185 | S | H | −CH₂−(4-Br-phenyl) |
| 186 | O | H | 3-I-phenyl |

TABLE 1-27

Structure: piperazine linked to 6,7-dimethoxyquinazoline with V=C(NR¹R²) group

| Compd. No. | V | R¹ | R² |
|---|---|---|---|
| 187 | O | H | 3-F-4-CH₃-phenyl |
| 188 | O | H | 3-Cl-4-CH₃-phenyl |
| 189 | S | H | 4-Cl-3-CF₃-phenyl |
| 190 | S | H | −CH₂−(3-Cl-4-CH₃-phenyl) |
| 191 | S | H | 4-Br-3-CH₃-phenyl |
| 192 | O | H | 3,4-di-F-phenyl |
| 193 | O | H | 3-Cl-4-F-phenyl |

TABLE 1-28

| Compd. No. | V | R¹ | R² |
|---|---|---|---|
| 194 | S | H | 4-bromo-3-chlorophenyl |
| 195 | S | H | -CH₂-(3,4-dichlorophenyl) |
| 196 | S | H | 4-methoxyphenyl |
| 197 | S | H | -CH₂-(3-methoxyphenyl) |
| 198 | O | H | -CH₂-(4-methoxyphenyl) |
| 199 | S | H | -CH₂-(4-methoxyphenyl) |
| 200 | O | H | -CH₂-(4-ethoxyphenyl) |
| 201 | O | H | 4-(n-propoxy)phenyl |
| 202 | O | H | 4-isopropoxyphenyl |

TABLE 1-29

| Compd. No. | V | R¹ | R² |
|---|---|---|---|
| 203 | O | H | -CH₂-(4-OCF₃-phenyl) |
| 204 | S | H | -CH₂-(4-OCF₃-phenyl) |
| 205 | S | H | -CH₂-(3,4-dimethoxyphenyl) |
| 206 | S | H | -(CH₂)₂-(3,4-dimethoxyphenyl) |
| 207 | S | H | 4-methoxy-3-cyclopentyloxyphenyl |
| 208 | S | H | -CH₂-(1,3-benzodioxol-5-yl) |
| 209 | S | H | 2,3-dihydro-1,4-benzodioxin-6-yl |

TABLE 1-30

[Structure: quinazoline with 6,7-dimethoxy substituents, connected to piperazine with C(=V)-N(R¹)(R²) group]

| Compd. No. | V | R¹ | R² |
|---|---|---|---|
| 210 | O | H | 4-methylphenyl fused with 15-crown-5 (benzo-crown ether) |
| 211 | O | H | 4-methylphenyl fused with 18-crown-6 (benzo-crown ether) |
| 212 | O | H | 3,4,5-trimethoxyphenyl (attached via methyl) |
| 213 | O | H | 3,4,5-trimethoxybenzyl (-CH₂-) |
| 214 | O | H | 4-(hydroxymethyl)phenyl |

TABLE 1-31

[Structure: quinazoline with 6,7-dimethoxy substituents, connected to piperazine with C(=V)-N(R¹)(R²) group]

| Compd. No. | V | R¹ | R² |
|---|---|---|---|
| 215 | O | H | 4-(1-hydroxyethyl)phenyl |
| 216 | O | H | 4-(acetoxy)phenyl |
| 217 | O | H | 3-(methylthio)phenyl |
| 218 | S | H | 4-(methylthio)phenyl |
| 219 | O | H | 4-(ethylthio)phenyl |
| 220 | S | H | 4-(trifluoromethylthio)phenyl |
| 221 | O | H | 4-aminophenyl |
| 222 | O | H | 4-(dimethylamino)phenyl |

TABLE 1-32
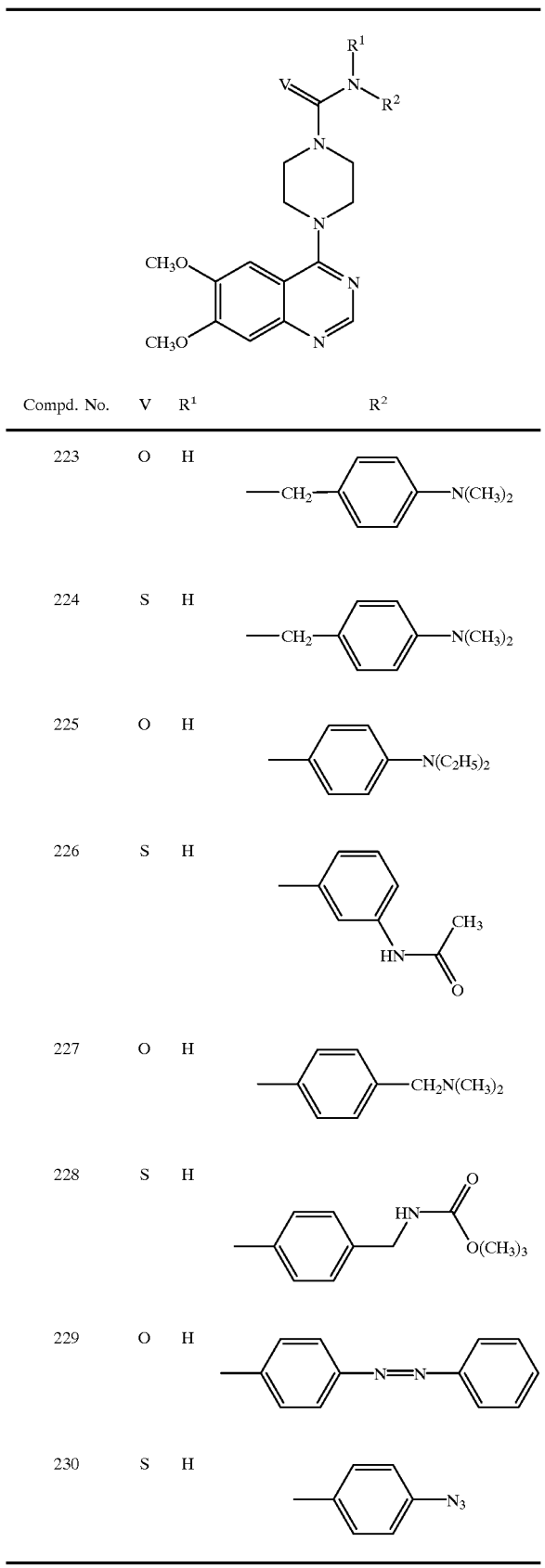
| Compd. No. | V | R¹ | R² |
|---|---|---|---|
| 223 | O | H | —CH₂—C₆H₄—N(CH₃)₂ |
| 224 | S | H | —CH₂—C₆H₄—N(CH₃)₂ |
| 225 | O | H | —C₆H₄—N(C₂H₅)₂ |
| 226 | S | H | —C₆H₄—NHC(O)CH₃ (3-position) |
| 227 | O | H | —C₆H₄—CH₂N(CH₃)₂ |
| 228 | S | H | —C₆H₄—CH₂NHC(O)O(CH₃)₃ |
| 229 | O | H | —C₆H₄—N=N—C₆H₅ |
| 230 | S | H | —C₆H₄—N₃ |
TABLE 1-33
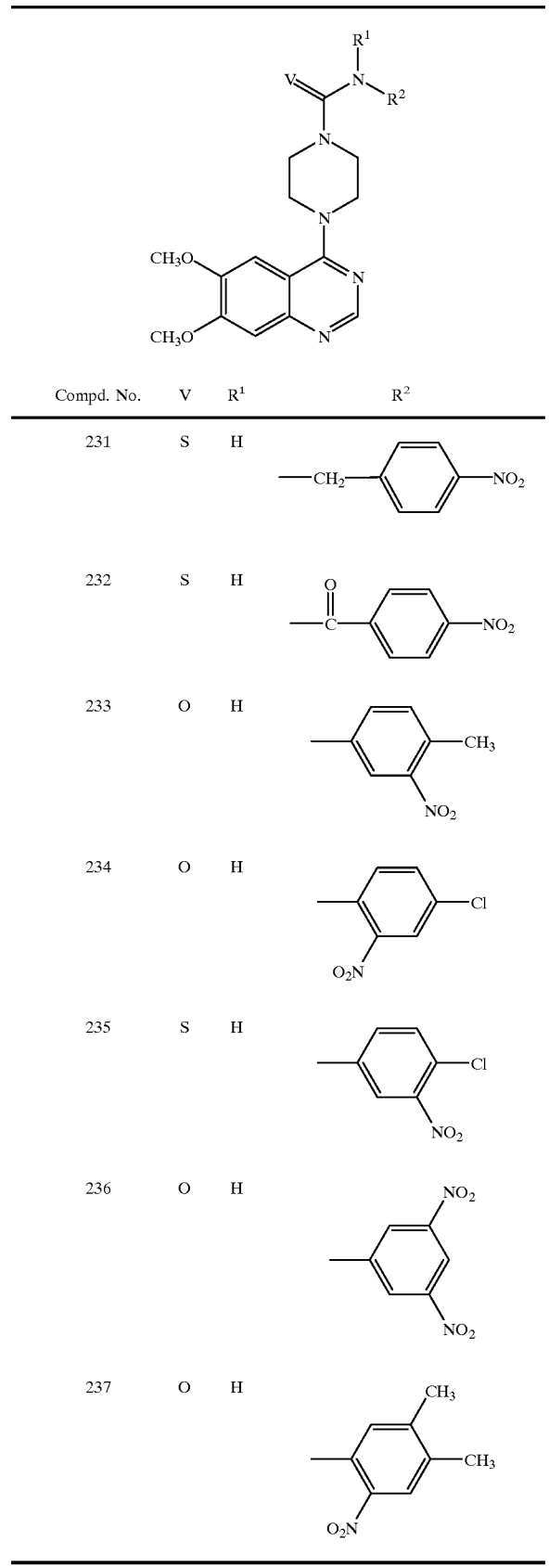
| Compd. No. | V | R¹ | R² |
|---|---|---|---|
| 231 | S | H | —CH₂—C₆H₄—NO₂ |
| 232 | S | H | —C(O)—C₆H₄—NO₂ |
| 233 | O | H | —C₆H₃(CH₃)(NO₂) |
| 234 | O | H | —C₆H₃(Cl)(O₂N) |
| 235 | S | H | —C₆H₃(Cl)(NO₂) |
| 236 | O | H | —C₆H₃(NO₂)₂ |
| 237 | O | H | —C₆H₂(CH₃)₂(O₂N) |

TABLE 1-34

[Structure: N,N-disubstituted carboxamide/thioamide of piperazine linked to 6,7-dimethoxyquinazolin-4-yl]

| Compd. No. | V | R¹ | R² |
|---|---|---|---|
| 238 | S | H | 3-cyanophenyl |
| 239 | O | H | 4-cyanophenyl |
| 240 | S | H | -CH₂-(4-cyanophenyl) |
| 241 | S | H | 3-(1-methylethenyl)phenyl |
| 242 | S | H | 4-acetylphenyl |
| 243 | O | H | 4-(trifluoroacetyl)phenyl |
| 244 | S | H | 4-(butanoyl)phenyl |
| 245 | O | H | 4-benzoylphenyl |

TABLE 1-35

[Structure: same as above]

| Compd. No. | V | R¹ | R² |
|---|---|---|---|
| 246 | S | H | 3-carboxyphenyl |
| 247 | O | H | 4-carboxyphenyl |
| 248 | O | H | 3-(ethoxycarbonyl)phenyl |
| 249 | S | H | 4-(methoxycarbonyl)phenyl |
| 250 | O | H | 4-(methylsulfinyl)phenyl |
| 251 | O | H | 4-(methylsulfonyl)phenyl |
| 252 | S | H | -CH₂-(4-methylsulfonylphenyl) |
| 253 | S | H | -CH₂-(4-sulfamoylphenyl) |

TABLE 1-36
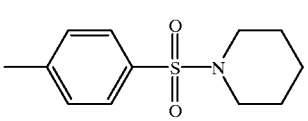
| Compd. No. | V | R¹ | R² |
|---|---|---|---|
| 254 | S | H | 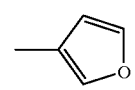 |
| 255 | O | H | 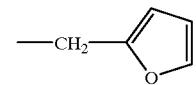 |
| 256 | O | H | 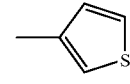 |
| 257 | O | H | 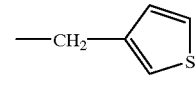 |
| 258 | O | H | 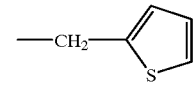 |
| 259 | O | H | 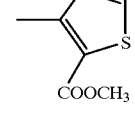 |
| 260 | S | H | 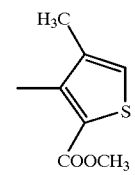 |
| 261 | S | H | 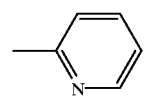 |
TABLE 1-37
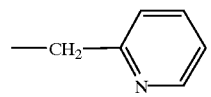
| Compd. No. | V | R¹ | R² |
|---|---|---|---|
| 262 | S | H | 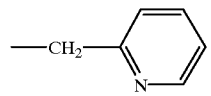 |
| 263 | O | H | 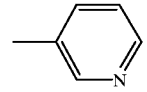 |
| 264 | S | H | 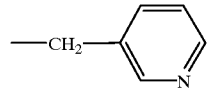 |
| 265 | O | H | 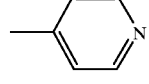 |
| 266 | O | H | 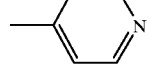 |
| 267 | O | H | 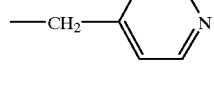 |
| 268 | S | H | 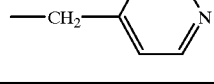 |
| 269 | O | H | — |
| 270 | S | H | — |

TABLE 1-38

| Compd. No. | V | R¹ | R² |
|---|---|---|---|
| 271 | O | H | 5-methyl-2-methylpyridin-yl |
| 272 | O | H | 5-methyl-2-chloropyridin-yl |
| 273 | O | H | 5-methyl-2-cyanopyridin-yl |
| 274 | O | H | 4-methyl-2,6-dichloropyridin-yl |
| 275 | O | H | —CH₂-(3-chloro-5-trifluoromethylpyridin-2-yl) |
| 276 | S | H | —CH₂-(3-chloro-5-trifluoromethylpyridin-2-yl) |
| 277 | S | H | 6-methyl-4-hydroxy-2-hydroxypyrimidin-yl |

TABLE 1-39

| Compd. No. | V | R¹ | R² |
|---|---|---|---|
| 278 | O | H | —CH₂-(5-methylpyrazin-2-yl) |
| 279 | S | H | 3-methyl-dihydrofuran-2(3H)-one |
| 280 | O | H | 4-(1H-pyrrol-1-yl)phenyl |
| 281 | S | H | —CH₂-(4-(1,2,3-thiadiazol-5-yl)phenyl) |
| 282 | S | H | 4-(pyridin-4-ylmethyl)phenyl |
| 283 | O | H | 5-methyl-2-(1H-pyrrol-1-yl)pyridin-yl |
| 284 | S | H | 4-thiocyanatophenyl |

TABLE 1-40

| Compd. No. | R³ | V | R² |
|---|---|---|---|
| 285 | H | S | -CH₂-phenyl |
| 286 | H | S | -CH₂-(pyridin-3-yl) |
| 287 | CH₃ | O | -(4-phenoxyphenyl) |
| 288 | CH₃ | S | -CH₂-phenyl |
| 289 | Cl | O | -(4-phenoxyphenyl) |
| 290 | Cl | S | -CH₂-phenyl |
| 291 | Cl | S | -CH₂-(pyridin-3-yl) |

TABLE 1-41

| Compd. No. | R⁴ | V | R² |
|---|---|---|---|
| 292 | CH₃ | O | -(4-phenoxyphenyl) |
| 293 | CH₃ | O | -(4-nitrophenyl) |
| 294 | CH₃ | S | -CH₂-phenyl |
| 295 | CH₃ | S | -CH₂-(pyridin-3-yl) |
| 296 | F | O | -(4-isopropylphenyl) |
| 297 | F | O | -(4-phenoxyphenyl) |
| 298 | F | O | -(4-acetylphenyl) |
| 299 | F | S | -CH₂-(pyridin-3-yl) |

TABLE 1-42
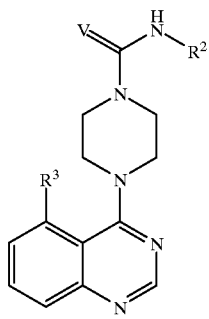
| Compd. No. | R⁴ | V | R² |
|---|---|---|---|
| 300 | Cl | O | -C₆H₄-CH(CH₃)₂ (4-isopropylphenyl) |
| 301 | Cl | O | -C₆H₄-O-C₆H₅ (4-phenoxyphenyl) |
| 302 | Cl | O | -C₆H₄-C(O)CH₃ (4-acetylphenyl) |
| 303 | Br | O | -C₆H₄-O-C₆H₅ |
| 304 | I | O | -C₆H₄-CH(CH₃)₂ |
| 305 | I | O | -C₆H₄-O-C₆H₅ |
| 306 | I | O | -C₆H₄-C(O)CH₃ |
TABLE 1-43
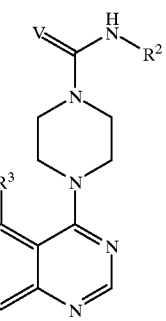
| Compd. No. | R⁴ | V | R² |
|---|---|---|---|
| 307 | OCH₃ | O | -C₆H₄-O-C₆H₅ |
| 308 | OCH₃ | O | -C₆H₄-NO₂ |
| 309 | OCH₃ | S | -CH₂-C₆H₅ |
| 310 | OCH₃ | S | -CH₂-(3-pyridyl) |
| 311 | NO₂ | O | -C₆H₄-O-C₆H₅ |
TABLE 1-44
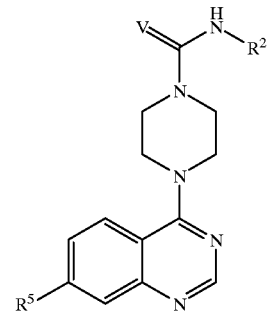
| Compd. No. | R⁵ | V | R² |
|---|---|---|---|
| 312 | CH₃ | O | -C₆H₄-O-C₆H₅ |

TABLE 1-44-continued
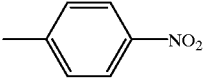
| Compd. No. | R⁵ | V | R² |
|---|---|---|---|
| 313 | CH₃ | O | 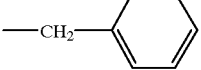 4-NO₂-phenyl |
| 314 | CH₃ | S | —CH₂-phenyl |
| 315 | CH₃ | S | —CH₂-(3-pyridyl) |
| 316 | Cl | O | 4-phenoxyphenyl |
| 317 | Cl | S | —CH₂-phenyl |
| 318 | OCH(CH₃)₂ | O | 4-phenoxyphenyl |
| 319 | OCH(CH₃)₂ | O | 4-NO₂-phenyl |
| 320 | OCH(CH₃)₂ | S | —CH₂-phenyl |
TABLE 1-45
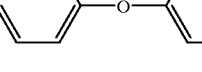
| Compd. No. | R⁵ | V | R² |
|---|---|---|---|
| 321 | NH₂ | O | 4-phenoxyphenyl |
| 322 | NO₂ | O | 4-phenoxyphenyl |
| 323 | COOCH₃ | O | 4-phenoxyphenyl |
| 324 | COOH | O | 4-phenoxyphenyl |
TABLE 1-46
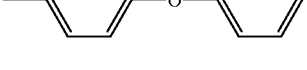
| Compd. No. | R⁶ | V | R² |
|---|---|---|---|
| 325 | Cl | O | 4-acetylphenyl |
| 326 | OCH₃ | O | 4-isopropylphenyl |

TABLE 1-46-continued
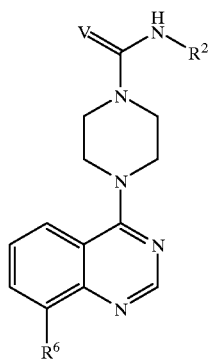
| Compd. No. | R⁶ | V | R² |
|---|---|---|---|
| 327 | OCH₃ | O |  |
TABLE 1-46-continued
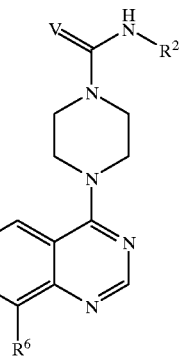
| Compd. No. | R⁶ | V | R² |
|---|---|---|---|
| 328 | OCH₃ | O |  |
TABLE 1-47
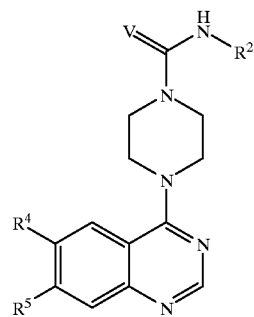
| Compd. No. | R⁴ | R⁵ | V | R² |
|---|---|---|---|---|
| 329 | F | F | O |  |
| 330 | F | F | S | —CH₂—⌬ |
| 331 | F | F | S | —CH₂—(3-pyridyl) |
| 332 | F | OC₂H₅ | O | —⌬—O—⌬ |

TABLE 1-47-continued

| Compd. No. | R⁴ | R⁵ | V | R² |
|---|---|---|---|---|
| 333 | OCH₃ | CH₃ | O | -C₆H₄-O-C₆H₅ (4-phenoxyphenyl) |
| 334 | OCH₃ | CH₃ | O | -C₆H₄-CN (4-cyanophenyl) |
| 335 | OCH₃ | OC₂H₅ | O | -C₆H₄-O-C₆H₅ (4-phenoxyphenyl) |
| 336 | OCH₃ | OC₂H₅ | O | -C₆H₄-Br (4-bromophenyl) |
| 337 | OCH₃ | OC₂H₅ | S | -CH₂-C₆H₅ |

TABLE 1-48

| Compd. No. | R⁴ | R⁵ | V | R² |
|---|---|---|---|---|
| 338 | OCH₃ | OC₂H₅ | S | -CH₂-(3-pyridyl) |

TABLE 1-48-continued
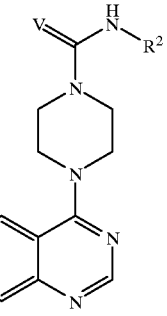
| Compd. No. | R⁴ | R⁵ | V | R² |
|---|---|---|---|---|
| 339 | OCH₃ | OCH(CH₃)₂ | O | 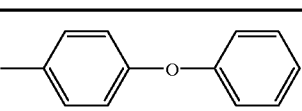 |
| 340 | OCH₃ | CH₃ | S | 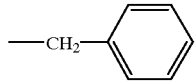 |
| 341 | OCH₃ | OCH(CH₃)₂ | S | 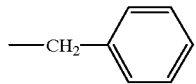 |
| 342 | OCH₃ | OCH(CH₃)₂ | S | 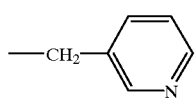 |
| 343 | OCH₃ | CH₃ | S | 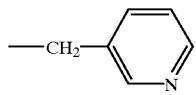 |
| 344 | OCH₃ | OH | O | 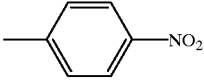 |
| 345 | OCH₃ | 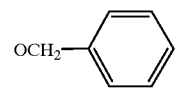 | O | 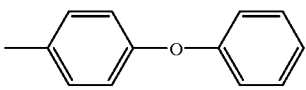 |

TABLE 1-49
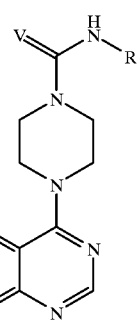
| Compd. No. | R⁴ | R⁵ | V | R² |
|---|---|---|---|---|
| 346 | OC$_2$H$_5$ | OCH$_3$ | O | 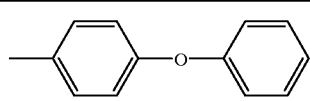 |
| 347 | OC$_2$H$_5$ | OCH$_3$ | O | 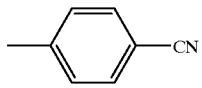 |
| 348 | OC$_2$H$_5$ | OCH$_3$ | S | 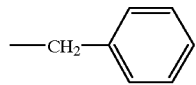 |
| 349 | OC$_2$H$_5$ | OCH$_3$ | S | 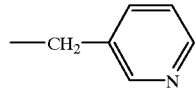 |
| 350 | OSO$_2$CH$_3$ | OCH$_3$ | O | 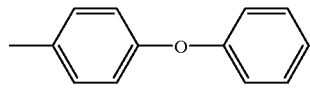 |
| 351 | OSO$_2$CH$_3$ | OCH$_3$ | S | 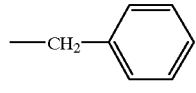 |
| 352 | OC$_2$H$_5$ | OC$_2$H$_5$ | O | 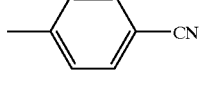 |
| 353 | OC$_2$H$_5$ | OC$_2$H$_5$ | S | 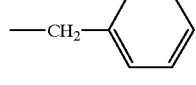 |
| 354 | OC$_2$H$_5$ | OC$_2$H$_5$ | S | 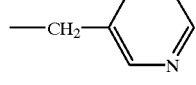 |

TABLE 1-50
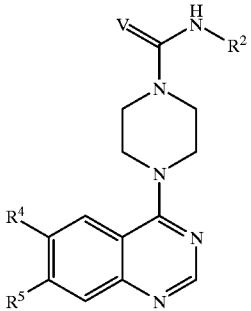
| Compd. No. | R⁴ | R⁵ | V | R² |
|---|---|---|---|---|
| 355 | OCH₂-C₆H₅ | OCH₂-C₆H₅ | O | -C₆H₄-O-C₆H₅ |
| 356 | NH₂ | Cl | O | -C₆H₄-O-C₆H₅ |
| 357 | NO₂ | Cl | O | -C₆H₄-O-C₆H₅ |
| 358 | NO₂ | Cl | S | -CH₂-C₆H₅ |
| 359 | NO₂ | NH₂ | O | -C₆H₄-O-C₆H₅ |
| 360 | HN-C(=O)-CH₃ | H | O | -C₆H₄-O-C₆H₅ |
| 361 | NO₂ | NHC₂H₅ | S | -CH₂-C₆H₅ |
| 362 | NO₂ | HN-C(=O)-CH₃ | O | -C₆H₄-O-C₆H₅ |

TABLE 1-51

| Compd. No. | R⁴ | R⁵ | V | R² |
|---|---|---|---|---|
| 363 | (CH=CH-CH=CH) | | O | -C₆H₄-O-C₆H₅ (4-phenoxyphenyl) |
| 364 | (CH=CH-CH=CH) | | O | -C₆H₄-NO₂ (4-nitrophenyl) |
| 365 | (CH=CH-CH=CH) | | S | -CH₂-C₆H₅ |
| 366 | (CH=CH-CH=CH) | | S | -CH₂-(3-pyridyl) |
| 367 | -O-CH₂-O- | | O | -C₆H₄-O-C₆H₅ |
| 368 | -O-CH₂-O- | | O | -C₆H₄-NO₂ |
| 369 | -O-CH₂-O- | | O | -C₆H₄-CN |
| 370 | -O-CH₂-O- | | S | -CH₂-C₆H₅ |

TABLE 1-51-continued

| Compd. No. | R⁴ | R⁵ | V | R² |
|---|---|---|---|---|
| 371 | -O-CH₂-O- | | S | -CH₂-(3-pyridyl) |

TABLE 1-52

| Compd. No. | R⁴ | R⁵ | V | R² |
|---|---|---|---|---|
| 372 | -O-CH₂-CH₂-O- | | O | -C₆H₄-O-C₆H₅ |
| 373 | -O-CH₂-CH₂-O- | | O | -C₆H₄-CN |
| 374 | -O-CH₂-CH₂-O- | | S | -CH₂-C₆H₅ |
| 375 | -O-CH₂-CH₂-O- | | S | -CH₂-(3-pyridyl) |

TABLE 1-53
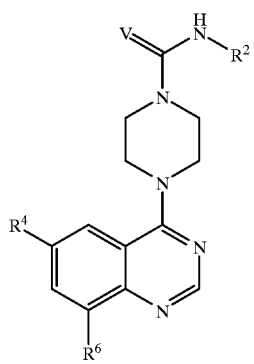
| Compd. No. | R⁴ | R⁶ | V | R² |
|---|---|---|---|---|
| 376 | Cl | Cl | O | —C₆H₄—CH(CH₃)₂ (p-isopropylphenyl) |
| 377 | Cl | Cl | O | —C₆H₄—O—C₆H₅ (p-phenoxyphenyl) |
| 378 | Cl | Cl | O | —C₆H₄—C(O)CH₃ (p-acetylphenyl) |
| 379 | I | I | O | —C₆H₄—CH(CH₃)₂ (p-isopropylphenyl) |
| 380 | I | I | O | —C₆H₄—O—C₆H₅ (p-phenoxyphenyl) |
| 381 | OCH₃ | OCH₃ | O | —C₆H₄—O—C₆H₅ (p-phenoxyphenyl) |
| 382 | OCH₃ | OCH₃ | S | —CH₂-(3-pyridyl) |

TABLE 1-54

| Compd. No. | R⁵ | R⁶ | V | R² |
|---|---|---|---|---|
| 383 | OCH₃ | OCH₃ | O | —C₆H₄—O—C₆H₅ (4-phenoxyphenyl) |
| 384 | OCH₃ | OCH₃ | S | —CH₂—C₆H₅ |
| 385 | OCH₃ | OCH₃ | S | —CH₂—(3-pyridyl) |

TABLE 1-55

| Compd. No. | R⁴ | R⁵ | V | R² |
|---|---|---|---|---|
| 386 | (CH₃)₂N—C(=O)—N(CH₃)— | | O | —C₆H₄—NO₂ (4-nitrophenyl) |

TABLE 1-55-continued
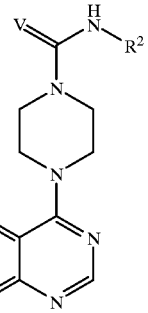
| Compd. No. | R⁴ | R⁵ | V | R² |
|---|---|---|---|---|
| 387 | 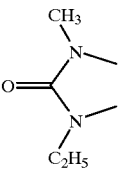 | | O | 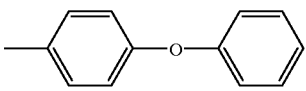 |
| 388 | 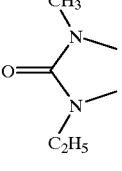 | | S | 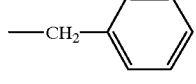 —CH₂— |
| 389 | 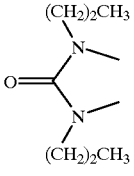 | | O | 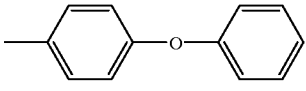 |
| 390 | 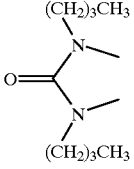 | | O | 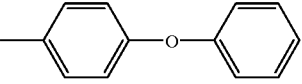 |

TABLE 1-56
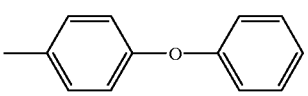
| Compd. No. | R⁸ | V | R² |
|---|---|---|---|
| 391 | $CH_3$ | O | 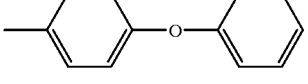 |
| 392 | Cl | O |  |
| 393 | 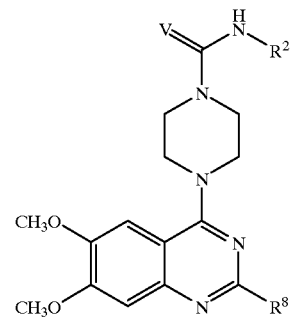 | O | 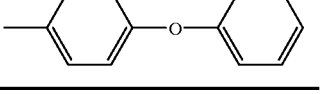 |
TABLE 1-57
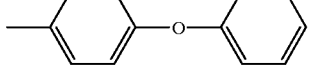
| Compd. No. | R⁴ | R⁸ | V | R² |
|---|---|---|---|---|
| 394 | H | H | O | 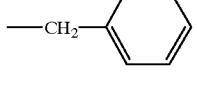 |
| 395 | H | H | S | 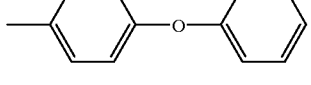 |
| 396 | H | H | S | 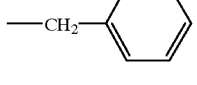 |
TABLE 1-57-continued
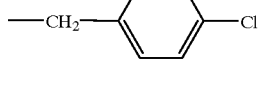
| Compd. No. | R⁴ | R⁸ | V | R² |
|---|---|---|---|---|
| 397 | H | $CF_3$ | O | 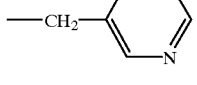 |
| 398 | $CF_3$ | H | S | 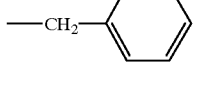 |
| 399 | Cl | H | O | 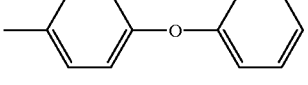 |
| 400 | Cl | H | S | 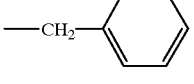 |
| 401 | Cl | H | S | 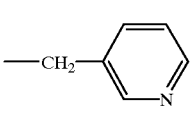 |
| 402 | Cl | H | S | 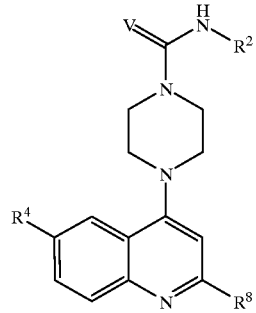 |
| 403 | $OCF_3$ | H | S | 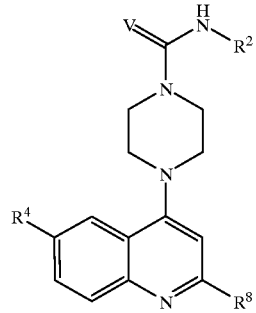 |

TABLE 1-58

| Compd. No. | R⁴ | R⁵ | R⁹ | V | R² |
|---|---|---|---|---|---|
| 404 | H | CF₃ | H | O | -C₆H₄-O-C₆H₅ (4-phenoxyphenyl) |
| 405 | H | Cl | H | S | -CH₂-C₆H₅ |
| 406 | H | Cl | H | S | -CH₂-(3-pyridyl) |
| 407 | OCH₃ | OCH₃ | H | O | -C₆H₄-O-C₆H₅ (4-phenoxyphenyl) |
| 408 | OCH₃ | OCH₃ | COOC₂H₅ | O | -C₆H₄-O-C₆H₅ (4-phenoxyphenyl) |
| 409 | OCH₃ | OCH₃ | COOC₂H₅ | S | -CH₂-C₆H₅ |
| 410 | OCH₃ | OCH₃ | COOC₂H₅ | S | -CH₂-(3-pyridyl) |

TABLE 1-59

| Compd. No. | R³ | R⁴ | R⁶ | R⁸ | V | R² |
|---|---|---|---|---|---|---|
| 411 | H | H | CF₃ | H | O | 4-phenoxyphenyl |
| 412 | H | H | Cl | H | O | 4-phenoxyphenyl |
| 413 | NO₂ | CH₃ | H | CF₃ | O | 4-phenoxyphenyl |

TABLE 1-60

| Compd. No. | R⁴ | R⁵ | R⁷ | V | R² |
|---|---|---|---|---|---|
| 414 | H | H | H | O | 4-phenoxyphenyl |
| 415 | H | H | H | O | 4-nitrophenyl |

TABLE 1-60-continued
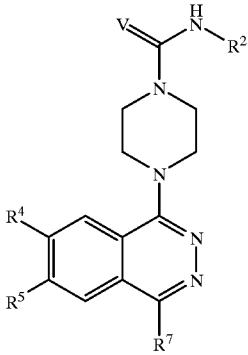
| Compd. No. | R⁴ | R⁵ | R⁷ | V | R² |
|---|---|---|---|---|---|
| 416 | H | H | Cl | O | 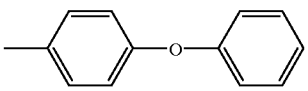 |
| 417 | H | H | Cl | O | 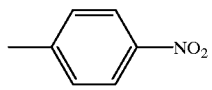 |
| 418 | H | H | —CH₂—C₆H₅ | O | 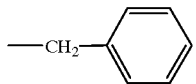 |
| 419 | 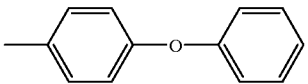 | | H | O | 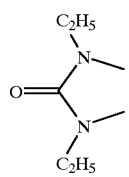 |
| 420 | 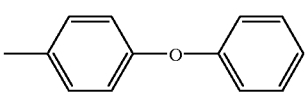 | | H | O | 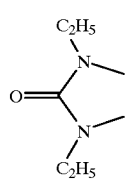 |
| 421 | 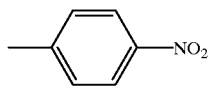 | | Cl | O | 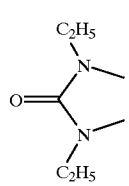 |

TABLE 1-61
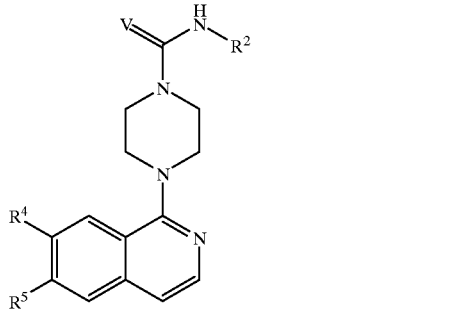
| Compd. No. | R⁴ | R⁵ | V | R² |
|---|---|---|---|---|
| 422 | H | H | O | 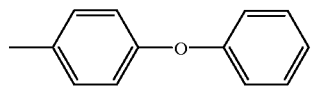 |
| 423 | OCH₃ | OCH₃ | O | 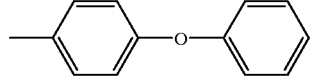 |
| 424 | OCH₃ | OCH₃ | S | 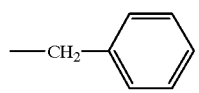 |
| 425 | OCH₃ | OCH₃ | S | 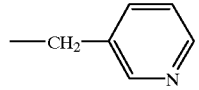 |
TABLE 1-62
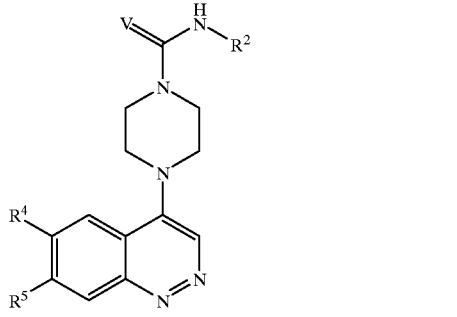
| Compd. No. | R⁴ | R⁵ | V | R² |
|---|---|---|---|---|
| 426 | OCH₃ | OCH₃ | O | 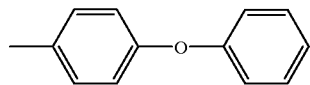 |
| 427 | OCH₃ | OCH₃ | S | 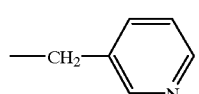 |

TABLE 1-63

[Structure: quinazoline with 6,7-dimethoxy groups, connected to a piperazine bearing two CH₃ substituents (with H₃C shown with wedge bond), and N-C(=V)-NH-R²]

| Compd. No. | V | R² |
|---|---|---|
| 428 | O | —C₆H₄—O—C₆H₅ (4-phenoxyphenyl) |
| 429 | O | —C₆H₄—NO₂ (4-nitrophenyl) |
| 430 | S | —CH₂—C₆H₅ (benzyl) |
| 431 | S | —CH₂—(3-pyridyl) |

TABLE 1-64

[Structure: quinazoline with 6,7-dimethoxy groups, connected to a 2,6-dimethylpiperazine, and N-C(=V)-NH-R²]

| Compd. No. | V | R² |
|---|---|---|
| 432 | O | —C₆H₄—NO₂ (4-nitrophenyl) |

TABLE 1-64-continued

[Same structure as Table 1-64]

| Compd. No. | V | R² |
|---|---|---|
| 433 | S | —CH₂—C₆H₅ (benzyl) |
| 434 | S | —CH₂—(3-pyridyl) |

TABLE 1-65

[Structure: quinazoline with 6,7-dimethoxy groups, connected to a homopiperazine (1,4-diazepane), and N-C(=V)-NH-R²]

| Compd. No. | V | R² |
|---|---|---|
| 435 | O | —C₆H₄—O—C₆H₅ (4-phenoxyphenyl) |
| 436 | S | —CH₂—C₆H₅ (benzyl) |
| 437 | S | —CH₂—(3-pyridyl) |

TABLE 1-66

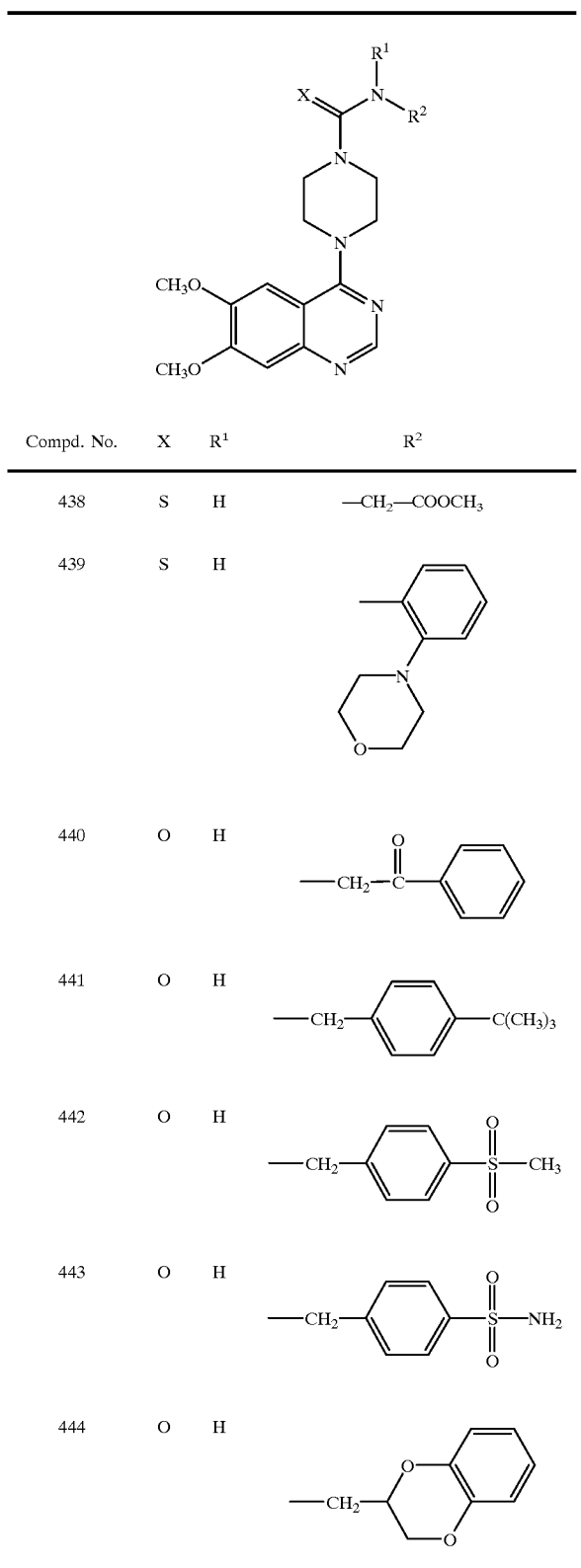

| Compd. No. | X | R¹ | R² |
|---|---|---|---|
| 438 | S | H | —CH₂—COOCH₃ |
| 439 | S | H | (2-morpholinophenyl) |
| 440 | O | H | —CH₂—C(=O)—phenyl |
| 441 | O | H | —CH₂—(4-C(CH₃)₃-phenyl) |
| 442 | O | H | —CH₂—(4-S(O)₂CH₃-phenyl) |
| 443 | O | H | —CH₂—(4-S(O)₂NH₂-phenyl) |
| 444 | O | H | —CH₂—(2,3-dihydro-1,4-benzodioxin-2-yl) |

TABLE 1-67

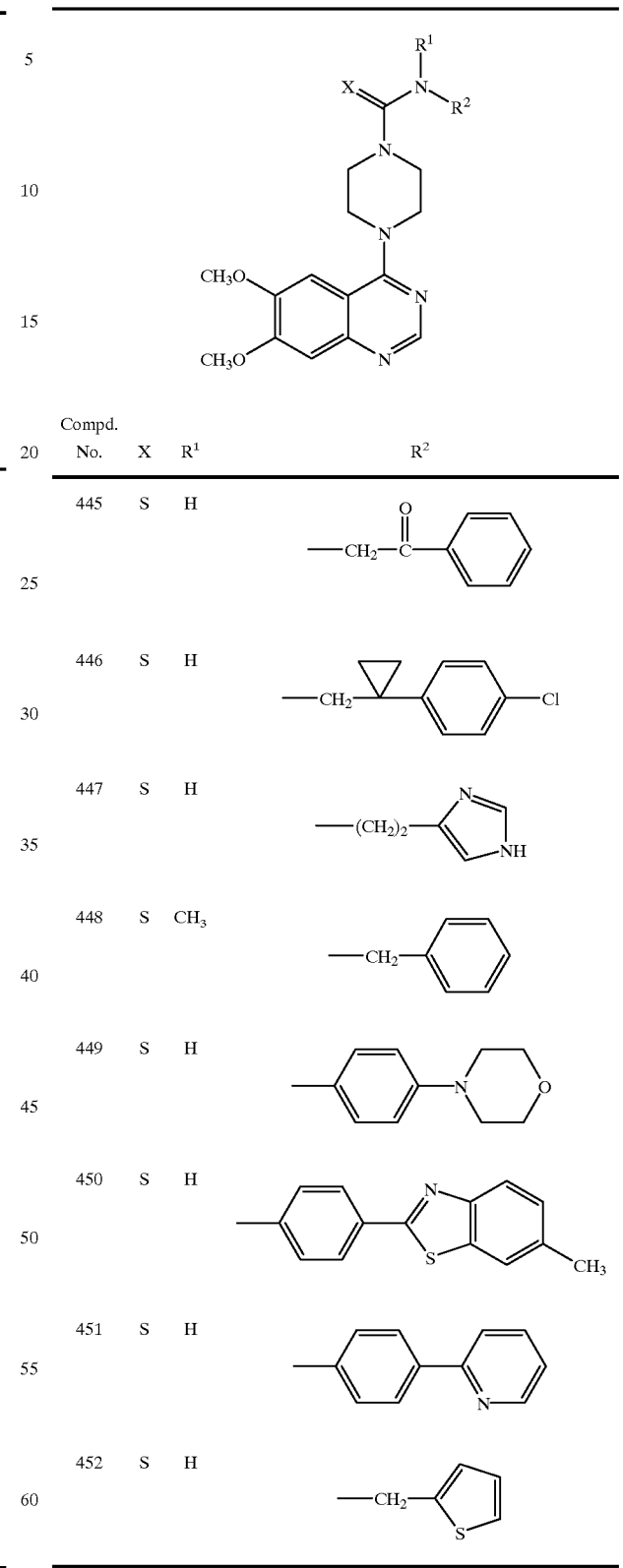

| Compd. No. | X | R¹ | R² |
|---|---|---|---|
| 445 | S | H | —CH₂—C(=O)—phenyl |
| 446 | S | H | —CH₂—(1-(4-chlorophenyl)cyclopropyl) |
| 447 | S | H | —(CH₂)₂—(1H-imidazol-4-yl) |
| 448 | S | CH₃ | —CH₂—phenyl |
| 449 | S | H | —(4-morpholinophenyl)methyl |
| 450 | S | H | —(4-(6-methylbenzothiazol-2-yl)phenyl)methyl |
| 451 | S | H | —(4-(pyridin-2-yl)phenyl)methyl |
| 452 | S | H | —CH₂—(thiophen-2-yl) |

TABLE 1-68

| Compd. No. | X | R¹ | R² |
|---|---|---|---|
| 453 | S | H | —(CH₂)₂-(2-pyridyl) |
| 454 | S | H | —CH₂-(2,3-dihydro-1,4-benzodioxin-2-yl) |
| 455 | S | H | —(4-(1,2,4-triazol-1-yl)phenyl) |
| 456 | S | H | —(4-(2-oxopyrrolidin-1-yl)phenyl) |
| 457 | O | H | —(4-(acetylamino)phenyl) |
| 458 | O | H | —(4-(3-ethylthioureido)phenyl) |
| 459 | O | H | —CH₂-(1,3-benzodioxol-5-yl) |

TABLE 1-69

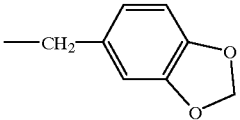

| Compd. No. | R⁴ | R⁵ | V | R² |
|---|---|---|---|---|
| 460 | OCH₃ | CH₃ | S | 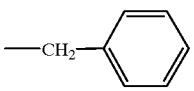 |
| 461 | NH₂ | NHC₂H₅ | S | 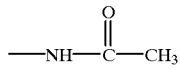 |
| 462 | 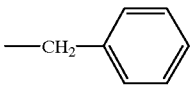 | NHC₂H₅ | S | 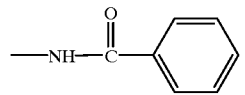 |
| 463 | 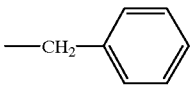 | NHC₂H₅ | S | —CH₂— |
| 464 | 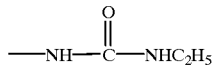 | NHC₂H₅ | S | |
| 465 | 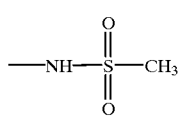 | NHC₂H₅ | S | 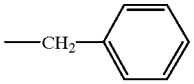 |
| 466 | OCH₃ | NHC₂H₅ | O | —CH₂CH₂Cl |

The pharmacological activities of the compounds of the present invention are shown below by Test Examples.

TEST EXAMPLE 1

Inhibitory Effect on Phosphorylation of PDGF Receptor

The test was carried out according to the method described in the literature [Dah-Shuhn et al., J. Biol. Chem., 266, 413–418 (1991)], using Chinese hamster ovary cells (CHO) wherein human β-PDGF receptor cDNA was introduced and expressed. The test result was expressed as the concentration of a test compound which inhibits the PDGF receptor phosphorylation by 50% ($IC_{50}$).

The results are shown in Table 2.

TABLE 2

| Compd. No. | Inhibitory effect on phosphorylation of PDGF receptor $IC_{50}$ (μM) |
|---|---|
| 9 | 0.67 |
| 19 | 0.11 |
| 45 | 0.16 |
| 54 | 0.71 |
| 60 | 0.05 |
| 71 | 0.94 |
| 77 | 0.26 |
| 78 | 0.58 |

TABLE 2-continued

| Compd. No. | Inhibitory effect on phosphorylation of PDGF receptor IC$_{50}$ ($\mu$M) |
|---|---|
| 79 | 0.12 |
| 98 | 0.22 |
| 104 | 0.34 |
| 105 | 0.44 |
| 109 | 0.41 |
| 115 | 0.36 |
| 121 | 0.12 |
| 124 | 0.28 |
| 125 | 0.05 |
| 135 | 0.46 |
| 177 | 0.77 |
| 178 | 0.41 |
| 180 | 1.00 |
| 203 | 1.39 |
| 208 | 0.03 |
| 228 | 0.29 |
| 229 | 0.31 |
| 239 | 0.21 |
| 240 | 0.50 |
| 241 | 0.40 |
| 254 | 0.46 |
| 255 | 0.66 |
| 283 | 1.40 |
| 292 | 0.76 |
| 297 | 0.33 |
| 312 | 0.26 |
| 335 | 0.21 |
| 339 | 0.64 |
| 346 | 0.28 |
| 350 | 0.23 |
| 357 | 0.19 |
| 366 | 1.47 |
| 367 | 0.20 |
| 394 | 0.19 |
| 408 | 0.21 |
| 414 | 0.93 |
| 426 | 1.12 |
| 433 | 0.38 |
| 435 | 0.66 |

TEST EXAMPLE 2

Growth Inhibition Against Smooth Muscle Cells

Vascular smooth muscle cells were isolated from a pig aorta by explantation and used for the test. The cells were put into wells of a 96-well plate (8000 cells/well) and cultured in Dulbecco's modified Eagle's medium (DMEM; Nissui Pharmaceutical Co., Ltd.) containing 10% fetal bovine serum (FBS; Hyclone) for 4 days. Then, the cells were further cultured in DMEM containing 0.1% FBS for 3 days, and were synchronized at the cell growth stationary phase.

To each well was added DMEM containing 0.1% FBS and a test sample at a varied concentration, and the cell growth was brought about by PDGF-BB (SIGMA, final concentration: 20 ng/ml). After culturing for 3 days, the cell growth was measured using the cell growth assay kit (Boehringer Mannheim) according to the XTT method [J. Immunol. Methods, 142, 257–265 (1991)], and the cell growth score was calculated by the following equation.

Cell growth score=100×{1−(M−P0)/(P100−P0)}

P100: Absorbance by XTT reagent when stimulated by PDGF-BB

P0: Absorbance by XTT reagent when not stimulated by PDGF-BB

M: Absorbance by XTT reagent after addition of a sample when stimulated by PDGF-BB The test result was expressed as the concentration of a test compound which inhibits the cell growth by 50% (IC$_{50}$). The results are shown in Table 3.

TABLE 3

| Compd. No. | Growth Inhibitory effect against smooth muscle cells IC$_{50}$ ($\mu$M) |
|---|---|
| 19 | 0.18 |
| 45 | 0.08 |
| 60 | 0.03 |
| 77 | 0.10 |
| 78 | 0.74 |
| 79 | 0.14 |

TEST EXAMPLE 3

Inhibitory Effect on Hypertrophy of Vascular Intima

Male SD rats (weight: 375–445 g, Charles River, golden standard) were anesthetized with sodium pentobarbital (50 mg/kg, i.p.), and then the neck of each animal was incised by the median incision, followed by retrograde insertion of a balloon catheter (2F, Edwards Laboratories) into the left external carotid. After the above treatment was repeated seven times, the catheter was pulled out, the left external carotid was ligated, and the wound was sutured. A test compound was suspended in a 0.5% solution of Tween 80 in an aqueous solution of sodium chloride to a concentration of 20 mg/ml in the case of intraperitoneal administration and in a 0.5% solution of methyl cellulose 400 to a concentration of 6 mg/ml in the case of oral administration. The suspension was administered once a day in the case of intraperitoneal administration and once or twice a day in the case of oral administration for a period of 15 days starting on the day before the balloon injury. On the 14th day after the balloon injury, the animal was killed and its left carotid was extirpated. The tissues were fixed with formalin, wrapped in paraffin and sliced, followed by Elastica Van Gieson staining. The area of the cross section of the vascular tissues (intima and media) was measured with an image analyzer (Luzex F, NIRECO) and the intima/media area ratio (I/M) was regarded as the degree of hypertrophy of the vascular intima. The administration route for each compound and the results are shown in Table 4.

TABLE 4

| | Dose for one administration | Number of the animals used | I/M ratio | Significant difference |
|---|---|---|---|---|
| Solvent-administered group | | 9 | 1.22 ± 0.10 | |
| Compound 77 | 100 mg/kg | 9 | 0.88 ± 0.09 | P<0.05 |
| Solvent-administered group | | 8 | 1.00 ± 0.11 | |
| Dihydrochloride of Compound 98 | 30 mg/kg | 10 | 0.69 ± 0.08 | P<0.05 |
| Solvent-administered group | | 9 | 0.95 ± 0.07 | |

TABLE 4-continued

| | | | | |
|---|---|---|---|---|
| Compound 208 | 30 mg/kg | 10 | 0.61 ± 0.07 | P<0.005 |
| Solvent-administered group | | 9 | 1.29 ± 0.04 | |
| Compound 239 | 30 mg/kg | 10 | 0.93 ± 0.05 | P<0.00005 |

| Administration route | |
|---|---|
| Compound 77 | Once a day by oral administration |
| Dihydrochloride of Compound 98 | Once a day by intraperitoneal administration |
| Compound 208 | Twice a day by oral administration |
| Compound 239 | Twice a day by oral administration |

From the above results, it is apparent that hypertrophy of vascular intima was significantly inhibited by administration of the compounds of the present invention (P<0.05, Student's t-test).

TEST EXAMPLE 4

Evaluation by the Use of a Rat Adjuvant Arthritis Model

Killed cells of *Mycobacterium butyricum* (Difco Laboratories Inc.) were disrupted in agate mortar and suspended in liquid paraffin to the final concentration of 6.6 mg/ml, followed by sterilization with high pressure steam. Then, 100 μl of the suspension was intradermaly injected into the right hind foot pad of each animal of groups of female 8-weeks-old Lewis rats (Charles River Japan) (6 animals/group) to induce adjuvant arthritis. A test compound was suspended in a 0.5% solution of methylcellulose to the final concentration of 3 mg/ml, and from just before the induction of arthritis, the suspension was orally administered in an amount of 1 ml/100 g of the body weight once a day, 5 days a week. To a control group was administered a 0.5% solution of methylcellulose. A normal group was given no adjuvant treatment or test compound administration. The administration of the test compound was continued till the 18th day after the adjuvant treatment. On the 17th day, the number of leukocytes in peripheral blood was counted, and on the 18th day, all the blood was collected, followed by dissection. The change in body weight with the passage of time, the change of edema in hind paw with the passage of time, the weight of spleen and thymus, the number of leukocytes in peripheral blood, the hydroxyproline content of urine, the glucosaminoglycan content of urine, the SH concentration in serum, the concentration of nitrogen monoxide in serum and the concentration of mucoprotein in serum were measured and evaluated. The volume of both hind paws was measured using a rat's hind foot edema measurement device (TK-101, Unicom). The number of leukocytes in peripheral blood was counted using an automatic multichannel blood cell counter (Sysmex K-2000, Toa Iyo Denshi Co., Ltd.). The hydroxyproline content of urine was measured according to the method described in Ikeda, et al., Annual Report of Tokyo Metropolitan Research Laboratories P. H., 36, 277 (1985), and the glucosaminoglycan content was measured according to the method described in Moriyama, et al., Hinyo Kiyo, 40, 565 (1994) and Klompmakers, et al., Analytical Biochemistry, 153, 80 (1986). The SH concentration in serum was measured according to the method described in Miesel, et al., Inflammation, 17, 595 (1993), and the concentration of nitrogen monoxide was measured according to the method of Tracey, et al., Journal of Pharmacology & Experimental Therapeutics, 272, 1011 (1995). The concentration of mucoprotein was measured using Aspro GP Kit (Otsuka Pharmaceutical Co., Ltd.). The percentage of inhibition for each indication was calculated according to the following equation.

% Inhibition={(Control group−Compound-administered group)/(Control group−Normal group)}×100

The results on Compound 239 are shown in Table 5.

TABLE 5

| Group | Volume of left hind foot (ml) | Inhibition rate (%) |
|---|---|---|
| Normal group | 1.12 ± 0.03 | — |
| Sensitized control group | 1.84 ± 0.18 | — |
| Compound-administered group | 1.52 ± 0.16 | 44 |

| Group | Body weight (g) | Inhibition rate (%) |
|---|---|---|
| Normal group | 191 ± 5 | — |
| Sensitized control group | 146 ± 4 | — |
| Compound-administered group | 159 ± 2* | 29 |

| Group | Weight of spleen (mg/10 g of body weight) | Inhibition rate (%) |
|---|---|---|
| Normal group | 21.4 ± 0.3 | — |
| Sensitized control group | 53.8 ± 3.8 | — |
| Compound-administered group | 40.4 ± 2.5* | 41 |

| Group | NO concentration (μM) | Inhibition rate (%) |
|---|---|---|
| Normal group | 11.1 ± 1.0 | — |
| Sensitized control group | 56.6 ± 7.0 | — |
| Compound-administered group | 37.6 ± 4.0 | 42 |

P<0.05 vs Sensitized control group

From the above results, it is apparent that Compound 239 inhibits the occurrence of adjuvant arthiritis.

TEST EXAMPLE 5

Activity on a Mesangial Proliferative Glomerulonephritis Model

Anti-rat Thy-1.1 monoclonal antibody OX-7 (Cedarlane) was administered to male Wistar-Kyoto rats (Charles River Japan, 160 g, 6 animals/group) in an amount of 1.0 mg/kg by intravenous administration through the tail vein. A test compound was suspended in a 0.5% solution of methylcellulose and the resulting suspension was administered to each of the rats twice a day for a period of 7 days starting on the day before the administration of OX-7. On the 7th day after the OX-7 administration, when mesangial cell growth and extracellular matrix hypertrophy became prominent, the left kidney of each rat was extirpated, fixed with 20% buffered formalin for 6 hours and wrapped in paraffin, followed by slicing. The obtained pieces were subjected to immune tissue staining using antibody PC10 (DAKO) against a proliferative cell nuclear antigen. After comparative staining with Methyl Green staining solution using diaminobenzidine as a color developer, the paraffin sections were enclosed. Half of the glomeruli in a kidney piece were observed and the number of the cells in one glomerulus which were positive to the proliferative cell nuclear antigen was calculated. The test for the significance of difference was carried out by the Wilcoxon test.

The results on Compound 208 are shown in Table 6.

TABLE 6

| Group | Number of cells which are positive to intranuclear antigen of proliferative cells |
| --- | --- |
| Normal group | 1.8 +/− 0.3 |
| Solvent-administered group | 8.7 +/− 0.4 |
| Compound-administered group | 6.1 +/− 0.9 |

From the above results, it is apparent that Compound 208 shows alleviating activity on mesangial proliferative glomerulonephritis.

Compounds (I) and pharmaceutically acceptable salts thereof can be administered as such, but it is usually preferred to administer them in the form of pharmaceutical compositions, which are used for animals and human beings.

It is preferred to employ the administration route which is the most effective for the treatment. For example, administration is made orally or non-orally by intrarectal, intraoral, subcutaneous, intramuscular or intravenous administration.

Examples of the forms for administration are capsules, tablets, granules, powders, syrups, emulsions, suppositories and injections.

Liquid compositions such as emulsions and syrups which are appropriate for oral administration can be prepared using water, sugars such as sucrose, sorbitol and fructose, glycols such as polyethylene glycol and propylene glycol, oils such as sesame oil, olive oil and soybean oil, preservatives such as p-hydroxybenzoates, flavors such as strawberry flavor and peppermint, etc.

Capsules, tablets, powders and granules can be prepared using excipients such as lactose, glucose, sucrose and mannitol, disintegrating agents such as starch and sodium alginate, lubricants such as magnesium stearate and talc, binders such as polyvinyl alcohol, hydroxypropyl cellulose and gelatin, surfactants such as fatty acid esters, plasticizers such as glycerin, etc.

Compositions suitable for non-oral administration preferably comprise a sterilized aqueous preparation containing an active compound which is isotonic to the recipient's blood. For example, injections are prepared using a carrier which comprises a salt solution, a glucose solution, or a mixture of a salt solution and a glucose solution.

Compositions for topical application are prepared by dissolving or suspending an active compound in one or more kinds of solvents such as mineral oil, petroleum and polyhydric alcohol, or other bases used for topical drugs.

Compositions for intestinal administration are prepared using ordinary carriers such as cacao fat, hydrogenated fat and hydrogenated fat carboxylic acid, and are provided as suppositories.

The compositions for non-oral administration may additionally be formulated to contain one or more kinds of additives selected from glycols, oils, flavors, preservatives (including antioxidants), excipients, disintegrating agents, lubricants, binders, surfactants and plasticizers which are used for the preparation of compositions for oral administration.

The effective dose and the administration schedule of Compound (I) or a pharmaceutically acceptable salt thereof will vary depending on the administration route, the patient's age and body weight, and the type or degree of the diseases to be treated. However, it is generally appropriate to administer Compound (I) or a pharmaceutically acceptable salt thereof in a dose of 0.01–1000 mg/adult/day, preferably 5–500 mg/adult/day, in one to several parts.

All the compounds of the present invention can be immediately applied to the treatment of kinase-dependent diseases of mammals as kinase inhibitors, specifically, those relating to tyrosine kinase. Specifically preferred are the compounds which have $IC_{50}$ within the range of 10 nM–10 $\mu$M. Specific compounds of the present invention which have an activity to specifically inhibit one of the three types of protein kinase (for example, kinase which phosphorylates tyrosine, kinase which phosphorylates tyrosine and threonine, and kinase which phosphorylates threonine) can be selected. Tyrosine kinase-dependent diseases include hyperproliferative malfunction which is caused or maintained by abnormal tyrosine kinase activity. Examples thereof include psoriasis, pulmonary fibrosis, glomerulonephritis, cancer, atherosclerosis and anti-angiopoiesis (for example, tumor growth and diabetic retinopathy). Current knowledge of the relationship between other classes of kinase and specific diseases is insufficient. However, compounds having specific PTK-inhibiting activity have a useful treatment effect. Other classes of kinase have also been recognized in the same manner. Quercetin, genistein and staurosporin, which are all PTK-inhibitors, inhibit many kinds of protein kinase in addition to tyrosine kinase. However, as a result of their lack of the specificity, their cytotoxicity is high. Therefore, a PTK-inhibitor (or an inhibitor of other classes of kinase) which is apt to bring about undesirable side effects because of the lack of selectivity can be identified by the use of an ordinary test to measure cytotoxicity.

BEST MODE FOR CARRYING OUT THE INVENTION

The present invention is further illustrated by the following Examples, Reference Examples and Preparation Examples, which are not to be construed as limiting the scope of the invention.

EXAMPLE 1

4-(6,7-Dimethoxy-4-quinazolinyl)-N-phenyl-1-piperazinecarboxamide (Compound 1)

In 5 ml of ethanol was dissolved 278 mg (1.0 mmol) of 6,7-dimethoxy-4-piperazinylquinazoline obtained by the method described in South African Patent No. 67 06512 (1968), and 0.109 ml (1.0 mmol) of phenyl isocyanate was added thereto. The mixture was heated under reflux for 10 minutes and then allowed to cool to room temperature. The precipitated crystals were collected by filtration and recrystallized from ethanol to give 174.3 mg of the desired compound as colorless crystals.

yield: 44% m.p.: 121–123° C.

$^1$H-NMR(CDCl$_3$) δ (ppm): 8.69(1H, s), 7.40–7.27(4H, m), 7.11–7.03(3H, m), 4.03(3H, s), 3.99(3H, s), 3.81–3.69 (8H, m).

FAB-Mass: 394(M$^+$+1)

IR(KBr) ν (cm$^{-1}$): 1636, 1507, 1446, 1429, 1240, 1215, 994.

In the following Examples 2–99, substantially the same procedure as in Example 1 was repeated, except that the corresponding isocyanate or isothiocyanate was used in place of phenyl isocyanate, to give the desired compound.

EXAMPLE 2

4-(6,7-Dimethoxy-4-quinazolinyl)-N-phenyl-1-piperazinethiocarboxamide (Compound 2)

Yield: 97%
m.p.: 230–232° C.
$^1$H-NMR(CDCl$_3$) δ (ppm): 8.66(1H, s), 7.38–7.15(6H, m), 7.09(1H, s), 4.08–4.05(4H, m), 4.02(3H, s), 3.98(3H, s), 3.85–3.81(4H, m).
FAB-Mass: 410(M$^+$+1)
IR(KBr) ν (cm$^{-1}$): 1584, 1509, 1481, 1431, 1342, 1209, 994.

EXAMPLE 3

N-Benzyl-4-(6,7-dimethoxy-4-quinazolinyl)-1-piperazinecarboxamide (Compound 3)

yield: 87%
m.p.: 167–168° C.
$^1$H-NMR(CDCl$_3$) δ (ppm): 8.67(1H, s), 7.39–7.27(6H, m), 7.10(1H, s), 4.47(2H, d, J=5.4 Hz), 4.03(3H, s), 3.99 (3H, s), 3.71–3.64(8H, m).
FAB-Mass: 408(M$^+$+1)
IR(KBr) ν (cm$^{-1}$): 1629, 1539, 1506, 1430, 1344, 1260, 1210, 988.

EXAMPLE 4

N-Benzoyl-4-(6,7-dimethoxy-4-quinazolinyl)-1-piperazinecarboxamide (Compound 4)

Yield: 87%
m.p.: 122–124° C.
$^1$H-NMR(CDCl$_3$) δ (ppm): 8.78(1H, s), 8.69(1H, s), 7.92 (2H, d, J=7.3 Hz), 7.59(1H, d, J=7.6 Hz), 7.48(2H, dd, J=7.6 Hz, 7.3 Hz), 7.28(1H, s), 7.10(1H, s), 4.03(3H, s), 3.99(3H, s), 3.79(8H, m).
FAB-Mass: 422(M$^+$+1)
IR(KBr) ν (cm$^{-1}$): 1629, 1539, 1506, 1430, 1344, 1260, 1210, 988.

EXAMPLE 5

N-Benzenesulfonyl-4-(6,7-dimethoxy-4-quinazolinyl)-1-piperazinecarboxamide (Compound 5)

Yield: 20%
m.p.: 98–100° C.
$^1$H-NMR(DMSO-d$_6$) δ (ppm): 8.43(1H, s), 8.22(1H, s), 7.72–7.69(2H, m), 7.32–7.30(3H, m), 7.12(1H, s), 7.04(1H, s), 3.83(3H, s), 3.81(3H, s), 3.51(4H, m), 3.43(4H, m).
FAB-Mass: 458(M$^+$+1)
IR(KBr) ν (cm$^{-1}$): 1625, 1501, 1440, 1284, 1220, 1131, 1083, 985, 875, 585.

EXAMPLE 6

4-(6,7-Dimethoxy-4-quinazolinyl)-N-(2-phenylethyl)-1-piperazinethiocarboxamide (Compound 6)

Yield: 100%
m.p.: 76–80° C.
$^1$H-NMR(CDCl$_3$) δ (ppm): 8.63(1H, s), 7.36–7.22(5H, m), 7.27(1H, s), 7.09(1H, s), 5.65(1H, brt, J=5.0 Hz), 4.02(3H, s), 4.01–3.94(6H, m), 3.98(3H, s), 3.83–3.79(4H, m), 2.99(2H, t, J=6.9 Hz).
FAB-Mass: 438(M$^+$+1)
IR(KBr) ν (cm$^{-1}$): 1537, 1504, 1475, 1452, 1429, 1340, 1238, 1209, 993.

EXAMPLE 7

4-(6,7-Dimethoxy-4-quinazolinyl)-N-(4-phenylbutyl)-1-piperazinethiocarboxamide (Compound 7)

Yield: 99%
m.p.: 112–114° C.
$^1$H-NMR(CDCl$_3$) δ (ppm): 8.64(1H, s), 7.31–7.25(2H, m), 7.24(1H, s), 7.20–7.17(3H, m), 7.10 (1H, s), 5.71(1H, brt, J=5.0 Hz), 4.07–4.03(4H, m), 4.02(3H, s), 3.98(3H, s), 3.86–3.82(4H, m), 3.72(2H, m), 2.67(2H, t, J=6.9 Hz), 1.71–1.68(4H, m).
FAB-Mass: 466(M$^+$+1)
IR(KBr) ν (cm$^{-1}$): 1576, 1546, 1506, 1480, 1433, 1414, 1344, 1247, 1210, 996, 934, 882, 850, 799, 749, 699.

EXAMPLE 8

4-(6,7-Dimethoxy-4-quinazolinyl)-N-(1-naphthyl)-1-piperazinecarboxamide (Compound 8)

Yield: 73%
m.p.: 254–256° C.
$^1$H-NMR(DMSO-d$_6$) δ (ppm): 8.74(1H, s), 8.60(1H, s), 7.99–7.90(2H, m), 7.76–7.74(1H, m), 7.53–7.43(3H, m), 7.26–7.23(2H, m), 3.95(3H, s), 3.95(3H, s), 3.78–3.65(8H, m).
FAB-Mass: 444(M$^+$+1)
IR(KBr) ν (cm$^{-1}$): 1633, 1506, 1429, 1391, 1238, 1213, 996.

EXAMPLE 9

4-(6,7-Dimethoxy-4-quinazolinyl)-N-(5-indanyl)-1-piperazinethiocarboxamide (Compound 9)

Yield: 100%
m.p.: 207–210° C.
$^1$H-NMR(CDCl$_3$) δ (ppm): 8.64(1H, s), 7.74(1H, brs), 7.23(1H, s), 7.16(1H, d, J=7.9 Hz), 7.08(1H, s), 7.04(1H, d, J=1.7 Hz), 6.93(1H, dd, J=7.9 Hz, 1.7 Hz), 4.08–4.04(4H, m), 4.00(3H, s), 3.98(3H, s), 3.82–3.79(4H, m), 2.90–2.83 (4H, m), 2.09–2.06(2H, m).
FAB-Mass: 450(M$^+$+1)
IR(KBr) ν (cm$^{-1}$): 1575, 1506, 1428, 1338, 1241, 1210, 1136, 993.

EXAMPLE 10

4-(6,7-Dimethoxy-4-quinazolinyl)-N-(1-pyrenyl)-1-piperazinethiocarboxamide (Compound 10)

Yield: 98%
m.p.: 140–145° C.
$^1$H-NMR(CDCl$_3$) δ (ppm): 8.59(1H, s), 8.19(1H, brs), 8.06–7.90(8H, m), 7.86(1H, d, J=8.3 Hz), 7.17(1H, s), 6.86(1H, s), 3.95(4H, m), 3.95(3H, s), 3.84(3H, s), 3.61–3.59(4H, m).

FAB-Mass: 534(M$^+$+1)

IR(KBr) ν (cm$^{-1}$): 1505, 1473, 1427, 1331, 1238, 1210, 993, 847.

EXAMPLE 11

4-(6,7-Dimethoxy-4-quinazolinyl)-N-(2,2-diphenylethyl)-1-piperazinethiocarboxamide (Compound 11)

Yield: 96% m.p.: 93–94° C.

$^1$H-NMR(CDCl$_3$) δ (ppm): 8.61(1H, s), 7.36–7.23(11H, m), 7.06(1H, s), 5.59(1H, brt, J=5.0 Hz), 4.47(1H, t, J=7.3 Hz), 4.33(2H, dd, J=7.3 Hz, 5.0 Hz), 4.01(3H, s), 3.97(3H, s), 3.87(4H, m), 3.75(4H, m).

FAB-Mass: 514(M$^+$+1)

IR(KBr) ν (cm$^{-1}$): 1576, 1504, 1475, 1450, 1429, 1348, 1240, 1209, 1136, 993, 704.

EXAMPLE 12

(dl)-4-(6,7-Dimethoxy-4-quinazolinyl)-N-(trans-2-phenylcyclopropyl)-1-piperazinecarboxamide (Compound 12)

Yield: 100% m.p.: 178–182° C.

$^1$H-NMR(CDCl$_3$) δ (ppm): 8.68(1H, s), 7.29–7.13(6H, m), 7.09(1H, s), 5.23(1H, brs), 4.02(3H, s), 3.98(3H, s), 3.67(4H, m), 3.62(4H, m), 2.87(1H, m), 2.06(1H, m), 1.21(2H, m).

FAB-Mass: 434(M$^+$+1)

IR(KBr) ν (cm$^{-1}$): 1622, 1504, 1429, 1350, 1257, 1211, 993.

EXAMPLE 13

N-Cyclohexyl-4-(6,7-dimethoxy-4-quinazolinyl)-1-piperazinecarboxamide (Compound 13)

Yield: 94% m.p.: 208–210° C.

$^1$H-NMR(CDCl$_3$) δ (ppm): 8.67(1H, s), 7.28(1H, s), 7.11(1H, s), 4.41(1H, d, J=7.4 Hz), 4.03(3H, s), 3.99(3H, s), 3.71–3.60(8H, m), 2.00–1.97(2H, m), 1.75–1.61(3H, m), 1.46–1.27(2H, m), 1.24–1.07(3H, m).

FAB-Mass: 400(M$^+$+1)

IR(KBr) ν (cm$^{-1}$): 1615, 1540, 1478, 1429, 1346, 1250, 1210, 992.

EXAMPLE 14

N-(1-Adamantyl-4-(6,7-dimethoxy-4-quinazolinyl)-1-piperazinecarboxamide (Compound 14)

Yield: 100% m.p.: 237–238° C.

$^1$H-NMR(CDCl$_3$) δ (ppm): 8.67(1H, s), 7.25(1H, s), 7.11(1H, s), 4.29(1H, brs), 4.03(3H, s), 3.99(3H, s), 3.71–3.67(4H, m), 3.58–3.54(4H, m), 2.09(3H, m), 2.02–2.01(6H, m), 1.69(6H, m).

FAB-Mass: 452(M$^+$+1)

IR(KBr) ν (cm$^{-1}$): 1324, 1535, 1504, 1430, 1235, 1210, 1134, 993.

EXAMPLE 15

N-Allyl-4-(6,7-dimethoxy-4-quinazolinyl)-1-piperazinethiocarboxamide (Compound 15)

Yield: 79% m.p.: 81–82° C.

$^1$H-NMR(CDCl$_3$) δ (ppm): 8.66(1H, s), 7.26(1H, s), 7.11(1H, s), 5.97(1H, ddt, J=16.8 Hz, 10.2 Hz, 5.9 Hz), 5.59(1H, brt, J=5.3 Hz), 5.31–5.21(2H, m), 4.38(2H, dt, J=5.9 Hz, 5.3 Hz), 4.10(4H, m), 4.03(3H, s), 3.99(3H, s), 3.87(4H, m).

FAB-Mass: 374(M$^+$+1)

IR(KBr) ν (cm$^{-1}$): 1576, 1506, 1475, 1429, 1350, 1240, 1209, 1136, 991.

EXAMPLE 16

4-(6,7-Dimethoxy-4-quinazolinyl)-N-(2-propynyl)-1-piperazinethiocarboxamide (Compound 16)

Yield: 79% m.p.: 158–160° C.

$^1$H-NMR(CDCl$_3$) δ (ppm): 8.70(1H, s), 7.27(1H, s), 7.08(1H, s), 5.19(1H, m), 4.76(2H, d, J=5.3 Hz), 4.03(3H, s), 3.99(3H, s), 3.71–3.67(4H, m), 3.65–3.61(4H, m), 1.77(1H, s).

FAB-Mass: 372(M$^+$+1)

IR(KBr) ν (cm$^{-1}$): 1629, 1612, 1573, 1510, 1448, 1432, 1242, 1216, 1154, 1042, 993, 938, 883, 848, 799.

EXAMPLE 17

4-(6,7-Dimethoxy-4-quinazolinyl)-N-(4-tolyl)-1-piperazinecarboxamide (Compound 17)

Yield: 91% m.p.: 225–228° C.

$^1$H-NMR(CDCl$_3$) δ (ppm): 8.67(1H, s), 7.26(2H, d, J=8.6 Hz), 7.25(1H, s), 7.08(1H, s), 7.04(2H, d, J=8.6 Hz), 7.01(1H, brs), 4.00(3H, s), 3.98(3H, s), 3.70(8H, m), 2.27(3H, s).

FAB-Mass: 407(M$^+$+1)

IR(KBr) ν (cm$^{-1}$): 1643, 1504, 1474, 1240, 1211, 1136, 993.

EXAMPLE 18

N-(4-Ethylphenyl)-4-(6,7-Dimethoxy-4-quinazolinyl)-1-piperazinecarboxamide (Compound 18)

Yield: 92% m.p.: 251–252° C.

$^1$H-NMR(CDCl$_3$) δ (ppm): 8.69(1H, s), 7.28(2H, d, J=7.9 Hz), 7.27(1H, s), 7.13(2H, d, J=7.9 Hz), 7.11(1H, s), 6.43(1H, brs), 4.03(3H, s), 4.00(3H, s), 3.74(8H, m), 2.61(2H, q, J=7.6 Hz), 1.21(3H, t, J=7.6 Hz).

FAB-Mass: 422(M$^+$+1)

IR(KBr) ν (cm$^{-1}$): 1641, 1519, 1506, 1417, 1250, 1211, 1134, 993.

EXAMPLE 19

4-(6,7-Dimethoxy-4-quinazolinyl)-N-(4-isopropylphenyl)-1-piperazinecarboxamide (Compound 19)

Yield: 70% m.p.: 252–254° C.

$^1$H-NMR(CDCl$_3$) δ (ppm): 8.65(1H, s), 8.00(1H, brs), 7.37(2H, d, J=8.2 Hz), 7.25(1H, s), 7.15(1H, s), 7.13(2H, d, J=8.2 Hz), 4.03(3H, s), 4.00(3H, s), 3.77(4H, m), 3.73(4H, m), 2.85(1H, m), 1.23(6H, d, J=6.9).

FAB-Mass: 436(M$^+$+1)

IR(KBr) ν (cm⁻¹): 1643, 1531, 1504, 1471, 1419, 1248, 1211, 1134, 993.

EXAMPLE 20

N-(4-Butylphenyl)-4-(6,7-dimethoxy-4-quinazolinyl)-1-piperazinecarboxamide (Compound 20)

Yield: 83% m.p.: 216–222° C.

$^1$H-NMR(CDCl$_3$) δ (ppm): 8.68(1H, s), 7.28(2H, d, J=8.3 Hz), 7.25(1H, s), 7.10(1H, s), 7.09(2H, d, J=8.3 Hz), 6.84 (1H, brs), 4.01(3H, s), 3.98(3H, s), 3.72(8H, m), 2.54(2H, t, J=7.3 Hz), 1.56(2H, tt, J=7.6 Hz, 7.3 Hz), 1.31(2H, tq, J=7.6 Hz, 7.3 Hz), 0.90(3H, t, J=7.3 Hz).

FAB-Mass: 450(M⁺+1)

IR(KBr) ν (cm⁻¹): 1617, 1504, 1417, 1244, 997.

EXAMPLE 21

N-(4-Butylphenyl)-4-(6,7-dimethoxy-4-quinazolinyl)-1-piperazinethiocarboxamide (Compound 21)

Yield: 80% m.p.: 171–173° C.

$^1$H-NMR(CDCl$_3$) δ (ppm): 8.65(1H, s), 7.63(1H, brs), 7.25(1H, s), 7.17–7.08(5H, m), 4.08–4.04(4H, m), 4.01(3H, s), 3.98(3H, s), 3.84–3.80(4H, m), 2.58(2H, t, J=7.6 Hz), 1.58(2H, tt, J=7.6 Hz, 7.6 Hz), 1.36(2H, tq, J=7.6 Hz, 7.3 Hz), 0.92(3H, t, J=7.3 Hz).

FAB-Mass: 466(M⁺+1)

IR(KBr) ν (cm⁻¹): 1574, 1505, 1472, 1426, 1339, 1244, 1210, 1190, 993, 937, 874.

EXAMPLE 22

N-(4-tert-Butylphenyl)-4-(6,7-dimethoxy-4-quinazolinyl)-1-piperazinethiocarboxamide (Compound 22)

Yield: 61% m.p.: 221–224° C.

$^1$H-NMR(CDCl$_3$) δ (ppm): 8.66(1H, s), 7.53(1H, brs), 7.36(2H, d, J=8.2 Hz), 7.25(1H, s), 7.13(2H, d, J=8.2 Hz), 7.09(1H, s), 4.08–4.04(4H, m), 4.02(3H, s), 3.98(3H, s), 3.85–3.82(4H, m), 1.30(9H, s).

FAB-Mass: 466(M⁺+1)

IR(KBr) ν (cm⁻¹): 1577, 1505, 1479, 1420, 1326, 1243, 1207, 991.

EXAMPLE 23

4-(6,7-Dimethoxy-4-quinazolinyl)-N-[4-(trifluoromethyl)phenyl]-1-piperazinecarboxamide (Compound 23)

Yield: 95% m.p.: 227–230° C.

$^1$H-NMR(CDCl$_3$) δ (ppm): 8.69(1H, s), 7.53(4H, m), 7.25(1H, s), 7.19(1H, brs), 7.10(1H, s), 4.01(3H, s), 3.99 (3H, s), 3.75(8H, m).

FAB-Mass: 462(M⁺+1)

IR(KBr) υ (cm⁻¹): 1651, 1537, 1504, 1474, 1419, 1327, 1244, 1211, 1115, 1066, 993.

EXAMPLE 24

4-(6,7-Dimethoxy-4-quinazolinyl)-N-(4-vinylphenyl)-1-piperazinethiocarboxamide (Compound 24)

Yield: 97% m.p.: 110–111° C.

$^1$H-NMR(CDCl$_3$)δ(ppm): 8.65(1H, s), 7.88(1H, brs), 7.36(2H, d, J=8.6 Hz), 7.23(1H, s), 7.15(2H, d, J=8.6 Hz), 7.08(1H, s), 6.65(1H, dd, J=17.5 Hz, 10.9 Hz), 5.68(1H, d, J=17.5 Hz), 5.22(1H, d, J=10.9 Hz), 4.07–4.04(4H, m), 4.00(3H, s), 3.97(3H, s), 3.83–3.79(4H, m).

P FAB-Mass: 436(M⁺+1)

IR(KBr) υ (cm⁻¹): 1576, 1505, 1476, 1427, 1334, 1239, 1209, 992.

EXAMPLE 25

N-(4-Decylphenyl)-4-(6,7-dimethoxy-4-quinazolinyl)-1-piperazinecarboxamide (Compound 25)

Yield: 86% m.p.: 120–121° C.

$^1$H-NMR(CDCl) δ(ppm): 8.65(1H, s), 7.77(1H, brs), 7.24 (1H, s), 7.14(2H, d, J=8.9 Hz), 7.10(1H, s), 7.10(2H, d, J=8.9 Hz), 4.07–4.02(4H, m), 4.00(3H, s), 3.98(3H, s), 3.95–3.79(4H, m), 2.57(2H, t, J=7.3 Hz), 1.56(2H, tt, J=7.3 Hz, 6.9 Hz), 1.30–1.23(14H, m), 0.87(3H, t, J=6.7 Hz).

FAB-Mass: 550(M⁺1)

IR(KBr) υ (cm⁻¹): 1576, 1506, 1428, 1336, 1247, 1208, 1135, 1020, 992, 858.

EXAMPLE 26

N-(4-Cyclohexylphenyl)-4-(6,7-dimethoxy-4-quinazolinyl)-1-piperazinecarboxamide (Compound 26)

Yield: 28% m.p.: 238–241° C.

$^1$H-NMR(CDCl$_3$) δ (ppm): 8.69(1H, s), 7.28(2H, d, J=8.6 Hz), 7.27(1H, s), 7.14(2H, d, J=8.6 Hz), 7.11(1H, s), 6.56 (1H, brs), 4.03(3H, s), 4.00(3H, s), 3.73(8H, m), 2.45(1H, m), 1.83–1.71(1H, m), 1.41–1.34(5H, m).

FAB-Mass: 476(M⁺+1)

IR(KBr) υ (cm⁻¹)1642, 1505, 1472, 1419, 1352, 1245, 1211, 1134, 994.

EXAMPLE 27

4-(6,7-Dimethoxy-4-quinazolinyl)-N-(2-biphenyl)-1-piperazinethiocarboxamide (Compound 27)

Yield: 80% m.p.: 94–95° C.

$^1$H-NMR(CDCl$_3$) δ (ppm): 8.62(1H, s), 7.60(2H, d, J=7.9 Hz), 7.47–7.25(9H, m), 7.12(H H, brs), 7.07(1H, s), 4.02 (3H, s), 3.98(3H, s), 3.97–3.95(4H, m), 3.78–3.75(4H, m).

FAB-Mass: 486(M⁺+1)

IR(KBr) υ (cm⁻¹): 1574, 1505, 1478, 1452, 1426, 1336, 1237, 1212, 1018, 990, 740.

EXAMPLE 28

N-(4-Biphenyl)-4-(6,7-dimethoxy-4-quinazolinyl)-1-piperazinecarboxamide (Compound 28)

Yield: 9% m.p.: 221–224 ° C.

$^3$H-NMR(CDCl$_3$) δ (ppm): 8.69(1H, s), 7.56–7.26(10H, m), 7.10(.H, s), 6.84(m H, brs), 4.02(3H, s), 3.98(3H, s), 3.75(8H, FAB-Mass: 470(M$^+$+1)

IR(KBr) υ (cm$^{-1}$):14,17,10,1238, 1212, 1136, 992.

EXAMPLE 29

4-(6,7-Dimethoxy-4-quinazolinyl)-N-(3,5-dimethylphenyl)-1-piperazinecarboxamide (Compound 29)

Yield: 74% m.p.: 223–226° C.

$^1$H-NMR(CDCl$_3$) δ (ppm): 8.69(1H, s), 7.26(1H, s), 7.11 (1H, s), 7.02(2H, s), 6.70(1H, s), 6.56(1H, s), 4.03(3H, s), 3.99(3H, s), 3.73(8H, m), 2.28(6H, s).

FAB-Mass: 422(M$^+$+1)

IR(KBr) υ (cm$^{-1}$): 1640, 1504, 1476, 1429, 1242, 1212, 996.

EXAMPLE 30

4-(6,7-Dimethoxy-4-quinazolinyl)-N-(3,4-dimethylphenyl)-1-piperazinecarboxamide (Compound 30)

Yield: 84% m.p.: 202–203° C.

$^1$H-NMR(CDCl$_3$) δ (ppm): 8.69(1H, s), 7.26(1H, s), 7.19 (1H, s), 7.10–7.01(3H, m), 6.74(1H, brs), 4.02(3H, s), 3.99(3H, s), 3.72(8H, m), 2.21(3H, s), 2.19(3H, s).

FAB-Mass: 422(M$^+$+1)

IR(KBr) υ (cm$^{-1}$): 1648, 1532, 1505, 1472, 1440, 1414, 1351, 1239, 1214, 1136, 992.

EXAMPLE 31

N-(2,6-Diisopropylphenyl)-4-(6,7-dimethoxy-4-quinazolinyl)-1-piperazinecarboxamide (Compound 31)

Yield: 75% m.p.: 280–282° C.

$^1$H-NMR(CDCl$_3$) δ (ppm): 8.71(1H, s), 7.28–7.24(2H, m), 7.18–7.13(3H, m), 4.04(3H, s), 4.01(3H, s), 3.71–3.66 (8H, m), 3.21–3.06(2H, m), 1.22(12H, d, J=6.4 Hz).

FAB-Mass: 477(M$^+$+1)

IR(KBr) υ (cm$^{-1}$): 1629, 1504, 1428, 1355, 1213, 996.

EXAMPLE 32

N-[3,5-Bis(trifluoromethyl)phenyl]-4-(6,7-dimethoxy-4-quinazolinyl)-1-piperazinecarboxamide (Compound 32)

Yield: 89% m.p.: 251–252° C.

$^1$H-NMR(CDCl$_3$) δ (ppm): 8.71(1H, s), 7.93(2H, s), 7.56 (3H, s), 7.26(1H, s), 7.11(1H, s), 6.80(1H, brs), 4.04(3H, s), 4.01(3H, s), 3.78(8H, m).

FAB-Mass: 529(M$^+$+1)

IR(KBr) υ (cm$^{-1}$): 1647, 1568, 1504, 1473, 1431, 1373, 1279, 1244, 1209, 1176, 1135, 995.

EXAMPLE 33

4-(6,7-Dimethoxy-4-quinazolinyl)-N-(3-isopropenyl-α, α-dimethybenzyl)-1-piperazinecarboxamide (Compound 33)

Yield: 90% m.p.: 190–191° C.

$^1$H-NMR(CDCl$_3$) δ (ppm): 8.65(1H, s), 7.48(1H, s), 7.28 (3H, m), 7.22(1H, s), 7.06(mH, s), 5.32(2H, brs), 5.05(1H, d, J=1.3 Hz), 4.98(1H, d, J=1.3 Hz), 3.99(3H, s), 3.94(3H, s), 3.65(4H, m), 3.58(4H, m), 2.12(3H, s), 1.71(6H. s).

FAB-Mass: 476(M$^+$+1)

IR(KBr) υ (cm$^{-1}$): 1632, 1504, 1473, 1429, 1387, 1352, 1254, 1211, 995.

EXAMPLE 34

4-(6,7-Dimethoxy-4-quinazolinyl)-N-(2-fluorophenyl)-1-piperazinecarboxamide (Compound 34)

Yield: 100% m.p. : 176–177° C.

$^1$H-NMR(CDCl$_3$) δ (ppm).: 8.70(1H, s) , 8.08(1H, m) , 7.28(1H, s), 7.14–6.97(3H, m), 7.12(1H, s), 6.74(1H, br), 4.03(3H, s), 4.01(3H, s), 3.77(8H, m).

PFAB-Mass: 412(M$^+$+1)

IR(KBr) υ (cm$^{-1}$):1643, 1506, 1479, 1448, 1433, 1242, 1215, 1138, 997, 754.

EXAMPLE 35

4-(6,7-Dimethoxy-4-quinazolinyl)-N-(3-fluorophenyl)-1-piperazinecarboxamide (Compound 35)

Yield: 90% m.p.: 214–220° C.

$^1$H-NMR(CDCl$_3$) δ (ppm): 8.69(1H, s), 7.33(2H, s), 7.27 (1H, s), 7.36–7.18(3H, m), 7.10(mH, s), 7.05(bH, m), 6.79–6.71(2H, m), 4.02(3H, s), 3.99(3H, s), 3.74(8H, m).

FAB-Mass: 412(M$^+$+1)

IR(KBr) υ (cm$^{-1}$): 1645, 1539, 1506, 1431, 1242, 1213, 995.

EXAMPLE 36

4-(6,7-Dimethoxy-4-quinazolinyl)-N-(4-fluorophenyl)-1-piperazinecarboxamide (Compound 36)

Yield: 100% m.p.: 198–202° C.

$^1$H-NMR(CDCl$_3$) δ (ppm): 8.69(1H, s), 7.32(2H, m)b, 7.25(H, s), 7.10(3H, s), 6.98(2H, m), 6.84(7.H, brs), 4.02 (3H, s), 3.99(3H, s), 3.73(8H, m).

FAB-Mass: 412(M$^+$+1)

IR(KBr) υ (cm$^{-1}$): 1633, 1506, 1429, 1236, 1209, 993.

EXAMPLE 37

4-(6,7-Dimethoxy-4-quinazolinyl)-N-(4-fluorophenyl)-1-piperazinethiocarboxamide (Compound 37)

Yield: 56% m.p.: 212–217° C.

$^1$H-NMR(CDCl$_3$) δ (ppm): 8.66(1H, s), 7.50(1H, brs), 7.28–7.18(3H, m), 7.10–7.01(3H, m), 4.12(4H, m), 4.02(3H, s), 3.99(3H, s), 3.85(4H, m).

FAB-Mass: 428(M$^+$+1)

IR(KBr) υ (cm$^{-1}$): 1508, 1479, 1456, 1419, 1340, 1207, 990.

EXAMPLE 38

N-(2-Chlorophenyl)-4-(6,7-dimethoxy-4-quinazolinyl)-1-piperazinecarboxamide (Compound 38)

Yield: 100% m.p.: 186–187° C.

$^1$H-NMR(CDCl$_3$) δ (ppm): 8.70(1H, s), 8.18(1H, dd, J=8.3 Hz, 1.7 Hz), 7.34(1H, dd, J=8.3 Hz, 1.3 Hz), 7.25(1H, ddd, J=8.3 Hz, 10 7.6 Hz, 1.3 Hz), 7.26(1H, s), 7.13(1H, brs), 7.12(1H, s), 6.97(1H, ddd, J=8.3 Hz, 7.6 Hz, 1.7 Hz), 4.03(3H, s), 4.01(3H, s), 3.78(8H, m).

FAB-Mass: 430(M$^+$+3), 428(M$^+$+1)

IR(KBr) υ (cm$^{-1}$): 1640, 1506, 1477, 1434, 1240, 1213, 995.

EXAMPLE 39

N-(3-Chlorophenyl)-4-(6,7-dimethoxy-4-quinazolinyl)-1-piperazinecarboxamide (Compound 39)

Yield: 86% m.p.: 223–224° C.

$^1$H-NMR(CDCl$_3$) δ (ppm): 8.69(1H, s), 7.48(1H, dd, J=2.0 Hz, 2.0 Hz), 7.29–7.15(3H, m), 7.09–6.98(3H, m), 4.02(3H, s), 3.99(3H, s), 3.73(8H, m).

FAB-Mass: 430(M$^+$+3), 428(M++1)

IR(KBr) υ (cm$^{-1}$): 1680, 1645, 1620, 1506, 1481, 1425, 1240, 1215, 990.

EXAMPLE 40

N-(4-Chlorophenyl)-4-(6,7-dimethoxy-4-quinazolinyl)-1-piperazinecarboxamide (Compound 40)

Yield: 100% m.p.: 217–219° C.

$^1$H-NMR(CDCl$_3$) δ (ppm): 8.58(1H, s), 8.17(2H, d, J=8.9Hz), 7.76(2H, d, J=8.9 Hz), 7.24(1H, s), 7.20(1H, s), 3.95(6H, s), 3.74–3.72(8H, m).

FAB-Mass: 430(M$^+$+3), 428(M$^+$+1)

IR(KBr) υ (cm$^{-1}$):1638, 1533, 1497, 1405, 1346, 1234, 1204, 988.

EXAMPLE 41

N-(4-Clorophenyl)-4-(6,7-Dimethoxy-4-quinazolinyl)-1-piperazinethiocarboxamide (Compound 41)

Yield: 96% m.p.: 199–204° C.

$^1$H-NMR(CDCl$_3$) δ (ppm): 8.66(1H, s), 7.67(1H, brs), 7.31(2H, d, J=8.6 Hz), 7.25(1H, s), 7.17(2H, d, J=8.6 Hz), 7.09(1H, s), 4.12(4H, m), 4.02(3H, s), 3.99(3H, s), 3.84(4H, m).

FAB-Mass: 446(M$^+$+3), 444(M$^+$+1)

IR(KBr) υ (cm$^{-1}$): 1574, 1506, 1492, 1479, 1423, 1344, 1327, 1209, 991.

EXAMPLE 42

N-(4-Chlorobenzyl)-4-(6,7-dimethoxy-4-quinazolinyl)-1-piperazinethiocarboxamide (Compound 42)

Yield: 77% m.p.: 218–220° C.

$^1$H-NMR(CDCl$_3$) δ (ppm): 8.62(1H, s), 7.29–7.27(4H, m), 7.22(1H, s), 7.10(1H, s), 6.09(1H, brt, J=5.0 Hz), 4.89(2H, d, J=5.0 Hz), 4.12–4.09(4H, m), 4.01(3H, s), 3.98(3H, s), 3.87–3.83(4H, m).

FAB-Mass: 460(M$^+$+3), 458(M$^+$+1)

IR(KBr) υ (cm$^{-1}$): 1575, 1532, 1502, 1475, 1428, 1394, 1322, 1235, 1208, 1135, 991, 938, 864, 799.

EXAMPLE 43

N-(4-Chlorobenzenesulfonyl) -4-(6,7-dirnethoxy-4-quinazolinyl)- 1-piperazinecarboxamide (Compound 43)

Yield: 67% m.p.: 228–234° C.

$^1$H-NMR(DMSO-d$_6$) δ (ppm): 8.53(1H, s), 8.32(1H, s), 7.80(2H, d, J=8.6 Hz), 7.46(2H, d, J=8.6 Hz ), 7.21 (1H, s), 7.04(1H, s), 3.93(3H, s), 3.91(3H, s), 3.59(4H, m), 3.53(4H, m).

FAB-Mass: 494(M$^+$+3), 492(M$^+$+1)

IR(KBr) υ (cm$^{-1}$): 1617, 1549, 1506, 1464, 1428, 1258, 1213, 1131, 1087, 993, 935, 893, 751, 631, 585.

EXAMPLE 44

N-(3-Bromophenyl)-4-(6,7-dimethoxy-4-quinazolinyl)-1-piperazinecarboxamide (Compound 44)

Yield: 87% m.p.: 221–222° C.

$^1$H-NMR(CDCl$_3$) δ (ppm): 8.68(1H, s), 7.62(1H, d, J=1.7 Hz), 7.30(6H, m), 7.25(2H, s), 7. 17–7.12(2H, m), 7.10(1H, s), 6.97(3H, brs), 4.02(3H, s), 3.99(3H, s), 3.73(8H, m).

FAB-Mass: 474(M++3), 472(M++1)

IR(KBr) υ (cm$^{-1}$): 1643, 1579, 1506, 1479, 1421, 1238, 1209, 995.

EXAMPLE 45

N-(4-Bromophenyl)-4-(6,7-dimethoxy-4-quinazolinyl)-1-piperazinecarboxamide (Compound 45)

Yield: 100% m.p.: 223–228° C.

$^1$H-NMR(CDCl$_3$) δ (ppm): 8.68(1H, s), 7.38(2H, d, J=1.7 Hz), 7.29(2H, d, J=8.9 Hz), 7.25(1H, s), 7.09(2H, s), 6.99(1H, brs), 4.01(3H, s), 3.99(3H, s), 3.72(8H, m).

FAB-Mass: 472( M$^+$+1)

IR(KBr) υ (cm$^{-1}$): 1640, 1531, 1504, 1489, 1410, 1239, 1212, 1135, 994.

EXAMPLE 46

4-(6,7-Dimethoxy-4-quinazolinyl)-N-(4-iodophenyl)-1-piperazinecarboxamide (Compound 46)

Yield: 86% m.p.: 238–242 CC $^1$H-NMR(CDCl$_3$) δ (ppm): 8.69(1H, s), 7.58(2H, d, J=8.3 Hz), 7.26(5H, s), 7.18(2H, d, J=8.3 Hz), 7.10(1H, s), 6.82(1H, brs), 4.02(3H, s), 4.00(3H, s), 3.73(8H, m).

FAB-Mass: 520(M$^+$+1)

IR(KBr) υ (cm$^{-1}$): 1645, 1584, 1525, 1505, 1487, 1407, 1238, 1212, 1135, 993.

EXAMPLE 47

4-(6,7-Dimethoxy-4-quinazolinyl)-N-(4-iodophenyl)-1-piperazinethiocarboxamide (Compound 47)

Yield: 94% m.p.: 129–132° C.

$^1$H-NMR(CDCl$_3$) δ (ppm): 8.93(1H, brs), 8.65(1H, s), 7.63(2H, d, J=8.6 Hz), 7.25(5H, s), 7.1 3(2H, d, J=8.6 Hz), 7.11(1H, s), 4.03–4.02(4H, m), 4.00(3H, s), 3.99(3H, s), 3.85(4H, m).

FAB-Mass: 536(M$^+$+1)

IR(KBr) 1)(cm$^{-1}$):1581, 1508, 1481, 1429, 1336, 1252, 1207, 1142, 993.

EXAMPLE 48

N-([4-Chloro-2-x(trifluoromethyl)phenyl]-4-(6,7-dimethoxy-4-quinazolinyl)-1-piperazinecarboxamide (Compound 48)

Yield: 97% m.p.: 189–190° C.

$^1$H-NMR(CDCl$_3$) δ (ppm): 8.70(1H, s), 8.05(2H, d, J=8.6 Hz), 7.55(1H, s), 7.49(2H, d, J=8.6 Hz), 7.26(1H, s), 7.11(1H, s), 6.91(1H, brs), 4.03(3H, s), 4.01(3H, s), 3.76(8H, m).

FAB-Mass: 498(M$^+$+3), 496(M$^+$+1)

IR(KBr) υ (cm$^{-1}$) 1628, 1506, 1479, 1437, 1309, 1263, 1240, 1213, 1124, 995.

EXAMPLE 49

N-[4-Chloro-3-(trifluoromethyl)phenyl]-4-(6,7-dimethoxy-4-quinazolinyl)-1-piperazinecarboxamide (Compound 49)

Yield: 83% mp:237–238° C.

$^1$H-NMR(CDCl$_3$) δ (ppm): 8.69(1H, s), 7.71(1H, d, J=2.3 Hz), 7.61(1H, dd, J=8.6 Hz, 2.3 Hz), 7.38(1H, d, J=8.6 Hz), 7.29(1H, brs), 7.25(1H, s), 7.10(1H, s), 4.02(3H, s), 4.00 (3H, s), 3.75(8H, m).

FAB-Mass: 498(M$^+$+3), 496(M$^+$+1)

IR(KBr) υ (cm$^{-1}$):1647, 1539, 1502, 1485, 1471, 1433, 1321, 1244, 1207, 1136, 993.

EXAMPLE 50

N-(2,4-Difluorophenyl)-4-(6,7-dimethoxy-4-quinazolinyl)-1-piperazinecarboxamide (Compound 50)

Yield: 35% m.p.: 174–175° C.

$^1$H-NMR(CDCl$_3$) δ (ppm): 8.71(1H, s), 8.02–7.97(1H, m), 7.28(1H, s), 7.12(1H, s), 6.91–6.85(2H, m), 4.04(3H, s), 4.00(3H, s), 3.89–3.71(8H, m).

FAB-Mass: 430(M$^+$+1)

IR(KBr) υ (cm$^{-1}$): 1616, 1500, 1424, 1351, 1238, 1208, 995.

EXAMPLE 51

N-(2,5-Difluorophenyl)-4-(6,7-dimethoxy-4-quinazolinyl)-1-piperazinecarboxamide (Compound 51)

Yield: 89% m.p.: 187–189° C.

$^1$H-NMR(CDCl$_3$) δ (ppm): 8.70(1H, s), 7.95(1H, m), 7.27(1H, s), 7.11(1H, s), 7.00(1H, m), 6.85(1H, br), 6.66 (1H, m), 4.03(3H, s), 4.01(3H, s), 3.77(8H, m).

FAB-Mass: 430(M$^+$+1)

IR(KBr) υ (cm 1): 1649, 1508, 1429, 1255, 1242, 1215, 1155, 997.

EXAMPLE 52

N-(2,6-Dichlorophenyl)-4-(6,7-dimethoxy-4-quinazolinyl)-1-piperazinecarboxamide (Compound 52)

Yield: 92% m.p.: 202–207° C.

$^1$H-NMR(CDCl$_3$) δ (ppm): 8.70(1H, s), 7.34(2H, d, J=7.9 Hz), 7.28(1H, s), 7.21(1H, d, J=7.9 Hz), 7.11(1H, s), 6.54 (1H, brs), 15 4.03(3H, s), 4.00(3H, s), 3.78–3.77(8H, m).

FAB-Mass: 464(M$^+$+1), 462(M$^+$+1)

IR(KBr) υ (cm$^{-1}$): 1634, 1506, 1428, 1250, 1211, 1135, 997, 933, 853, 799.

EXAMPLE 53

N-(2,4-Dichlorophenyl)-4-(6,7-dimethoxy-4-quinazolinyl)-1-piperazinecarboxamide (Compound 53)

Yield: 100% m.p.: 166–167° C.

$^1$H-NMR(CDCl$_3$) δ (ppm): 8.70(1H, s), 8.15(1H, d, J=8.9 Hz), 7.36(1H, d, J=2.3 Hz), 7.27(1H, s), 7.23(1H, dd, J=8.9 Hz, 2.3 Hz), 7.12(1H, s), 7.07(1H, brs), 4.03(3H, s), 4.01 (3H, s), 3.78(8H, m).

FAB-Mass: 464(M$^+$+3), 462(M$^+$+1)

IR(KBr) υ (cm$^{-1}$): 1676, 1576, 1506, 1474, 1431, 1238, 1207, 1136, 991

EXAMPLE 54

N-(3,4-Dichlorophenyl)-4-(6,7-dimethoxy-4-quinazolinyl)-1-piperazinecarboxarnide (Compound 54)

Yield: 100% m.p.: 221–222° C.

$^1$H-NMR(CDCl$_3$) δ (ppm): 8.69(1H, s), 7.60(1H, d, J=2.3 Hz), 5 7.33(1H, a, J=8.6 Hz)g 7.26(1H, s), 7.23(1H, dd, J=8.6 Hz, 2.3 Hz), 7.10(1H, s), 6.89(1H, brs), 4.02(3H, s), 4.00(3H, s), 3.74(8H, m).

FAB-Mass: 464(M$^+$+3), 462(M$^+$+1)

IR(KBr) υ (cm$^{-1}$): 1645, 1587, 1502, 1477, 1431, 1394, 1244, 1207, 1135, 993.

EXAMPLE 55

N-(3,5-Dichlorophenyl)-4-(6,7-dimethoxy-4-quinazolinyl)-1-piperazinecarboxamide (Compound 55)

Yield: 93% m.p.: 139–140° C.

$^1$H-NMR(CDCl$_3$) δ (ppm) : 8.67(1H, s), 7.75(1H, brs), 7.39(2H, d, J=2.0 Hz), 7.25(1H, s), 7.09(1H, s), 6.97(1H, d, J=2.0Hz), 4.02(3H, s), 3.99(3H, s), 3.76–3.70(8H, m).

FAB-Mass: 464(M$^+$+3), 462(M$^+$+1)

IR(KBr) υ (cm$^{-1}$): 1641, 1585, 1504, 1473, 1416, 1244, 1209, 1136, 993.

EXAMPLE 56

4-(6,7-Dimethoxy-4-quinazolinyl)-N-(4-methoxyphenyl)-1-piperazinecarboxamide (Compound 56)

Yield: 87% m.p.: 221–223° C.

$^1$H-NMR(CDCl$_3$) δ (ppm): 8.69(1H, s), 7.29–7.24(3H, m), 7.12(1H, s), 6.86(2H, d, J=8.9 Hz), 4.03(3H, s), 4.00 (3H, s), 3.79(3H, s), 3.76–3.72(8H, m).

FAB-Mass: 424(M$^+$+1)

EXAMPLE 57

4-(6,7-Dimethoxy-4-quinazolinyl)-N-(4-ethoxyphenyl)-1-piperazinecarboxamide (Compound 57)

Yield: 100% m.p.: 165–166° C.

$^1$H-NMR(CDCl$_3$) δ (ppm): 8.69(1H, s), 8.16(2H, d, J=9.6 Hz), 7.29(1H, s), 7.13(1H, s), 6.96(2H, d, J=9.6 Hz), 6.86 (1H, brs), 4.13(2H, q, J=6.9 Hz), 4.04(3H, s), 4.01(3H, s), 3.79–3.77(8H, m), 1.47(3H, t, J=6.9 Hz).

FAB-Mass: 438(M$^+$+1)

IR(KBr) υ (cm$^{-1}$): 1662, 1538, 1506, 1452, 1425, 1358, 1250, 1211, 991.

EXAMPLE 58

N-(4-Butoxyphenyl)-4-(6,7-dimethoxy-4-quinazolinyl)-1-piperazinecarboxamide (Compound 58)

Yield: 91% m.p.: 213–214° C.

$^1$H-NMR(CDCl$_3$) δ (ppm): 8.68(1H, s), 7.25(2H, d, J=8.9 Hz), 7.25(1H, s), 7.09(1H, s), 6.82(2H, d, J=8.9 Hz), 6.79

(1H, brs), 4.01(3H, s), 3.98(3H, s), 3.90(2H, t, J=6.6 Hz), 3.70(8H, m), 1.73(2H, tt, J=7.3 Hz, 6.6 Hz), 1.46(2H, tq, J=7.3 Hz, 7.3 Hz), 0.94(3H, t, J=7.3 Hz).

FAB-Mass: 466(M$^+$+1)

IR(KBr) υ (cm$^{-1}$): 1637, 1574, 1511, 1419, 1238, 1211, 993.

EXAMPLE 59

4-(6,7-Dimethoxy-4-quinazolinyl)-N-[4-(trifluoromethoxy)phenyl]-1-piperazinecarboxamide (Compound 59)

Yield: 87% m.p.: 204–205° C.

$^1$H-NMR(CDCl$_3$) δ (ppm): 8.68(1H, s), 7.42(2H, d, J=8.9 Hz), 7.25(1H, s), 7.14(2H, d, J=8.9 Hz), 7.10(1H, s), 4.01(3H, s), 3.99(3H, s), 3.74(8H, m).

FAB-Mass: 478(M$^+$+1)

IR(KBr) υ (cm$^{-1}$): 1644, 1500, 1417, 1250, 1205, 1158, 996, 928, 847, 799.

EXAMPLE 60

4-(6,7-Dimethoxy-4-quinazolinyl)-N-(4-phenoxyphenyl)-1-piperazinecarboxamide (Compound 60)

Yield: 97% m.p.: 218–219° C.

$^1$H-NMR(CDCl$_3$) δ (ppm): 8.70(1H, s), 7.37–7.26(5H, m), 7.12(1H, s), 7.07(1H, m), 7.00–6.97(4H, m), 6.46(1H, brs), 4.03(3H, s), 4.00(3H, s), 3.76(8H, m).

FAB-Mass: 486(M$^+$+1)

IR(KBr) υ (cm$^{-1}$): 1633, 1541, 1506, 1421, 1248, 1234, 993.

EXAMPLE 61

4-(6,7-Dimethoxy-4-quinazolinyl)-N-(4-phenoxyphenyl)-1-piperazinethiocarboxamide (Compound 61)

Yield: 74% m.p.: 242–243° C.

$^1$H-NMR(CDCl$_3$) δ (ppm): 8.67(1H, s), 7.38–7.31(2H, m), 7.27(1H, s), 7.26(1H, brs), 7.21–6.96(8H, m), 4.12–4.08(4H, m), 4.03(3H, s), 3.99(3H, s), 3.88–3.84(4H, m).

FAB-Mass: 502(M$^+$+1)

IR(KBr) υ (cm$^{-1}$): 1576, 1506, 1484, 1432, 1398, 1339, 1241, 1212, 993.

EXAMPLE 62

4-(6,7-Dimethoxy-4-quinazolinyl)-N-14-(4-nitrophenoxy)phenyl]-1-piperazinethiocarboxamide (Compound 62)

Yield: 87% m.p.: 204–207° C.

$^1$H-NMR(CDCl$_3$) δ (ppm): 8.67(1H, s), 8.20(2H, d, J=8.9 Hz), 7.56(1H, brs), 7.34(2H, d, J=8.9 Hz), 7.28(1H, s), 7.11(1H, s), 7.09(2H, d, J=8.9 Hz), 7.04(2H, d, J=8.9 Hz), 4.18–4.14(4H, m), 4.03(3H, s), 4.00(3H, s), 3.91–3.87(4H, m).

FAB-Mass: 547(M$^+$+1)

IR(KBr) υ (cm$^{-1}$): 1579, 1505, 1480, 1420, 1337, 1240, 1208, 992, 878, 844.

EXAMPLE 63

N-(4-Benzyloxyphenyl)-4-(6,7-dimethoxy-4-quinazolinyl)-1-piperazinethiocarboxamide (Compound 63)

Yield: 83% m.p.: 103–105° C.

$^1$H-NMR(CDCl$_3$) δ (ppm): 8.65(1H, s), 7.63(1H, brs), 7.43–7.29(5H, m), 7.24(1H, s), 7.15(2H, d, J=8.9 Hz), 7.09(1H, s), 6.94(2H, d, J=8.9 Hz), 5.03(2H, s), 4.08(4H, m), 4.01(3H, s), 3.97(3H, s), 3.82(4H, m).

FAB-Mass: 516(M$^+$+1)

IR(KBr) υ (cm$^{-1}$): 1543, 1508, 1475, 1427, 1336, 1238, 1209, 1016, 991.

EXAMPLE 64

N-(2,4-Dimethoxyphenyl)-4-(6,7-dimethoxy-4-quinazolinyl)-1-piperazinecarboxamide (Compound 64)

Yield: 100% m.p.: 187–188° C.

$^1$H-NMR(CDCl$_3$) δ (ppm): 8.69(1H, s), 7.98(1H, d, J=6.9 Hz), 7.27(1H, s), 7.13(1H, s), 6.89(1H, brs), 6.51–6.48(2H, m), 4.04(3H, s), 4.01(3H, s), 3.87(3H, s), 3.80(3H, s), 3.76(8H, m).

FAB-Mass: 454(M$^+$+1)

IR(KBr) υ (cm$^{-1}$): 1640, 1600, 1533, 1502, 1454, 1236, 1207, 990.

EXAMPLE 65

N-(2,5-Dimethoxyphenyl)-4-(6,7-Dimethoxy-4-quinazolinyl)-1-piperazinecarboxamide (Compound 65)

Yield: 93% m.p.: 215–217° C.

$^1$H-NMR(CDCl$_3$) δ (ppm): 8.70(1H, s), 7.92(1H, d, J=3.3 Hz), 7.27(1H, s), 7.24(1H, brs), 7.13(1H, s), 6.79(1H, d, J=8.9 Hz), 6.52(1H, dd, J=8.9 Hz, 3.3 Hz), 4.04(3H, s), 4.01(3H, s), 3.86(3H, s), 3.79(3H, s), 3.77(8H, m).

FAB-Mass: 454(M$^+$+1)

IR(KBr) υ (cm$^{-1}$): 1659, 1531, 1502, 1429, 1236, 1209, 1134, 993.

EXAMPLE 66

N-(3,4-Dimethoxyphenyl)-4-(6,7-dimethoxy-4-quinazolinyl)-1-piperazinethiocarboxamide (Compound 66)

Yield: 100% mp.: 174–176° C.

$^1$H-NMR(CDCl$_3$) δ (ppm): 8.65(1H, s), 7.60(1H, brs), 7.25(1H, s), 7.10(1H, s), 6.84–6.73(3H, m), 4.12–4.08(4H, m), 4.02(3H, s), 3.98(3H, s), 3.86(3H.s), 3.86–3.85(4H, m), 3.85(3H, s).

FAB-Mass: 470(M$^+$+1)

IR(KBr) υ (cm$^{-1}$): 1504, 1479, 1344, 1257, 1240, 1211, 1132, 1025, 991.

EXAMPLE 67

N-(3,5-Dimethoxyphenyl)-4-(6,7-dimethoxy-4-quinazolinyl)-1-piperazinethiocarboxamide (Compound 67)

Yield: 83% m.p.: 240–241° C.

$^1$H-NMR(CDCl$_3$+DMSO-d$_6$) δ (ppm): 9.17(1H, brs), 8.60(1H, s), 7.22(1H, s), 7.17(1H, s), 6.54(2H, d, J=2.3 Hz), 6.24(1H, d, J=2.3 Hz), 4.15(4H, m), 4.01(3H, s), 4.00(3H, s), 3.84(4H, m), 3.77(3H, s), 3.76(3H, s).

FAB-Mass: 470(M$^+$+1)

IR(KBr) υ (cm$^{-1}$): 1605, 1502, 1477, 1425, 1211, 1182, 993.

EXAMPLE 68

4-(6,7-Dimethoxy-4-quinazolinyl)-N-(3,4-methylenedioxyphenyl)-1-piperazinethiocarboxamide (Compound 68)

Yield: 100% m.p.: 207–211° C.

$^1$H-NMR(CDCl$_3$) δ (ppm): 8.66(1H, s), 7.60(1H, brs), 7.25(1H, s), 7.10(1H, s), 6.79–6.75(2H, m), 6.63(1H, dd, J=8.3 Hz, 2.0 Hz), 5.98(2H, s), 4.10(4H, m), 4.02(3H, s), 3.99(3H, s), 3.84(4H, m).

FAB-Mass: 454(M$^+$+1)

IR(KBr) υ (cm$^{-1}$): 1541, 1504, 1479, 1431, 1346, 1242, 1209, 1136, 1036, 991, 935, 854.

EXAMPLE 69

4-(6,7-Dimethoxy-4-quinazolinyl)-N-(4-methylthiophenyl)-1-piperazinecarboxamide (Compound 69)

Yield: 84% m.p.: 231–233° C.

$^1$H-NMR(CDCl$_3$) δ (ppm): 8.69(1H, s), 7.33(2H, d, J=8.9 Hz), 7.28(1H, s), 7.22(2H, d, J=8.9 Hz), 7.10(1H, s), 6.75 (1H, brs), 4.02(3H, s), 3.99(3H, s), 3.73(8H, m), 2.45(3H, s).

FAB-Mass: 440(M$^+$+1)

IR(KBr) υ (cm$^{-1}$): 1597, 1576, 1506, 1429, 1348, 1292, 1209, 991.

EXAMPLE 70

4-(6,7-Dimethoxy-4-quinazolinyl)-N-[4-(4-nitrophenylthio)phenyl]-1-piperazinethiocarboxamide (Compound 70)

Yield: 59% m.p.: 144–146° C.

$^1$H-NMR(CDCl$_3$) δ (ppm): 8.67(1H, s), 8.07(2H, d, J=8.9 Hz), 7.67(1H, brs), 7.52(2H, d, J=8.6 Hz), 7.36(2H, d, J=8.6 Hz), 7.27(1H, s), 7.19-(2H, d, J=8.9 Hz), 7.11(1H, s), 4.17–4.15(4H, m), 4.03(3H, s), 4.00(3H, s), 3.90–3.86(4H, m).

FAB-Mass: 563(M$^+$+1)

IR(KBr) υ (cm$^{-1}$): 1576, 1507, 1479, 1456, 1416, 1335, 1209, 992, 854.

EXAMPLE 71

4-(6,7-Dimethoxy-4-quinazolinyl)-N-(4-dimethylaminophenyl)-1-piperazinethiocarboxamide (Compound 71)

Yield: 73% m.p.: 226–227° C.

$^1$H-NMR(CDCl$_3$) δ (ppm): 8.65(1H, s), 7.28(1H, s), 7.27 (1H, brs), 7.10(1H, s), 7.07(2H, d, J=8.9 Hz), 6.69(2H, d, J=8.9 Hz), 4.09–4.05(4H, m), 4.03(3H, s), 3.99(3H, s), 3.86–3.82(4H, m).

FAB-Mass: 453(M$^+$+1)

IR(KBr) υ (cm$^{-1}$): 1576, 1506, 1476, 1427, 1338, 1211, 991.

EXAMPLE 72

N-(4-Diethylaminophenyl)-4-(6,7-dimethoxy-4-quinazolinyl)-1-piperazinethiocarboxamide (Compound 72)

Yield: 100% m.p.: 147–148° C.

$^1$H-NMR(CDCl$_3$) δ (ppm): 8.64(1H, s), 7.67(1H, brs), 7.23(1H, s), 7.09(1H, s), 7.04(2H, d, J=8.9 Hz), 6.60(2H, d, J=8.9 Hz), 4.10–4.07(4H, m), 4.00(3H, s), 3.97(3H, s), 3.82–3.81(4H, m), 3.31(4H, q, J=6.9 Hz), 1.13(6H, t, J=6.9 Hz).

FAB-Mass: 481(M$^+$+1)

IR(KBr) υ (cm$^{-1}$): 1616, 1576, 1520, 1446, 1429, 1396, 1339, 1256, 1210, 1137, 992.

EXAMPLE 73

4-(6,7-Dimethoxy-4-quinazolinyl)-N-[4-(5-dimethylamino-1-naphthalenesulfonylamino)phenyl]-1-piperazinethiocarboxamide (Compound 73)

Yield: 99% m.p.: 153–156° C.

$^1$H-NMR(CDCl$_3$) δ (ppm): 8.65(1H, s), 8.47(1H, d, J=8.6 Hz), 8.33(1H, d, J=8.6 Hz), 8.16(1H, dd, J=7.6 Hz, 1.3 Hz), 7.55–7.49(2H, m), 7.41(1H, dd, J=8.6 Hz, 7.6 Hz), 7.27(1H, s), 7.15(1H, d, J=7.6 Hz), 7.07(1H, s), 6.99(2H, d, J=8.9 Hz), 6.89(2H, d, J=8.9 Hz), 4.04–4.02(4H, m), 4.00(3H, s), 3.93(3H, s), 3.78(4H, m), 2.85(6H, s).

FAB-Mass: 658(M$^+$+1)

IR(KBr) υ (cm$^{-1}$): 1576, 1507, 1475, 1429, 1327, 1210, 1142, 992, 791.

EXAMPLE 74

4-(6,7-Dimethoxy-4-quinazolinyl)-N-[4-(4-dimethylaminophenylazo)phenyl]-1-piperazinethiocarboxamide (Compound 74)

Yield: 100% m.p.: 148–149° C.

$^1$H-NMR(DMSO-d$_6$) δ (ppm): 9.62(1H, brs), 8.57(1H, s), 7.78(2H, d, J=8.3 Hz), 7.74(2H, d, J=8.6 Hz), 7.53(2H, d, J=8.6 Hz), 25 7.26(1H, s), 7.24(1H, s), 6.83(2H, d, J=8.3 Hz), 4.16(4H, m), 3.94(3H, s), 3.94(3H, s), 3.87(4H, m), 3.06(6H, s).

FAB-Mass: 557(M$^+$+1)

IR(KBr) υ (cm$^{-1}$): 1601, 1506, 1425, 1363, 990.

EXAMPLE 75

4-(6,7-Dimethoxy-4-quinazolinyl)-N-(2-nitrophenyl)-1-piperazinecarboxamide (Compound 75)

Yield: 13% m.p.: 217–218° C.

$^1$H-NMR(CDCl$_3$) δ (ppm): 10.33(1H, brs), 8.71(1H, s), 8.66(1H, dd, J=8.6 Hz, 1.3 Hz), 8.23(1H, dd, J=8.2 Hz, 1.7 Hz), 7.64(1H, ddd, J=8.6 Hz, 7.3 Hz, 1.7 Hz), 7.28(1H, s), 7.12(1H, s), 7.10(1H, ddd, J=8.2 Hz, 7.3 Hz, 1.3 Hz), 4.04(3H, s), 4.02(3H, s), 3.86–3.83(4H, m), 3.81–3.79(4H, m).

FAB-Mass: 439(M$^+$+1)

IR(KBr) υ (cm$^{-1}$): 1660, 1509, 1453, 1430, 1336, 1211, 989, 745.

EXAMPLE 76

4-(6,7-Dimethoxy-4-quinazolinyl)-N-(3-nitrophenyl)-1-piperazinecarboxamide (Compound 76)

Yield: 89% m.p. 123–125° C.

$^1$H-NMR(CDCl$_3$) δ (ppm): 8.68(1H, s), 8.23(1H, dd, J=2.3 Hz, 2.0 Hz), 7.88-7.83(2H, m), 7.49(1H, brs), 7.42(1H, dd, J=8.3 Hz, 8.3 Hz), 7.25(1H, s), 7.11(1H, s), 4.02(3H, s), 4.00(3H, s), 3.79–3.75(8H, m).

FAB-Mass: 439(M$^+$+1)

IR(KBr) υ (cm$^{-1}$): 1640, 1522, 1503, 1475, 1431, 1336.

EXAMPLE 77

4-(6,7-Dimethoxy-4-quinazolinyl)-N-(4-nitrophenyl)-1-piperazinecarboxamide (Compound 77)

Yield: 90% m.p.: 272–274° C.

$^1$H-NMR(DMSO-d$_6$) δ (ppm): 9.33(1H, brs), 8.56(1H, s), 8.15(2H, d, J=9.4 Hz), 8.58(1H, s), 7.75(2H, d, J=9.4 Hz), 7.23(1H, s), 7.19(1H, s), 3.93(6H, s), 3.72–3.70(8H, m).

FAB-Mass: 439(M$^+$+1)

IR(KBr) υ (cm$^{-1}$): 1664, 1504, 1426, 1324, 1240, 1208, 995.

EXAMPLE 78

4-(6,7-Dimethoxy-4-quinazolinyl)-N-(2-nitrophenyl)-1-piperazinethiocarboxamide (Compound 78)

Yield: 100% m.p.: 177–178° C.

$^1$H-NMR(CDCl$_3$) δ (ppm): 10.14(1H, brs), 8.69(1H, s), 8.52(1H, 5 dd, J=8.6 Hz, 1.0Hz), 8.16(1H, dd, J=8.6 Hz, 1.3 Hz), 7.64(1H, ddd, J=8.6 Hz, 8.3 Hz, 1.3 Hz), 7.29(1H, s), 7.21(1H, ddd, J=8.6 Hz, 8.3 Hz, 1.0 Hz), 7.13(1H, s), 4.29(4H, m), 4.04(3H, s), 4.01(3H, s), 3.94(4H, m).

FAB-Mass: 455(M$^+$+1)

IR(KBr) υ (cm$^{-1}$): 1575, 1504, 1471, 1400, 1338, 1236, 991.

EXAMPLE 79

4-(6,7-Dimethoxy-4-quinazolinyl)-N-(3-nitrophenyl)-1-piperazinethiocarboxamide (Compound 79)

Yield: 83% m.p.: 140–143° C.

$^1$H-NMR(DMSO-d$_6$) δ (ppm): 9.76(1H, brs), 8.56(1H, s), 8.32(1H, d, J=2.0Hz), 7.95(1H, m), 7.87(1H, dd, J=8.3 Hz, 1.0 Hz), 7.59(1H, dd, J=8.3 Hz, 8.3 Hz), 7.26(1H, s), 7.24(1H, s), 4.18(4H, m), 3.94(3H, s), 3.94(3H, s), 3.88(4H, m).

FAB-Mass: 455(M$^+$+1)

IR(KBr) υ (cm$^{-1}$): 1529, 1504, 1477, 1429, 1348, 1240, 1209, 993.

EXAMPLE 80

4-(6,7-Dimethoxy-4-quinazolinyl)-N-(4-nitrophenyl)-1-piperazinethiocarboxamide (Compound 80)

Yield: 67% m.p.: 221–224° C.

$^1$H-NMR(CDCl$_3$) δ (ppm): 8.68(1H, s), 8.22(2H, d, J=8.9 Hz), 7.65(1H, brs), 7.37(2H, d, J=8.9 Hz), 7.27(1H, s), 7.09(1H, s), 4.13(4H, m), 4.03(3H, s), 4.00(3H, s), 3.88(4H, m).

FAB-Mass: 455(M$^+$+1)

IR(KBr) υ (cm 1): 1576, 1506, 1429, 1348, 1292, 1209, 991.

EXAMPLE 81

4-(6,7-Dimethoxy-4-quinazolinyl)-N-(4-fluoro-3-nitrophenyl)-1-piperazinecarboxamide (Compound 81)

Yield: 77% m.p.: 243–245° C.

$^1$H-NMR(CDCl$_3$) δ (ppm): 8.74(1H, s), 8.63(1H, m), 8.28(1H, dd, J=6.6 Hz, 2.6 Hz), 7.93(1H, m), 7.26(1H, s), 7.19(1H, brs), 7.14(1H, s), 4.04(3H, s), 4.01(3H, s), 3.98–3.95(4H, m), 3.78–3.72(4H, m).

FAB-Mass: 457(M$^+$+1)

IR(KBr) υ (cm$^{-1}$): 1640, 1537, 1504, 1350, 1242, 1207, 990.

EXAMPLE 82

N-(2-Chloro-4-nitrophenyl)-4-(6,7-dimethoxy-4-quinazolinyl)-1-piperazinecarboxamide (Compound 82)

Yield: 93% m.p.: 194–195° C.

$^1$H-NMR(CDCl$_3$) δ (ppm): 8.71(1H, s), 8.52(1H, d, J=8.9 Hz), 8.30(1H, d, J=2.5 Hz), 8.16(1H, dd, J=8.9 Hz, 2.5 Hz), 7.43(1H, brs), 7.28(1H, s), 7.11(1H, s), 4.04(3H, s), 4.01(3H, s), 3.82(8H, m).

FAB-Mass: 475(M$^+$+3), 473(M$^+$+1)

IR(KBr) υ (cm$^{-1}$): 1686, 1506, 1479, 1430, 1340, 1236, 1209, 1135, 991, 742.

EXAMPLE 83

N-(4-Chloro-3-nitrophenyl)-4-(6,7-dimethoxy-4-quinazolinyl)-1-piperazinecarboxamide (Compound 83)

Yield: 64% m.p.: 253–255° C.

$^1$H-NMR(CDCl$_3$) δ (ppm): 8.70(1H, s), 8.04(1H, d, J=2.3 Hz), 7.60(1H, dd, J=8.9 Hz, 2.3 Hz), 7.46(1H, d, J=8.9 Hz), 7.28(1H, s), 7.10(1H, s), 6.62(1H, brs), 4.04(3H, s), 4.00(3H, s), 3.77(8H, m).

FAB-Mass: 475(M$^+$+3), 473(M$^+$+1)

IR(KBr) υ (cm$^{-1}$): 1646, 1525, 1500, 1472, 1428, 1338, 1243, 1209, 1135, 992.

EXAMPLE 84

N-(3-Cyanophenyl)-4-(6,7-dimethoxy-4-quinazolinyl)-1-piperazinecarboxamide (Compound 84)

Yield: 100% m.p.: 240–244° C.

$^1$H-NMR(CDCl$_3$) δ (ppm): 8.68(1H, s), 7.76(1H, s), 7.68(1H, d, J=7.9 Hz), 7.44–7.27(3H, m), 7.24(1H, s), 7.10(1H, s), 4.01(3H, s), 3.99(3H, s), 3.76(8H, m).

FAB-Mass: 419(M$^+$+1)

IR(KBr) υ (cm$^{-1}$): 2208, 1666, 1547, 1504, 1477, 1429, 1242, 1209, 993.

EXAMPLE 85

N-(4-Cyanophenyl)-4-(6,7-dimethoxy-4-quinazolinyl)-1-piperazinethiocarboxamide (Compound 85)

Yield: 87% m.p.: 247–252° C.

¹H-NMR(CDCl₃) δ (ppm): 8.67(1H, s), 7.86(1H, brs), 7.62(2H, d, J=8.6 Hz), 7.37(2H, d, J=8.6 Hz), 7.28(1H, s), 7.10(1H, s), 4.16–4.08(4H, m), 4.03(3H, s), 3.99(3H, s), 3.89–3.84(4H, m).

FAB-Mass: 435(M⁺+1)

IR(KBr) υ (cm⁻¹): 2220, 1506, 1483, 1427, 1298, 1215, 991.

EXAMPLE 86

N-(3-Acetylphenyl)-4-(6,7-dimethoxy-4-quinazolinyl)-1-piperazinecarboxamide (Compound 86)

Yield: 77% m.p.: 241–245° C.

¹H-NMR(CDCl₃) δ (ppm): 8.68(1H, s), 8.26(1H, m), 8.05(1H, brs), 7.84(1H, m), 7.57(1H, m), 7.37(1H, m), 7.24(1H, s), 7.13(1H, s), 4.03(3H, s), 4.00(3H, s), 3.98(4H, m), 3.79–3.73(4H, m), 2.59(3H, s).

FAB-Mass: 436(M⁺+1)

IR(KBr) υ (cm⁻¹): 1665, 1539, 1505, 1480, 1426, 1383, 1307, 1244, 1205, 1133, 993.

EXAMPLE 87

N-(4-Acetylphenyl)-4-(6,7-dimethoxy-4-quinazolinyl)-1-piperazinecarboxamide (Compound 87)

Yield: 100% m.p.: 220–222° C.

¹H-NMR(CDCl₃) δ (ppm): 8.69(1H, s), 7.91(2H, d, J=8.6 Hz), 7.52(2H, d, J=8.6 Hz), 7.26(1H, s), 7.23(1H, brs), 7.10(1H, s), 4.02(3H, s), 3.99(3H, s), 3.77(8H, m), 2.57(3H, s).

FAB-Mass: 436(M⁺+1)

IR(KBr) υ (cm⁻¹): 1662, 1583, 1504, 1473, 1415, 1238, 1211, 993.

EXAMPLE 88

N-(4-Benzoylphenyl)-4-(6,7-dimethoxy-4-quinazolinyl)-1-piperazinethiocarboxamide (Compound 88)

Yield: 100% m.p.: 222–223° C.

¹H-NMR(CDCl₃) δ (ppm): 8.67(1H, s), 7.81(2H, d, J=8.6 Hz), 7.77(2H, dd, J=7.9 Hz, 1.7 Hz), 7.59(1H, dd, J=7.3 Hz, 1.7 Hz), 7.48(2H, dd, J=7.9 Hz, 7.3 Hz), 7.30(2H, d, J=8.6 Hz), 7.27(1H, brs), 7.26(1H, s), 7.09(1H, s), 4.12(4H, m), 4.02(3H, s), 3.99(3H, s), 3.86(4H, m).

FAB-Mass: 514(M⁺+1)

IR(KBr) υ (cm⁻¹): 1504, 1425, 1303, 1282, 1209, 990.

EXAMPLE 89

4-(6,7-Dimethoxy-4-quinazolinyl)-N-(4-ethoxycarbonylphenyl)-1-piperazinecarboxamide (Compound 89)

Yield: 96% m.p.: 242–246° C.

¹H-NMR(CDCl₃) δ (ppm): 8.69(1H, s), 7.98(2H, d, J=8.9 Hz), 5 7.49(2H, d, J=8.9 Hz), 7.26(1H, s), 7.10(1H, s), 4.35(2H, q, J=7.4 Hz), 4.02(3H, s), 3.99(3H, s), 3.73(8H, m), 1.38(3H, t, J=7.4 Hz).

FAB-Mass: 466(M⁺+1)

IR(KBr) υ (cm⁻¹): 1700, 1659, 1504, 1417, 1281, 1213, 1174, 991.

EXAMPLE 90

N-(4-Butoxycarbonylphenyl)-4-(6,7-dimethoxy-4-quinazolinyl)-1-piperazinecarboxamide (Compound 90)

Yield: 81% m.p.: 226–227° C.

¹H-NMR(CDCl₃) δ (ppm): 8.69(1H, s), 7.98(2H, d, J=7.9 Hz), 7.48(2H, d, J=7.9 Hz), 7.26(1H, s), 7.10(1H, s), 6.96(1H, brs), 4.29(2H, t, J=6.6 Hz), 4.02(3H, s), 3.99(3H, s), 3.76(8H, m), 1.74(2H, tt, J=7.3 Hz, 6.6 Hz), 1.48(2H, tq, J=7.6 Hz, 7.3 Hz), 0.97(3H, t, J=7.6 Hz).

FAB-Mass: 494(M⁺+1)

IR(KBr) υ (cm⁻¹): 1705, 1654, 1507, 1418, 1283, 1240, 1214, 1177, 994.

EXAMPLE 91

N-[3,5-Bis(methoxycarbonyl)phenyl]-4-(6,7-dimethoxy-4-quinazolinyl)-1-piperazinecarboxamide (Compound 91)

Yield: 93% m.p.: 252–253° C.

¹H-NMR(CDCl₃) δ (ppm): 8.70(1H, s), 8.37(1H, d, J=1.7 Hz), 8.27(2H, d, J=1.7 Hz), 7.28(1H, s), 7.12(1H, s), 6.84(1H, brs), 4.04(3H, s), 4.01(3H, s), 3.93(6H, s), 3.78(8H, m).

FAB-Mass: 510(M⁺+1)

IR(KBr) υ (cm⁻¹): 1727, 1658, 1633, 1549, 1504, 1428, 1336, 1241, 1212, 1129, 994, 755.

EXAMPLE 92

(d1)-N-[4-(2,3,4,5-Tetrahydro-2-oxofuran-3-ylcarbamoyl)phenyl]-4-(6,7-dimethoxy-4-quinazolinyl)-1-piperazinethiocarboxamide (Compound 92)

Yield: 71% m.p.: 174–178° C.

1H-NMR(CDCl₃) δ (ppm): 8.67(1H, s), 7.73(2H, d, J=8.6 Hz), 7.67(1H, brs), 7.25(1H, s), 7.21(2H, d, J=8.6 Hz), 7.09(1H, s), 6.88(1H, br), 4.73(1H, m), 4.56(1H, m), 4.36(1H, m), 4.08–4.02(4H, m), 4.03(3H, s), 4.00(3H, s), 3.89–3.82(4H, m), 2.90(1H, m), 2.33(1H, m).

FAB-Mass: 537(M⁺+1)

IR(KBr) υ (cm⁻¹): 1762, 1650, 1578, 1505, 1476, 1424, 1305, 1209, 1020, 991, 853.

EXAMPLE 93

4-(6,7-Dimethoxy-4-quinazolinyl)-N-(4-sulfamoylphenyl)-1-piperazinethiocarboxamide (Compound 93)

Yield: 100% m.p.: 172–180° C.

¹H-NMR(DMSO-d₆) δ (ppm): 9.63(1H, brs), 8.54(1H, s), 7.73(2H, 25 d, J=8.4 Hz), 7.51(2H, d, J=8.4 Hz), 7.26(1H, s), 7.24(2H, s), 7.22(1H, s), 4.13(4H, m), 3.93(3H, s), 3.85(4H, m).

FAB-Mass: 489(M⁺+1)

IR(KBr) υ (cm⁻¹): 1583, 1508, 1479, 1419, 1336, 1205, 1159, 991.

EXAMPLE 94

4-(6,7-Dimethoxy-4-quinazolinyl)-N-furfuryl-1-piperazinethiocarboxamide (Compound 94)

Yield: 99% m.p.: 189–190° C.

¹H-NMR(CDCl₃) δ (ppm): 8.63(1H, s), 7.37(1H, d, J=1.6 Hz), 7.24(1H, s), 7.10(1H, s), 6.33(2H, m), 6.13(1H, brt, J=4.6 Hz), 4.91(2H, d, J=4.6 Hz), 4.12–4.08(4H, m), 4.02 (3H, s), 3.98(3H, s), 3.86–3.82(4H, m).

FAB-Mass: 414(M⁺+1)

IR(KBr) υ (cm⁻¹): 1578, 1505, 1477, 1424, 1353, 1242, 1210, 1138, 990.

EXAMPLE 95

4-(6,7-Dimethoxy-4-quinazolinyl)-N-(2-furoyl)-1-piperazinethiocarboxamide (Compound 95)

Yield: 44% m.p.: 187–189° C.

¹H-NMR(CDCl₃) δ (ppm): 8.69(1H, s), 8.68(1H, brs), 7.58(1H, d, J=1.7 Hz), 7.31-7.22(2H, m), 7.09(1H, s), 6.58 (1H, dd, J=3.6,1.7 Hz), 4.04(3H, s), 4.00(3H, s), 3.95–3.90 (8H, m).

FAB-Mass: 428(M⁺+1)

IR(KBr) υ (cm⁻¹): 1687, 1616, 1585, 1505, 1471, 1451, 1423, 1236, 1207, 1170, 1023, 990, 834.

EXAMPLE 96

4-(6,7-Dimethoxy-4-quinazolinyl)-N-[2-(2-thienyl)ethyl]-1-piperazinecarboxamide (Compound 96)

Yield: 83% m.p.: 184–185° C.

¹H-NMR(CDCl₃) δ(ppm): 8.67(1H, s), 7.26(1H, s), 7.17 (1H, dd, J=5.3 Hz, 1.3 Hz), 7.10(1H, s), 6.97(1H, dd, J=5.3 Hz, 3.6 Hz), 6.86(1H, dd, J=3.6 Hz, 1.3 Hz), 4.80(1H, brt, J=5.6 Hz), 4.03(3H, s), 3.99(3H, s), 3.70–3.67(4H, m), 3.61–3.52(6H, m), 3.08(2H, t, J=6.6 Hz).

FAB-Mass: 428(M⁺+1)

IR(KBr) υ (cm⁻¹): 1617, 1539, 1505, 1429, 1350, 1212, 1135, 992, 848.

EXAMPLE 97

4-(6,7-Dimethoxy-4-quinazolinyl)-N-(3-pyridyl)-1-piperazinethiocarboxamide (Compound 97)

Yield: 100% m.p.: 169–171° C.

¹H-NMR(CDCl₃) δ (ppm): 8.65(1H, s), 8.52(1H, brs), 8.43(1H, d, 10 J=2.6 Hz), 8.35(1H, dd, J=4.6 Hz, 1.3 Hz), 7.81(1H, ddd, J=8.3 Hz, 2.6 Hz, 1.3 Hz), 7.29(1H, dd, J=8.3 Hz, 4.6 Hz), 7.23(1H, s), 7.10(1H, s), 4.20–4.16(4H, m), 4.01(3H, s), 3.99(3H, s), 3.88–3.85(4H, m).

FAB-Mass: 411(M⁺+1)

IR(KBr) υ (cm⁻¹): 1575, 1533, 1505, 1474, 1432, 1313, 1241, 1209, 1017, 990, 872, 713.

EXAMPLE 98

4-(6,7-Dimethoxy-4-quinazolinyl)-N-(3-picolyl)-1-piperazinethiocarboxamide (Compound 98)

Yield: 100% m.p.: 104–106° C.

¹H-NMR(CDCl₃) δ (ppm): 8.64(1H, s), 8.53(1H, s), 8.52 (1H, m), 7.77(1H, d, J=7.9 Hz), 7.29(1H, dd, J=7.9 Hz, 4.6 Hz), 7.27(1H, s), 7.10(1H, s), 6.20(1H, brt, J=5.3 Hz), 4.97(2H, d, J=5.3 Hz), 4.14–4.10(4H, m), 4.02(3H, s), 3.98(3H, s), 3.88–3.84(4H, m).

FAB-Mass: 425(M⁺+1)

IR(KBr) υ (cm⁻¹): 1582, 1509, 1479, 1450, 1429, 1354, 1340, 1245, 1208, 1140, 1032, 994, 944, 883, 851, 712.

EXAMPLE 99

N-(1,4-Dihydroxy-6-phthalazinyl)-4-(6,7-dimethoxy-4-quinazolinyl)-1-piperazinethiocarboxamide (Compound 99)

Yield: 93% m.p.: 153–155° C.

¹H-NMR(CDCl₃+DMSO-d₆) δ (ppm): 8.59(1H, s), 8.07–7.96(3H, m), 7.23(1H, s), 7.21(1H, s), 4.22(4H, m), 4.00(3H, s), 4.00(3H, s), 3.88(4H, m).

FAB-Mass: 494(M⁺+1)

IR(KBr) υ (cm⁻¹): 1645, 1581, 1508, 1487, 1434, 1317, 1211, 991.

EXAMPLE 100

4-(6,7-Dimethoxy-4-quinazolinyl)-N-[4-(piperidinomethyl)phenyl]-1-piperazinecarboxamide (Compound 100)

In 10 ml of toluene was suspended 593.5 mg (2.16 mmol) of 6,7-dimethoxy-4-piperazinylquinazoline obtained by the method described in South African Patent No. 67 06512 (1968), and 362.6 ml (2.16 mmol) of 4-(chloromethyl) phenyl isocyanate was added thereto, followed by stirring at room temperature for 3 hours. After the reaction mixture was filtered, the obtained crystals were washed with diisopropyl ether and dried under reduced pressure to give 916.8 mg (2.08 mmol, 96%) of N-[4-(chloromethyl)phenyl]-4-(6,7-dimethoxy-4-quinazolinyl)-1-piperazinecarboxamide. In 10 ml of dimethylformamide was dissolved 422.9 mg (0.96 mmol) of the obtained N-l4-(chloromethyl)phenyl]-4-(6,7-dimethoxy-4-quinazolinyl)-1-piperazinecarboxamide, and 0.28 ml (2.83 mmol) of piperidine was added thereto, followed by stirring at room temperature for 7 hours. Then, the reaction mixture was poured into water and the precipitated crystals were collected by filtration, followed by purification by silica gel column chromatography to give 430.9 mg (0.88 mmol) of the desired compound as colorless crystals.

Yield: 92% m.p.: 122–123° C.

¹H-NMR(CDCl₃) δ (ppm): 8.69(1H, s), 7.33(2H, d, J=8.9 Hz), 35 7.27(1H, s), 7.25(2H, d, J=8.9 Hz), 7.11(1H, s), 6.67(1H, brs), 4.03(3H, s), 4.00(3H, s), 3.74(8H, m), 2.39 (4H, m), 1.60–1.56(4H, m), 1.44–1.42(4H, m).

FAB-Mass: 491(M⁺+1)

IR(KBr) υ (cm⁻¹): 1645, 1505, 1471, 1417, 1349, 1238, 1212, 1136, 993.

EXAMPLE 101

N-(4-Benzylaminomethylphenyl)-4-(6,7-dimethoxy-4-quinazolinyl)-1-piperazinecarboxamide (Compound 101)

Substantially the same procedure as in Example 100 was repeated, except that benzylamine was used in place of piperidine, to give the desired compound.

Yield: 76%

¹H-NMR(CDCl₃₊DMSO-d₆) δ (ppm): 9.68(1H, br), 8.83 (1H, brs), 8.57(1H, s), 7.68(1H, s), 7.60–7.56(5H, m), 7.43–7.39(4H, m), 7.27(1H, s), 4.22(4H, m), 4.08(3H, s), 4.08–4.01(4H, m), 4.03(3H, s), 3.87(4H, m).

FAB-Mass: 513(M⁺+1)

IR(KBr) υ (cm⁻¹): 1625, 1495, 1418, 1313, 1283, 1212, 1134, 989.

EXAMPLE 102

4-(6,7-Dimethoxy-4-quinazolinyl)-N-(4-(4-pyridylmethylaminomethyl)phenyl]-1-piperazinecarboxamide trihydrochloride (Compound 102)

Substantially the same procedure as in Example 100 was repeated, except that 4-aminomethylpyridine was used in place of piperidine, to give a free form of the desired compound. In 15 ml of methanol was dissolved 208.6 mg of the obtained free form under ice-cooling, and 5 ml of a saturated solution of hydrochloric acid in ethyl acetate was added thereto, followed by stirring. After the solvent was evaporated, the residue was recrystallized from methanol/ethyl acetate to give 102.1 mg of the desired compound.

Yield: 21% m.p.: 182–185° C. (hydrochloride)

$^1$-NMR (free base, CDCl$_3$)δ (ppm): 8.68(1H, s), 8.53(2H, d, J=5.0 Hz), 7.38–7.24(7H, m), 7.10(1H, s), 6.96(1H, brs), 4.01(3H, s), 3.99(3H, s), 3.80(2H, s), 3.74–3.70(10H, m), 1.97(1H, br).

FAB-Mass: 514(M$^+$+1)

IR (hydrochloride, KBr) υ (cm$^{-1}$): 1626, 1520, 1504, 1421, 1391, 1313, 1284, 1246, 1219, 989.

EXAMPLE 103

N-(4-Nitrophenyl)-4-(4-quinazolinyl)-1-piperazinecarboxamide (Compound 103)

Substantially the same procedure as in Example 77 was repeated, except that 4-piperazinylquinazoline obtained according to the method described in South African Patent No. 67 06512 (1968) was used in place of 6,7-dimethoxy-4-piperazinylquinazoline, to give the desired compound.

Yield: 88% m.p.: 155–158° C.

$^1$H-NMR(CDCl$_3$) δ (ppm): 8.74(1H, s), 8.40(1H, brs), 8.11(2H, d, J=9.2 Hz), 7.92-7.89(2H, m), 7.77(1H, dd, J=7.9 Hz, 7.9 Hz), 7.63(2H, d, J=9.2 Hz), 7.51(1H, dd, J=7.9 Hz, 7.9 Hz), 3.84(8H, m).

FAB-Mass: 379(M$^+$+1)

IR(KBr) υ (cm$^{-1}$): 1670, 1558, 1500, 1476, 1419, 1404, 1346, 1329, 1304, 1261, 1242, 1223, 1109, 939.

EXAMPLE 104

N-(4-Phenoxyphenyl)-4-(4-quinazolinyl)-1-piperazinecarboxamide (Compound 104)

Substantially the same procedure as in Example 60 was repeated, except that 4-piperazinylquinazoline obtained according to the method described in South African Patent No. 67 06512 (1968) was used in place of 6,7-dimethoxy-4-piperazinylquinazoline, to give the desired compound.

Yield: 42% m.p.: 74–75° C.

$^1$H-NMR(CDCl$_3$) δ (ppm): 8.76(1H, s), 7.94–7.88(2H, m), 7.76(1H, dd, J=8.6 Hz, 6.9 Hz), 7.49(1H, dd, J=8.2 Hz, 6.9 Hz), 7.35–7.27(4H, m), 7.06(1H, m), 6.98–6.95(4H, m), 6.86(1H, brs), 3.85–3.82(4H, m), 3.76–3.72(4H, m).

FAB-Mass: 426(M$^+$+1)

IR(KBr) υ (cm 1): 1645, 1568, 1538, 1505, 1416, 1350, 1225, 1165, 1014, 993, 937, 869, 836, 770, 750, 688.

EXAMPLE 105

4-(6,7-Diethoxy-4-quinazolinyl)-N-(4-nitrophenyl)-1-piperazinecarboxamide (Compound 105)

Substantially the same procedure as in Example 77 was repeated, except that 6,7-diethoxy-4-piperazinylquinazoline obtained according to the method described in South African Patent No. 67 06512 (1968) was used in place of 6,7-dimethoxy-4-piperazinylquinazoline, to give the desired compound.

Yield: 22% m.p.: 120–121° C.

$^1$H-NMR(CDCl$_3$) δ (ppm): 8.68(1H, s), 8.21(2H, d, J=8.9 Hz), 7.58(2H, d, J=8.9 Hz), 7.26(1H, s), 7.11(1H, s), 6.87 (1H, brs), 4.26(2H, q, J=6.9 Hz), 4.19(2H, q, J=6.9 Hz), 1.56(3H, t, 25 J=6.9 Hz), 1.56(3H, t, J=6.9).

FAB-Mass: 467(M$^+$+1)

IR(KBr) υ (cm$^{-1}$): 1652, 1548, 1502, 1329, 1238, 1205, 1112, 934, 852, 752.

EXAMPLE 106

4-(6,7-Diethoxy-4-quinazolinyl)-N-(4-phenoxyphenyl)-1-piperazinecarboxamide (Compound 106)

Substantially the same procedure as in Example 60 was repeated, except that 6,7-diethoxy-4-piperazinylquinazoline obtained according to the method described in South African Patent No. 67 06512 (1968) was used in place of 6,7-dimethoxy-4-piperazinylquinazoline, to give the desired compound.

Yield: 21% m.p.: 187–190° C.

$^1$H-NMR(CDCl$_3$) δ (ppm): 8.68(1H, s), 7.37–7.25(5H, m), 7.13(1H, s), 7.07(1H, m), 7.00–6.97(4H, m), 6.41(1H, brs), 4.24(2H, q, J=6.9 Hz), 4.18(2H, q, J=6.9 Hz), 3.74(8H, m), 1.56(3H, t, J=6.9 Hz), 1.56(3H, t, J=6.9 Hz).

FAB-Mass: 514(M$^+$+1)

IR(KBr) υ (cm$^{-1}$): 1632, 1533, 1508, 1489, 1417, 1227, 995, 933, 8.68, 856, 847, 752.

EXAMPLE 107

N-(4-Nitrophenyl)-4-(6,7,8-trimethoxy-4-quinazolinyl)-1-piperazinecarboxamide (Compound 107)

Substantially the same procedure as in Example 77 was repeated, except that 4-piperazinyl-6,7,8-trimethoxyquinazoline obtained according to the method described in South African Patent No. 67 06512 (1968) was used in place of 6,7-dimethoxy-4-piperazinylquinazoline, to give the desired compound.

Yield: 43% m.p.: 197–199° C.

$^1$H-NMR(CDCl$_3$) δ (ppm): 8.72(1H, s), 8.16(2H, d, J=8.6 Hz), 7.62(1H, brs), 7.61(2H, d, J=8.6 Hz), 6.93(1H, s), 4.12(3H, s), 4.07(3H, s), 3.98(3H, s), 3.79–3.77(8H, m).

FAB-Mass: 469(M$^+$+1)

IR(KBr) υ (cm 1): 1674, 1611, 1545, 1500, 1479, 1417, 1329, 1302, 1124, 992, 851, 752.

EXAMPLE 108

-N-(4-Phenoxyphenyl)-4-(6,7,8-trimethoxy-4-quinazolinyl)-1-piperazinecarboxamide (Compound 108)

Substantially the same procedure as in Example 60 was repeated, except that 4-piperazinyl-6,7,8-trimethoxyquinazoline obtained according to the method described in South African Patent No. 67 06512 (1968) was used in place of 6,7-dimethoxy-4-piperazinylquinazoline, to give the desired compound.

Yield: 55% m.p.: 83–84° C.

$^1$H-NMR(CDCl$_3$) δ (ppm): 8.74(1H, s), 7.34(2H, d, J=8.9 Hz), 10 7.30(2H, m), 7.06(1H, m), 6.98(1H, s), 6.98–6.93 (4H, m), 6.82(1H, brs), 4.13(3H, s), 4.07(3H, s), 3.96(3H, s), 3.73(8H, m).

FAB-Mass: 516(M$^+$+1)

IR(KBr) υ (cm$^{-1}$): 1645, 1508, 1489, 1416, 1227, 1124, 991.

EXAMPLE 109

4-(7-Ethylamino-6-nitro-4-quinazolinyl)-N-(4-phenoxyphenyl)-1-piperazinecarboxamide (Compound 109)

Substantially the same procedure as in Example 60 was repeated, except that 7-ethylamino-6-nitro-4-piperazinylquinazoline obtained according to the method described in WO 95/06648 was used in place of 6,7-dimethoxy-4-piperazinylquinazoline, to give the desired compound.

Yield: 67% m.p.: 242–244° C.

$^1$H-NMR(CDCl$_3$) δ (ppm): 8.88(1H, s), 8.53(1H, s), 7.65 (1H, brt, J=5.0 Hz), 7.35–7.27(4H, m), 7.08–6.95(6H, m), 6.68(1H, brs), 4.03–3.99(4H, m), 3.79–3.76(4H, m), 3.39 (2H, dt, J=7.3 Hz, 5.0 Hz), 1.41(3H, t, J=7.3 Hz).

FAB-Mass: 514(M$^+$+1)

IR(KBr) υ (cm$^{-1}$): 1645, 1621, 1545, 1508, 1487, 1419, 1346, 1326, 1222.

EXAMPLE 110

4-(2-Phenyl-4-quinazolinyl)-N-(4-nitrophenyl)-1-piperazinecarboxamide (Compound 110)

Substantially the same procedure as in Example 77 was repeated, except that 2-phenyl-4-piperazinylquinazoline obtained according to the method described in U.S. Pat. No. 4,306,065 (1981) was used in place of 6,7-dimethoxy-4-piperazinylquinazoline, to give the desired compound.

Yield: 35% m.p.: 236–238 QC $^1$H-NMR(DMSO-d$_6$) $^6$(ppm): 9.37(1H, brs), 8.54–8.51 (2H, m), 8.18(2H, d, J=7.9 Hz), 8.11(1H, d, J=8.6 Hz), 7.94–7.83(2H, m), 7.78(2H, d, J=7.9 Hz), 7.59–7.52(4H, m), 3.95(4H, m), 3.82(4H, m).

FAB-Mass: 455(M$^+$+1)

IR(KBr) υ (cm$^{-1}$): 1687, 1537, 1500, 1493, 1327, 1225, 1109.

EXAMPLE 111

4-(6,7-Dimethoxy-2-phenyl-4-quinazolinyl)-N-(4-nitrophenyl)-1-piperazinecarboxamide (Compound 111) Substantially the same procedure as in Example 77 was repeated, except that 6,7-dimethoxy-2-phenyl-4-piperazinylquinazoline obtained according to the method described in U.S. Pat. No. 4,306,065 (1981) was used in place of 6,7-dimethoxy-4-piperazinylquinazoline, to give the desired compound.

Yield: 68% m.p.: 156–157 QC $^1$H-NMR(DMSO-d$_6$) δ (ppm): 9.34(1H, brs), 8.49(2H, m), 8.18(2H, d, J=9.2 Hz), 7.77(2H, d, J=9.2 Hz), 7.52–7.49 (3H, m), 7.33(1H, s), 7.24(1H, s), 3.98(3H, s), 3.96(3H, s), 3.81(8H, m).

FAB-Mass: 515(M$^+$+1)

IR(KBr) υ (cm$^{-1}$): 1676, 1551, 1504, 1419, 1327, 1238, 1111, 997, 852.

EXAMPLE 112

4-(6,7-Dimethoxy-4-quinazolinyl)-N-(4-nitrophenyl)-1-homopiperazinecarboxamide (Compound 112)

Substantially the same procedure as in Example 77 was repeated, except that 6,7-dimethoxy-4-homopiperazinylquinazoline obtained according to the method described in South African Patent No. 67 06512 (1968) was used in place of 6,7-dimethoxy-4-piperazinylquinazoline, to give the desired compound.

Yield: 22% m.p.: 243–244° C.

$^1$H-NMR(DMSO-d$_6$) δ (ppm): 9.30(1H, brs), 8.73(1H, s), 8.06(2H, d, J=8.9 Hz), 7.63(2H, d, J=8.9 Hz), 7.45(1H, s), 7.26(1H, s), 4.32(2H, m), 4.19(2H, m), 3.97(2H, m), 3.97 (3H, s), 3.92(3H, s), 3.70(2H, m), 2.11(2H, m).

FAB-Mass: 453(M$^+$+1)

IR(KBr) υ (cm$^{-1}$): 1666, 1622, 1577, 1549, 1521, 1500, 1331, 1213, 1110, 856, 750.

EXAMPLE 113

4-(6,7-Dimethoxy-1-isoquinolyl)-N-(4-nitrophenyl)-1-piperazinecarboxamide (Compound 113)

Substantially the same procedure as in Example 77 was repeated, except that 6,7-dimethoxy-1-piperazinylisoquinoline obtained according to the method described in South African Patent No. 67 06512 (1968) was used in place of 6,7-dimethoxy-4-piperazinylquinazoline, to give the desired compound.

Yield: 73% m.p.: 247–248° C.

$^1$H-NMR(CDCl$_{3+}$ DMSO-d$_6$) δ (ppm): 8.99(1H, s), 8.13 (2H, d, J=9.2 Hz), 8.05(1H, d, J=5.6 Hz), 7.75(2H, d, J=9.2 Hz), 7.39(1H, s), 7.24(1H, d, J=5.6 Hz), 7.11(1H, s), 4.02 (3H, s), 4.02(3H, s), 3.85-3.83(4H, m), 3.39(4H, m).

GAB-Mass: 438(M$^+$+1)

IR(KBr) υ (cm 1): 1670, 1506, 1425, 1336, 1234, 1216, 1111, 991.

EXAMPLE 114

4-(3-Chloro-6,7-dimethoxy-1-isoquinolyl)-N-(4-nitrophenyl)-1-piperazinecarboxamide (Compound 114) Substantially the same procedure as in Example.77 was repeated, except that 3-chloro-6,7-dimethoxy-1-piperazinylisoquinoline obtained according to the method described in South African Patent No. 67 06512 (1968) was used in place of 6,7-dimethoxy-4-piperazinylquinazoline, to give the desired compound.

Yield: 55% m.p.: 227–228° C.

$^1$H-NMR(CDCl$_3$+DMSO-d$_6$) δ (ppm): 8.90(1H, brs), 8.13(2H, d, J=9.2 Hz), 7.73(2H, d, J=9.2 Hz), 7.30(1H, s), 7.25(1H, s), 7.01(1H, s), 4.02(3H, s), 4.02(3H, s), 3.84–3.82 (4H, m), 3.44(4H, m).

FAB-Mass: 474(M$^+$+3), 472(M$^+$+1)

IR(KBr) υ (cm$^{-1}$): 1650, 1512, 1500, 1424, 1348, 1248, 1215, 1165, 1141, 994, 943, 855, 749.

EXAMPLE 115

4-(7-Chloro-4-quinolyl)-N-(4-phenoxyphenyl)-1-piperazinecarboxamide (Compound 115)

Substantially the same procedure as in Example 60 was repeated, except that 7-chloro-4-piperazinylquinoline obtained according to the method described in Ind. J. Chem., 26B, 550–555 (1987) was used in place of 6,7-dimethoxy-4-piperazinylquinazoline, to give the desired compound.

Yield: 100% m.p.: 159–161° C.

$^1$H-NMR(CDCl$_3$) δ (ppm): 8.75(1H, d, J=5.3 Hz), 8.07 (1H, d, =2.0 Hz), 7.96(1H, d, J=9.2 Hz), 7.46(1H, dd, J=9.2 Hz, 2.0 Hz), 7.36–7.27(4H, m), 7.05(1H, m), 7.00–6.96(4H, m), 6.86(1H, d, J=5.3 Hz), 6.68(1H, brs), 3.81–3.77(4H, m), 3.26–3.23(4H, m).

FAB-Mass: 461(M$^+$+3), 459(M$^+$+1)

IR(KBr) υ (cm$^{-1}$): 1639, 1538, 1503, 1488, 1418, 1381, 1243, 1226, 997, 868.

EXAMPLE 116

4-(6,7-Dimethoxy-4-quinazolinyl)-N,N-diphenyl-1-piperazinecarboxamide (Compound 116)

In 10 ml of dimethylformamide was dissolved 400 mg (1.46 mmol) of 6,7-dimethoxy-4-piperazinylquinazoline obtained according to the method described in South African Patent No. 67 06512 (1968), and 1.02 ml (7.32 mmol) of triethylamine was added thereto. To the resulting mixture was added 406 mg (1.75 mmol) of diphenylcarbamoyl chloride, followed by overnight stirring at room temperature. After the reaction mixture was poured into water, the precipitated crystals were collected by filtration, followed by purification by silica gel column chromatography to give 680 mg of the desired compound as colorless crystals.

Yield: 99% m.p.: 196–197° C.

$^1$H-NMR(CDCl$_3$) δ (ppm): 8.65(1H, s), 7.36–7.28(5H, m), 7.24(1H, s), 7.18–7.08(5H, m), 7.04(1H, s), 4.02(3H, s), 3.97(3H, s), 3.61–3.59(4H, m), 3.56–3.54(4H, m).

FAB-Mass: 470(M$^+$+1)

IR(KBr) υ (cm$^{-1}$): 1662, 1505, 1471, 1418, 1230, 1206, 1133, 996, 748, 697.

EXAMPLE 117

4-(6,7-Dimethoxy-4-quinazolinyl)-N-(4-morpholinophenyl)-1-piperazinecarboxamide (Compound 117) To a solution of 2.60 g (14.6 mmol) of 4-morpholinoaniline in 20 ml of methylene chloride were added 14.07 ml (105 mmol) of triethylamine and 3.53 g (17.5 mmol) of 4-nitrophenyl hloroformate under ice-cooling, followed by stirring at room emperature for 7 hours. After the solvent was evaporated, ater was added to the residue, and the precipitated crystals ere collected by filtration, washed water, and dried to give 4-morpholino-N-(4-nitrophenoxycarbonyl)aniline.

The above-obtained N-(4-nitrophenyloxycarbonyl)anilin-4-yl morpholine and 800 mg (2.92 mmol) of 6,7-dimethoxy-4-piperazinylquinazoline obtained according to the method described in South African Patent No. 67 06512 (1968) were heated at 100° C. in 10 ml of N-methylpyrrolidone with stirring for 12 hours. After the reaction mixture was poured into water, the precipitated crystals were collected by filtration, washed with water, and dried, followed by purification by silica gel column chromatography to give 950.0 mg (1.99 mmol) of the desired compound as colorless crystals.

Yield: 68% m.p.: 254–256° C.

$^1$H-NMR(CDCl$_3$) δ (ppm): 8.69(1H, s), 7.28(2H, d, J=8.9 Hz), 7.27(1H, s), 7.12(1H, s), 6.88(2H, d, J=8.9 Hz), 6.34 (1H, brs), 4.03(3H, s), 4.00(3H, s), 3.88–3.84(4H, m), 3.74(8H, m), 3.13–3.09(4H, m).

FAB-Mass: 479(M$^+$+1)

IR(KBr) υ (cm$^{-1}$): 1635, 1574, 1506, 1472, 1422, 1232, 1212, 1135, 994, 933, 821.

EXAMPLE 118

4-(6,7-Dimethoxy-4-quinazolinyl)-N-(5-indolyl)-1-piperazinecarboxamide (Compound 118)

Substantially the same procedure as in Example 117 was repeated, except that 5-aminoindole was used in place of 4-morpholinoaniline, to give the desired compound.

Yield: 30% m.p.: 209–210° C.

$^1$H-NMR(CDCl$_3$) δ (ppm): 9.01(1H, brs), 8.67(1H, s), 7.55(1H, s), 7.29–7.17(2H, m), 7.11–7.02(4H, m), 6.39(1H, brs), 3.99(3H, s), 3.94(3H, s), 3.65(8H, m).

FAB-Mass: 433(M$^+$+1)

IR(KBr) υ (cm$^{-1}$): 1623, 1547, 1505, 1474, 1451, 1429, 1239, 1211, 996.

EXAMPLE 119

N-[2-(4-Chlorophenyl)ethyl]-4-(6,7-dimethoxy-4-quinazolinyl)-1-piperazinecarboxamide (Compound 119)

In 15 ml of dimethylformamide, 666.8 mg (1.52 mmol) of 4-(6,7-dimethoxy-4-piperazinylquinazolinyl)-1-piperazinecarboxylic acid 4-nitrophenyl ester obtained according to the method described in South African Patent No. 67 06512 (1968) and 1.06 ml (7.57 mmol) of 2-(4-chlorophenyl)ethylamine were heated at 80° C. with stirring for 3 hours. After the reaction mixture was poured into water and extracted with chloroform, the obtained organic layer was washed with water and dried over anhydrous sodium sulfate. After the solvent was evaporated, the residue was purified by silica gel column chromatography to give 485.2 mg of the desired compound as colorless crystals.

Yield: 70% m.p.: 177–178° C.

$^1$H-NMR(CDCl$_3$) δ (ppm): 8.65(1H, s), 7.31(2H, d, J=8.6 Hz), 7.24(1H, s), 7.13(2H, d, J=8.6 Hz), 7.09(1H, s), 5.02 (1H, brt, J=5.6 Hz), 4.02(3H, s), 3.98(3H, s), 3.67–3.65(4H, m), 3.60–3.58(4H, m), 3.50(2H, m), 2.83(2H, t, J=6.9 Hz).

FAB-Mass: 458(M$^+$+3), 456(M$^+$+1)

IR(KBr) υ (cm$^{-1}$): 1622, 1539, 1506, 1353, 1243, 1212, 1134, 993, 845.

EXAMPLE 120

N-[2-(4-Bromophenyl)ethyl]-4-(6,7-dimethoxy-4-quinazolinyl)- 1-piperazinecarboxamide (Compound 120)

Substantially the same procedure as in Example 119 was repeated, except that 2-(4-bromophenyl) ethylamine was used in place of 2-(4-chlorophenyl)ethylamine, to give the desired compound.

Yield: 72% m.p.: 174–175° C.

$^1$H-NMR(CDCl$_3$) δ (ppm): 8.67(1H, s), 7.43(2H, d, J=8.3 Hz), 7.25(1H, s), 7.09(2H, d, J=8.3 Hz), 7.09(1H, s), 4.67 (1H, brt, J=5.6 Hz), 4.03(3H, s), 3.99(3H, s), 3.69–3.65(4H, m), 3.58–3.56(4H, m), 3.52(2H, m), 2.81(2H, t, J=6.9 Hz).

FAB-Mass: 502(M++3), 500(M++1)

IR(KBr) υ (cm⁻¹): 1624, 1540, 1506, 1355, 1237, 1212, 993.

EXAMPLE 121

4-(1,3-Dihydro-1,3-dimethyl-2-oxo-2H-imidazo[4,5-g]quinazolin-8-yl)-N-(4-phenoxyphenyl)-1-piperazinecarboxamide (Compound 121)

Substantially the same procedure as in Example 60 was repeated, except that 1,3-dihydro-1,3-dimethyl-2-oxo-8-piperazinyl-2H-imidazo[4,5-g]quinazoline obtained in Reference Example 1 was used in place of 6,7-dimethoxy-4-piperazinylquinazoline, to give the desired compound.

Yield: 73% (3 steps)

m.p.: 250–255° C.

¹H-NMR(CDCl₃) δ (ppm): 8.73(1H, s), 7.41(1H, s), 7.37–7.25(5H, m), 7.07(1H, m), 7.01–6.96(4H, m), 6.67(1H, brs), 3.78(8H, m), 3.51(3H, s), 3.51(3H, s).

FAB-Mass: 510(M++1)

IR(KBr) υ (cm⁻¹): 1735, 1715, 1642, 1543, 1505, 1488, 1224.

EXAMPLE 122

4-(1,3-Diethyl-1,3-dihydro-2-oxo-2H-imidazo[4,5-g]quinazolin-8-yl)-N-(4-phenoxyphenyl)-1-piperazinecarboxamide (Compound 122)

Substantially the same procedure as in Example 60 was repeated, except that 1,3-diethyl-1,3-dihydro-2-oxo-8-piperazinyl-2H-imidazo[4,5-g]quinazoline obtained in 5 Reference Example 2 was used in place of 6,7-dimethoxy-4-piperazinylquinazoline, to give the desired compound.

Yield: 66% m.p.: 168–169° C.

¹H-NMR(CDCl₃) δ (ppm): 8.71(1H, s), 7.45(1H, s), 7.37–7.26(5H, m), 7.05(1H, m), 6.97–6.94(5H, m), 4.04–4.00(4H, m), 3.77(8H, m), 1.43–1.36(6H, m).

FAB-Mass: 538(M++1)

IR(KBr) υ (cm⁻¹): 1732, 1717, 1645, 1539, 1489, 1416, 1220.

EXAMPLE 123

4-(3-Ethyl-1,3-dihydro-2-oxo-2H-imidazo[4,5-g]quinazolin-8-yl)-N-(4-phenoxyphenyl)-1-piperazinecarboxamide (Compound 123)

To a solution of 197.5 mg (0.38 mmol) of N-(4-phenoxyphenyl)-4-(7-ethylamino-6-nitro-4-quinazolinyl)-1-piperazinecarboxamide (Compound 109) obtained in Example 109 in 4 ml of ethanol was added 30 mg of 10% palladium-carbon, followed by stirring for 7.5 hours in a stream of hydrogen. The catalyst was separared by filtration with Celite and the solvent was evaporated. The obtained residue was dissolved in 10 ml of dimethylformamide, and 187.2 mg (1.15 mmol) of carbonyldiimidazole was added thereto, followed by stirring at 80° C. for 2 hours in an atmosphere of argon. After the reaction mixture was poured into water, the precipitated crystals were collected by filtration, washed with water, and dried, followed by purification by silica gel column chromatography to give 65.7 mg (0.13 mmol) of the desired compound as colorless crystals.

Yield: 34% m.p.: 248–251° C.

¹H-NMR(CDCl₃) δ (ppm): 9.23(1H, brs), 8.73(1H, s), 7.46(1H, s), 7.36–7.28(5H, m), 7.07(1H, m), 6.99–6.92(4H, m), 6.55(1H, brs), 4.04(2H, q, J=7.3 Hz), 3.96(4H, m), 3.71(4H, m), 1.42(3H, t, J=7.3 Hz).

FAB-Mass: 510(M++1)

IR(KBr) υ (cm 1): 1722, 1645, 1506, 1489, 1225.

EXAMPLE 124

4-(3-Ethyl-3H-1,2,3-triazolo[4,5-g]quinazolin-8-yl)-N-(4-phenoxyphenyl)-1-piperazinecarboxamide (Compound 124) To a solution of 394.8 mg (0.77 mmol) of N-(4-phenoxyphenyl)-4-(7-ethylamino-6-nitro-4-quinazolinyl)-1-piperazinecarboxamide (Compound 109) obtained in Example 109 in 8 ml of ethanol was added 60 mg of 10% palladium-carbon, followed by stirring for 7.5 hours in a stream of hydrogen. The catalyst was separated by filtration with Celite and the solvent was evaporated. The obtained residue was dissolved in a mixture of 10 ml of water, 1 ml of concentrated hydrochloric acid and 10 ml of acetic acid, and 106.2 mg (1.54 mmol) of sodium nitrite was added thereto under ice-cooling, followed by stirring at the same temperature for 4 hours. After the reaction mixture was poured into a saturated aqueous solution of sodium bicarbonate, the precipitated crystals were collected by filtration, washed with water, and dried, followed by purification by silica gel column chromatography to give 119.3 mg (0.24 mmol) of the desired compound as colorless crystals.

Yield: 31% m.p.: 167–168° C.

¹H-NMR(CDCl₃) δ (ppm): 8.73(1H, s), 8.03(1H, s), 7.38–7.27(5H, m), 7.06(1H, m), 6.99–6.95(4H, m), 6.78(1H, brs), 4.80(2H, q, J=7.3 Hz), 4.01–3.97(4H, m), 3.83–3.80 (4H, m), 1.71(3H, t, J=7.3 Hz).

FAB-Mass: 495(M++1)

IR(KBr) υ (cm⁻¹): 1641, 1545, 1504, 1487, 1416, 1350, 1223, 1211, 991.

In the following Examples 125–136, substantially the same procedure as in Example 1 was repeated, except that the corresponding isocyanate or isothiocyanate was used in place of phenyl isocyanate, to give the desired compound.

EXAMPLE 125

N-Benzyl-4-(6,7-dimethoxy-4-quinazolinyl)-1-piperazinethiocarboxamide (Compound 125)

Yield: 61% m.p.: 187–189° C.

¹H-NMR(CDCl₃) δ (ppm): 8.63(1H, s), 7.34–7.30(5H, m), 7.24(1H, 15 s), 7.10(1H, s), 5.98(1H, brt, J=5.0 Hz), 4.90(2H, d, J=5.0 Hz), 4.12–4.07(4H, m), 4.01(3H, s), 3.98(3H, s), 3.87–3.83(4H, m).

FAB-Mass: 424(M++1)

IR(KBr) υ (cm⁻¹): 1541, 1504, 1479, 1433, 1340, 1244, 1209, 989.

EXAMPLE 126

(dl)-4-(6,7-Dimethoxy-4-quinazolinyl)-N-(1-phenylethyl)-1-piperazinethiocarboxamide (Compound 126)

Yield: 81% m.p.: 98–99° C.

¹H-NMR(CDCl₃) δ (ppm): 8.63(1H, s), 7.41-7.25(5H, m), 7.24(1H, s), 7.10(1H, s), 5.93(1H, brd, J=7.3 Hz), 5.85(1H, dq, J=7.3 Hz, 6.6 Hz), 4.09–4.06(4H, m), 4.01(3H, s), 3.97(3H, s), 3.8614 3.83(4H, m), 1.63(3H, d, J=6.6 Hz).

FAB-Mass: 438(M$^+$+1)

IR(KBr) υ (cm$^{-1}$): 1576, 1506, 1475, 1429, 1348, 1240, 1211, 1136, 991, 700.

EXAMPLE 127

(S)-4-(6,7-Dimethoxy-4-quinazolinyl)-N-(1-phenylethyl)- 1-piperazinecarboxamide (Compound 127)

Yield: 77%

$^1$H-NMR(CDCl$_3$) δ (ppm): 8.67(1H, s), 7.37–7.26(5H, m), 7.24(1H, s), 7.09(1H, s), 5.06(1H8 dq, J=6.9 Hz, 6.6 Hz), 4.98(m H, brd, Js6.6 Hz)9, 4.02(3H, s)3.97(3H, s), 3.66–3.63(8H, m), 1.52(3H, d, J=6.9 Hz).

FAB-Mass: 422(M$^+$+1)

IR(KBr) υ (cm$^{-1}$): 1618, 1574, 1535, 1504, 1473, 1437, 1394, 1348, 1250, 1213, 1134, 993.

EXAMPLE 128

(R)-4-(6,7-Dimethoxy-4-quinazolinyl) -N-(1-phenylethyl)-1-piperazinecarboxamide (Compound 128)

Yield: 72% m.p.: 189–190° C.

$^1$H-NMR(CDCl$_3$) δ (ppm): 8.67(1H, s), 7.36–7.23(5H, m), 7.27(1H, s), 7.09(1H, s), 5.06(1H, dq, J=7.3 Hz, 6.6 Hz), 4.81(1H, d, J=7.3 Hz), 4.02(3H, s), 3.98(3H, s), 3.69–3.61 (8H, m), 1.53(3H, d, J=6.6 Hz).

FAB-Mass: 422(M$^+$+1)

IR(KBr) υ (cm$^{-1}$): 1574, 1535, 1504, 1473, 1437, 1394, 1348, 1331, 1252, 1213, 1134, 993.

EXAMPLE 129

(S)-4-(6,7-Dimethoxy-4-quinazolinyl)-N-(1-phenylethyl)-1-piperazinethiocarboxamide (Compound 129)

Yield: 88% m.p.: 98–100° C.

$^1$NMR(CDCl$_3$) δ (ppm): 8.63(1H, s), 7.40–7.28(5H, m), 7.24(1H, s), 7.10(1H, s), 5.85–5.81(2H, m), 4.09–4.06(4H, m), 4.02(3H, s), 3.98(3H, s), 3.87–3.83(4H, m), 1.63(3H, d, J=6.3 Hz).

FAB-Mass: 438(M$^+$+1)

IR(KBr) υ (cm$^{-1}$): 1506, 1475, 1429, 1348, 1240, 1209.

EXAMPLE 130

(R)-4-(6,7-Dimethoxy-4-quinazolinyl)-N-(1-phenylethyl)-1-piperazinethiocarboxamide (Compound 130)

Yield: 82% m.p.: 99–101° C.

$^1$H-NMR(CDCl$_3$) δ (ppm): 8.63(1H, s), 7.41–7.26(5H, m), 7.24(1H, s), 7.10(1H, s), 5.93–5.81(2H, m), 4.09–4.07 (4H, m), 4.02(3H, s), 3.98(3H, s), 3.87–3.83(4H, m), 1.63 (3H, d, J=6.6 Hz).

FAB-Mass: 438(M$^+$+1)

IR(KBr) υ (cm$^{-1}$): 1576, 1506, 1475, 1429, 1346, 1240, 1209, 1136, 991, 935, 849, 700.

EXAMPLE 131

(S)-4-(6,7-Dimethoxy-4-quinazolinyl)-N-(1-methoxycabonyl-2-phenylethyl)-1-piperazinecarboxamide (Compound 131)

Yield: 71% m.p.: 167–168° C.

$^1$H-NMR(CDCl$_3$) δ (ppm): 8.68(1H, s), 7.34–7.23(5H, m), 7.14(1H, s), 7.08(1H, s), 4.98(1H, brd, J=7.3 Hz), 4.83(1H, dt, J=7.3 Hz, 5.6 Hz), 4.03(3H, s), 3.99(3H, s), 3.76(3H, s), 3.67–3.65(4H, m), 3.61–3.57(4H, m), 3.16(2H, d, J=5.6 Hz).

FAB-Mass: 480(M$^+$+1)

IR(KBr) υ (cm$^{-1}$): 1749, 1624, 1576, 1541, 1504, 1475, 1437, 1350, 1211, 993.

EXAMPLE 132

4-(6,7-Dimethoxy-4-quinazolinyl)-N-(1-naphthylmethyl)-1-piperazinethiocarboxamide (Compound 132)

Yield: 100% m.p.: 164–165° C.

$^1$H-NMR(CDCl$_3$) δ (ppm): 8.58(1H, s), 8.02(1H, d, J=7.6 Hz), 7.88–7.79(2H, m), 7.57–7.29(4H, m), 7.19(1H, s), 7.05(1H, s), 5.97(1H, brt, J=4.3 Hz), 5.28(2H, d, J=4.3 Hz), 4.05–4.01(4H, m), 3.98(3H, s), 3.95(3H, s), 3.80–3.76(4H, ut).

FAB-Mass: 474(M$^+$+1)

IR(KBr) υ (cm$^{-1}$)1574, 1537, 1506, 1429, 1344, 1249, 1207, 1134, 989, 933, 879, 858, 791, 768.

EXAMPLE 133

4-4(6,7-Dimethoxy-4-quinazolinyl)-N-diphenylmethyl-1-piperazinethiocarboxamide (Compound 133)

Yield: 89% m.p.: 128–129° C.

$^1$H-NMR(CDCl$_3$) δ (ppm): 8.62(1H, s), 7.36–7.23(11H, m), 7.09(3H, s), 7.00(1H, d, J=7.3 Hz), 6.27(4H, brd, J=7.3 Hz), 4.13–4.08(4H, m), 4.00(3H, s), 3.96(3H, s), 3.86–3.82 (4H, m).

FAB-Mass: 500(M$^+$+1)

IR(KBr) υ (cm$^{-1}$): 1574, 1504, 1473, 1450, 1427, 1340, 1236, 1207, 993, 698.

EXAMPLE 134

(dl)-4-(6,7-Dimethoxy-4-quinazolinyl)-N-(1,2-diphenylethyl)1-piperazinethiocarboxamide (Compound 134)

Yield: 97% m.p.: 168–169° C.

$^1$H-NMR(CDCl$_3$) δ (ppm): 8.63(1H, s), 7.33–7.18(9H, m), 7.11–7.07(3H, m), 5.97–5.91(2H, m), 4.05–3.93(4H, m), 4.01(3H, s), 3.98(3H, s), 3.81–3.79(4H, m), 3.36–3.18 (2H, m).

FAB-Mass: 514(M$^+$+1)

IR(KBr) υ (cm$^{-1}$): 1576, 1531, 1504, 1473, 1429, 1342, 1236, 1211, 993, 933, 856, 702.

EXAMPLE 135

4-(6,7-Dimethoxy-4-quinazolinyl)-N-(3-phenylpropyl)-1-piperazinethiocarboxamide (Compound 135)

Yield: 74% m.p.: 147–148° C.

$^1$H-NMR(CDCl$_3$) δ (ppm): 8.65(1H, s), 7.34–7.21(6H, m), 7.08(1H, s), 5.53(1H, brt, J=4.9 Hz), 4.02(3H, s), 3.98(3H, s), 3.87–3.74(10H, m), 2.75(2H, t, J=7.3 Hz), 2.04(2H, tt, J=7.3 Hz, 6.6 Hz).

FAB-Mass: 452(M$^+$+1)

IR(KBr) υ (cm$^{-1}$): 1549, 1504, 1473, 1450, 1429, 1350, 1240, 1211, 991.

EXAMPLE 136

N-(2-Anthryl)-1-(6,7-dimethoxy-4-quinazolinyl)-1-piperazinethiocarboxamide (Compound 136)

Yield: 100%

$^1$H-NMR(CDCl$_3$) δ (ppm): 8.66(1H, s), 8.37(1H, s), 8.29 (1H, s), 7.98–7.93(3H, m), 7.70-7.54(2H, m), 7.48–7.38(3H, m), 7.26(1H, s), 7.06(1H, s), 4.13–4.03(4H, m), 4.02(3H, s), 3.96(3H, s), 3.86–3.79(4H, m).

FAB-Mass: 510(M$^+$+1)

EXAMPLE 137

4-(6,7-Dimethoxy-4-quinazolinyl)-N-methyl-N-phenyl-1-piperazinecarboxamide (Compound 137)

Substantially the same procedure as in Example 116 was repeated, except that the corresponding N-methyl-N-phenylcarbamoyl chloride was used in place of diphenyl-carbamoyl chloride, to give the desired compound.

Yield: 95% m.p.: 187–188° C.

$^1$H-NMR(CDCl$_3$) δ (ppm): 8.62(1H, s), 7.39–7.31(2H, m), 7.22(1H, s), 7.21–7.11(3H, m), 7.02(1H, s), 4.01(3H, s), 3.95(3H, s), 3.46(8H, m), 3.28(3H, s).

FAB-Mass: 408(M$^+$+1)

IR(KBr) υ (cm$^{-1}$): 1633, 1570, 1506, 1430, 1344, 991.

In the following Examples 138-149, substantially the same procedure as in Example 1 was repeated, except that the corresponding isocyanate or isothiocyanate was used in place of phenyl isocyanate, to give the desired compound.

EXAMPLE 138

N-Cyclohexylmethyl-4-(6,7-dimethoxy-4-quinazolinyl)-1-piperazinethiocarboxamide (Compound 138)

Yield: 73% m.p.: 170–171° C.

$^1$H-NMR(CDCl$_3$) δ (ppm): 8.64(1H, s), 7.25(1H, s), 7.12 (1H, s), 5.86(1H, brt, J=5.3 Hz), 4.12–4.08(4H, m), 4.03(3H, s), 3.99(3H, s), 3.88–3.84(4H, m), 3.56(2H, dd, J=6.6 Hz, 5.3 Hz), 1.78–1.65(6H, m), 1.32–1.14(3H, m), 1.05–0.92 (2H, m).

FAB-Mass: 430(M$^+$+1)

IR(KBr) υ (cm$^{-1}$): 2924, 2852, 1578, 1541, 1506, 1477, 1427, 1338, 1247, 1209, 1136, 993, 933, 852.

EXAMPLE 139

4-(6,7-Dimethoxy-4-quinazolinyl)-N-[(3aα,4β,5β,7β,7aα)-hexahydro-4,7-methano-5-(1H-indenyl)]-1-piperazinethiocarboxamide (Compound 139)

Yield: 90% m.p.: 130–133° C.

$^1$H-NMR(CDCl$_3$) δ (ppm): 8.65(1H, s), 7.26(1H, s), 7.11 (1H, s), 5.77–5.70(2H, m), 5.41(1H, m), 4.29(1H, m), 4.06 (4H, m), 4.03(3H, s), 3.98(3H, s), 3.87–3.83(4H, m), 3.16–0.97(10H, m).

FAB-Mass: 466(M$^{30}$ +1)

IR(KBr) υ (cm$^{-1}$): 1574, 1504, 1473, 1429, 1346, 1240, 1209, 993, 935, 856.

EXAMPLE 140

(dl)-4-(6,7-Dimethoxy-4-quinazolinyl)-N-(2-tetrahydropyranyl)-1-piperazinecarboxamide (Compound 140)

Yield: 87% m.p.: 199–200° C.

$^1$H-NMR(CDCl$_3$) δ (ppm): 8.67(1H, s), 7.26(1H, S), 7.09(1H, s), 5.44(1H, d, J=-8.9 Hz), 5.09(1H, ddd, J=10.6 Hz, 8.9 Hz, 2.0 Hz), 4.05–4.03(4H, m), 3.99(3H, S), 3.68–3.59(9H, m), 1.93–1.81(2H, m), 1.68–1.38(4H, m).

FAB-Mass: 402(M$^+$+1)

IR(KBr) 1)(cm$^{-1}$): 2935, 2862, 1624, 1541, 1535, 1502, 1479, 1431, 1350, 1247, 1211, 1134, 1078, 1032, 997, 939, 872.

EXAMPLE 141

(dl)-4-(6,7-Dimethoxy-4-quinazolinyl)-N-tetrahydrofurfuryl-1-piperazinethiocarboxamide (Compound 141)

Yield: 88% m.p.: 195–196° C.

$^1$H-NMR(CDCl$_3$) δ (ppm): 8.65(1H, s), 7.26(1H, s), 7.11 (1H, s), 6.17(1H, brt, J=5.9 Hz), 4.21–4.08(6H, m), 4.03(3H, s), 3.99(3H, s), 3.92–3.74(6H, m), 3.45(H, m)6, 2.09–1.88 (3H, m), 1.62(2H, m).

FAB-Mass: 418(M$^+$+1)

IR(KBr) υ (cm$^{-1}$): 1574, 1543, 1504, 1471, 1417, 1350, 1240, 1209, 1136, 1066, 989, 931, 875, 843.

EXAMPLE 142

4-4(6,7-Dimethoxy-4-quinazolinyl)-N-(2-morpholinoethyl)-1-piperazinethiocarboxamide (Compound 142)

Yield: 70% m.p.: 79–81° C.

$^1$H-NMR(CDCl$_3$) δ (ppm): 8.66(1H, s), 7.26(1H, s), 7.12 (1H, s), 6.55(1H, brt, J=3.6 Hz), 4.10-4.06(4H, m), 4.03(3H, s), 3.99(3H, s), 3.89–3.86(4H, m), 3.77–3.70(6H, m), 2.66–2.62(2H, m), 2.52–2.49(4H, m).

FAB-Mass: 447(M$^+$+1)

IR(KBr) υ (cm$^{-1}$): 1578, 1506, 1477, 1429, 1350, 1238, 1209, 1114, 991.

EXAMPLE 143

N-Cinnamoyl-4-(6,7-dimethoxy-4-quinazolinyl)--1-piperazinethiocarboxamide (Compound 143)

Yield: 307% m.p.: 218–2186° C.

$^1$H-NMR(CDCl$_3$) δ (ppm): 8.70(1H, brs), 8.70(1H, s), 7.74(3H, d, J=15.5 Hz), 7.55–7.51(2H, m), 7.43–7.38(3H, m), 7.29(1H, s), 7.10(1H, s), 6.57(3H, d, J=15.5 Hz), 4.39–4.30(2H, m), 4.04(3H, s), 4.00(3H, s), 3.97 3.90(6H, m).

FAB-Mass: 464(M$^+$+1)

IR(KBr) υ (cm$^{-1}$): 1668, 1618, 1578, 1502, 1477, 1429, 1354, 1336, 1242, 1209, 1184, 1134, 987.

EXAMPLE 144

4-(6,7-Dimethoxy-4-quinazolinyl)-N-(3-tolyl)-1-piperazinecarboxamide (Compound 144)

Yield: 79% m.p.: 218–219° C.

¹H-NMR(CDCl₃) δ (ppm): 8.69(1H, s), 7.27(1H, d, J=7.3 Hz), 7.26(1H, s), 7.20–7.13(2H, m), 7.10(1H, s), 6.86(1H, m), 6.76(1H, brs), 4.02(3H, s), 3.99(3H, s), 3.72(8H, m), 2.31(3H, s).

FAB-Mass: 408(M⁺+1)

IR(KBr) 1)(cm⁻¹) : 1632, 1545, 1506, 1477, 1425, 1400, 1350, 1248, 1209, 995.

EXAMPLE 145

4-(6,7-Dimethoxy-4-quinazolinyl)-N-(3-tolyl)-1-piperazinethiocarboxamide (Compound 145)

Yield: 78% m.p.: 199–201° C.

¹H-NMR(CDC₃) δ (ppm): 8.65(1H, s), 7.72(1H, brs), 7.24(1H, s), 7.21(5H, dd, J=7.6 Hz, 2.6 Hz), 7.08((H, s), 7.00–6.96(3H, m), 4.06–4.04(4H, m), 4.01(3H, s), 3.98(3H, s), 3.83–3.79(4H, m), 2.33(3H, s).

FAB-Mass: 424(M⁺+1)

IR(KBr) υ (cm⁻¹): 1576, 1533, 1502, 1473, 1446, 1421, 1385, 1335, 1240, 1211, 1134, 1018, 991, 931, 851.

EXAMPLE 146

4-(6,7-Dimethoxy-4-quinazolinyl)-N-(4-tolyl)-1-piperazinethiocarboxamide (Compound 146)

Yield: 82% m.p.: 204–205° C.

¹H-NMR(CDCl₃) δ (ppm): 8.65(1H, s), 7.82(1H, brs), 7.23(1H, s), 7.13(2H, d, J=8.6 Hz), 7.10(1H, s), 7.10(2H, d, J=8.6 Hz), 4.08–4.05(4H, m), 4.00(3H, s), 3.98(3H, s), 3.83–3.79(4H, m)), 2.31(3H, s).

FAB-Mass: 424(M⁺+1)

IR(KBr) υ (cm⁻¹): 1578, 1541, 1504, 1473, 1446, 1390, 1342, 1244, 1209, 991.

EXAMPLE 147

4-(6,7-Dimethoxy-4-quinazolinyl)-N-(4-methylbenzyl)-1-piperazinethiocarboxamide (Compound 147)

Yield: 89% m.p.: 202–204° C.

¹H-NMR(CDCl₃) δ (ppm): 8.64(1H, s), 7.28(1H, s), 7.26 (2H, d, J=7.9 Hz), 7.17(2H, d, J=7.9 Hz), 7.10(1H, s), 5.84(1H, brt, J=4.3 Hz), 4.85(2H, d, J=4.3 Hz), 4.10–4.07 (4H, m), 4.02(3H, s), 3.98(3H, s), 3.86–3.82(4H, m), 2.35 (3H, s).

FAB-Mass: 438(M⁺+1)

IR(KBr) υ (cm⁻¹): 1539, 1504, 1477, 1431, 1348, 1238, 1205, 991.

EXAMPLE 148

4-(6,7-Dimethoxy-4-quinazolinyl)-N-(3-ethylphenyl)-1-piperazinecarboxamide (Compound 148)

Yield: 78% m.p.: 207–208° C.

¹H-NMR(CDCl₃) δ (ppm): 8.69(1H, s), 7.27–7.24(2H, m), 7.21–7.16(2H, m), 7.11(1H, s), 6.91(1H, m), 6.63(1H, brs), 4.03(3H, s), 4.00(3H, s), 3.74(8H, m), 2.62(2H, q, J=7.6 Hz), 1.22(3H, t, J=7.6 Hz).

FAB-Mass: 421(M⁺+1)

IR(KBr) υ (cm⁻¹): 1637, 1543, 1504, 1475, 1429, 1240, 1209, 996.

EXAMPLE 149

4-(6,7-Dimethoxy-4-quinazolinyl)-N-(3-ethylphenyl)-1-piperazinethiocarboxamide (Compound 149)

Yield: 79% m.p.: 195–197° C.

¹H-NMR(CDCl₃) δ (ppm): 8.65(1H, s), 7.61(1H, brs), 7.31–7.22(2H, m), 7.08(1H, s), 7.01-6.99(3H, m), 4.07–4.03 (4H, m), 4.01(3H, s), 3.98(3H, s), 3.83–3.79(4H, m), 2.63 (2H, q, J=7.4 Hz), 1.22(3H, t, J=7.4 Hz).

FAB-Mass: 438(M⁺+1)

IR(KBr) υ (cm⁻¹): 1578, 1533, 1506, 1473, 1421, 1335, 1240, 1211, 1134, 1018, 991, 930, 849.

EXAMPLE 150

4-(6,7-Dimethoxy-4-quinazolinyl)-N-(3-isopropylphenyl)-1-piperazinecarboxamide (Compound 150)

To a solution of 2.05 g (9.39 mmol) of di-tert-butyl dicarbonate in 30 ml of dichloromethane was added 108 mg (0.88 mmol) of 4-(N,N-dimethylamino)pyridine. After the mixture was stirred at room temperature for 5 minutes, 1.26 ml (8.95 mmol) of ³-isopropylaniline was added thereto, followed by further stirring at room temperature for 30 minutes. To the reaction mixture was added 548 mg (2.00 mmol) of 6,7-dimethoxy-4-piperazinylquinazoline obtained by the method described in South African Patent No. 67 06512 (1968), followed by stirring at room temperature for 30 minutes. After the solvent was evaporated, the residue was purified by silica gel chromatography and recrystallized from ethyl acetate to give the desired compound as colorless crystals.

Yield: 63% m.p.: 196–197° C.

¹H-NMR(CDCl₃) δ (ppm): 8.70(1H, s), 7.2714 7.20(4H, m), 7.12(1H, s), 6.94(1H, dd, J=7.3 Hz, 1.6 Hz), 6.42(1H, brs), 4.04(3H, s), 4.00(3H, s), 3.76(8H, m), 2.89(1H, m), 1.25(6H, d, J=6.9 Hz).

FAB-Mass: 436(M⁺+1)

IR(KBr) υ (cm⁻¹): 1637, 1521, 1449, 1429, 1238, 1211, 993, 795.

EXAMPLE 151

4-(6,7-Dimethoxy-4-quinazolinyl)-N-(3-isopropylphenyl)-1-piperazinethiocarboxamide (Compound 151)

To a solution of 696 mg (3.00 mmol) of commercially available 1,1'-thiocarbonyl-di-2(1H)-pyridone in 10 ml of dichloromethane was added slowly 0.42 ml (2.98 mmol) of 3-isopropylaniline. After stirring at room temperature for one hour, 548 mg (2.00 mmol) of 6,7-dimethoxy-4-piperazinylquinazoline obtained by the method described in South African Patent No. 67 06512 (1968) was added to the reaction mixture, followed by further stirring at room temperature for one hour. To the reaction mixture was added water, followed by extraction with chloroform. The organic layer was washed with a saturated aqueous solution of sodium chloride and dried over magnesium sulfate. After the solvent was evaporated, the residue was purified by silica gel chromatography and recrystallized from chloroform-diisopropyl ether to give the desired compound as colorless crystals.

Yield: 39% m.p.: 169–171° C.

¹H-NMR(CDCl₃) δ(ppm): 8.66(1H, s), 7.32–7.24(3H, m), 7.09(1H, s), 7.06–7.00(3H, m), 4.07–4.04(4H, m), 4.03(3H, s), 3.99(3H, s), 3.84–3.80(4H, m), 2.9(1H, m), 1.25(6H, d, J=6.9 Hz).

FAB-Mass: 452(M⁺+1)

IR(KBr) υ (cm⁻¹): 1539, 1506, 1479, 1429, 1238, 1209, 993, 797.

EXAMPLE 152

4-(6,7-Dimethoxy-4-quinazolinyl)-N-(4-isopropylphenyl)-1-piperazinethiocarboxamide (Compound 152)

Substantially the same procedure as in Example 1 was repeated, except that the corresponding 4-isopropylphenyl isothiocyanate was used in place of phenyl isocyanate, to give the desired compound.

Yield: 84% m.p.: 194–195° C.

¹H-NMR(CDCl₃) δ (ppm): 8.66(1H, s), 7.56(1H, brs), 7.28(1H, s), 7.26(2H, d, J=8.3 Hz), 7.12(2H, d, J=8.3 Hz), 7.09(1H, s), 4.08–4.04(4H, m), 4.01(3H, s), 3.98(3H, s), 3.84–3.81(4H, m), 2.89(1H, m), 1.23(6H, d, J=6.9 Hz).

FAB-Mass: 452(M⁺+1)

IR(KBr) υ (cm⁻¹): 1578, 1541, 1510, 1475, 1446, 1425, 1390, 1342, 1250, 1211, 1136, 1016, 991, 937.

EXAMPLE 153

4-(6,7-Dimethoxy-4-quinazolinyl)-N-(4-isopropylbenzyl)-1-piperazinecarboxamide (Compound 153)

Substantially the same procedure as in Example 119 was repeated, except that the corresponding 4-isopropylbenzylamine was used in place of 2-(4-chlorophenyl)ethylamine, to give the desired compound.

Yield: 31% m.p.: 135–136° C.

¹H-NMR(CDCl₃) δ (ppm): 8.67(1H, s), 7.27(2H, d, J=8.3 Hz), 7.27(1H, s), 7.21(2H, d, J=8.3 Hz), 7.09(1H, s), 4.88 (1H, brt, J=5.3 Hz), 4.43(2H, d, J=5.3 Hz), 4.03(3H, s), 3.98(3H, s), 3.70 -3.63(8H, m), 2.90(1H, m), 1.24(6H, d, J=6.9 Hz).

FAB-Mass: 450(M⁺+1)

IR(KBr) υ (cm⁻¹) : 1628, 1545, 1502, 1471, 1431, 1352, 1254, 1207, 1134, 993, 852, 798.

EXAMPLE 154

4-(6,17-Dimethoxy-4-guinazolinyl) -N-(4-isopropylbenzyl)-1-piperazinethiocarboxamide (Compound 154)

To a solution of 0.181 ml (2.37 mmol) of thiophosgene in 10 ml of dichloromethane were added slowly 353.1 mg (2.37 mmol) of 4-isopropylbenzylamine and 0.76 ml (5.45 mmol) of triethylamine under ice-cooling. After the mixture was stirred at the same temperature for 1.5 hours, 500 mg (1.82 mmol) of 6,7-dimethoxy-4-piperazinylquinazoline obtained according to the method described in South African Patent No. 67 06512 (1968) was added thereto, followed by overnight stirring at room temperature. After the solvent was evaporated, the residue was purified by silica gel chromatography to give the desired compound as colorless crystals.

Yield: 86% m.p.: 178–179° C.

¹H-NMR(CDCl₃) δ (ppm): 8.62(1H, s), 7.35–7.20(5H, m), 7.10(1H, s), 5.91(1H, br), 4.85(2H, d, J=4.6 Hz), 4.12–4.07(4H, m), 4.01(3H, s), 3.98(3H, s), 3.86–3.82(4H, m), 2.90(1H, m), 1.24(6H, d, J=6.9 Hz).

FAB-Mass: 466(M⁺+1)

IR(KBr) υ (cm⁻¹): 2872, 1541, 1506, 1475, 1429, 1346, 1236, 1205, 1136, 991, 935.

EXAMPLE 155

4-(6,7-Dimethoxy-4-quinazolinyl)-N-(4-isobutylphenyl)-1-piperazinecarboxamide (Compound 155)

Substantially the same procedure as in Example 164 was repeated, except that the corresponding 4-isobutylbenzoic acid was used in place of 4-vinylbenzoic acid, to give the desired compound.

Yield: 61% m.p.: 215–217° C.

1H-NMR(CDCl₃) δ (ppm): 8.70(1H, s), 7.28(2H, d, J=7.6 Hz), 7.26(1H, s), 7.11(1H, s), 7.09(2H, d, J=7.6 Hz), 6.37 (1H, brs), 4.04(3H, s), 4.00(3H, s), 3.75(8H, m), 2.43(2H, d, J=6.9 Hz), 10 1.83(1H, m), 0.89(6H, d, J=6.9 Hz).

FAB-Mass: 398(M⁺+1)

IR(KBr) υ (cm⁻¹): 1643, 1573, 1502, 1415, 1245, 1211, 1133, 993, 846.

EXAMPLE 156

N-(4-tert-Butylphenyl)-4-(6,7-dimethoxy-4-quinazolinyl)-1-piperazinecarboxamide (Compound 156)

Substantially the same procedure as in Example 117 was repeated, except that the corresponding 4-tert-butylaniline was used in place of 4-morpholinoaniline, to give the desired compound.

Yield: 20% m.p.: 109–111° C.

¹H-NMR(CDCl₃) δ (ppm): 8.68(1H, s), 7.43(1H, brs), 7.37–7.28(5H, m), 7.13(1H, s), 4.03(3H, s), 4.00(3H, s), 3.77–3.75(8H, m), 1.30(9H, s).

FAB-Mass: 450(M⁺+1)

IR(KBr) υ (cm⁻¹): 1662, 1508, 1475, 1429, 1354, 1246, 1211, 993.

EXAMPLE 157

N-(4-tert-Butylbenzyl)-4-(6,7-dimethoxy-4-quinazolinyl)-1-piperazinethiocarboxamide (Compound 157)

Substantially the same procedure as in Example 154 was repeated, except that the corresponding 4-tert-butylbenzylamine was used in place of 4-isopropylbenzylamine to give the desired compound.

Yield: 91% mp:104–105° C.

¹H-NMR(CDCl₃) δ (ppm): 8.62(1H, s), 7.37(2H, d, J=8.3 Hz), 7.29(2H, d, J=8.3 Hz), 7.22(1H, s), 7.10(1H, s), 6.11 (1H, brt, J=4.3 Hz) , 4.86(2H, d, J=4.3 Hz) ,4.12–4.06(4H, m) , 4.00(3H, s), 3.98(3H, s), 3.86–3.82(4H, m), 1.31(9H, s).

FAB-Mass: 480(M⁺+1)

IR(KBr) υ (cm⁻¹): 1508, 1475, 1431, 1350, 1240, 1209.

EXAMPLE 158

N-(4-Dif luoromethoxyphenyl)-4-(6,7-dimethoxy-4-quinazolinyl)-1-piperazinecarboxamide (Compound 158)

Substantially the same procedure as in Example 164 was repeated, except that the corresponding 4-difluoromethoxybenzoic acid was used in place of 4-vinylbenzoic acid, to give the desired compound.

Yield: 15% m.p.: 190–192° C.

$^1$H-NMR(CDCl$_3$) δ (ppm): 8.70(1H, s), 7.37(2H, d, J=8.9 Hz), 7.27(2H, d), 7.J8(Hz, s), 7.08(2H, s, J=8.9 Hz), 6.50 (1H, brs), 6.46(3H, t, J=7. 4 Hz),, 4.04(3H, s), 4.00(3H, s), 3.76(8H, m).

FAB-Mass: 460(M$^+$+1)

IR(KBr) υ (cm$^{-1}$): 1646, 1573, 1538, 1508, 1436, 1234, 1209, 1132, 1027, 993, 927, 846, 777.

EXAMPLE 159

4-(6,7-Dimethoxy-4-quinazolinyl)-N-(4-trifluoromethylphenyl))-1-piperazinethiocarboxamide (Compound 159)

Substantially the same procedure as in Example 1 was repeated, except that the corresponding 4-trifluoromethylphenyl isothiocyanate was used in place of phenyl isocyanate, to give the desired compound.

Yield: 82% m.p.: 117–119° C.

$^1$H-NMR(CDCl$_3$) δ (ppm): 8.65(1H, s), 8.18(1H, brs), 7.56(2H, d, J=8.6 Hz), 7.33(2H, d, J=8.6 Hz), 7.23(1H, s), 7.09(1H, s), 4.12–4.07(4H, m), 4.00(3H, s), 3.98(3H, s), 3.86–3.83(4H, m).

FAB-Mass: 478(M$^+$+1)

IR(KBr) υ (cm$^{-1}$): 1581, 1508, 1479, 1430, 1325, 1207, 1162, 1113, 1066, 993.

EXAMPLE 160

4-(6,7-Dimethoxy-4-quinazolinyl)-N-(4-trifluoromethylbenzyl)-1-piperazinecarboxamide (Compound 160)

Substantially the same procedure as in Example 119 was repeated, except that the corresponding 4-trifluoromethylbenzylamine was used in place of 2-(4-chlorophenyl)ethylamine, to give the desired compound.

Yield: 60% m.p.: 195–197° C.

$^1$H-NMR(CDCl$_3$) δ (ppm): 8.67(1H, s), 7.59(2H, d, J=8.3 Hz), 7.44(2H, d, J=8.3 Hz), 7.25(1H, s), 7.09(1H, s), 5.10 (1H, brt, J=5.6 Hz), 4.52(2H, d, J=5.6 Hz), 4.03(3H, s), 3.99(3H, s), 3.71–3.65(8H, m).

FAB-Mass: 476(M$^+$+1)

IR(KBr) υ (cm$^{-1}$): 1620, 1504, 1475, 1429, 1327, 1255, 1211, 1161, 1111, 1066, 993.

EXAMPLE 161

4-(6,7-Dimethoxy-4-quinazolinyl)-N-(4-trifluoromethylbenzyl)-1-piperazinethiocarboxamide (Compound 161)

Substantially the same procedure as in Example 154 was repeated, except that the corresponding 4-trifluoromethylbenzylamine was used in place of 4-isopropylbenzylamine, to give the desired compound.

Yield: 99% m.p.: 216–217° C.

$^1$H-NMR(CDCl$_3$) δ (ppm): 8.64(1H, s), 7.61(2H, d, J=7.9 Hz), 7.47(2H, d, J=7.9 Hz), 7.24(1H, s), 7.10(1H, s), 6.07 (1H, brt, J=5.3 Hz), 5.01(2H, d, J=5.3 Hz), 4.14–4.10(4H, m), 4.02(3H, s), 3.98(3H, s), 3.89–3.85(4H, m).

FAB-Mass: 492(M$^+$+1)

IR(KBr) υ (cm$^{-1}$): 1531, 1500, 1473, 1429, 1329, 1234, 1207, 1159, 1113, 1066, 989.

EXAMPLE 162

4-(6,7-Dimethoxy-4-quinazolinyl)-N-(3-trifluoromethylphenyl)-1-piperazinecarboxamide (Compound 162)

Substantially the same procedure as in Example 1 was repeated, except that the corresponding 3-trifluoromethylphenyl isocyanate was used in place of phenyl isocyanate, to give the desired compound.

Yield: 100% m.p.: 180–181° C.

$^1$H-NMR(CDCl$_3$) δ (ppm): 8.69(1H, s), 7.67(1H, brs), 7.61(1H, d, J=8.3 Hz), 7.41–7.28(3H, m), 7.24(1H, s), 7.09(1H, s), 4.01(3H, s), 3.99(3H, s), 3.77–3.71(8H, m).

FAB-Mass: 462(M$^+$+1)

IR(KBr) υ (cm$^{-1}$): 1647, 1554, 1502, 1471, 1431, 1335, 1244, 1207, 1124, 993.

EXAMPLE 163

4-(6,7-Dimethoxy-4-quinazolinyl)-N-(3-trifluoromethylphenyl)-1-piperazinethiocarboxamide (Compound 163)

Substantially the same procedure as in Example 1 was repeated, except that the corresponding 3-trifluoromethylphenyl isothiocyanate was used in place of phenyl isocyanate, to give the desired compound.

Yield: 86% m.p. 171–172° C.

$^1$H-NMR(CDCl$_3$) δ (ppm): 8.67(4H, s)$_1$ 7.54(1H, brs), 7.48–7.41(3H, m), 7.27(1H, s), 7.27(1H, d, J=2.3 Hz), 7.10(1H, s), 4.16–4.11(4H5 m), 4.03(3H, s), 3.99(3H, s), 3.89–3.85(4H, m).

FAB-Mass: 478(M$^+$+1)

IR(KBr) υ (cm$^{-1}$): 1576, 1543, 1506, 1477, 1431, 1333, 1238, 1211, 1165, 1119, 995.

EXAMPLE 164

4-(6,7-Dimethoxy-4-quinazolinyl)-N-(4-vinylphenyl)-1-piperaziinecarboxamide (Compound 164)

To a suspension of 1.48 g (10.0 mmol) of 4-vinylbenzoic acid in 20 ml of toluene were added 1.39 ml (10.0 mmol) of triethylamine and 2.15 ml (10.0 mmol) of diphenyiphosphoryl azide. After the mixture was heated at 70° C. with stirring for 2 hours, 548 mg (2.00 mmol) of 6,7-dimethoxy-4-piperazinyiquinazoline obtained according to the method described in South African Patent No. 6706512 (1968) was added thereto, followed by heating under reflux for one hour. After the reaction mixture was allowed to cool to room temperature, water was added thereto, followed by extraction with chloroform. The organic layer was washed with a saturated aqueous solution of sodium chloride and dried over magnesium sulfate. After the solvent was evaporated, the residue was purified by silica gel chromatography and recrystallized from ethyl acetate to give the desired compound as colorless crystals.

Yield: 54% m.p.: 214–216° C.

$^1$H-NMR(CDCl$_3$) δ (ppm): 8.70(1H, s), 7.36(4H, s), 7.27 (1H, s), 7.11(1H, s), 6.65(1H, dd, J=17.5 Hz, 10.9 Hz), 6.50(1H, brs), 5.67(1H, d, J=17.5 Hz), 5.18(1H, d, J=10.9 Hz), 4.03(3H, s), 4.00(3H, s), 3.75(8H, m).

FAB-Mass: 420(M⁺+1)

IR(KBr) υ (cm⁻¹)1619, 1577, 1504, 1477, 1421, 1303, 1236, 1211, 1039, 991, 939, 910.

EXAMPLE 165

4-(6,7-Dimethoxy-4-quinazolinyl)-N-(4-isopropenylbenzyl)-1-piperazinecarboxamide (Compound 165)

Substantially the same procedure as in Example 263 was repeated, except that the corresponding 4-isopropenylbenzylamine was used in place of 2-picolylamine, to give the desired compound.

Yield: 17% m.p.: 123–124° C.

$^1$H-NMR(CDCl$_3$) δ (ppm): 8.68(1H, s), 7.47(2H, d, J=8.3 Hz), 7.31(2H, d, J=8.3 Hz), 7.26(1H, s), 7.10(1H, s), 5.37 (1H, s), 5.09(1H, s), 4.79(1H, br), 4.46(2H, d, J=5.6 Hz), 4.03(3H, s), 3.99(3H, s), 3.71–3.68(4H, m), 3.66–3.63(4H, m), 2.15(3H, s).

FAB-Mass: 476(M⁺+1)

IR(KBr) υ (cm⁻¹): 1621, 1540, 1506, 1429, 1351, 1253, 1209, 991, 846.

EXAMPLE 166

4-(6,7-Dimethoxy-4-quinazolinyl)-N-(4-isopropenylbenzyl)-1-piperazinethiocarboxamide (Compound 166)

Substantially the same procedure as in Example 154 was repeated, except that the corresponding 4-isopropenylbenzylamine was used in place of 4-isopropylbenzylamine, to give the desired compound.

Yield: 21%

$^1$H-NMR(CDCl$_3$) δ (ppm): 8.65(1H, s), 7.47(2H, d, J=8.5 Hz), 7.33(2H, d, J=8.5 Hz), 7.26(1H, s), 7.11(1H, s), 5.70 (1H, br), 5.36(1H, s), 5.11(1H, s), 4.89(2H, d, J=4.6 Hz), 4.11–4.07(4H, m), 4.03(3H,s), 3.99(3H, s), 3.88–3.84(4H, m), 2.16(3H, s).

EXAMPLE 167

4-(6,7-Dimethoxy-4-quinazolinyl)-N-[4-[1-(2-methyl-1-propenyl)]benzyl)-1-piperazinecarboxamide (Compound 167)

Substantially the same procedure as in Example 263 was repeated, except that the corresponding 4-[1-(2-methyl-1-propenyl)]benzylamine was used in place of 2-picolylamine, to give the desired compound.

Yield: 16% m.p.: 168–169° C.

$^1$H-NMR(CDCl$_3$) δ (ppm): 8.68(1H, s), 7.28(2H, d, J=8.3 Hz), 10 7.26(1H, s), 7.21(2H, d, J=8.3 Hz), 7.10(1H, s), 6.25(1H, s), 4.78(1H, brt, J=4.9 Hz), 4,45(2H, d, J=4.9 Hz), 4.03(3H, s), 3.99(3H, s), 3.71–3.68(4H, m), 3.66–3.63(4H, m), 1.91(3H, s), 1.86(3H, s).

FAB-Mass: 462(M⁺+1)

IR(KBr) υ (cm⁻¹): 1623, 1542, 1504, 1436, 1427, 1253, 1209, 991, 848.

EXAMPLE 168

4-(6,7-Dimethoxy-4-quinazolinyl)-N-(4-[1-(2-methyl-1-propenyl)]benzyl)-1-piperazinethiocarboxamide (Compound 168)

Substantially the same procedure as in Example 154 was repeated, except that the corresponding 4-[1-(2-methyl-1-propenyl)]benzylamine was used in place of 4-isopropylbenzylamine, to give the desired compound.

Yield: 31%

$^1$H-NMR(CDCl$_3$) δ (ppm): 8.65(1H, s), 7.31(2H, d, J=8.3 Hz), 7.26(1H, s), 7.22(2H, d, J=8.3 Hz), 7.11(1H, s), 6.25 (1H, s), 5.70(1H, br), 4.87(2H, d, J=4.6 Hz), 4.11–4.07(4H, m), 4.03(3H, s), 3.99(3H, s), 3.88–3.85(4H, m), 1.91(3H, s), 1.87(3H, s).

In the following Examples 169–171, substantially the same procedure as in Example 1 was repeated, except that the corresponding isothiocyanate was used in place of phenyl isocyanate, to give the desired compound.

EXAMPLE 169

4-(6,7-Dimethoxy-4-quinazolinyl)-N-[trans-4-(4-propylcyclohexyl)phenyl]-1-piperazinethiocarboxamide (Compound 169)

Yield: 83% m.p.: 106–109° C.

$^1$H-NMR(CDCl$_3$) δ (ppm): 8.65(1H, s), 7.53(1H, brs), 7.25(1H, s), 7.18(2H, d, J=8.6 Hz), 7.10(2H, d, J=8.6 Hz), 7.08(1H, s), 4.07–4.03(4H, m), 4.01(3H, s), 3.98(3H, s), 3.84–3.80(4H, m), 10 2.43(1H, tt, J=12.2 Hz, 3.0 Hz), 1.91–1.84(4H, m), 1.48–1.15(7H, m), 1.10–0.95(2H, m), 0.90(3H, t, J=7.3 Hz).

FAB-Mass: 534(M⁺+1)

IR(KBr) υ (cm⁻¹): 2920, 1576, 1506, 1473, 1427, 1236, 1209, 1134, 1014, 991, 854.

EXAMPLE 170

4-(6,7-Dimethoxy-4-quinazolinyl)-N-{4-[1-(4-hexylbicyclo[2.2.2]octyl)]phenyl}-1-piperazinethiocarboxamide (Compound 170)

Yield: 70% m.p.: 148–149° C.

$^1$H-NMR(CDCl$_3$) δ (ppm): 8.66(1H, s), 7.45(1H, brs), 7.28(2H, d, J=6.9 Hz), 7.28(2H, d, J=6.9 Hz), 7.25(1H, s), 7.08(1H, s), 4.06–4.03(4H, m), 4.02(3H, s), 3.98(3H, s), 3.84–3.80(4H, m), 1.83–1.74(6H, m), 1.49-1.44(6H, m), 1.31–1.13(10H, m), 0.89(3H, t, J=6.6 Hz).

FAB-Mass: 602(M⁺+1)

IR(KBr) υ (cm⁻¹): 2927, 2854, 1508, 1483, 1473, 1454, 1430, 1332, 1238, 1215, 1138, 995, 941, 854.

EXAMPLE 171

4-(6,7-Dimethoxy-4-quinazolinyl)-N-(3-fluorobenzyl)-1-piperazinethiocarboxamide(Compound 171)

Yield: 75% m.p.: 100–102° C.

$^1$H-NMR(CDCl$_3$) δ (ppm): 8.63(1H, s), 7.32(1H, m), 7.28(1H, s), 7.27–6.95(4H, m), 6.09(1H, brt, J=5.0 Hz), 4.93(2H, d, J=5.0 Hz), 4.14-4.10(4H, m), 4.02(3H, s), 3.99 (3H, s), 3.88–3.85(4H, m).

FAB-Mass: 442(M⁺+1)

IR(KBr) υ (cm⁻¹): 1579, 1506, 1481, 1450, 1435, 1338, 1250, 1206, 1138, 991.

EXAMPLE 172

4-(6,7-Dimethoxy-4-quinazolinyl)-N-(4-fluorobenzyl)-1-piperazinecarboxamide (Compound 172)

Substantially the same procedure as in Example 263 was repeated, except that the corresponding 4-fluorobenzylamine was used in place of 2-picolylamine, to give the desired compound.

Yield: 53% m.p.: 200–201° C.

$^1$H-NMR(CDCl$_3$) δ (ppm): 8.67(1H, s), 7.31(2H, m), 7.26(1H, s), 7.10(1H, s), 7.04(2H, m), 4.86(1H, brt, J=5.6 Hz), 4.43(2H, d, J=5.6 Hz), 4.03(3H, s)., 3.99(3H, s), 3.70–3.68(4H, m), 3.65–3.63(4H, m).

FAB-Mass: 426(M$^+$+1)

IR(KBr) υ (cm$^{-1}$): 1576, 1506, 1475, 1429, 1350, 1240, 1209, 1136, 991.

In the following Examples 173–182, substantially the same procedure as in Example 1 was repeated, except that the corresponding isocyanate or isothiocyanate was used in place of phenyl isocyanate, to give the desired compound.

EXAMPLE 173

4-(6,7-Dimethoxy-4-quinazolinyl)-N-(4-fluorobenzyl)-1-piperazinethiocarboxamide (Compound 173)

Yield: 78% m.p.: 217–218° C.

$^1$H-NMR(CDCl$_3$) δ (ppm): 8.62(1H, s), 7.33(2H, m), 7.23(1H, s), 7.10(1H, s), 7.02(2H, m), 6.14(1H, brt, J=5.0 Hz), 4.88(2H, d, J=5.0Hz), 4.12–4.07(4H, m), 4.01(3H, s), 3.98(3H, s), 3.87–3.83(4H, m).

FAB-Mass: 442(M$^+$+1)

IR(KBr) υ (cm$^{-1}$): 1533, 1506, 1477, 1452, 1431, 1406, 1327, 1236, 1211, 1136, 991, 937, 864.

EXAMPLE 174

(dl)-4-(6,7-Dimethoxy-4-quinazolinyl)-N-[1-(4-fluorophenyl)ethyl]-1-piperazinethiocarboxamide (Compound 174)

Yield: 84% m.p.: 95–97° C.

$^1$H-NMR(CDCl$_3$) δ (ppm): 8.61(1H, s), 7.34(2H, dd, J=6.9 Hz, 5.0 Hz), 7.22(1H, s), 7.10(1H, s), 7.00(2H, dd, J=8.9 Hz, 6.9 Hz), 6.13(1H, brd, J=7.6 Hz), 5.84(1H, dq, J=7.6 Hz, 6.9 Hz), 4.09–4.07(4H, m), 4.01(3H, s), 3.97(3H, s), 3.86–3.85(4H, m), 1.60(3H, d, J=6.9 Hz).

FAB-Mass: 456(M$^+$+1)

IR(KBr) υ (cm$^{-1}$): 1576, 1508, 1475, 1429, 1348, 1209, 993, 839.

EXAMPLE 175

N-(3-Chlorophenyl)-4-(6,7-dimethoxy-4-quinazolinyl)-1-piperazinethiocarboxamide (Compound 175)

Yield: 79% m.p.: 222–224° C.

$^1$H-NMR(CDCl$_3$+DMSO-d$_6$) δ (ppm): 8.78(1H, brs), 8.67(1H, s), 7.35(2H, m), 7.28-7.26(2H, m), 7.16–7.13(2H, m), 4.17–4.16(4H, m), 4.04(3H, s), 4.01(3H, s), 3.87–3.85 (4H, m).

FAB-Mass: 446(M$^+$+3), 444(M$^+$+1)

IR(KBr) υ (cm$^{-1}$): 1522, 1508, 1479, 1426, 1317, 1238, 1213, 994.

EXAMPLE 176

N-(2-Chlorobenzyl)-4-(6,7-dimethoxy-4-quinazolinyl)-1-piperazinethiocarboxamide(Compound 176)

Yield: 89% m.p.: 175–176° C.

$^1$H-NMR(CDCl$_3$) d(ppm): 8.62(1H, s), 7.51(1H, dd, J=6.9 Hz, 2.3 Hz), 7.37(1H, dd, J=6.6 Hz, 1.7 Hz), 7.30–7.23(3H, m), 7.10(1H, s), 6.32(1H, brt, J=5.6 Hz), 5.01(2H, d, J=5.6 Hz), 4.12–4.07(4H, m), 4.02(3H, s), 3.98(3H, s), 3.87–3.83(4H, m).

FAB-Mass: 460(M$^+$+3), 458(M$^+$+1)

IR(KBr) υ (cm$^{-1}$): 1549, 1504, 1481, 1429, 1348, 1240, 1207, 1136, 991, 847.

EXAMPLE 177

N-(3-Chlorobenzyl)-4-(6,7-dimethoxy-4-quinazolinyl)-1-piperazinethiocarboxamide(Compound 177)

Yield: 98% m.p.: 117–119° C.

$^1$H-NMR(CDCl$_3$) δ (ppm): 8.60(1H, s), 7.30–7.20(5H, m), 7.08(1H, s), 6.30(1H, brt, J=5.3 Hz), 4.89(2H, d, J=5.3 Hz), 4.12–4.07(4H, m), 3.99(3H, s), 3.96(3H, s), 3.85–3.82 (4H, m).

FAB-Mass: 460(M$^+$+3), 458(M$^+$+1)

IR(KBr) υ (cm$^{-1}$): 1576, 1506, 1483, 1437, 1406, 1354, 1329, 1254, 1205, 991, 858.

EXAMPLE 178

N-(4-Chlorobenzyl)-4-(6,7-dimethoxy-4-quinazolinyl)-1-piperazinecarboxamide (Compound 178)

Yield: 76% m.p.: 203–204° C.

$^1$H-NMR(CDCl$_3$) δ (ppm): 8.67(1H, s), 7.32–7.18(5H, m), 7.09(1H, s), 5.04(1H, brt, J=5.6 Hz), 4.43(2H, d, J=5.6 Hz), 4.02(3H, s), 3.98(3H, s), 3.70–3.68(4H, m), 3.65-3.63 (4H, m).

FAB-Mass: 444(M$^+$+3), 442(M$^+$+1)

IR(KBr) υ (cm$^{-1}$): 1626, 1541, 1504, 1475, 1429, 1350, 1255, 1211, 993.

EXAMPLE 179

N-(4-Chlorobenzoyl)-4-(6,7-dimethoxy-4-quinazolinyl)-1-piperazinethiocarboxamide (Compound 179)

Yield: 15% m.p.: 166–168° C.

$^1$H-NMR(CDCl$_3$) δ (ppm): 8.78(1H, br), 8.69(1H, s), 7.82(2H, d, 10 J=8.2 Hz), 7.47(2H, d, J=8.2 Hz), 7.28(1H, s), 7.10(1H, s), 4.41(2H, m), 4.03(3H, s), 4.00(3H, s), 3.89(6H, m).

FAB-Mass: 474(M$^+$+3), 472(M$^+$+1)

IR(KBr) υ (cm$^{-1}$): 1670, 1579, 1504, 1425, 1350, 1242, 1211, 1096, 1016, 991, 851, 750.

EXAMPLE 180

N-[2-(4-Chlorophenyl)ethyl]-4-(6,7-dimethoxy-4-quinazolinyl)-1-piperazinethiocarboxamide (Compound 180)

Yield: 74% m.p.: 106–109° C.

$^1$H-NMR(CDCl$_3$) δ (ppm): 8.63(1H, s), 7.29(2H, d, J=8.3 Hz), 7.25(1H, s), 7.17(2H, d, J=8.3 Hz), 7.10(1H, s), 5.73 (1H, brt, J=5.3 Hz), 4.02(3H, s), 4.01–3.91(6H, m), 3.98(3H, s), 3.85–3.81(4H, m), 2.97(2H, t, J=6.9 Hz).

FAB-Mass: 474(M$^+$+3), 472(M$^+$+1)

(KBr) υ (cm$^{-1}$): 1579, 1506, 1487, 1429, 1344, 1240, 1213, 1012, 993.

EXAMPLE 181

N-(3-Bromophenyl)-4-(6,7-dimethoxy-4-quinazolinyl)-1-piperazinethiocarboxamide (Compound 181)

Yield: 81% m.p.: 220–222° C.

$^1$H-NMR(CDCl$_3$) δ (ppm): 8.67(1H, s), 7.51(1H, brs), 7.37(1H, dd, J=2.0 Hz, 1.7 Hz), 7.32-7.14(4H, m), 7.09(1H, s), 4.10–4.06(4H, m), 4.03(3H, s), 3.99(3H, s), 3.86–3.83 (4H, m).

FAB-Mass: 490(M +3), 488(M$^+$+1)

IR(KBr) υ (cm$^{-1}$): 1572, 1508, 1477, 1425, 1315, 1236, 1213, 993, 870.

EXAMPLE 182

N-(4-Bromophenyl)-4-(6,7-dimethoxy-4-quinazolinyl)-1-piperazinethiocarboxamide (Compound 182)

Yield: 78% m.p.: 170–171° C.

$^1$H-NMR(CDCl$_3$) δ (ppm): 8.66(1H, s), 7.63(1H, brs), 7.45(2H, d, J=8.6 Hz), 7.24(1H, s), 7.11(2H, d, J=8.6 Hz), 7.09(1H, s), 4.10–4.07(4H, m), 4.01(3H, s), 3.99(3H, s), 3.85–3.82(4H, m).

FAB-Mass: 490(M$^+$+3), 488(M$^+$+1)

IR(KBr) υ (cm$^{-1}$): 1504, 1473, 1425, 1344, 1209.

EXAMPLE 183

N-(4-Bromophenyl)-4-(6,7-dimethoxy-4-quinazolinyl)-N-methyl-1-piperazinecarboxamide (Compound 183)

To a solution of 1.01 g (2.15 mmol) of N-(4-bromophenyl)-4-(6,7-dimethoxy-4-quinazolinyl)-1-piperazinecarboxamide obtained in Example 45 in 15 ml of dimethylformamide was added 171.9 mg (4.30 mmol) of 60% sodium hydride under ice-cooling, followed by stirring at room temperature for 30 minutes. To the reaction mixture was added 0.27 ml (4.34 mmol) of methyl iodide, followed by overnight stirring at room temperature. The resulting mixture was poured into water, and sodium chloride was added thereto. The precipitated crystals were collected by filtration, washed with water, and dried, followed by purification by silica gel column chromatography to give the desired compound as colorless crystals.

Yield: 81%

$^1$H-NMR(CDCl$_3$) δ (ppm): 8.64(1H, s), 7.47(2H, d, J=8.6 Hz), 7.24(1H, s), 7.04(2H, d, J=8.6HZ), 7.02(1H, s), 4.02 (3H, s), 3.97(3H, s), 3.51–3.43(8H, m), 3.25(3H, s).

FAB-Mass: 488(M$^+$+3), 486(M$^+$+1)

EXAMPLE 184

N-(4-Bromobenzyl)-4-(6,7-dimethoxy-4-quinazolinyl)-1-piperazinecarboxamide (Compound 184)

Substantially the same procedure as in Example 119 was repeated, except that the corresponding 4-bromobenzylamine was used in place of 2-(4-chlorophenyl)ethylamine, to give the desired compound.

Yield: 55% m.p.: 211-212 OC $^1$H-NMR(CDCl$_3$) δ (ppm): 8.67(1H, s), 7.45(2H, d, J=7.2 Hz), 7.25(1H, s), 7.21(2H, d, J=7.2 Hz), 7.09(1H, s), 4.99 (1H, brt, J=5.6 Hz), 4.41(2H, d, J=5.6 Hz), 4.03(3H, s), 3.98(3H, s), 3.70–3.63(8H, m).

FAB-Mass: 488(M$^+$+3), 486(M$^+$+1) IR(KBr) υ (cm$^{-1}$): 1626, 1574, 1539, 1504, 1473, 1429, 1352, 1255, 1209, 1134, 993.

EXAMPLE 185

N-(4-Bromobenzyl)-4-(6,7-dimethoxy-4-quinazolinyl)-1-piperazinethiocarboxamide (Compound 185)

To a solution of 502.3 mg (1.42 mmol) of 4-(6,7-dimethoxy-4-quinazolinyl)-1-piperazinethiocarboxylic acid chloride obtained in Reference Example 6 in 10 ml of dimethylformamide were added 1.00 ml (7.17 mmol) of triethylamine and 950 mg (4.27 mmol) of 4-bromobenzylamine hydrochloride. The mixture was stirred overnight at room temperature in an atmosphere of argon. The reaction mixture was poured into water, and sodium chloride was added thereto. The precipitated crystals were collected by filtration, washed with water, and dried, followed by purification by silica gel column chromatography to give the desired compound as colorless crystals.

Yield: 76% m.p.: 217–218° C.

$^1$H-NMR(CDCl$_3$) δ (ppm): 8.61(1H, s), 7.43(2H, d, J=8.2 Hz), 7.22(2H, d, J=8.2 Hz), 7.21(1H, s), 7.09(1H, s), 6.29 (1H, brt, J=5.0 Hz), 4.87(2H, d, J=5.0 Hz), 4.11–4.09(4H, m), 4.01(3H, s), 3.98(3H, s), 3.87–3.83(4H, m).

FAB-Mass: 504(M$^+$+3), 502(M$^+$+1)

IR(KBr) υ (cm$^{-1}$): 1533, 1498, 1473, 1425, 1394, 1319, 1234, 1207, 1134, 989, 935, 864, 795.

In the following Examples 186–197, substantially the same procedure as in Example 1 was repeated, except that the corresponding isocyanate or isothiocyanate was used in place of phenyl isocyanate, to give the desired compound.

EXAMPLE 186

4-(6,7-Dimethoxy-4-quinazolinyl)-N-(3-iodophenyl)-1-piperazinecarboxamide (Compound 186)

Yield: 93% m.p.: 205–208° C.

$^1$H-NMR(CDCl$_3$) δ (ppm): 8.67(1H, s), 7.77(1H, brs), 7.38–7.32(2H, m), 7.24(1H, s), 7.08(1H, s), 7.00–6.93(2H, m), 4.01(3H, s), 3.98(3H, s), 3.72(8H, m).

FAB-Mass: 520(M$^+$+1)

IR(KBr) υ (cm$^{-1}$): 1637, 1578, 1506, 1475, 1419, 1238, 1209, 995.

EXAMPLE 187

4-(6,7-Dimethoxy-4-quinazolinyl)-N-(3-fluoro-4-methylphenyl)-1-piperazinecarboxamide (Compound 187)

Yield: 87%

$^1$H-NMR(CDCl$_3$) δ (ppm): 8.71(1H, s), 7.67(1H, brs), 7.27(2H, m), 7.12(1H, s), 7.05(2H, m), 4.03(3H, s), 4.01 (3H, s), 3.76–3.73(8H, m), 2.20(3H, s).

FAB-Mass: 426(M$^+$+1)

EXAMPLE 188

N-(3-Chloro-4-methylphenyl)-4-(6,7-dimethoxy-4-quinazolinyl)-1-piperazinecarboxamide (Compound 188)

Yield: 91% m.p.: 217–218° C.

$^1$H-NMR(CDCl$_3$) δ (ppm): 8.67(1H, s), 7.45(1H, brs), 7.42(1H, s), 7.23(1H, s), 7.18(1H, d, J=8.2 Hz), 7.08(1H, s), 7.07(1H, d, J=8.2 Hz), 4.00(3H, s), 3.97(3H, s), 3.72–3.70 (8H, m), 2.26(3H, s).

FAB-Mass: 424(M$^+$+3), 422(M$^+$+1)

IR(KBr) υ (cm$^{-1}$): 1641, 1576, 1502, 1471, 1429, 1400, 1244, 1207, 993.

EXAMPLE 189

N-(4-Chloro-3-trifluoromethylphenyl)-4-(6,7-dimethoxy-4-quinazolinyl)-1-piperazinethiocarboxamide (Compound 189)

Yield: 79%

$^1$H-NMR(DMSO-d$_6$) δ (ppm): 9.71(1H, brs), 8.56(1H, s), 7.91(1H, d, J=2.3 Hz), 7.72(1H, dd, J=8.6 Hz, 2.3 Hz), 7.66(1H, d, J=8.6 Hz), 7.25(1H, s), 7.24(1H, s), 4.16(4H, m), 3.94(3H, s), 3.94(3H, s), 3.87(4H, m).

FAB-Mass: 514(M$^+$+3), 512(M$^+$+1)

EXAMPLE 190

N-(3-Chloro-4-methylbenzyl)-4-(6,7-dimethoxy-4-quinazolinyl)-1-piperazinethiocarboxamide (Compound 190)

Yield: 85% m.p.: 108–110° C.

$^1$H-NMR(CDCl$_3$) δ (ppm): 8.62(1H, s), 7.35-7.12(3H, m), 7.23(1H, s), 7.10(1H, s), 6.13(1H, brt, J=5.3 Hz), 4.93(2H, d, J=5.3 Hz), 4.12–4.07(4H, m), 4.02(3H, s), 3.98(3H, s), 3.87–3.83(4H, m).

FAB-Mass: 474(M$^+$+3), 472(MW +1)

IR(KBr) V (cm$^{-1}$): 1576, 1504, 1477, 1429, 1350, 1240, 1209, 1136, 993.

EXAMPLE 191

N-(4-Bromo-3-methylphenyl)-4-(6,7-dimethoxy-4-quinazolinyl)-1-piperazinethiocarboxamide (Compound 191)

Yield: 74% m.p.: 160–161° C.

$^1$H-NMR(CDCl$_3$) δ (ppm): 8.67(1H, s), 7.49(1H, d, J=8.3 Hz), 7.36(1H, brs), 7.27(1H, s), 7.24(1H, d, J=2.6 Hz), 7.09(1H, s), 6.92(1H, dd, J=8.3 Hz, 2.6 Hz), 4.10–4.06(4H, m), 4.03(3H, s), 3.99(3H, s), 3.86–3.82(4H, m), 2.38(3H, s).

FAB-Mass: 504(M$^+$+3), 502(M$^+$+1)

IR(KBr) υ (cm$^{-1}$): 1576, 1504, 1477, 1429, 1319, 1209, 993.

EXAMPLE 192

N-(3,4-Difluorophenyl)-4-(6,7-dimethoxy-4-quinazolinyl)-1-piperazinecarboxamide (Compound 192)

Yield: 82%

$^1$H-NMR(CDCl$_3$) δ (ppm): 8.67(1H, s), 7.42(1H, m), 7.30–7.24(2H, 25 m), 7.09(1H, s), 7.05-6.97(2H, m), 4.01 (3H, s), 3.99(3H, s), 3.73(8H, m).

FAB-Mass: 430(M$^+$+1)

EXAMPLE 193

N-(3-Chloro-4-fluorophenyl)-4-(6,7-dimethoxy-4-quinazolinyl)-1-piperazinecarboxamide (Compound 193)

Yield: 93% m.p.: 200–201° C.

$^1$H-NMR(CDCl$_3$) δ (ppm): 8.68(1H, s), 7.52(1H, dd, J=6.6 Hz, 35 2.6 Hz), 7.25(1H, s), 7.21(1H, ddd, J=8.9 Hz, 6.9 Hz, 2.6 Hz), 7.11(1H, brs), 7.10(1H, s), 7.03(1H, dd, J=8.9 Hz, 8.6 Hz), 4.02(3H, s), 3.99(3H, s), 3.73(8H, m).

FAB-Mass: 448(M$^+$+3), 446(M$^+$+1) IR(KBr) υ (cm$^{-1}$): 1645, 1535, 1506, 1473, 1454, 1412, 1244, 1209, 1136, 993, 852, 814.

EXAMPLE 194

N-(4-Bromo-3-chlorophenyl)-4-(6,7-dimethoxy-4-quinazolinyl)1-piperazinethiocarboxamide (Compound 194)

Yield: 89% m.p.: 169–172° C.

$^1$H-NMR(CDCl$_3$+DMSO-d$_6$) 86(ppm): 9.07(H, brs), 8.67 (dH, s), 7.59–7.50(2H, m), 7.28–7.23(2H, m), 7.14(1H, s), 4.21–4.19(4H, m), 4.05(3H, s), 4.01(3H, s), 3.88–3.87(4H, m).

FAB-Mass: 526(M$^+$+5), 524(M$^+$+3), 522(M$^+$+1)

IR(KBr) υ (cm$^{-1}$): 1525, 1504, 1471, 1429, 1417, 1313, 1209, 1018, 993.

EXAMPLE 195

N-(3,4-Dichlorobenzyl)-4-(6,7-dimethoxy-4-quinazolinyl)-1-piperazinethiocarboxamide (Compound 195)

Yield: 91% m.p.: 197–200° C.

$^1$H-NMR(CDCl$_3$) δ (ppm): 8.63(1H, s), 7.43(1H, d, J=2.0 Hz), 7.40(1H, d, J=8.3 Hz), 7.24(1H, s), 7.21 (1H, dd, J=8.3 Hz, 2.0 Hz), 7.10(1H, s), 6.20(1H, brt, J=5.0 Hz), 4.90(2H, d, J=5.0 Hz), 4.15–4.10(4H, m), 4.02(3H, s), 3.99(3H, s), 3.89–3.85(4H, m).

FAB-Mass: 494(M$^+$+3), 492(M$^+$+1)

IR(KBr) υ (cm$^{-1}$): 1579, 1506, 1475, 1446, 1429, 1396, 1346, 1327, 1248, 1207, 1140, 993.

EXAMPLE 196

4-(6,7-Dimethoxy-4-quinazolinyl)-N-(4-methoxyphenyl)-1-piperazinethiocarboxamide (Compound 196)

Yield 84% m.p.: 196–197° C.

$^1$H-NMR(CDCl$_3$) δ (ppm): 8.66(1H, s) , 7.46(1H, brs), 7.28(1H, ) 7.15(2H, d, J=8.9 Hz), 7.10(1H, s), 6.88(2H, d, J=8.9 Hz), 4.09–4.07(4H, m), 4.02(3H, s), 399(3H, s), 3.85–3.82(4H, m), 3.80(3H, s).

FAB-Mass: 440(M$^+$+1)

IR(KBr) υ (cm$^{-1}$): 1539, 1508, 1431, 1336, 1240, 1209, 1039, 993, 867.

EXAMPLE 197

4-(6,7-Dimethoxy-4-quinazolinyl)-N-(3-methoxybenzyl)-1-piperazinethiocarboxamide (Compound 197)

Yield: 85% m.p.: 146–147° C.

$^1$H-NMR(CDCl$_3$) δ (ppm): 8.65(1H, s), 7.29(2H, m), 7.27(6H, s), 7.11(1H, s), 6.96–6.92(2H, m), 6.86(1H, dd, J=8.3 Hz, 1.7 Hz), 5.73(2H, brt, J=4.6 Hz), 4.8(2H, d, J=4.6 Hz), 4.11–4.07(4H, m), 4.03(3H, s), 3.99(3H, s), 3.88–3.84 (4H, m), 3.82(3H, s).

FAB-Mass: 454(M$^+$+1)

IR(KBr) υ (cm$^{-1}$): 1541, 1500, 1477, 1435, 1352, 1327, 1244, 1207, 991.

EXAMPLE 198

4-(6,7-Dimethoxy-4-quinazolinyl)-N-(4-methoxybenzyl)-1-piperazinecarboxamide (Compound 198)

Substantially the same procedure as in Example 263 was repeated, except that the corresponding 4-methoxybenzylamine was used in place of 2-picolylamine, to give the desired compound.

Yield: 34% m.p.: 147–148° C.

$^1$H-NMR(CDCl$_3$) δ (ppm): 8.67(1H, s), 7.27(2H, d, J=7.6 Hz), 7.26(1H, s), 7.09(6H, s), 6.88(2H, d, J=7.6 Hz), 4.77 (1H, brt, J=5.3 Hz), 4.40(2H, a, J=5.3 Hz), 4.03(3111 s), 3.98(3H, s), 3.81(3H, s), 3.70–3.67(4H, in), 3.64–3.61(4H, in).

FAB-Mass: 438(M$^+$+1)

IR(KBr) υ (cm$^{-1}$): 1623, 1575, 1540, 1504, 1429, 1351, 1243, 1209, 1133, 1029, 993, 848.

EXAMPLE 199

4-(6,7-Dimethoxy-4-quinazolinyl)-N-(4-methoxybenzyl)-1-piperazinethiocarboxamide (Compound 199)

Substantially the same procedure as in Example 1 was repeated, except that the corresponding 4-methoxybenzyl isothiocyanate was used in place of phenyl isocyanate, to give the desired compound.

Yield: 72% m.p.: 201–204° C.

$^1$H-NMR(CDCl$_3$) δ (ppm): 8.64(1H, s), 7.30(2H, d, J=8.6 Hz), 7.27(1H, s), 7.10(1H, s), 6.90(2H, d, J=8.6 Hz), 5.69 (1H, brt, J=4.3 Hz), 4.82(2H, d, J=4.3 Hz), 4.10–4.06(4H, m), 4.03(3H, s), 3.98(3H, s), 3.87–3.83(4H, m), 3.82(3H, s).

FAB-Mass: 454(M$^+$+1)

IR(KBr) υ (cm$^{-1}$): 1506, 1477, 1449, 1431, 1346, 1248, 1209, 991.

EXAMPLE 200

4-(6,7-Dimethoxy-4-quinazolinyl)-N-(4-ethoxybenzyl)-1-piperazinecarboxamide (Compound 200)

Substantially the same procedure as in Example 263 was repeated, except that the corresponding 4-ethoxybenzylamine was used in place of 2-picolylamine, to give the desired compound.

Yield: 39% m.p.: 176–177° C.

$^1$H-NMR(CDCl$_3$) δ (ppm): 8.67(1H, s), 7.26(1H, s), 7.25 (2H, d,.

J=8.3 Hz), 7.09(1H, s), 6.87(2H, d, J=8.3 Hz), 4.75(1H, brt, 35 J=5.33 Hz), 4.39(2H, d, J=5.3 Hz), 4.04(23H, q, J=6.9 Hz)8, 4.02(31, s), 3.98(3H, s) , 3.69–3.67(4H, m) , 3.64–3.62(4H, m) , 1.41(3H t, J=6.9 Hz).

FAB-Mass: 452(M$^+$+1)

IR(KBr) υ (cm$^{-1}$)1629, 1575, 1527, 1429, 1234, 1209, 1043, 995.

EXAMPLE 201

4(6,7-Dimethoxy-4-quinazolinyl)-N-(4-propoxyphenyl)-1-piperazinecarboxamide (Compound 201)

Substantially the same procedure as in Example 164 was repeated, except that the corresponding 4-propoxybenzoic acid was used in place of 4-vinylbenzoic acid, to give the desired dcompound.

Yield: 67% m.p.: 218–220° C.

$^1$H-NMR(CDCl$_3$) δ (ppm): 8.70(1H, s), 7.26(1H, s), 7.25 (2H, d, J=8.5 Hz), 7.11(1H, s), 6.86(2H, d, J=8.5 Hz), 6.35(1H, brs), 4.03(3H, s), 4.00(3H, s), 3.89(2H, t, J=6.6 Hz), 3.74(8H, m), 1.79(2H, m), 1.02(3H, t, J=6.8 Hz).

FAB-Mass: 452(M$^+$+1)

IR(KBr) υ (cm$^{-1}$): 1637, 1573, 1508, 1473, 1419, 1234, 1211, 1133, 993.

EXAMPLE 202

4-(6,7-Dimethoxy-4-quinazolinyl)-N-(4-isopropoxyphenyl)-1-piperazinecarboxamide (Compound 202)

Substantially the same procedure as in Example 164 was repeated, except that the corresponding 4-isopropoxybenzoic acid was used in place of 4-vinylbenzoic acid, to give the desired compound.

Yield: 67% m.p.: 220–222° C.

$^1$H-NMR(CDCl$_3$) δ (ppm): 8.70(1H, s), 7.26(1H, s), 7.25 (2H, d, J=8.6 Hz), 7.11(1H, s), 6.85(2H, d, J=8.6 Hz), 6.35(1H, brs), 4.49(1H, m), 4.03(3H, s), 4.00(3H, s), 3.74 (8H, m), 1.31(6H, d, J=5.9 Hz).

FAB-Mass: 452(M$^+$+1)

IR(KBr) υ (cm$^{-1}$): 1637, 1573, 1535, 1504, 1473, 1234, 1211, 1133, 993.

EXAMPLE 203

4-(6,7-Dimethoxy-4-quinazolinyl)-N-(4-trifluoromethoxybenzyl)-1-piperazinecarboxamide (Compound 203)

Substantially the same procedure as in Example 263 was repeated, except that the corresponding 4-trifluoromethoxybenzylamine was used in place of 2-picolylamine, to give the desired compound.

m.p.: 176–177° C.

$^1$H-NMR(CDCl$_3$) δ (ppm): 8.67(1H, s), 7.37(2H, d, J=8.4 Hz), 7.26(1H, s), 7.19(2H, d, J=8.4 Hz), 7.10(1H, s), 4.93 (1H, brt, J=5.3 Hz), 4.47(2H, d, J=5.3 Hz)., 4.03(3H, s), 3.99(3H, s), 3.71–3.69(4H, m), 3.66–3.64(4H, m).

FAB-Mass: 492(M$^+$+1)

IR(KBr) υ (cm$^{-1}$): 1629, 1573, 1540, 1504, 1473, 1430, 1249, 1209, 1135, 993.

EXAMPLE 204

4-(6,7-Dimethoxy-4-quinazolinyl)-N-(4-trifluoromethoxybenzyl)-1-piperazinethiocarboxamide (Compound 204)

Substantially the same procedure as in Example 154 was repeated, except that the corresponding 4-trifluoromethoxybenzylamine was used in place of 4-isopropylbenzylamine, to give the desired compound.

Yield: 95% m.p.: 131–132° C.

$^1$H-NMR(CDCl$_3$) δ (ppm): 8.63(1H, s), 7.40(2H, d, J=8.6 Hz), 35 7.24(1H, s), 7.20(2H, d, J=8.6 Hz), 7.10(1H, s), 6.00(1H, brt, J=4.9 Hz) , 4.94(2H, d, J=4.9 Hz) , 4.13–4.07 (4H, m), 4.02(3H, s) , 3.98(3H, s), 3.88–3.84(4H,m)

FAB-Mass: 508(M$^+$+1)

IR(KBr) υ (cm$^{-1}$):1508, 1477, 1431, 1350, 1263, 1213, 1163, 991.

EXAMPLE 205

N-(3,4-Dimethoxybenzyl)-4-(6,7-dimethoxy-4-quinazolinyl)-1-piperazinethiocarboxamide (Compound 205)

Substantially the same procedure as in Example 1 was repeated, except that the corresponding 3,4-dimethoxybenzyl isothiocyanate was used in place of phenyl isocyanate, to give the desired compound.

Yield: 82% m.p.: 196–197° C.

$^1$H-NMR(CDCl$_3$) δ (ppm): 8.64(1H, s), 7.28(1H, s), 7.11(1H, s), 6.90–6.83(3H, m), 5.78(1H, brt, J=4.6 Hz), 4.82(2H, d, J=4.6 Hz), 4.11–4.07(4H,m), 4.03(3H,s), 3.98(3H,s),3.88(3H, s), 3.88(3H, s), 3.87–3.83(4H, m).

FAB-Mass: 484(M$^+$+1)

IR(KBr) υ (cm$^{-1}$):516, 1504, 1477, 1431, 1352, 1263, 1236, 1209, 1137, 1028, 991, 849.

EXAMPLE 206

N-[2-(3,4-Dimethoxyphenyl)ethyl]-4-(6,7-dimethoxy-4-quinazolinyl)-1-piperazinethiocarboxamide (Compound 206)

Substantially the same procedure as in Example 1 was repeated, except that the corresponding 2-(3,4-dimethoxyphenyl)ethyl isothiocyanate was used in place of phenyl isocyanate, to give the desired compound.

Yield: 71% m.p.: 98–100° C.

$^1$H-NMR(CDCl$_3$) δ (ppm): 8.63(1H, s), 7.25(1H, s), 7.10(1H, s), 6.84–6.75(3H, m), 5.69(1H, brt, J=5.3 Hz), 4.03(3H, s), 4.01–3.93(6H, m), 3.98(3H, s), 3.88(3H, s), 3.87(3H, S), 3.84–3.80(4H, m), 2.93(2H, t, J=7.3 Hz).

FAB-Mass: 498(M$^+$+1)

IR(KBr) υ (cm$^{-1}$): 1576, 1506, 1475, 1429, 1344, 1261, 1236, 1211, 1138, 1028, 993.

EXAMPLE 207

N-(3-Cyclopentyloxy-4-methoxyphenyl)-4-(6,7-dimethoxy-4-quinazolinyl)-1-piperazinethiocarboxamide (Compound 207)

Substantially the same procedure as in Example 154 was repeated, except that the corresponding 3-cyclopentyloxy-4-methoxyaniline was used in place of 4-isopropylbenzylamine, to give the desired compound.

Yield: 77%

$^1$H-NMR(CDCl$_3$) δ (ppm): 8.64(1H, s), 7.78(1H, brs), 7.23(1H, s), 7.09(1H, s), 6.84(1H, d, J=2.3 Hz), 6.80(1H, d, J=8.6 Hz), 6.71(1H, dd, J=8.6 Hz, 2.3 Hz), 4.69(1H, m), 4.09–4.04(4H, m), 4.01(3H, s), 3.98(3H, s), 3.95–3.81(4H, m), 3.81(3H, s), 1.98–1.76(6H, m), 1.58(2H, m).

FAB-Mass: 524(M$^+$+1)

In the following Examples 208–212, substantially the same procedure as in Example 1 was repeated, except that the corresponding isocyanate or isothiocyanate was used in place of phenyl isocyanate, to give the desired compound.

EXAMPLE 208

4-(6,7-Dimethoxy-4-quinazolinyl)-N-(3,4-methylenedioxybenzyl)-1-piperazinethiocarboxamide (Compound 208)

Yield: 72% m.p.: 113–114° C.

$^1$H-NMR(CDCl$_3$) δ (ppm): 8.63(1H, s), 7.24(1H, s), 7.10(1H, s), 6.87(1H, d, J=1.3 Hz), 6.81(1H, dd, J=7.9 Hz, 1.3 Hz), 6.77(1H, d, J=7.9 Hz), 5.95(2H, s), 5.89(1H, brt, J=5.0 Hz), 4.79(2H, d, J=5.0 Hz), 4.11–4.07(4H, n), 4.02(3H, s), 3.98(3H, s)4 3.87–3.83(4H, m).

FAB-Mass: 468(M$^+$+1)

IR(KBr) 1(cm$^{-1}$): 1579, 1504, 1483, 1452, 1352, 1238, 1215, 1038, 991, 935, 849.

EXAMPLE 209

4-(6,7-Dimethoxy-4-quinazolinyl)-N-(3,4-ethylenedioxyphenyl)-1-piperazinethiocarboxamide (Compound 209)

Yield: 81% m.p. : 165–166° C.

$^1$H-NMR(CDCl$_3$) δ (ppm) : 8.64(1H, s), 7.56(1H, brs), 7.24(1H, s), 7.09(1H, s), 6.81(1H, dd, J=8.6 Hz, 2.3 Hz), 6.74(1H, d, J=2.3 Hz), 6.67(1H, d, J=8.6 Hz), 4.23–4.22(4H, m), 4.07–4.04(4H, m), 4.01(3H, s), 3.98(3H, s), 3.83–3.81(4H, m).

FAB-Mass: 468(M$^+$+1)

IR(KBr) υ (cm$^{-1}$): 1533, 1508, 1479, 1433, 1340, 1246, 1207, 1068, 991.

EXAMPLE 210

4-(6,7-Dimethoxy-4-quinazolinyl)-N-[2-(6,7,9,10,12,13,15,16-octahydro-5,8,11,14,17-pentaoxabenzocyclopentadecenyl)]-1-piperazinecarboxamide (Compound 210)

Yield: 15% m.p.: 163–164° C.

$^1$H-NMR(CDCl$_3$) δ (ppm): 8.69(1H, s), 7.25(1H, s), 7.19(1H, s), 7.09(1H, s), 6.79-6.76(2H, m), 6.65(1H, brs), 4.14–4.09(4H, 30 m), 4.03(3H, s), 4.00(3H, s), 3.91–3.86(4H, m), 3.75(16H, m).

FAB-Mass: 584(M$^+$+1)

IR(KBr) υ (cm$^{-1}$): 1633, 1572, 1512, 1506, 1477, 1425, 1352, 1242, 1211, 1134, 996, 856, 800.

EXAMPLE 211

4-(6,7-Dimethoxy-4-quinazolinyl)-N-[2-(6,7,9,10,12,13,15,16,18,19-decahydro-5,8,11,14,17,20-hexaoxabenzocyclooctadecenyl)]-1-piperazinecarboxamide (Compound 211)

Yield: 39%

$^1$H-NMR(CDCl$_3$) δ (ppm): 8.67(1H, s), 7.28–7.26(2H, m), 7.20(1H, brs), 7.11(1H, s), 6.89(1H, dd, J=8.6 Hz, 2.0 Hz), 6.72(1H, d, J=8.6 Hz), 4.09(4H, m), 4.03(3H, s), 4.00(3H, s), 3.86(4H, m), 3.74–3.67(20H, m).

FAB-Mass: 628(M$^+$+1)

EXAMPLE 212

4-(6,7-Dimethoxy-4-quinazolinyl)-N-(3,4,5-trimethoxyphenyl)-1-piperazinecarboxamide (Compound 212)

Yield: 100% m.p.: 198–199° C.

$^1$H-NMR(CDCl$_3$) δ (ppm): 8.69(1H, s), 7.26(1H, s), 7.11(1H, s), 6.78(1H, brs), 6.72(2H, s), 4.02(3H, s), 3.99(3H, s), 3.82(6H, 20 s), 3.82(3H, s), 3.74(8H, m).

FAB-Mass: 484(M$^+$+1)

IR(KBr) υ (cm$^{-1}$): 1630, 1606, 1506, 1452, 1425, 1236, 1209, 1126, 997.

EXAMPLE 213

4-(6,7-Dimethoxy-4-quinazolinyl)-N-(3,4,5-trimethoxybenzyl)-1-piperazinecarboxamide (Compound 213)

Substantially the same procedure as in Example 119 was repeated, except that the corresponding 3,4,5-trimethoxybenzylamine was used in place of 2-(4-chlorophenyl)ethylamine, to give the desired compound.

Yield: 53%

$^1$H-NMR(CDCl$_3$) δ (ppm): 8.67(1H, s), 7.28(1H, s), 7.10 (1H, s), 35 6.56(2H, s), 4.93(1H, brt, J=5.3 Hz), 4.40(2H, d, J=5.3 Hz), 4.03(3H, s), 3.98(3H, s), 3.86(3H, s), 3.81(6H, s), 3.68–3.67(8H, m).

FAB-Mass: 498(M$^+$+1)

EXAMPLE 214

4-(6,7-Dimethoxy-4-quinazolinyl)-N-(4-hydroxymethylbenzyl)-1-piperazinecarboxamide (Compound 214)

To a solution of 1.50 g (5.48 mmol) of 6,7-dimethoxy-4-piperazinylquinazoline obtained according to the method described in South African Patent No. 67 06512 (1968) in 40 ml of dimethylformamide was added 1.10 g (6.56 mmol) of 4-(chloromethyl)phenyl isocyanate, followed by overnight stirring at room temperature. The reaction mixture was poured into water, and sodium chloride was added thereto. The precipitated crystals were collected by filtration, washed with water, and dried, followed by purification by silica gel column chromatography to give the desired compound as colorless crystals.

Yield: 25% m.p.: 228–229° C.

$^1$H-NMR(CDCl$_3$) δ (ppm): 8.68(1H, s), 7.38–7.32(5H, m), 7.11(1H, s), 6.68(1H, br), 4.64(2H, s), 4.03(3H, s), 4.00(3H, s), 3.73(8H, m), 1.74(1H, br).

FAB-Mass: 424(M$^+$+1)

IR(KBr) υ (cm$^{-1}$): 3125, 1657, 1597, 1529, 1508, 1470, 1423, 1360, 1308, 1230, 1205, 991, 931, 854.

EXAMPLE 215

(dl)-4-(6,7-Dimethoxy-4-quinazolinyl)-N-[4-(1-hydroxyethyl)phenyl]-1-piperazinecarboxamide (Compound 215)

To a suspension of 38 mg (1.0 mmol) of sodium borohydride in 50 ml of isopropyl alcohol was added 435 mg (1.00 mmol) of N-(4-acetylphenyl)-4-(6,7-dimethoxy-4-guinazolinyl)-1-piperazinecarboxamide obtained in Example 87, followed by overnight stirring at room temperature. After the solvent was evaporated, the residue was dissolved in chloroform. The resulting solution was washed successively with 1 N hydrochloric acid, water, a saturated aqueous solution of sodium hydrogencarbonate and a saturated aqueous solution of sodium chloride, and then dried over magnesium sulfate. After the solvent was evaporated, the residue was purified by silica gel chromatography and recrystallized from ethyl acetate to give the desired compound as colorless crystals.

Yield: 98% m.p.: 228–230° C.

$^1$H-NMR(CDCl$_3$) δ (ppm): 8.70(1H, s), 7.36(2H, d, J=9.2 Hz), 7.32(2H, d, J=9.2 Hz), 7.28(1H, s), 7.12(1H, s), 6.43 (1H, brs), 4.87(1H, q, J=6.3 Hz), 4.04(3H, s), 4.00(3H, s), 3.75(8H, m), 15 1.48(3H, d, J=6.3 Hz).

FAB-Mass: 398(M$^+$+1)

IR(KBr) υ (cm$^{-1}$): 3330, 1664, 1577, 1506, 1475, 1417, 1241, 1211, 1137, 993.

EXAMPLE 216

N-(4-Acetoxyphenyl)-4-(6,7-dimethoxy-4-quinazolinyl)-1-piperazinecarboxamide (Compound 216)

Substantially the same procedure as in Example 164 was repeated, except that the corresponding 4-acetoxybenzoic acid was used in place of 4-vinylbenzoic acid, to give the desired compound.

Yield: 67% m.p.: 197–199° C.

$^1$H-NMR(CDCl$_3$) δ (ppm): 8.70(1H, s), 7.39(2H, d, J=8.9 Hz), 7.28(1H, s), 7.12(1H, s), 7.04(2H, d, J=8.9 Hz), 6.45 (1H, brs), 4.04(3H, s), 4.00(3H, s), 3.75(8H, m), 2.29(3H, s).

FAB-Mass: 452(M ++1)

IR(KBr) υ (cm$^{-1}$): 1730, 1631, 1505, 1450, 1429, 1241, 1211, 993, 916,

EXAMPLE 217

4-(6,7-Dimethoxy-4-quinazolinyl)-N-(3-methylthiophenyl)-1-piperazinecarboxamide (Compound 217)

Substantially the same procedure as in Example 1 was repeated, except that the corresponding 3-methylthiophenyl isocyanate was used in place of phenyl isocyanate, to give the desired compound.

Yield: 96% m.p.: 180–181° C.

$^1$H-NMR(CDCl$_3$) δ (ppm): 8.56(1H, s), 7.35(bH, brs), 7.26(2H, s), 7d12(H, s), 7.05–7.03(2H, m), 6.97(sH, m), 6.76(1H, m), 3.89(3H, s), 3.86(3H, s), 3.61–3.59(8H, m), 2.30(3H, s).

FAB-Mass: 440(M$^+$+1)

IR(KBr) υ (cm$^{-1}$): 151, 1583, 1537, 1504, 1477, 1421, 1242, 1209, 993.

EXAMPLE 218

4-(6,7-Dimethoxy-4-quinazolinyl)-N-(4-methylthiophenyl)-1-piperazinethiocarboxamide (Compound 218)

Substantially the same procedure as in Example 154 was repeated, except that the corresponding 4-methylthioaniline was used in place of 4-isopropylbenzylamine, to give the desired compound.

Yield: 77% m.p.: 214–216° C.

$^1$H-NMR(DMSO-d$_6$) δ (ppm): 9.41(1H, brs), 8.55((H, s), 7.28(2H, d, J=8.9 Hz), 7.25(1H, s), 7.23(1H, s), 7.21(2H, a, J=8.9 Hz), 4.13–4.02(4H, m), 3.94(3H, s), 3.94(3H, m), 3.90–3.85(4H, m), 2.47(3H, s).

FAB-Mass: 456(M$^+$+1)

IR(KBr) υ (cm$^{-1}$): 1514, 1433, 1336, 1238, 1211, 993.

EXAMPLE 219

4-(6,7-Dimethoxy-4-quinazolinyl)-N-(4-ethylthiophenyl)-1-piperazinecarboxamide (Compound 219)

Substantially the same procedure as in Example 164 was repeated, except that the corresponding 4-ethylthiobenzoic acid was used in place of 4-vinylbenzoic acid, to give the desired compound.

Yield: 77% m.p.: 208–209° C.

$^1$H-NMR(CDCl$_3$) δ (ppm): 8.70(1H, s), 7.32(4H, s), 7.27 (1H, s), 7.11(1H, s), 6.45(1H, brs), 4.03(3H, s), 4.00(3H, s), 3.75(8H, m), 2.89(2H, q, J=7.3 Hz), 1.28(3H, t, J=7.3 Hz).

FAB-Mass: 454(M$^+$+1)

IR(KBr) υ (cm$^{-1}$): 1641, 1573, 1502, 1448, 1436, 1236, 1211, 1135, 991, 846.

EXAMPLE 220

4-(6,7-Dimethoxy-4-quinazolinyl)-N-(4-trifluoromethylthiophenyl)-1piperazinethiocarboxamide (Compound 220)

Substantially the same procedure as in Example 154 was repeated, except that the corresponding 4-trifluoromethylthioaniline was used in place of 4-isopropylbenzylamine, to give the desired compound.

Yield: 87% m.p.: 128–131° C.

$^1$H-NMR(CDCl$_3$) δ (ppm): 8.66(1H, s), 8.17(1H, brs), 7.59(2H, d, 25 J=7.9 Hz), 7.29(2H, d, J=7.9 Hz), 7.23(1H, s), 7.08(1H, s), 4.10–4.07(4H, m), 4.00(3H, s), 3.98(3H, s), 3.86–3.83(4H, m).

FAB-Mass: 510(M$^+$+1) IR(KBr) υ (cm$^{-1}$): 1578, 1506, 1477, 1458, 1427, 1346, 1238, 1209, 1155, 1128, 1109, 989, 851.

EXAMPLE 221

N-(4-Aminophenyl)-4-(6,7-dimethoxy-4-quinazolinyl)-1-piperazinecarboxamide (Compound 221)

In 50 ml of ethanol was suspended 1.5 g (3.7 mmol) of 4-(6,7-dimethoxy-4-quinazolinyl)-N-(4-nitrophenyl)-1-piperazinecarboxamide obtained in Example 77, and a suspension of 500 mg of 10% palladium-carbon in 10 ml of water and 10 ml of ethanol was added thereto, followed by stirring in a stream of hydrogen at room temperature for 5 hours. After the catalyst was separated by filtration using Celite, the solvent was evaporated. Then, the residue was purified by silica gel chromatography and recrystallized from ethyl acetate to give the desired compound as colorless crystals.

Yield: 29% m.p.: 215–217° C.

1H-NMR(CDCl$_3$) δ (ppm): 8.69(1H, s), 7.26(1H, s), 7.13(2H, d, J=9.0 Hz), 7.11(1H, s), 6.65(2H, d, J=9.0 Hz), 6.26(1H, brs), 4.03(3H, s), 3.99(3H, s), 3.72(8H, m), 3.56 (2H, brs).

FAB-Mass: 409(M$^+$+1)

IR(KBr) υ (cm$^{-1}$): 1556, 1508, 1406, 1257, 1213, 910, 835, 711.

EXAMPLE 222

4-(6,7-Dimethoxy-4-quinazolinyl)-N-(4-dimethylaminophenyl)-1-piperazinecarboxamide (Compound 222)

Substantially the same procedure as in Example 164 was repeated, except that the corresponding 4-dimethylaminobenzoic acid was used in place of 4-vinylbenzoic acid, to give the desired compound.

Yield: 63% m.p.: 252–254° C.

$^1$H-NMR(CDCl$_3$) δ (ppm): 8.69(1H, s), 7.26(1H, s), 7.20 (2H, d, J=8.9 Hz), 7.11(1H, s), 6.71(2H, d, J=8.9 Hz), 6.31(1H, brs), 4.03(3H, s), 4.00(3H, s), 3.72(8H, m), 2.91 (6H, s).

FAB-Mass: 437(M$^+$+1)

IR(KBr) υ (cm$^{-1}$): 1631, 1523, 1504, 1483, 1450, 1348, 1255, 1209, 1135, 993, 937, 848.

EXAMPLE 223

4-(6,7-Dimethoxy-4-quinazolinyl)-N-(4-dimethylaminobenzyl)-1-piperazinecarboxamide (Compound 223)

Substantially the same procedure as in Example 263 was repeated, except that the corresponding 4-dimethylaminobenzylamine was used in place of 2-picolylamine, to give the desired compound.

Yield: 28% m.p.: 188–190° C.

$^1$H-NMR(CDCl$_3$) δ (ppm): 8.67(1H, s), 7.26(1H, s), 7.21 (2H, d, 10 J=9.0 Hz), 7.09(1H, s), 6.72(2H, d, J=9.0 Hz), 4.66(1H, brt, J=5.2 Hz), 4.36(2H, d, J=5.2 Hz), 4.03(3H, s), 3.99(3H, s), 3.70–3.67(4H, m), 3.63–3.61(4H, m), 2.95(6H, s).

FAB-Mass: 451(M$^+$+1)

IR(KBr) υ (cm$^{-1}$): 1646, 1575, 1521, 1506, 1475, 1430, 1351, 1247, 1213, 1133, 993.

EXAMPLE 224

4-(6,7-Dimethoxy-4-quinazolinyl)-N-(4-dimethylaminobenzyl)-1-piperazinethiocarboxamide (Compound 224)

Substantially the same procedure as in Example 185 was repeated, except that the corresponding 4-dimethylaminobenzylamine was used in place of 4-bromobenzylamine, to give the desired compound.

Yield: 71% m.p.: 177–178° C.

$^1$H-NMR(CDCl$_3$) δ (ppm): 8.63(1H, s), 7.24(2H, d, J=8.6 Hz), 7.24(1H, s), 7.10(1H, s), 6.71(2H, d, J=8.6 Hz), 5.73 (1H, brt, J=4.3 Hz), 4.75(2H, d, J=4.3 Hz), 4.08–4.04(4H, m), 4.02(3H, s), 3.98(3H, s), 3.85–3.81(4H, m), 2.95(6H, s).

FAB-Mass: 467(M$^+$+1)

IR(KBr) υ (cm$^{-1}$): 1522, 1504, 1475, 1431, 1352, 1327, 1211, 991.

EXAMPLE 225

N-(4-Diethylaminophenyl)-4-(6,7-dimethoxy-4-quinazolinyl)-1-piperazinecarboxamide (Compound 225)

Substantially the same procedure as in Example 164 was repeated, except that the corresponding 4-diethylaminobenzoic acid was used in place of 4-vinylbenzoic acid, to give the desired compound.

Yield: 32% m.p.: 221–223° C.

$^1$H-NMR(CDCl$_3$) δ (ppm): 8.69(1H, s), 7.26(1H, s), 7.17 (2H, d, 10 J=9.0 Hz), 7.12(5H, s), 6.64(2H, d, J=9.1 Hz), 6.22(mH, brs), 4.03(3H, s), 4.00(3H, s), 3.73(8H, m), 3.32 (4H, q, J=6.9 Hz), 1.13(6.(, t, J=6.9 Hz).

FAB-Mass: 465(M$^+$+1)

IR(KBr) υ (cm$^{-1}$): 1633, 1575, 1506, 1475, 1423, 1351, 1245, 1211, 1133, 993.

EXAMPLE 226

N-(3-Acetamidophenyl)-4-(6,7-dimethoxy-4-quinazolinyl)-1-piperazinethiocarboxamide (Compound 226)

Substantially the same procedure as in Example 1 was repeated, except that the corresponding 3-acetamidophenyl isothiocyanate was used in place of phenyl isocyanate, to give the desired compound.

Yield: 92% m.p.: 207–208° C.

$^1$H-NMR(CDCl$_3$) δ (ppm): 8.66(1H, s), 8.07(1H, brs), 7.90(2H, s), 7.56(Hz, brs), 7.25(sH, s), 7.19(2H , m, 7.11 (11z , m), 7.09(bs, s), 6.97(11, d, J=7.9 Hz), 4.02(4H, m), 4.02(3H, s), 3.99(3H, s), 3.79(4H, m), 2.10(3z, s).

FAB-Mass: 467(M$^+$+1)

IR(KBr) 1(cm$^{-1}$): 1662, 1574, 1506, 1481, 1429, 1336, 1242, 1225, 1211, 991.

EXAMPLE 227

4-(6,7-Dimethoxy-4-quinazolinyl)-N-[4-(N,N-dimethylaminomethyl)phenyl]-1-piperazinecarboxamide (Compound 227)

Substantially the same procedure as in Example 100 was repeated, except that the corresponding dimethylamine was used in place of piperidine, to give the desired compound.

Yield: 56% m.p.: 213–215° C.

$^1$H-NMR(CDCl$_3$) δ (ppm): 8.69(1H, s), 7.42(2H, d, J=8.3 Hz), 7.32(2H, d, J=8.3 Hz), 7.26(1H, s), 7.11(1H, s), 6.78 (1H, brs), 10 4.04(3H, s), 4.00(3H, s), 3.76(8H, m), 3.60(2H, s), 2.38(6H, s).

FAB-Mass: 451(M$^+$+1)

IR(KBr) υ (cm$^{-1}$): 1646, 1575, 1504, 1473, 1429, 1241, 1211, 1133, 993, 858, 848.

EXAMPLE 228

N-[4-(N-tert-Butoxycarbonylaminomethyl)phenyl]-4-(6,7-dimethoxy-4-quinazolinyl)-1-piperazinethiocarboxamide (Compound 228)

Substantially the same procedure as in Example 1 was repeated, except that the corresponding 4-(N-tert-butoxycarbonylaminomethyl)phenyl isothiocyanate was used in place of phenyl isocyanate, to give the desired compound.

C Yield: 93% m.p.: 123–126° C.

$^1$H-NMR(CDCl$_3$) δ (ppm):8.65(1H, s),7.93(1H, brs), 7.24 (1H, s), 7.22(2H, d, J=8.9 Hz), 7.16(2H, d, J=8.9 Hz), 7.09(1H, s), 5.18(1H, br), 4.26(2H, d, J=5.6 Hz), 4.07(4H, m), 4.01(3H, s), 3.98(3H, s), 3.82–3.79(4H, m), 1.45(9H, s).

FAB-Mass: 539(M$^+$+1)

IR(KBr) υ (cm$^{-1}$): 1695, 1583, 1531, 1506, 1479, 1429, 1336, 1252, 1207.

EXAMPLE 229

4-(6,7-Dimethoxy-4-quinazolinyl)-N-(4-phenylazophenyl)- 1-piperazinecarboxamide (Compound 229) Substantially the same procedure as in Example 164 was repeated, except that the corresponding 4-phenylazobenzoic acid was used in place of 4-vinylbenzoic acid, to give the desired compound.

Yield: 65% m.p.: 244–246° C.

$^1$H-NMR(CDCl$_3$) δ (ppm): 8.71(1H, s), 7.94–7.87(4H, m), 7.59–7.42(5H, m), 7.28(1H, s), 7.11(1H, s), 6.73(1H, brs), 4.04(3H, s), 4.01(3H, s), 3.78(8H, m).

FAB-Mass: 498(M$^+$+1)

IR(KBr) (cm$^{-1}$): 1645, 1506, 1473, 1436, 1242, 1211, 993, 846.

EXAMPLE 230

N-(4-Azidophenyl)-4-(6,7-dimethoxy-4-quinazolinyl)-1-piperazinethiocarboxamide (Compound 230)

Substantially the same procedure as in Example 1 was repeated, except that the corresponding 4-azidophenyl isothiocyanate was used in place of phenyl isocyanate, to give the desired compound.

Yield: 86%

$^1$H-NMR(CDCl$_3$) δ (ppm): 8.66(1H, s), 7.57(1H, brs), 7.27(2H, d, J=8.6 Hz), 7.22(1H, s), 7.10(1H, s), 7.01(2H, d, J=8.6 Hz), 4.16–4.09(4H, m), 4.02(3H, s), 3.99(3H, s), 3.87–3.83(4H, m).

FAB-Mass: 451(M$^+$+1)

EXAMPLE 231

4-(6,7-Dimethoxy-4-quinazolinyl)-N-(4-nitrobenzyl)-1-piperazinethiocarboxamide (Compound 231)

Substantially the same procedure as in Example 185 was repeated, except that the corresponding 4-nitrobenzylamine was used in place of 4-bromobenzylamine, to give the desired compound.

Yield: 85% m.p.: 214–216° C.

$^1$H-NMR(CDCl$_3$) δ (ppm): 8.64(1H, s), 8.17(2H, d, J=8.6 Hz), 7.51(2H, d, J=8.6 Hz), 7.26(1H, s), 7.11(1H, s), 6.16 (1H, brt, J=5.3 Hz), 5..09(2H, d, J=5.3 Hz), 4.17–4.14(4H, m), 4.03(3H, s), 3.99(3H, s), 3.91–3.87(4H, m).

IR(KBr) V (cm$^{-1}$): 1502, 1475, 1427, 1346, 1327, 1234, 1205, 1134, 989, 860.

In the following Examples 232–242, substantially the same procedure as in Example 1 was repeated, except that the corresponding isocyanate or isothiocyanate was used in place of phenyl isocyanate, to give the desired compound.

EXAMPLE 232

4-(6,7-Dimethoxy-4-quinazolinyl)-N-(4-nitrobenzoyl)-1-piperazinethiocarboxamide (Compound 232)

Yield: 27% m.p.: 103–105° C.

$^1$H-NMR(CDCl$_3$) δ (ppm): 8.68(1H, s), 8.34(2H, d, J=8.9 Hz), 8.06(2H, d, J=8.9 Hz), 7.29(1H, brs), 7.27(1H, s), 7.10(1H, s), 4.41(2H, m), 4.03(3H, s), 4.00(3H, s), 3.91(6H, m).

FAB-Mass: 483(M$^+$+1)

IR(KBr) υ (cm$^{-1}$): 1579, 1506, 1475, 1427, 1348, 1244, 1211, 991, 833, 717.

EXAMPLE 233

4-(6,7-Dimethoxy-4-quinazolinyl)-N-(4-methyl-3-nitrophenyl)-1-piperazinecarboxamide (Compound 233)

Yield: 94%

$^1$H-NMR(DMSO-d$_6$) d(ppm): 9.04(1H, brs), 8.58(1H, s), 8.27(1H, 30 s), 7.75(1H, d, J=8.5 Hz), 7.38(1H, d, J=8.5

Hz), 7.25(1H, s), 7.20(1H, s), 3.94(4H, m), 3.71(4H, m), 3.36(3H, s), 3.36(3H, s), 2.45(3H, s).

FAB-Mass: 453(M$^+$+1)

EXAMPLE 234

N-(4-Chloro-2-nitrophenyl)-4-(6,7-dimethoxy-4-quinazolinyl)-1-piperazinecarboxamide (Compound 234)

Yield: 89% m.p.: 205–206° C.

$^1$H-NMR(CDCl$_3$) δ (ppm): 10.10(1H, brs), 8.66(1H, s), 8.57(1H, d, J=9.2 Hz), 8.18(1H, d, J=2.3 Hz), 7.59(1H, dd, J=9.2 Hz, 2.3 Hz), 7.26(1H, s), 7.15(1H, s), 4.04(3H, s), 4.02(3H, s), 4.00–3.82(8H, m).

FAB-Mass: 475(M$^+$+3), 473(M$^+$+1)

IR(KBr) υ (cm$^{-1}$): 1686, 1660, 1578, 1508, 1429, 1358, 1335, 1267, 1238, 1209, 991.

EXAMPLE 235

N-(4-Chloro-3-nitrophenyl)-4-(6,7-dimethoxy-4-quinazolinyl)-1-piperazinethiocarboxamide (Compound 235)

Yield: 74%

$^1$-NMR(DMSO-d$_6$) δ (ppm): 9.81(1H, brs), 8.56(1H, s), 8.15(1H, d, J=2.3 Hz), 7.76-7.67(2H, m), 7.25(1H, s), 7.24(1H, s), 4.16(4H, m), 3.94(3H, s), 3.94(3H, s), 3.87(4H, m).

FAB-Mass: 491(M$^+$+3), 489(M$^+$+1)

EXAMPLE 236

4-(6,7-Dimethoxy-4-quinazolinyl)-N-(3,4-dinitrophenyl)-1-piperazinecarboxamide (Compound 236)

Yield: 82% m.p.: 273–274° C.

$^1$H-NMR(DMSO-d$_6$) δ (ppm): 9.60(1H, brs), 8.87(2H, s), 8.58(1H, s), 8.40(1H, s), 7.25(1H, s), 7.20(1H, s), 3.94(3H, s), 3.94(3H, s), 3.76–3.74(8H, m).

FAB-Mass: 484(M$^+$+1)

IR(KBr) υ (cm$^{-1}$): 1645, 1535, 1502, 1471, 1427, 1346, 1252, 1209, 1136, 991, 729.

EXAMPLE 237

4-(6,7-Dimethoxy-4-quinazolinyl)-N-(4,5-dimethyl-2-nitrophenyl)-1-piperazinecarboxamide (Compound 237)

Yield: 76% m.p.: 213–215° C.

$^1$H-NMR(CDCl$_3$) δ (ppm): 10.28(1H, brs), 8.70(1H, s), 8.43(1H, s), 7.98(1H, s), 7.28(1H, s), 7.13(1H, s), 4.04(3H, s), 4.02(3H, s), 3.85-3.78(8H, m), 2.34(3H, s), 2.27(3H, s).

FAB-Mass: 467(M$^+$+1)

IR(KBr) υ (cm$^{-1}$): 1686, 1578, 1508, 1448, 1329, 1246, 1209, 993.

EXAMPLE 238

N-(3-Cyanophenyl)-4-(6,7-dimethoxy-4-quinazolinyl)-1-piperazinethiocarboxamide (Compound 238)

Yield: 79% m.p.: 169–170° C.

$^1$H-NMR(CDCl$_3$) δ (ppm): 8.67(1H, s), 7.58–7.54(2H, m), 7.48–7.45(2H, m), 7.27(1H, s), 7.27(1H, brs), 7.11(1H, s), 4.17–4.15(4H, m), 4.03(3H, s), 4.00(3H, s), 3.91–3.87(4H, m).

FAB-Mass: 435(M$^+$+1)

IR(KBr) υ (cm$^{-1}$): 2220, 1578, 1541, 1506, 1479, 1429, 1313, 1240, 1211, 993.

EXAMPLE 239

N-(4-Cyanophenyl)-4-(6,7-dimethoxy-4-quinazolinyl)-1-piperazinecarboxamide (Compound 239)

Yield: 90% m.p.: 274–275° C.

$^1$H-NMR(DMSO-d$_6$) δ (ppm): 9.15(1H, brs), 8.58(1H, s), 7.70(4H, s), 7.24(1H, s), 7.19(1H, s), 3.94(3H, s), 3.94(3H, s), 3.71–3.70(8H, m).

FAB-Mass: 419(M$^+$+1)

IR(KBr) υ (cm$^{-1}$): 2222, 1659, 1593, 1524, 1429, 1385, 1360, 1319, 1248, 1234, 1209, 1136, 996, 933, 837.

EXAMPLE 240

N-(4-Cyanobenzyl)-4-(6,7-dimethoxy-4-quinazolinyl)-1-piperazinethiocarboxamide (Compound 240)

Yield: 87% m.p.: 186–187° C.

$^1$H-NMR(CDCl$_3$) δ (ppm): 8.62(1H, s), 7.58(2H, d, J=8.4 Hz), 7.45(2H, d, J=8.4 Hz), 7.24(1H, s), 7.11(1H, s), 6.37 (1H, brt, J=5.4 Hz), 5.03(2H, d, J=5.4 Hz), 4.16–4.12(4H, m), 4.02(3H, s), 3.98(3H, s), 3.89–3.85(4H, m).

FAB-Mass: 449(M$^+$+1)

IR(KBr) υ (cm$^{-1}$): 2220, 1543, 1502, 1475, 1414, 1387, 1333, 1236, 1207, 1134, 1014, 989, 931.

EXAMPLE 241

N-(3-Acetylphenyl)-4-(6,7-dimethoxy-4-quinazolinyl)-1-piperazinethiocarboxamide (Compound 241)

Yield: 71% m.p.: 192–193° C.

$^1$H-NMR(CDCl$_3$) δ (ppm): 8.66(1H, s), 7.80(1H, brs), 7.75(1H, d, J=7.6 Hz), 7.54–7.43(3H, m), 7.26(1H, s), 7.10(1H, s), 4.15–4.11(4H, m), 4.03(3H, s), 3.99(3H, s), 3.88–3.86(4H, m), 2.60(3H, s).

FAB-Mass: 452(M$^+$+1)

IR(KBr) 1)(cm$^{-1}$): 1666, 1541, 1506, 1473, 1448, 1425, 1302, 1236, 1203, 1188, 991.

EXAMPLE 242

N-(4-Acetylphenyl)-4-(6,7-dimethoxy-4-quinazolinyl)-1-piperazinethiocarboxamide (Compound 242)

Yield: 79% m.p.: 256–257° C.

$^1$H-NMR(DMSO-d$_6$) $^6$(ppm): 9.69(1H, brs), 8.55(1H, s), 7.90(2H, d, J=8.3 Hz), 7.52(2H, d, J=8.3 Hz), 7.25(1H, s), 7.24(1H, s), 4.13(4H, m), 3.94(3H, s), 3.94(3H, s), 3.85(4H, m), 2.54(3H, s).

FAB-Mass: 452(M$^+$+1)

IR(KBr) υ (cm$^{-1}$): 1678, 1574, 1506, 1429, 1358, 1319, 1269, 1240, 1211, 1136, 993, 941, 870.

EXAMPLE 243

4-(6,7-Dimethoxy-4-quinazolinyl)-N-(4-trifluoroacetylphenyl)-1-piperazinecarboxamide (Compound 243)

Substantially the same procedure as in Example 164 was repeated, except that the corresponding 4-trifluoroacetylbenzoic acid was used in place of 4-vinylbenzoic acid, to give the desired compound.

Yield: 15% m.p.: 144–146° C.

$^1$H-NMR(CDCl$_3$) δ (ppm): 8.70(1H, s), 8.05(2H, d, J=8.4 Hz), 7.59(2H, d, J=8.4 Hz), 7.28(1H, s), 7.11(1H, s), 6.80 (1H, brs), 4.04(3H, s), 4.01(3H, s), 3.79(8H, m).

FAB-Mass: 490(M$^+$+1)

IR(KBr) υ (cm$^{-1}$): 1654, 1641, 1589, 1577, 1506, 1473, 1423, 1232, 1207, 1168, 991, 939, 769.

EXAMPLE 244

N-(4-Butyrylphenyl)-4-(6,7-dimethoxy-4-quinazolinyl)-1-piperazinethiocarboxamide (Compound 244)

Substantially the same procedure as in Example 154 was repeated, except that the corresponding 4-butyrylaniline was used in place of 4-isopropylbenzylamine, to give the desired compound.

Yield: 86% m.p.: 218–219° C.

$^1$H-NMR(DMSO-d$_6$) δ (ppm): 9.69(1H, brs), 8.55(1H, s), 7.91(2H, d, J=8.9 Hz), 7.51(2H, d, J=8.9 Hz), 7.25(1H, s), 7.24(1H, s), 4.14–4.12(4H, m), 3.94(3H, s), 3.94(3H, s), 3.86–3.85(4H, m), 2.96(2H, t, J=7.3 Hz), 1.64(2H, tq, J=7.3 Hz, 7.3 Hz), 0.93(3H, t, J=7.3 Hz).

FAB-Mass: 480(M$^+$+1)

IR(KBr) υ (cm$^{-1}$): 1680, 1576, 1508, 1462, 1429, 1313, 1238, 1211, 993.

EXAMPLE 245

N-(4-Benzoylphenyl)-4-(6,7-dimethoxy-4-quinazolinyl)-1-piperazinecarboxamide (Compound 245)

Substantially the same procedure as in Example 164 was repeated, except that the corresponding 4-benzoylbenzoic acid was used in place of 4-vinylbenzoic acid, to give the desired compound.

Yield: 55% m.p.: 240–241° C.

$^1$H-NMR(DMSO-d$_6$) δ (ppm): 9.34(1H, brs), 8.58(1H, s), 7.76(2H, 15 d, J=8.6 Hz), 7.72(4H, m), 7.58(1H, m), 7.54 (2H, d, J=8.6 Hz), 7.24(1H, s), 7.20(1H, s), 3.94(3H, s), 3.94(3H, s), 3.73–3.71(8H, m).

FAB-Mass: 498(M$^+$+1)

IR(KBr) υ (cm$^{-1}$): 1637, 1616, 1508, 1473, 1438, 1238, 1211, 991, 848.

EXAMPLE 246

N-(3-Carboxyphenyl)-4-(6,7-dimethoxy-4-quinazolinyl)-1-piperazinethiocarboxamide (Compound 246)

Substantially the same procedure as in Example 1 was repeated, except that the corresponding 3-carboxyphenyl isothiocyanate was used in place of phenyl isocyanate, to give the desired compound.

Yield: 96%

$^1$H-NMR(DMSO-d$_6$) δ (ppm): 9.62(1H, brs), 8.55(1H, s), 7.94(1H, s), 7.72(1H, d, J=7.6 Hz), 7.48(1H, d, J=8.3 Hz), 7.32(1H, dd, J=8.3 Hz, 7.6 Hz), 7.25(1H, s), 7.23(1H, s), 4.16(4H, m), 3.94(3H, s), 3.94(3H, s), 3.85(4H, m).

FAB-Mass: 454(M$^+$+1)

IR(KBr) 1(cm$^{-1}$): 3360, 1549, 1506, 1431, 1394, 1338, 1211.

EXAMPLE 247

N-(4-Carboxyphenyl)-4-(6,7-dimethoxy-4-quinazolinyl)-1-piperazinecarboxamide (Compound 247)

To a solution of 390 mg (0.84 mmol) of 4-(6,7-dimethoxy-4-quinazolinyl)-N-(4-ethoxycarbonylphenyl)-1-piperazinecarboxamide obtained in Example 89 in 10 ml of 1,4-dioxane were added 70.4 mg (1.68 mmol) of lithium hydroxide monohydrate and 1 ml of water, followed by stirring at room temperature for 4.5 hours. To the resulting mixture was further added 70.4 mg (1.68 mmol) of lithium hydroxide monohydrate, followed by overnight stirring at room temperature. After the solvent was evaporated, water was added to the residue, and the resulting mixture was adjusted to pH 4 with 4 N hydrochloric acid. The precipitated crystals were collected by filtration, washed with water, and dried, followed by purification by silica gel column chromatography to give the desired compound as colorless crystals. F Yield: 100%

$^1$H-NMR(DMSO-d$_6$) $^6$(ppm): 8.86(1H, brs), 8.57(1H, s), 7.87(2H, d, J=8.3 Hz), 7.50(2H, d, J=8.3 Hz), 7.24(1H, s), 7.20(1H, s), 3.94(3H, s), 3.94(3H, s), 3.70(4H, m), 3.42(4H, m).

FAB-Mass: 438(M$^+$+1)

IR(KBr) υ (cm$^{-1}$): 3360, 1601, 1506, 1412, 1385, 1246, 1213, 993.

In the following Examples 248 and 249, substantially the same procedure as in Example 1 was repeated, except that the corresponding isocyanate or isothiocyanate was used in place of phenyl isocyanate, to give the desired compound.

EXAMPLE 248

4-(6,7-Dimethoxy-4-quinazolinyl)-N-(3-ethoxycarbonylphenyl)-1-piperazinecarboxamide (Compound 248)

Yield: 92% m.p.: 187–188° C.

$^1$H-NMR(CDCl$_3$) δ (ppm): 8.69(1H, s), 7.92(1H, d, J=1.7 Hz), 7.78–7.71(2H, m), 7.36(1H, m), 7.26(1H, s), 7.11(1H, s), 7.06(1H, brs), 4.25(2H, q, J=7.3 Hz), 4.02(3H, s), 3.99 (3H, s), 3.75(8H, m), 1.37(3H, t, J=7.3 Hz).

FAB-Mass: 466(M$^+$+1)

IR(KBr) υ (cm$^{-1}$): 1699, 1668, 1539, 1506, 1489, 1431, 1352, 1300, 1242, 1209, 997, 760.

EXAMPLE 249

4-(6,7-Dimethoxy-4-quinazolinyl)-N-(4-methoxycarbonylphenyl)-1-piperazinethiocarboxamide (Compound 249)

Yield: 75% m.p.: 208–209° C.

$^1$H-NMR(CDCl$_3$) δ (ppm): 8.67(1H, s), 8.02(2H, d, J=8.9 Hz), 7.55(1H, brs), 7.27(1H, s), 7.22(2H, d, J=8.9 Hz), 7.08(1H, s), 4.09–4.05(4H, m), 4.03(3H, s), 3.99(3H, s), 3.91(3H, s), 3.86–3.82(4H, m).

FAB-Mass: 468(M$^+$+1)

IR(KBr) (cm$^{-1}$): 1716, 1578, 1527, 1508, 1477, 1431, 1284, 1211, 991.

EXAMPLE 250

(dl)-4-(6,7-Dimethoxy-4-quinazolinyl)-N-(4-methylsulfinylphenyl)-1-piperazinecarboxamide (Compound 250)

To a solution of 646.8 mg (1.47 mmol) of 4-(6,7-dimethoxy-4-quinazolinyl)-N-(4-methylthiophenyl)-1-piperazinecarboxamide obtained in Example 69 in 15 ml of dichloromethane was added 381.4 mg (2.21 mmol) of m-chloroperbenzoic acid under ice-cooling, followed by stirring in an atmosphere of argon at the same temperature for 6 hours. To the reaction mixture was added a 0.1 N aqueous solution of sodium thiosulfate, followed by further stirring at room temperature for 30 minutes. The organic layer was separated, washed with a saturated aqueous solution of sodium chloride, and then dried over anhydrous sodium sulfate. After the solvent was evaporated, the residue was purified by silica gel column chromatography to give the desired compound as colorless crystals.

Yield: 72%

$^1$H-NMR(CDCl$_3$) 6 (ppm): 8.69(1H, s), 7.58(1H, brs), 7.56(2H, d, J=6.3 Hz), 7.29(1H, s), 7.28(2H, d, J=6.3 Hz), 7.11(1H, s), 4.03(3H, s), 4.00(3H, s), 3.77–3.73(8H, m), 2.72(3H, s).

FAB-Mass: 456(M$^+$+1)

IR(KBr) υ (cm$^{-1}$): 1670, 1541, 1508, 1481, 1433, 1242, 1213, 1026, 993.

EXAMPLE 251

4-(6,7-Dimethoxy-4-quinazolinyl)-N-(4-mesylphenyl)-1-piperazinecarboxamide (Compound 251)

Substantially the same procedure as in Example 250 was repeated using 780.0 mg (1.78 mmol) of 4-(6,7-dimethoxy-4-quinazolinyl)-N-(4-methylthiophenyl)-1-piperazinecarboxamide obtained in Example 69 and 918.9 mg (5.33 mmol) of m-chloroperbenzoic acid to give the desired compound as colorless crystals.

Yield: 44% m.p.: 266–269° C.

$^1$H-NMR(CDCl$_3$+DMSO-d$_6$) 6 (ppm): 9.07(1H, brs), 8.57(1H, s), 7.77(4H, m), 7.22(1H, s), 7.17(1H, s), 3.97(3H, s), 3.97(3H, s), 3.76–3.71(8H, m), 3.08(3H, s).

FAB-Mass: 472(M$^+$+1)

IR(KBr) υ (cm$^{-1}$): 1653, 1591, 1533, 1504, 1471, 1419, 1321, 1298, 1236, 1209, 1147, 991, 770.

EXAMPLE 252

4-(6,7-Dimethoxy-4-quinazolinyl)-N-(4-mesylbenzyl)-1-piperazinethiocarboxamide (Compound 252)

Substantially the same procedure as in Example 185 was repeated, except that the corresponding 4-mesylbenzylamine was used in place of 4-bromobenzylamine, to give the desired compound.

Yield: 83%

$^1$H-NMR(CDCl$_3$) δ (ppm): 8.64(1H, s), 7.65(2H, d, J=8.2 Hz), 7.38(2H, d, J=8.2 Hz), 7.25(1H, s), 7.13(1H, s), 6.89 (1H, brt, J=5.6 Hz), 5.06(2H, d, J=5.6 Hz), 4.20–4.16(4H, m), 4.03(3H, s), 4.00(3H, s), 3.90–3.87(4H, m), 3.01(3H, s).

EXAMPLE 253

4-(6,7-Dimethoxy-4-quinazolinyl)-N-(4-sulfamoylbenzyl)-1-piperazinethiocarboxamide (Compound 253)

Substantially the same procedure as in Example 185 was repeated, except that the corresponding 4-sulfamoylbenzylamine was used in place of 4-bromobenzylamine, to give the desired compound.

Yield: 66%

$^1$H-NMR(DMSO-d$_6$) δ (ppm): 8.54(1H, s), 8.41(1H, brt, J=4.3 Hz), 7.76(2H, d, J=7.9 Hz), 7.47(2H, d, J=7.9 Hz), 7.31(2H, brs), 7.24(1H, s), 7.23(1H, s), 4.87(2H, d, J=4.3 Hz), 4.07–4.05(4H, m), 3.93(3H, s), 3.93(3H, s). 3.82–3.81 (4H, m). FAB-Mass: 503(M$^+$+1)

EXAMPLE 254

4-(6,7-Dimethoxy-4-quinazolinyl)-N-(4-piperidinosulfonylphenyl)-1-piperazinethiocarboxamide (Compound 254)

Substantially the same procedure as in Example 1 was repeated, except that the corresponding 4-piperidinosulfonylphenyl isothiocyanate was used in place of phenyl isocyanate, to give the desired compound.

Yield: 100%

$^1$H-NMR(CDCl$_3$) δ (ppm): 8.66(1H, s), 8.16(1H, brs), 7.55(2H, d, J=8.6 Hz), 7.42(2H, d, J=8.6 Hz), 7.25(1H, s), 7.12(1H, s), 4.20–4.17(4H, m), 4.02(3H, s), 4.01(3H, s), 3.91–3.89(4H, m), 2.99–2.95(4H, m), 1.63(4H, m), 1.44–1.42(2H, m).

FAB-Mass: 557(M$^+$+1)

IR(KBr) υ (cm$^{-1}$): 1593, 1579, 1504, 1477, 1427, 1327, 1242, 1213, 1163, 1093, 991, 737.

EXAMPLE 255

4-(6,7-Dimethoxy-4-quinazolinyl)-N-(3-furyl)-1-piperazinecarboxamide (Compound 255)

Substantially the same procedure as in Example 265 was repeated, except that the corresponding 3-furoyl chloride was used in place of nicotinoyl chloride, to give the desired compound.

Yield: 32% m.p.: 213–215° C.

$^1$H-NMR(CDCl$_3$) δ (ppm): 8.69(1H, s), 7.84(1H, d, J=1.7 Hz), 7.31(1H, dd, J=1.7 Hz, 1.3 Hz), 7.27(1H, s), 7.11(1H, s), 20 6.33(1H, d, J=1.3 Hz), 6.27(1H, brs), 4.04(3H, s), 4.00(3H, s), 3.73(8H, m).

FAB-Mass: 384(M$^+$+1) IR(KBr) υ (cm$^{-1}$): 1637, 1556, 1504, 1475, 1430, 1349, 1336, 1255, 1209, 991.

EXAMPLE 256

4-(6,7-Dimethoxy-4-quinazolinyl)-N-furfuryl-1-piperazinecarboxamide (Compound 256)

Substantially the same procedure as in Example 263 was repeated, except that the corresponding furfurylamine was used in place of 2-picolylamine, to give the desired compound.

Yield: 63% m.p.: 168–170° C.

$^1$H-NMR(CDCl$_3$) δ (ppm): 8.68(1H, s), 7.37(1H, d, J=1.6 Hz), 7.26(1H, s), 7.09(1H, s), 6.34(1H, dd, J=3.1 Hz, 1.6 Hz), 6.26(1H, d, J=3.1 Hz), 4.84(1H, brt, J=5.3 Hz), 4.46 (2H, d, J=5.3 Hz), 4.03(3H, s), 3.99(3H, s), 3.70–3.67(4H, m), 3.65–3.62(4H,m).

FAB-Mass: 398(M$^+$+1)

IR(KBr) υ (cm$^{-1}$): 1633, 1542, 1504, 1475, 1430, 1344, 1332, 1238, 1211, 991, 856, 738.

EXAMPLE 257

4-(6,7-Dimethoxy-4-quinazolinyl)-N-(3-thienyl)-1-piperazinecarboxamide (Compound 257)

Substantially the same procedure as in Example 265 was repeated, except that the corresponding 3-thiophenecarbonyl chloride was used in place of nicotinoyl chloride, to give the desired compound.

Yield: 81% m.p.: 239–241° C.

$^1$H-NMR(CDCl$_3$) δ (ppm): 8.69(1H, s), 7.31(1H, dd, J=3.1 Hz, 1.3 Hz), 7.27(1H, s), 7.23(1H, dd, J=5.1 Hz, 3.1 Hz), 7.11(1H, s), 7.00(1H, dd, J=5.1 Hz, 1.3 Hz), 6.72(1H, brs), 4.04(3H, s), 4.00(3H, s), 3.74(8H, m).

FAB-Mass: 398(M$^+$+1)

IR(KBr) υ (cm$^{-1}$): 1637, 1535, 1504, 1473, 1411, 1251, 1211, 993, 846, 773.

EXAMPLE 258

4-(6,7-Dimethoxy-4-quinazolinyl)-N-(3-thienylmethyl)-1-piperazinecarboxamide (Compound 258)

Substantially the same procedure as in Example 164 was repeated, except that the corresponding 3-thiophenecarboxylic acid was used in place of 4-vinylbenzoic acid, to give the desired compound.

Yield: 48% m.p.: 178–179° C.

$^1$H-NMR(CDCl$_3$) δ (ppm): 8.68(1H, s), 7.31(1H, dd, J=5.0 Hz, 35 3.0 Hz), 7.26(1H, s), 7.19(1H, dd, J=3.0 Hz, 1.3 Hz), 7.09(1H, dd, J=5.0 Hz, 1.3 Hz), 7.08(1H, s), 4.78(1H, brt, J=5.1 Hz), 4.48(2H, d, J=5.1 Hz), 4.03(3H, s), 3.99(3H, s), 3.70–3.68(4H, m), 3.64–3.62(4H, m).

FAB-Mass: 414(M$^+$+1)

IR(KBr) υ (cm$^{-1}$): 1637, 1556, 1504, 1475, 1430, 1349, 1336, 1255, 1209, 991.

EXAMPLE 259

4-(6,7-Dimethoxy-4-quinazolinyl)-N-(2-thienylmethyl)-1-piperazinecarboxamide (Compound 259)

Substantially the same procedure as in Example 263 was repeated, except that the corresponding 2-thienylmethylamine was used in place of 2-picolylamine, to give the desired compound.

Yield: 42% m.p.: 168–170° C.

$^1$H-NMR(CDCl$_3$) δ (ppm): 8.69(1H, s), 7.27–7.23(2H, m), 7.10(1H, s), 7.01–6.95(2H, m), 4.85(1H, br), 4.65(2H, d, J=4.0 Hz), 4.03(3H, s), 3.99(3H, s), 3.70–3.68(4H, m), 3.65–3.63(4H, m).

FAB-Mass: 414(M$^+$+1)

IR(KBr) υ (cm$^{-1}$): 1626, 1544, 1502, 1431, 1350, 1282, 1207, 993, 856.

EXAMPLE 260

44-(6,7-Dimethoxy-4-quinazolinyl)-N-(2-methoxycarbonyl-3-thienyl)-1-piperazinethiocarboxamide (Compound 260)

Substantially the same procedure as in Example 1 was repeated, except that the corresponding 3-isothiocyanatothiophene-2-carboxylic acid methyl ester was used in place of phenyl isocyanate, to give the desired compound.

Yield: 75% m.p.: 226–228° C.

$^1$H-NMR(CDCl$_3$) δ (ppm): 10.82(1H, brs), 8.77(1H, d, J=5.6 Hz), 8.68(1H, s), 7.48(1H, d, J=5.6 Hz), 7.28(1H, s), 7.13(1H, s), 4.32–4.28(4H, m), 4.04(3H, s), 4.01(3H, s), 3.95–3.91(4H, m), 3.90(3H, s).

FAB-Mass: 474(M$^+$+1)

IR(KBr) υ (cm$^{-1}$): 1682, 1589, 1502, 1473, 1458, 1425, 1333, 1254, 1203, 1134, 1092, 991, 781.

EXAMPLE 261

4-(6,7-Dimethoxy-4-quinazolinyl)-N-(2-methoxycarbonyl-4-methyl-3-thienyl)-1-piperazinethiocarboxamide (Compound 261)

Substantially the same procedure as in Example 1 was repeated, except that the corresponding 3-isothiocyanato-4-methylthiophene-2-carboxylic acid methyl ester was used in place of phenyl isocyanate, to give the desired compound.

Yield: 78% m.p.: 113–116° C.

$^1$H-NMR(CDCl$_3$) δ (ppm): 8.68(1H, s), 8.54(1H,brs), 7.29(1H, s), 7.17(1H, s), 7.13(1H, s), 4.30–4.26(4H, m), 4.04(3H, s), 4.01(3H, s), 3.93–3.89(4H, m), 3.85(3H, s), 2.27(3H, s).

FAB-Mass: 488(M$^+$+1)

IR(KBr) υ (cm$^{-1}$): 1700, 1572, 1504, 1475, 1431, 1346, 1279, 1242, 1209, 991.

EXAMPLE 262

4-(6,7-Dimethoxy-4-quinazolinyl)-N-(2-pyridyl)-1-piperazinethiocarboxamide (Compound 262)

Substantially the same procedure as in Example 154 was repeated, except that the corresponding 2-aminopyridine was used in place of 4-isopropylbenzylamine, to give the desired compound.

Yield: 30% m.p.: 208–210° C.

$^1$H-NMR(DMSO-d$_6$) δ (ppm): 9.90(1H, brs), 8.55(1H, s), 8.29(1H, dd, J=5.3 Hz, 1.3 Hz), 7.71(1H, ddd, J=8.1 Hz, 7.1 Hz, 1.3 Hz), 7.61(1H, d, J=8.1 Hz), 7.24(1H, s),7.23(1H, s), 7.05(1H, dd, J=7.1 Hz, 5.3 Hz), 4.11(3H, s), 3.93(8H, m), 3.83(3H, s).

FAB-Mass: 411(M$^+$+1)

IR(KBr) υ (cm$^{-1}$): 1577, 1519, 1504, 1477, 1421, 1303, 1236, 1039, 991, 939, 769.

EXAMPLE 263

4-(6,7-Dimethoxy-4-quinazolinyl)-N-(2-picolyl)-1-piperazinecarboxamide (Compound 263)

To a solution of 954 mg (3.30 mmol) of 4-methoxyphenyl-4-nitrophenyl carbonate obtained according to the method described in Synthetic Communications, 26, 331 (1996) in 20 ml of acetonitrile was added 5 ml of a solution of 324 mg (3.00 mmol) of 2-picolylamine in acetonitrile, followed by stirring at room temperature for 3 hours. To the resulting mixture were added 548 mg (2.00 mmol) of 6,7-dimethoxy-4-piperazinylquinazoline obtained according to the method described in South African Patent No. 67 06512 (1968) and 0.328 ml (2.19 mmol) of 1,8-diazabicyclo[5.4.0]-7-undecene, followed by heating under reflux for 3 hours. After the reaction mixture was allowed to cool to room temperature, the solvent was evaporated, and chloroform was added to the residue. The resulting mixture was washed with a 10% aqueous solution of sodium hydroxide three times and then with a saturated aqueous solution of sodium chloride, and dried over magnesium sulfate. After the solvent was evaporated, the residue was purified by silica gel chromatography and recrystallized from ethyl acetate to give the desired compound as colorless crystals.

Yield: 49% m.p.: 181–182° C.

$^1$H-NMR(CDCl$_3$) δ (ppm): 8.67(1H, s), 8.55(1H, d, J=4.3 Hz), 7.68(1H, m), 7.30(1H, d, J=8.9 Hz), 7.26(1H, s), 7.20(1H, m), 7.12(1H, s), 6.03(1H, brt, J=4.6 Hz), 4.58(2H, d, J=4.6 Hz), 4.03(3H, s), 3.99(3H, s), 3.71(8H, m).

FAB-Mass: 395(M$^+$+1)

IR(KBr) υ (cm$^{-1}$): 1631, 1569, 1546, 1504, 1473, 1436, 1344, 1263, 1236, 1209, 1132, 987, 854, 752.

EXAMPLE 264

4-(6,7-Dimethoxy-4-quinazolinyl)-N-(2-picolyl)-1-piperazinethiocarboxamide (Compound 264)

Substantially the same procedure as in Example 185 was repeated, except that the corresponding 2-picolylamine was used in place of 4-bromobenzylamine, to give the desired compound.

Yield: 56% m.p.: 175–176° C.

$^1$H-NMR(CDCl$_3$) δ (ppm): 8.67(1H, s), 8.54(1H, d, J=5.0 Hz), 7.74–7.68(2H, m), 7.33–7.22(3H, m), 7.14(1H, s), 4.97(2H, d, J=3.6 Hz), 4.21–4.17(4H, m), 4.03(3H, s), 4.00(3H, s), 3.91–3.87(4H, m).

IR(KBr) υ (cm$^{-1}$): 1576, 1545, 1504, 1477, 1427, 1352, 1242, 1207, 1136, 989, 933, 843.

EXAMPLE 265

4-(6,7-Dimethoxy-4-quinazolinyl)-N-(3-pyridyl)-1-piperazinecarboxamide (Compound 265)

To a suspension of 5.9 g (33 mmol) of nicotinoyl chloride hydrochloride in 50 ml of diethyl ether was added 50 ml of an aqueous solution of 12.0 g (185 mmol) of sodium azide under ice-cooling, followed by vigorous stirring at room temperature. After the organic layer was separated, the water layer was extracted with ether. Then, the combined organic layers were washed with a saturated aqueous solution of sodium chloride, and dried over magnesium sulfate. After the solvent was evaporated at a temperature below 30° C., the residue was dissolved in 40 ml of toluene. To the resulting solution was added 548 mg (2.00 mmol) of 6,7-dimethoxy-4-piperazinylquinazoline obtained according to the method described in South African Patent No.67 06512 (1968), followed by heating at 70° C. with stirring for 3 hours. After the reaction mixture was allowed to cool to room temperature, the solvent was evaporated, and the residue was purified by silica gel chromatography and recrystallized from ethyl acetate to give the desired compound as colorless crystals.

Yield: 25% m.p.: 208–209° C.

$^1$H-NMR(CDCl$_3$) δ (ppm): 8.70(1H, s), 8.48(1H, d, J=2.7 Hz), 8.30(1H, dd, J=4.8 Hz, 1.6 Hz), 8.00(1H, m), 7.26(1H, s), 7.25(1H, m), 7.11(1H, s), 6.66(1H, brs), 4.03(3H, s), 4.00(3H, s), 3.77(8H, m).

FAB-Mass: 395(M$^+$+1)

IR(KBr) υ (cm$^{-1}$): 1672, 1575, 1546, 1504, 1483, 1430, 1234, 1201, 1133, 993.

EXAMPLE 266

4-(6,7-Dimethoxy-4-quinazolinyl)-N-(3-picolyl)-1-piperazinecarboxamide (Compound 266)

Substantially the same procedure as in Example 119 was repeated, except that the corresponding 3-picolylamine was used in place of 2-(4-chlorophenyl)ethylamine, to give the desired compound.

Yield: 12% m.p.: 188–189° C.

$^1$H-NMR(CDCl$_3$) δ (ppm): 8.68(1H, s), 8.57(1H, d, J=2.3 Hz), 8.53(1H, dd, J=5.0 Hz, 1.7 Hz), 7.70(1H, ddd, J=7.9 Hz, 2.3 Hz, 1.7 Hz), 7.30–7.26(2H, m), 7.09(1H, s), 5.04 (1H, brt, J=5.6 Hz), 4.49(2H, d, J=5.6 Hz), 4.03(3H, s), 3.99(3H, s), 3.71–3.64(8H, m).

FAB-Mass: 409(M$^+$+1)

IR(KBr) υ (cm$^{-1}$): 1626, 1574, 1537, 1504, 1487, 1435, 1346, 1242, 1213, 1136, 993, 849, 716.

EXAMPLE 267

4-(6,7-Dimethoxy-4-quinazolinyl)-N-(4-pyridyl)-1-piperazinecarboxamide (Compound 267)

Substantially the same procedure as in Example 265 was repeated, except that isonicotinoyl chloride hydrochloride was used in place of nicotinoyl chloride, to give the desired compound.

Yield: 76% m.p.: 141–143° C.

$^1$H-NMR(CDCl$_3$) δ (ppm): 8.70(1H, s), 8.46(2H, d, J=4.9 Hz), 7.37(2H, d, J=4.9 Hz), 7.26(1H, s), 7.11(1H, s), 6.71 (1H, brs), 4.04(3H, s), 4.01(3H, s), 3.77(8H, m).

FAB-Mass: 395(M$^+$+1)

IR(KBr) υ (cm$^{-1}$): 1660, 1579, 1546, 1508, 1475, 1430, 1240, 1213, 989, 939, 852, 827.

EXAMPLE 268

4-(6,7-Dimethoxy-4-quinazolinyl)-N-(4-pyridyl)-1-piperazinethiocarboxamide (Compound 268)

Substantially the same procedure as in Example 154 was repeated, except that the corresponding 4-aminopyridine was used in place of 4-isopropylbenzylamine, to give the desired compound.

Yield: 43% m.p.: 218–220° C.

$^1$H-NMR(CDCl$_3$) δ (ppm): 8.70(1H, s), 8.52(2H, d, J=6.3 Hz), 7.28(1H, s), 7.26(1H, brs), 7.08(1H, s), 7.07(2H, d, J=6.3 Hz), 4.10–4.07(4H, m), 4.04(3H, s), 4.00(3H, s), 3.88–3.64(4H, m).

FAB-Mass: 411(M$^+$+1)

IR(KBr) υ (cm$^{-1}$): 1580, 1508, 1479, 1425, 1405, 1344, 1251, 1207, 1141, 991, 944, 852, 821.

EXAMPLE 269

4-(6,7-Dimethoxy-4-quinazolinyl)-N-(4-picolyl)-1-piperazinecarboxamide (Compound 269)

Substantially the same procedure as in Example 119 was repeated, except that the corresponding 4-picolylamine was used in place of 2-(4-chlorophenyl)ethylamine, to give the desired compound.

Yield: 45%

$^1$H-NMR(CDCl$_3$) δ (ppm): 8.67(1H, s), 8.53(2H, d, J=5.3 Hz), 7.28(1H, s), 7.23(2H, d, J=5.3 Hz), 7.10(1H, s), 5.35

(1H, brt, J=5.9 Hz), 4.48(2H, d, J=5.9 Hz), 4.02(3H, s), 3.99(3H, s), 3.70–3.69(8H, m).

FAB-Mass: 409(M$^+$+1)

EXAMPLE 270

4-(6,7-Dimethoxy-4-quinazolinyl)-N-(4-picolyl)-1-piperazinethiocarboxamide (Compound 270)

Substantially the same procedure as in Example 1 was repeated, except that the corresponding 4-picolylisothiocyanate was used in place of phenyl isocyanate, to give the desired compound.

Yield: 59% m.p.: 236–239° C.

$^1$H-NMR(CDCl$_3$) δ (ppm): 8.66(1H, s), 8.57(2H, d, J=5.7 Hz), 7.27(2H, d, J=5.7 Hz), 7.26(1H, s), 7.11(1H, s), 6.09 (1H, brt, J=5.3 Hz), 5.00(2H, d, J=5.3), 4.16–4.12(4H, m), 4.03(3H, s), 3.99(3H, s), 3.91–3.87(4H, m).

FAB-Mass: 425(M$^+$+1)

IR(KBr) υ (cm$^{-1}$): 1577, 1535, 1504, 1479, 1430, 1336, 1241, 1211, 1135, 993, 935, 865, 798.

In the following Examples 271–273, substantially the same 30 procedure as in Example 265 was repeated, except that the corresponding carboxylic acid halide was used in place of nicotinoyl chloride, to give the desired compound.

EXAMPLE 271

4-(6,7-Dimethoxy-4-quinazolinyl)-N-(2-methyl-5-pyridyl)- 1-piperazinecarboxamide (Compound 271)

Yield: 6% m.p.: 240–241° C.

$^1$H-NMR(CDCl$_3$) δ (ppm): 8.70(1H, s), 8.35(1H, d, J=2.6 Hz), 7.88(1H, dd, J=8.8 Hz, 2.6 Hz), 7.27(1H, s), 7.12(1H, d, J=8.8 Hz), 7.11(1H, s), 6.46(1H, brs), 4.04(3H, s), 4.01 (3H, s), 3.77(8H, m), 2.52(3H, s).

FAB-Mass: 409(M$^+$+1),

IR(KBr) υ (cm$^{-1}$): 1676, 1618, 1504, 1448, 1429, 1236, 1209, 993.

EXAMPLE 272

N-(2-Chloro-5-pyridyl)-4-(6,7-dimethoxy-4-quinazolinyl)-1-piperazinecarboxamide (Compound 272)

Yield: 53% m.p.: 238–240° C.

$^1$H-NMR(CDCl$_3$) δ (ppm): 8.70(1H, s), 8.27(1H, d, J=2.6 Hz), 8.01(1H, dd, J=8.5 Hz, 2.6 Hz), 7.29(1H, d, J=8.5 Hz), 7.26(1H, s), 7.11(1H, s), 6.62(1H, brs), 4.04(3H, s), 4.00 (3H, s), 3.77(8H, m).

FAB-Mass: 431(M$^+$+3), 429(M$^+$+1) IR(KBr) 1) (cm$^{-1}$) 1637, 1571, 1508, 1465, 1351, 1240, 1213, 995.

EXAMPLE 273

N-(2-Cyano-5-pyridyl)-4-(6,7-dimethoxy-4-quinazolinyl)-1-piperazinecarboxamide (Compound 273)

Yield: 12% m.p.: 275–277° C.

1H-NMR(DMSO-d$_6$) δ (ppm): 9.38(1H, brs), 8.83(1H, d, J=2.3 Hz), 8.58(1H, s), 8.14(1H, dd, J=8.9 Hz, 2.3 Hz), 7.91(1H, d, J=8.9 Hz), 7.25(1H, s), 7.20(1H, s), 3.93(3H, s), 3.93(3H, s), 3.73(8H, m).

FAB-Mass: 420(M$^+$+1)

IR(KBr) υ (cm$^{-1}$): 2233, 1666, 1575, 1523, 1427, 1236, 1211, 1135, 993.

EXAMPLE 274

N-(2,6-Dichloro-4-pyridyl)-4-(6,7-dimethoxy-4-quinazolinyl)-1-piperazinecarboxamide (Compound 274)

Substantially the same procedure as in Example 1 was repeated, except that the corresponding 2,6-dichloro-4-pyridyl isocyanate was used in place of phenyl isocyanate, to give the desired compound.

Yield: 56% m.p.: 267–270° C.

$^1$H-NMR(CDCl$_3$) δ(ppm): 8.67(1H, s), 7.61(1H, brs), 7.44(2H, s), 7.28(1H, s), 7.09(1H, s), 4.03(3H, s), 4.00(3H, s), 3.75(8H, m).

FAB-Mass: 467(M++5), 465(M$^+$+3), 463(M$^+$+1)

IR(KBr) υ (cm$^{-1}$): 1682, 1578, 1504, 1477, 1431, 1248, 1215, 1163, 1099, 991, 845.

EXAMPLE 275

N-(3-Chloro-5-trifluoromethyl-2-picolyl)-4-(6,7-dimethoxy-4-quinazolinyl)-1-piperazinecarboxamide (Compound 275)

Substantially the same procedure as in Example 119 was repeated, except that the corresponding 3-chloro-5-trifluoromethyl-2-picolylamine was used in place of 2-(4-chlorophenyl)ethylamine, to give the desired compound.

Yield: 40%

$^1$H-NMR(CDCl$_3$) δ (ppm): 8.83(1H, s), 8.62(1H, s), 8.01 (1H, s), 30 7.27(1H, br), 7.27(1H, s), 7.10(1H, s), 5.06(2H, d, J=4.0 Hz), 4.07(3H, s), 4.03–3.97(8H, m), 4.01(3H, s).

EXAMPLE 276

N-(3-Chloro-5-trifluoromethyl-2-picolyl)-4-(6,7-dimethoxy-4-quinazolinyl)-1-piperazinethiocarboxamide (Compound 276)

Substantially the same procedure as in Example 185 was repeated, except that the corresponding 3-chloro-5-trifluoromethyl-2-picolylamine was used in place of 4-bromobenzylamine, to give the desired compound.

Yield: 76% m.p.: 182–183° C.

$^1$H-NMR(CDCl$_3$) δ (ppm): 8.76(1H, d, J=1.7 Hz), 8.67 (1H, s), 8.00(1H, d, J=1.7 Hz), 7.60(1H, br), 7.27(1H, s), 7.14(1H, s), 5.10(2H, d, J=2.6 Hz), 4.27–4.18(4H, m), 4.04(3H, s), 4.00(3H, s), 3.98–3.89(4H, m).

FAB-Mass: 529(M$^+$+3), 527(M$^+$+1)

IR(KBr) υ (cm$^{-1}$): 1506, 1475, 1448, 1429, 1354, 1329, 1234, 1209, 1134, 1122, 1095, 1061, 993.

EXAMPLE 277

N-(2,6-Dihydroxy-4-pyrimidinyl)-4-(6,7-dimethoxy-4-quinazolinyl)-1-piperazinethiocarboxamide (Compound 277)

Substantially the same procedure as in Example 1 was repeated, except that the corresponding 2,6-dihydroxy-4-pyrimidinyl isothiocyanate was used in place of phenyl isocyanate, to give the desired compound.

Yield: 40% m.p.: 283–285° C.

$^1$H-NMR(DMSO-d$_6$) δ (ppm): 11.25(1H, br), 10.85(1H, br), 8.65(1H, brs), 8.54(1H, s), 7.46(1H, s), 7.24(1H, s), 7.23(1H, s), 4.11(4H, m), 3.94(3H, s), 3.94(3H, s), 3.83(4H, m).

FAB-Mass: 444(M$^+$+1)

IR(KBr) υ (cm$^{-1}$): 1682, 1504, 1483, 1433, 1346, 1207, 991.

EXAMPLE 278

4-(6,7-Dimethoxy-4-quinazolinyl)-N-(5-methyl-2-pyrazinylmethyl)-1-piperazinecarboxamide (Compound 278)

Substantially the same procedure as in Example 263 was repeated, except that the corresponding 5-methyl-2-pyrazinylmethylamine was used in place of 2-picolylamine, to give the desired compound.

Yield: 59% m.p.: 202–204° C.

$^1$H-NMR (CDCl$_3$) δ (ppm): 8.68 (1H, s), 8.52 (1H, s), 8.39 (1H, s), 7.26 (1H, s), 7.10 (1H, s), 5.65 (1H, brt, J=4.9 Hz), 4.58 (2H, d, J=4.9 Hz), 4.03 (3H, s), 3.99 (3H, s), 3.69 (8H, m), 2.57 (3H, s).

FAB-Mass: 424 (M$^+$+1)

IR (KBr) σ (cm$^{-1}$); 1648, 1504, 1450, 1423, 1243, 1205, 993.

EXAMPLE 279

4-(6,7-Dimethoxy-4-quinazolinyl)-N-(2,3,4,5-tetrahydro-2-oxo-3-furyl)-1-piperazinethiocarboxamide (Compound 279)

Substantially the same procedure as in Example 1 was repeated, except that the corresponding 2,3,4,5-tetrahydro-2-oxo-3-furyl isothiocyanate was used in place of phenyl isocyanate to give the desired compound.

Yield: 73% m.p.: 147–148° C.

$^1$H-NMR (CDCl$_3$) δ (ppm): 8.66 (1H, s), 7.27 (1H, s), 7.11 (1H, s), 6.47 (1H, d, J=5.6 Hz), 5.40 (1H, m), 4.51 (1H, m), 4.31 (1H, m), 4.17–4.09 (4H, m), 4.04 (3H, s), 4.00 (3H, s), 3.88–3.80 (4H, m), 3.13 (1H, m), 2.17 (1H, m).

FAB-Mass: 418 (M$^+$+1)

IR (KBr) σ (cm$^{-1}$): 1774, 1578, 1508, 1481, 1427, 1348, 1211, 1140, 1020, 991, 941.

EXAMPLE 280

4-(6,7-Dimethoxy-4-quinazolinyl)-N-[4-(1-pyrrolyl)phenyl]-1-piperazinecarboxamide (Compound 280)

Substantially the same procedure as in Example 164 was repeated, except that the corresponding 4-(1-pyrrolyl)benzoic acid was used in place of 4-vinylbenzoic acid, to give the desired compound.

Yield: 98% m.p.: 224–226° C.

$^1$H-NMR (CDCl$_3$) δ (ppm): 8.70 (1H, s), 7.44 (2H, d, J=8.9 Hz), 7.33 (2H, d, J=8.9 Hz), 7.26 (1H, s), 7.12 (1H, s), 7.04 (2H, d, J=2.2 Hz), 6.59 (1H, brs), 6.33 (2H, d, J=2.2 Hz), 4.04 (3H, s), 4.00 (3H, s), 3.77 (8H, m).

FAB-Mass: 459 (M$^+$+1)

IR (KBr) σ (cm$^{-1}$): 1656, 1523, 1427, 1328, 1309, 1232, 1205, 991, 846, 723.

EXAMPLE 281

4-(6,7-Dimethoxy-4-quinazolinyl)-N-{4-[5-(1,2,3-thiadiazolyl)]benzyl}-1-piperazinethiocarboxamide (Compound 281)

Substantially the same procedure as in Example 154 was repeated, except that the corresponding 4-[5-(1,2,3-thiadiazolyl)benzylamine was used in place of 4-isopropylbenzylamine, to give the desired compound.

Yield: 96% m.p.: 225–226° C.

$^1$H-NMR (DMSO-d$_6$) δ (ppm): 9.58 (1H, s), 8.54 (1H, s), 8.38 (1H, br), 8.09 (2H, d, J=7.9 Hz), 7.49 (2H, d, J=7.9 Hz), 7.24 (1H, s), 7.23 (1H, s), 4.89 (2H, br), 4.08–3.99 (4H, m), 3.93 (3H, s), 3.93 (3H, s), 3.88–3.81 (4H, m).

FAB-Mass: 508 (M$^+$+1)

IR (KBr) σ (cm$^{-1}$): 1508, 1479, 1456, 1427, 1363, 1346, 1238, 1132, 991.

EXAMPLE 282

4-(6,7-Dimethoxy-4-quinazolinyl)-N-[4-(4-picolyl)phenyl]-1-piperazinethiocarboxamide (Compound 282)

Substantially the same procedure as in Example 154 was repeated, except that the corresponding 4-picolylaniline was used in place of 4-isopropylbenzylamine, to give the desired compound.

Yield: 67% m.p.: 198–200° C.

$^1$H-NMR (CDCl$_3$) δ (ppm): 8.66 (1H, s), 8.50 (2H, d, J=4.6 Hz), 7.49 (1H, brs), 7.27 (1H, s), 7.19–7.09 (7H, m), 4.13–4.08 (4H, m), 4.03 (3H, s), 3.99 (3H, s), 3.95 (2H, s), 3.87–3.83 (4H, m).

FAB-Mass: 501 (M$^+$+1)

IR (KBr) σ (cm$^{-1}$): 1502, 1475, 1419, 1344, 1230, 1209, 991.

EXAMPLE 283

4-(6,7-Dimethoxy-4-quinazolinyl)-N-[2-(1-pyrrolyl)-5-pyridyl]-1-piperazinecarboxamide (Compound 283)

Substantially the same procedure as in Example 265 was repeated, except that 2-(1-pyrrolyl)pyridine-5-carboxylic acid chloride was used in place of nicotinoyl chloride, to give the desired compound.

Yield: 60% m.p.: 252–254° C.

$^1$H-NMR (CDCl$_3$) δ (ppm): 8.71 (1H, s), 8.27 (1H, d, J=2.5 Hz), 8.06 (1H, dd, J=8.9 Hz, 2.5 Hz), 7.45 (2H, d, J=2.2 Hz), 7.30 (1H, d, J=8.9 Hz), 7.28 (1H, s), 7.12 (1H, s), 6.51 (1H, brs), 6.35 (2H, d, J=2.2 Hz), 4.04 (3H, s), 4.01 (3H, s), 3.78 (8H, m).

FAB-Mass: 460 (M$^+$+1)

IR (KBr) σ (cm$^{-1}$): 1646, 1540, 1502, 1429, 1245, 1234, 1211, 993.

EXAMPLE 284

4-(6,7-Dimethoxy-4-quinazolinyl)-N-(4-thiocyanatophenyl)-1-piperazinethiocarboxamide (Compound 284)

Substantially the same procedure as in Example 154 was repeated, except that the corresponding 4-thiocyanatoaniline was used in place of 4-isopropylbenzylamine, to give the desired compound.

Yield: 58%

$^1$H-NMR (CDCl$_3$) δ (ppm): 8.67 (1H, s), 7.74 (1H, brs), 7.50 (2H, d, J=8.6 Hz), 7.34 (2H, d, J=8.6 Hz), 7.25 (1H, s), 7.10 (1H, s), 4.26–4.11 (4H, m), 4.02 (3H, s), 3.99 (3H, s), 3.88–3.85 (4H, m).

FAB-Mass: 467 (M$^+$+1)

In the following Examples 285 and 286, substantially the same procedure as in Example 1 was repeated, except that 4-(1-piperazinyl)quinazoline was used in place of 6,7-dimethoxy-4-piperazinylquinazoline, and the corresponding isothiocyanate was used in place of phenyl isocyanate, to give the desired compound.

EXAMPLE 285

N-Benzyl-4-(4-quinazolinyl)-1-piperazinethiocarboxamide (Compound 285)

Yield: 52% m.p.: 68–70° C.

$^1$H-NMR (CDCl$_3$) δ (ppm): 8.64 (1H, s), 7.90–7.83 (2H, m), 7.74 (1H, m), 7.47 (1H, m), 7.34–7.21 (5H, m), 6.70 (1H, brt, J=5.3 Hz), 4.90 (2H, d, J=5.3 Hz), 4.11–4.08 (4H, m), 3.94–3.91 (4H, m).

FAB-Mass: 364 (M$^+$+1)

IR (KBr) σ (cm$^{-1}$): 1568, 1539, 1500, 1444, 1402, 1348, 1012, 939, 773, 698.

EXAMPLE 286

N-(3-Picolyl)-4-(4-quinazolinyl)-1-piperazinethiocarboxamide (Compound 286)

Yield: 61% m.p.: 193–194° C.

$^1$H-NMR (CDCl$_3$) δ (ppm): 8.65 (1H, s), 8.43–8.39 (2H, m), 7.91–7.83 (2H, m), 7.78–7.71 (2H, m), 7.48 (1H, ddd, J=7.9 Hz, 7.3 Hz, 0.7 Hz), 7.29–7.21 (2H, m), 4.93 (2H, d, J=5.3 Hz), 4.18–4.14 (4H, m), 3.97–3.93 (4H, m).

FAB-Mass: 365 (M$^+$+1)

IR (KBr) σ (cm$^{-1}$): 1568, 1537, 1495, 1400, 1346, 1325, 1236, 1005, 775.

In the following Examples 287 and 288, substantially the same procedure as in Example 1 was repeated, except that 5-methyl-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 287

4-(5-Methyl-4-quinazolinyl)-N-(4-phenoxyphenyl)-1-piperazinecarboxamide (Compound 287)

Yield: 80% m.p.: 187–188° C.

$^1$H-NMR (CDCl$_3$) δ (ppm): 8.63 (1H, s), 7.72 (1H, d, J=8.3 Hz), 7.61 (1H, dd, J=8.3 Hz, 6.9 Hz), 7.36–7.23 (6H, m), 7.03 (1H, m), 6.95–6.88 (4H, m), 3.72–3.53 (6H, m), 3.42–3.38 (2H, m), 2.73 (3H, s).

FAB-Mass: 440 (M$^+$+1)

IR (KBr) σ (cm$^{-1}$): 1641, 1541, 1508, 1489, 1419, 1250, 1217, 997.

EXAMPLE 288

N-Benzyl-4-(5-methyl-4-quinazolinyl)-1-piperazinethiocarboxamide (Compound 288)

Yield: 84% m.p.: 165–167° C.

$^1$H-NMR (CDCl$_3$) δ (ppm): 8.55 (1H, s), 7.69–7.58 (2H, m), 7.31–7.19 (6H, m), 6.60 (1H, brt, J=5.0 Hz), 4.87 (2H, d, J=5.0 Hz), 3.98–3.94 (4H, m), 3.70–3.61 (2H, br), 3.48 (2H, br), 2.72 (3H, s).

FAB-Mass: 378 (M$^+$+1)

IR (KBr) σ (cm$^{-1}$) 1541, 1491, 1439, 1414, 1341, 1236, 1009, 818, 700.

In the following Examples 289–291, substantially the same procedure as in Example 1 was repeated, except that 5-chloro-4-(1-piperazinyl)quinazoline was used in place of 6,7-dimethoxy-4-piperazinylquinazoline, and the corresponding isocyanate or isothiocyanate was used in place of phenyl isocyanate, to give the desired compound.

EXAMPLE 289

4-(5-Chloro-4-quinazolinyl)-N-(4-phenoxyphenyl)-1-piperazinecarboxamide (Compound 289)

Yield: 33%

$^1$H-NMR (CDCl$_3$) δ (ppm): 8.65 (1H, s), 7.82 (1H, d, J=7.3 Hz), 7.64 (1H, dd, J=7.9 Hz, 7.3 Hz), 7.51 (1H, dd, J=7.9 Hz, 1.3 Hz), 7.33–7.27 (4H, m), 7.06 (1H, m), 6.98–6.95 (4H, m), 6.62 (1H, brs), 3.82–3.54 (8H, m).

FAB-Mass: 462 (M$^+$+3), 460 (M$^+$+1)

EXAMPLE 290

N-Benzyl-4-(5-chloro-4-quinazolinyl)-1-piperazinethiocarboxamide (Compound 290)

Yield: 90%

$^1$H-NMR (CDCl$_3$) δ (ppm): 8.58 (1H, s), 7.77 (1H, dd, J=8.3 Hz, 1.3 Hz), 7.62 (1H, dd, J=8.3 Hz, 7.6 Hz), 7.49 (1H, dd, J=7.6 Hz, 1.3 Hz), 7.33–7.24 (5H, m), 6.34 (1H, brt, J=5.0 Hz), 4.88 (2H, d, J=5.0 Hz), 4.01 (4H, m), 3.81 (2H, br), 3.74–3.72 (2H, br).

FAB-Mass: 400 (M$^+$+3), 398 (M$^+$+1)

EXAMPLE 291

4-(5-Chloro-4-quinazolinyl)-N-(3-picolyl)-1-piperazinethiocarboxamide dihydrochloride (Compound 291)

Yield: 30% m.p.: 150–152° C. (hydrochloride)

$^1$H-NMR (free base, CDCl$_3$) δ (ppm): 8.61 (1H, s), 8.47 (1H, dd, J=4.9 Hz, 1.7 Hz), 8.41 (1H, d, J=2.3 Hz), 7.79 (1H, dd, J=8.6 Hz, 1.3 Hz), 7.78 (1H, dd, J=7.9 Hz, 2.3 Hz, 1.7 Hz), 7.63 (1H, dd, J=8.6 Hz, 7.6 Hz), 7.50 (1H, dd, J=7.6 Hz, 1.3 Hz), 7.25 (1H, dd, J=7.9 Hz, 4.9 Hz), 6.66 (1H, brt, J=5.0 Hz), 4.93 (2H, d, J=5.0 Hz), 4.06 (4H, m), 3.86–3.72 (2H, br), 3.70–3.57 (2H, br).

FAB-Mass: 401 (M$^+$+3), 399 (M$^+$+1)

IR(hydrochloride, KBr) σ (cm$^{-1}$): 1605, 1539, 1414, 1389, 1360, 1327, 1279, 683.

In the following Examples 292–295, substantially the same procedure as in Example 1 was repeated, except that 6-methyl-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 292

4-(6-Methyl-4-quinazolinyl)-N-(4-phenoxyphenyl)-1-piperazinecarboxamide (Compound 292)

Yield: 85% m.p.: 244–246° C.

¹H-NMR (CDCl₃) δ (ppm): 8.71 (1H, s), 7.81 (1H, d, J=8.6 Hz), 7.64 (1H, d, J=1.3 Hz), 7.58 (1H, dd, J=8.6 Hz, 1.3 Hz), 7.35 (2H, d, J=8.9 Hz), 7.36–7.23 (3H, m), 7.04 (1H, m), 6.96–6.92 (4H, m), 3.77–3.75 (8H, m), 2.51 (3H, s).

FAB-Mass: 440 (M⁺+1)

IR (KBr) σ (cm⁻¹): 1641, 1605, 1580, 1508, 1489, 1263, 1234, 833, 750, 694.

EXAMPLE 293

4-(6-Methyl-4-quinazolinyl)-N-(4-nitrophenyl)-1-piperazinecarboxamide (Compound 293)

Yield: 52% m.p.: 126–129° C.

¹H-NMR (CDCl₃) δ (ppm): 8.70 (1H, s), 8.13 (2H, d, J=9.2 Hz), 7.87 (1H, s), 7.81 (1H, d, J=7.6 Hz), 7.62 (1H, d, J=7.6 Hz), 7.60 (2H, d, J=9.2 Hz), 3.82 (8H, m), 2.53 (3H, s).

FAB-Mass: 393 (M⁺+1)

IR (KBr) σ (cm⁻¹): 1672, 1558, 1512, 1500, 1479, 1419, 1335, 1304, 1261.

EXAMPLE 294

N-Benzyl-4-(6-methyl-4-quinazolinyl)-1-piperazinethiocarboxamide (Compound 294)

Yield: 46%.

¹H-NMR (CDCl₃+DMSO-d₆) δ (ppm): 8.64 (1H, s), 7.80–7.49 (4H, m), 7.38–7.21 (5H, m), 4.95 (2H, d, J=5.3 Hz), 4.17–4.13 (4H, m), 3.94–3.90 (4H, m), 2.52 (3H, s).

EXAMPLE 295

4-(6-Methyl-4-quinazolinyl)-N-(3-picolyl)-1-piperazinethiocarboxamide (Compound 295)

Yield: 71% m.p.: 128–129° C.

¹H-NMR (CDCl₃) δ (ppm): 8.66 (1H, s), 8.51–8.49 (2H, m), 7.82–7.76 (2H, m), 7.66 (1H, d, J=1.7 Hz), 7.59 (1H, dd, J=8.6 Hz, 1.7 Hz), 7.28 (1H, m), 6.46 (1H, brt, J=5.3 Hz), 4.96 (2H, d, J=5.3 Hz), 4.16–4.12 (4H, m), 3.96–3.92 (4H, m), 2.52 (3H, s).

FAB-Mass: 379 (M⁺+1)

IR (KBr) σ (cm⁻¹): 1574, 1539, 1512, 1479, 1446, 1431, 1406, 1387, 1356, 1331.

In the following Examples 296–299, substantially the same procedure as in Example 1 was repeated, except that 6-fluoro-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 296

4-(6-Fluoro-4-quinazolinyl)-N-(4-isopropylphenyl)-1-piperazinecarboxamide (Compound 296)

Yield: 39% m.p.: 139–140° C.

¹H-NMR (CDCl₃) δ (ppm): 8.77 (1H, s), 7.95 (1H, m), 7.59–7.51 (2H, m), 7.28 (2H, d, J=8.6 Hz), 7.18 (2H, d, J=8.6 Hz), 6.34 (1H, brs), 3.86–3.82 (4H, m), 3.77–3.73 (4H, m), 2.88 (1H, m), 1.23 (6H, d, J=6.9 Hz).

FAB-Mass: 394 (M⁺+1)

IR (KBr) σ (cm⁻¹): 1645, 1538, 1506, 1419, 1247, 1238, 995, 908, 838, 829.

EXAMPLE 297

4-(6-Fluoro-4-quinazolinyl)-N-(4-phenoxyphenyl)-1-piperazinecarboxamide (Compound 297)

Yield: 42% m.p.: 186–187° C.

¹H-NMR (CDCl₃) δ (ppm): 8.77 (1H, s), 7.97 (1H, m), 7.59–7.51 (2H, m), 7.37–7.26 (4H, m), 7.10 (1H, m), 7.00–6.96 (4H, m), 6.43 (1H, brs), 3.86–3.82 (4H, m), 3.77–3.73 (4H, m).

FAB-Mass: 444 (M⁺+1)

IR (KBr) σ (cm⁻¹): 1641, 1589, 1571, 1542, 1506, 1415, 1230, 995, 908, 837.

EXAMPLE 298

N-(4-Acetylphenyl)-4-(6-fluoro-4-quinazolinyl)-1-piperazinecarboxamide (Compound 298)

Yield: 25% m.p.: 184–185° C.

¹H-NMR (CDCl₃) δ (ppm): 8.77 (1H, s), 7.95 (1H, m), 7.94 (2H, d, J=8.9 Hz), 7.60–7.48 (2H, m), 7.51 (2H, d, J=8.9 Hz), 6.69 (1H, brs), 3.87–3.84 (4H, m), 3.80–3.77 (4H, m), 2.58 (3H, s).

FAB-Mass: 394 (M⁺+1)

IR (KBr) σ (cm⁻¹): 1648, 1645, 1544, 1513, 1419, 1355, 1242, 993, 838.

EXAMPLE 299

4-(6-Fluoro-4-quinazolinyl)-N-(3-picolyl)-1-piperazinethiocarboxamide (Compound 299)

Yield: 36% m.p.: 170–172° C.

¹H-NMR (CDCl₃) δ (ppm): 8.72 (1H, s), 8.59 (1H, d, J=1.6 Hz), 8.56 (1H, dd, J=4.9 Hz, 1.6 Hz), 7.95 (1H, m), 7.77 (1H, ddd, J=7.2 Hz, 1.6 Hz, 1.6 Hz), 7.57 (1H, m), 7.52 (1H, m), 7.30 (1H, m), 5.86 (1H, brt, J=4.9 Hz) 4.97 (2H, d, J=4.9 Hz), 4.14–4.11 (4H,m), 3.98–3.94 (4H, m).

FAB-Mass: 383 (M⁺+1)

IR (KBr) σ (cm⁻¹): 1556, 1508, 1405, 1257, 1213, 1018, 910, 835, 711.

In the following Examples 300–302, substantially the same procedure as in Example 1 was repeated, except that 6-chloro-4-(1-piperazinyl)quinazoline was used in place of 6,7-dimethoxy-4-(1-piperazinyl)quinazoline, and the corresponding isocyanate was used in place of phenyl isocyanate, to give the desired compound.

EXAMPLE 300

4-(6-Chloro-4-quinazolinyl)-N-(4-isopropylphenyl)-1-piperazinecarboxamide (Compound 300)

Yield: 29% m.p.: 192–193° C.

¹H-NMR (CDCl₃) δ (ppm): 8.76 (1H, s), 7.90–7.87 (2H, m), 7.70 (1H, dd, J=9.2 Hz, 2.3 Hz), 7.28 (2H, d, J=9.0 Hz), 7.17 (2H, d, J=9.0 Hz), 6.35 (1H, brs), 3.89–3.86 (4H, m), 3.78–3.73 (4H, m), 2.88 (1H, m), 1.23 (6H, d, J=6.9 Hz).

FAB-Mass: 412 (M⁺+3), 410 (M⁺+1)

IR (KBr) σ (cm⁻¹): 1643, 1594, 1535, 1502, 1419, 1245, 991, 835.

EXAMPLE 301

4-(6-Chloro-4-quinazolinyl)-N-(4-phenoxyphenyl)-1-piperazinecarboxamide (Compound 301)

Yield: 35% m.p.: 116–120° C.

¹H-NMR (CDCl₃) δ (ppm): 8.89 (1H, s), 7.90 (1H, d, J=1.3 Hz), 7.85 (1H, dd, J=8.1 Hz, 1.3 Hz), 7.43 (1H, d, J=8.1 Hz), 7.35–7.28 (4H, m), 7.10 (1H, m), 7.01–6.97 (4H, m), 6.36 (1H, brs), 3.93–3.89 (4H, m), 3.77–3.73 (4H, m).

FAB-Mass: 462 (M⁺+3), 460 (M⁺+1)

IR (KBr) σ (cm⁻¹): 1648, 1539, 1506, 1488, 1417, 1224, 993, 946.

EXAMPLE 302

N-(4-Acetylphenyl)-4-(6-chloro-4-quinazolinyl)-1-piperazinecarboxamide (Compound 302)

Yield: 18% m.p.: 207–208° C.

¹H-NMR (CDCl₃) δ (ppm): 8.77 (1H, s), 7.94 (2H, d, J=8.9 Hz), 7.92–7.82 (2H, m), 7.51 (2H, d, J=8.9 Hz), 7.45 (1H, m), 6.64 (1H, brs), 3.96–3.92 (4H, m), 3.82–3.78 (4H, m) 2.59 (3H, s).

FAB-Mass: 412 (M⁺+3), 410 (M⁺+1)

IR (KBr) σ (cm⁻¹): 1677, 1668, 1527, 1495, 1270, 1234, 1172, 993, 950, 839, 777.

EXAMPLE 303

4-(6-Bromo-4-quinazolinyl)-N-(4-phenoxyphenyl)-1-piperazinecarboxamide (Compound 303)

Substantially the same procedure as in Example 60 was repeated, except that 6-bromo-4-(1-piperazinyl)quinazoline was used in place of 6,7-dimethoxy-4-(1-piperazinyl)quinazoline, to give the desired compound.

Yield: 29% m.p.: 169–170° C.

¹H-NMR (CDCl₃) δ (ppm): 8.77 (1H, s), 8.05 (1H, d, J=1.0 Hz), 7.87–7.79 (2H, m), 7.37–7.28 (4H, m), 7.08 (1H, m), 7.02–6.96 (4H, m), 6.44 (1H, brs), 3.90–3.85 (4H, m), 3.79–3.63 (4H, m).

FAB-Mass: 506 (M⁺+3), 504 (M⁺+1)

IR (KBr) σ (cm⁻¹): 1633, 1531, 1504, 1489, 1416, 1227, 833.

In the following Examples 304–306, substantially the same procedure as in Example 1 was repeated, except that 6-iodo-4-(1-piperazinyl)quinzoline was used in place of 6,7-dimethoxy-4-(1-piperazinyl)quinazoline, and the corresponding isocyanate was used in place of phenyl isocyanate, to give the desired compound.

EXAMPLE 304

4-(6-Iodo-4-quinazolinyl)-N-(4-isopropylphenyl)-1-piperazinecarboxamide (Compound 304)

Yield: 14% m.p.: 211–212° C.

¹H-NMR (CDCl₃) δ (ppm): 8.76 (1H, s), 8.26 (1H, d, J=1.8 Hz), 8.00 (1H, dd, J=8.9 Hz, 1.8 Hz), 7.66 (1H, d, J=8.9 Hz), 7.28 (2H, d, J=8.6 Hz), 7.17 (2H, d, J=8.6 Hz), 6.36 (1H, brs), 3.90–3.86 (4H, m), 3.76–3.72 (4H, m), 2.88 (1H, m), 1.23 (6H, d, J=6.9 Hz).

FAB-Mass: 502 (M⁺+1)

IR (KBr) σ (cm⁻¹): 1643, 1594, 1556, 1531, 1496, 1417, 1245, 991, 831.

EXAMPLE 305

4-(6-Iodo-4-quinazolinyl)-N-(4-phenoxyphenyl)-1-piperazinecarboxamide (Compound 305)

Yield: 43% m.p.: 184–185° C.

¹H-NMR (CDCl₃) δ (ppm): 8.76 (1H, s), 8.27 (1H, d, J=2.0 Hz), 8.00 (1H, dd, J=8.9 Hz, 2.0 Hz), 7.66 (1H, d, J=8.9 Hz), 7.36–7.28 (4H, m), 7.08 (1H, m), 7.01–6.97 (4H, m), 6.40 (1H, brs), 3.91–3.87 (4H, m), 3.77–3.73 (4H, m).

FAB-Mass: 552 (M⁺+1)

IR (KBr) σ (cm⁻¹): 1637, 1540, 1508, 1488, 1413, 1226, 1012, 993, 840.

EXAMPLE 306

N-(4-Acetylphenyl)-4-(6-iodo-4-quinazolinyl)-1-piperazinecarboxamide (Compound 306)

Yield: 7%

¹H-NMR (CDCl₃) δ (ppm): 8.78 (1H, s), 8,27 (1H, d, J=1.6 Hz), 8.01 (1H, dd, J=8.9 Hz, 1.6 Hz), 7.93 (2H, d, J=8.5 Hz), 7.67 (1H, d, J=8.9 Hz), 7.50 (2H, d, J=8.5 Hz), 6.68 (1H, brs), 3.92–3.88 (4H, m), 3.80–3.76 (4H, m), 2.58 (3H, s).

FAB-Mass: 502 (M⁺+1)

In the following Examples 307–310, substantially the same procedure as in Example 1 was repeated, except that 6-methoxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 307

4-(6-Methoxy-4-quinazolinyl)-N-(4-phenoxyphenyl)-1-piperazinecarboxamide (Compound 307)

Yield: 100% m.p.: 139–140° C.

¹H-NMR (CDCl₃) δ (ppm): 8.70 (1H, s), 7.86 (1H, d, J=8.9 Hz), 7.43 (1H, dd, J=8.9 Hz, 2.3 Hz), 7.35–7.25 (4H, m), 7.14 (1H, d, J=2.3 Hz), 7.07–7.01 (2H, m), 6.96–6.93 (4H, m), 3.90 (3H, s), 3.74 (8H, m).

FAB-Mass: 456 (M⁺+1)

IR (KBr) σ (cm⁻¹): 1637, 1539, 1508, 1489, 1417, 1227, 843.

EXAMPLE 308

4-(6-Methoxy-4-quinazolinyl)-N-(4-nitrophenyl)-1-piperazinecarboxamide (Compound 308)

Yield: 76% m.p.: 228–229° C.

¹H-NMR (CDCl₃) δ (ppm): 8.68 (1H, s), 8.12 (2H, d, J=9.2 Hz), 7.89 (1H, brs), 7.85 (1H, d, J=8.9 Hz), 7.59 (2H, d, J=9.2 Hz), 7.44 (1H, dd, J=8.9 Hz, 2.6 Hz), 7.15 (1H, d, J=2.6 Hz), 3.92 (3H, s), 3.80–3.79 (8H, m).

FAB-Mass: 409 (M⁺+1)

IR (KBr) σ (cm$^{-1}$): 1651, 1541, 1502, 1475, 1417, 1325, 1240, 1109, 985, 841.

EXAMPLE 309

N-Benzyl-4-(6-methoxy-4-quinazolinyl)-1-piperazinethiocarboxamide (Compound 309)

Yield: 79% m.p.: 68–70° C.

$^1$H-NMR (CDCl$_3$) δ (ppm): 8.59 (1H, s), 7.82 (1H, d, J=9.2 Hz), 7.43 (1H, dd, J=9.2 Hz, 2.3 Hz), 7.35–7.24 (5H, m), 7.15 (1H, d, J=2.3 Hz), 6.68 (1H, brt, J=4.6 Hz), 4.91 (2H, d, J=4.6 Hz), 4.10–4.09 (4H, m), 3.91 (3H, s), 3.89–3.87 (4H, m).

FAB-Mass: 394 (M$^+$+1)

IR (KBr) σ (cm$^{-1}$): 1541, 1508, 1448, 1335, 1228.

EXAMPLE 310

4-(6-Methoxy-4-quinazolinyl)-N-(3-picolyl)-1-piperazinethiocarboxamide (Compound 310)

Yield: 81% m.p.: 139–140° C.

$^1$H-NMR (CDCl$_3$) δ (ppm): 8.59 (1H, s), 8.42–8.40 (2H, m), 7.80–7.75 (2H, m), 7.41 (1H, dd, J=8.9 Hz, 2.3 Hz), 7.34 (1H, br), 7.24 (1H, dd, J=7.9 Hz, 4.9 Hz), 7.14 (1H, d, J=2.3 Hz), 4.94 (2H, d, J=5.3 Hz), 4.16–4.14 (4H, m), 3.90 (3H, s), 3.90–3.87 (4H, m).

FAB-Mass: 395 (M$^+$+1)

IR (KBr) σ (cm$^{-1}$): 1549, 1502, 1425, 1406, 1257, 1227, 1016, 943, 849, 714.

EXAMPLE 311

4-(6-Nitro-4-quinazolinyl)-N-(4-phenoxyphenyl)-1-piperazinecarboxamide (Compound 311)

Substantially the same procedure as in Example 60 was repeated, except that 6-nitro-4-(1-piperazinyl)quinazoline was used in place of 6,7-dimethoxy-4-(1-piperazinyl)quinazoline, to give the desired compound.

Yield: 98% m.p.: 170–171° C.

$^1$H-NMR (CDCl$_3$) δ (ppm): 8.89 (1H, brs), 8.77 (1H, s), 8.51 (1H, d, J=8.9 Hz), 8.29 (1H, s), 7.98 (1H, d, J=8.9 Hz), 7.47–7.44 (2H, m), 7.34–7.28 (2H, m), 7.06 (1H, m), 6.97–6.94 (4H, m), 4.14–4.11 (4H, m), 4.09–4.06 (4H, m).

FAB-Mass: 471 (M$^+$+1)

IR (KBr) σ (cm$^{-1}$): 1633, 1581, 1506, 1416, 1356, 1325, 1225, 847, 748.

In the following Examples 312–315, substantially the same procedure as in Example 1 was repeated, except that 7-methyl-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 312

4-(7-Methyl-4-quinazolinyl)-N-(4-phenoxyphenyl)-1-piperazinecarboxamide (Compound 312)

Yield: 93% m.p.: 184–185° C.

$^1$H-NMR (CDCl$_3$) δ (ppm): 8.72 (1H, s), 7.79 (1H, d, J=8.6 Hz), 7.69 (1H, s), 7.37–7.26 (5H, m), 7.06 (1H, m), 6.99–6.93 (4H, m), 6.86 (1H, brs), 3.84–3.81 (4H, m), 3.75–3.68 (4H, m), 2.53 (3H, s).

FAB-Mass: 440 (M$^+$+1)

IR (KBr) σ (cm$^{-1}$): 1626, 1525, 1508, 1489, 1421, 1227.

EXAMPLE 313

4-(7-Methyl-4-quinazolinyl)-N-(4-nitrophenyl)-1-piperazinecarboxamide (Compound 313)

Yield: 65% m.p.: 251–254° C.

$^1$H-NMR (CDCl$_3$) δ (ppm): 8.65 (1H, s), 8.08 (1H, brs), 8.06 (2H, d, J=9.2 Hz), 7.74 (1H, d, J=9.3 Hz), 7.62 (1H, d, J=1.3 Hz), 7.57 (2H, d, J=9.2 Hz), 7.29 (1H, dd, J=9.3 Hz, 1.3 Hz), 3.78 (8H, m), 2.48 (3H, s).

FAB-Mass: 393 (M$^+$+1)

IR (KBr) σ (cm$^{-1}$): 1680, 1597, 1551, 1498, 1450, 1416, 1390, 1331, 1304, 1234, 1198, 1111, 993, 752.

EXAMPLE 314

N-Benzyl-4-(7-methyl-4-quinazolinyl)-1-piperazinethiocarboxamide (Compound 314)

Yield: 78% m.p.: 177–178° C.

$^1$H-NMR (CDCl$_3$) δ (ppm): 8.65 (1H, s), 7.81 (1H, m), 7.65 (1H, m), 7.39–7.26 (6H, m), 6.87 (1H, br), 4.96 (2H, d, J=4.0 Hz), 4.15–4.13 (4H, m), 3.95 (4H, m), 2.55 (3H, s).

FAB-Mass: 378 (M$^+$+1)

IR (KBr) σ (cm$^{-1}$): 1566, 1541, 1495, 1448, 1414, 1338, 1219, 1012, 694.

EXAMPLE 315

4-(7-Methyl-4-quinazolinyl)-N-(3-picolyl)-1-piperazinethiocarboxamide dihydrochloride (Compound 315)

Yield: 87% m.p.: 180–183° C. (hydrochloride)

$^1$H-NMR (free base, CDCl$_3$) δ (ppm): 8.63 (1H, s), 8.47–8.45 (2H, m), 7.81–7.76 (2H, m), 7.64 (1H, s), 7.32–7.23 (2H, m), 6.82 (1H, brt, J=5.3 Hz), 4.95 (2H, d, J=5.3 Hz), 4.16–4.12 (4H, m), 3.97–3.93 (4H, m), 2.52 (3H, s).

FAB-Mass: 379 (M$^+$+1)

IR (hydrochloride, KBr) σ (cm$^{-1}$): 1525, 1473, 1444, 1419, 1396, 1360, 1323.

In the following Examples 316 and 317, substantially the same procedure as in Example 1 was repeated, except that 7-chloro-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 316

4-(7-Chloro-4-quinazolinyl)-N-(4-phenoxyphenyl)-1-piperazinecarboxamide (Compound 316)

Yield: 13%

FAB-Mass: 462 (M$^+$+3), 460 (M$^+$+1)

EXAMPLE 317

N-Benzyl-4-(7-chloro-4-quinazolinyl)-1-piperazinethiocarboxamide (Compound 317)

Yield: 79% m.p.: 70–71° C.

¹H-NMR (CDCl₃) δ (ppm): 8.67 (1H, s), 7.88 (1H, d, J=2.0 Hz), 7.83 (1H, d, J=8.9 Hz), 7.41 (1H, dd, J=8.9 Hz, 2.0 Hz), 7.36–7.29 (5H, m), 5.84 (1H, brt, J=4.9 Hz), 4.89 (2H, d, J=4.9 Hz), 4.12–4.07 (4H, m), 4.00–3.96 (4H, m).

FAB-Mass: 400 (M⁺+3), 398 (M⁺+1)

IR (KBr) σ (cm⁻¹): 1562, 1537, 1495, 1454, 1439, 1335.

In the following Examples 318–320, substantially the same procedure as in Example 1 was repeated, except that 7-isopropoxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 318

4-(7-Isopropoxy-4-quinazolinyl)-N-(4-phenoxyphenyl)-1-piperazinecarboxamide (Compound 318)

Yield: 23% m.p.: 181–182° C.

¹H-NMR (CDCl₃) δ (ppm): 8.65 (1H, s), 8.02 (1H, d, J=8.9 Hz), 7.37–7.27 (5H, m), 7.19 (1H, dd, J=8.9 Hz, 2.6 Hz), 7.11–6.94 (5H, m), 6.71 (1H, brs), 5.60 (1H, m), 3.77–3.70 (4H, m), 3.48–3.45 (4H, m), 1.46 (6H, d, J=6.3 Hz).

FAB-Mass: 484 (M⁺+1)

IR (KBr) σ (cm⁻¹): 1660, 1614, 1572, 1531, 1508, 1491, 1429, 1219, 1113, 837, 750, 689.

EXAMPLE 319

4-(7-Isopropoxy-4-quinazolinyl)-N-(4-nitrophenyl)-1-piperazinecarboxamide (Compound 319)

Yield: 23%

¹H-NMR (CDCl₃) δ (ppm): 8.65 (1H, s), 8.15 (2H, d, J=8.9 Hz), 8.03 (1H, d, J=8.9 Hz), 7.70 (2H, d, J=8.9 Hz), 7.35–7.13 (3H, m), 5.60 (1H, m), 4.05 (4H, m), 3.80–3.78 (4H, m), 1.46 (6H, d, J=6.3 Hz).

FAB-Mass: 437 (M⁺+1)

EXAMPLE 320

N-Benzyl-4-(7-isopropoxy-4-quinazolinyl)-1-piperazinethiocarboxamide (Compound 320)

Yield: 24%

¹H-NMR (CDCl₃) δ (ppm): 8.60 (1H, s), 8.00 (1H, d, J=9.2 Hz), 7.37–7.29 (5H, m), 7.10 (1H, dd, J=9.2 Hz, 2.3 Hz), 6.98 (1H, d, J=2.3 Hz), 6.26 (1H, brt, J=5.0 Hz), 5.57 (1H, m), 4.89 (2H, d, J=5.0 Hz), 4.70–4.06 (4H, m), 3.54–3.51 (4H, m), 1.45 (6H, d, J=6.3 Hz).

FAB-Mass: 422 (M⁺+1)

EXAMPLE 321

4-(7-Amino-4-quinazolinyl)-N-(4-phenoxyphenyl)-1-piperazinecarboxamide (Compound 321)

To a solution of 455.6 mg (0.97 mmol) of 4-(7-nitro-4-quinazolinyl)-N-(4-phenoxyphenyl)-1-piperazinecarboxamide obtained in Example 322 in 10 ml of ethanol was added a suspension of 100 mg of 10% palladium-carbon in 5 ml of ethanol and 2 ml of water, followed by stirring in a stream of hydrogen at room temperature for 4 hours. After the catalyst was separated by filtration using Celite, the solvent was evaporated. The residue was purified by silica gel chromatography to give the desired compound as colorless crystals.

Yield: 45%

¹H-NMR (CDCl₃) δ (ppm): 8.68 (1H, s), 7.77 (1H, d, J=8.3 Hz), 7.55 (1H, brs), 7.35–7.29 (4H, m), 7.07–6.97 (7H, m), 6.35 (2H, brs), 3.84–3.82 (4H, m), 3.75–3.73 (4H, m).

EXAMPLE 322

4-(7-Nitro-4-quinazolinyl)-N-(4-phenoxyphenyl)-1-piperazinecarboxamide (Compound 322)

Substantially the same procedure as in Example 60 was repeated, except that 7-nitro-4-(1-piperazinyl)quinazoline was used in place of 6,7-dimethoxy-4-(1-piperazinyl) quinazoline, to give the desired compound.

Yield: 24% m.p.: 146–148° C.

¹H-NMR (CDCl₃) δ (ppm): 8.82 (1H, s), 8.73 (1H, d, J=2.3 Hz), 8.21 (1H, dd, J=8.9 Hz, 2.3 Hz), 8.04 (1H, d, J=8.9 Hz), 7.35–7.27 (4H, m), 7.06 (1H, m), 6.98–6.94 (4H, m), 6.80 (1H, brs), 3.95–3.92 (4H, m), 3.78–3.74 (4H, m).

FAB-Mass: 471 (M⁺+1)

IR (KBr) σ (cm⁻¹): 1635, 1587, 1541, 1529, 1508, 1489, 1417, 1346, 1227, 996, 808, 743.

EXAMPLE 323

4-(7-Methoxycarbonyl-4-quinazolinyl)-N-(4-phenoxyphenyl)-1-piperazinecarboxamide (Compound 323)

Substantially the same procedure as in Example 60 was repeated, except that 7-methoxycarbonyl-4-(1-piperazinyl) quinazoline was used in place of 6,7-dimethoxy-4-(1-piperazinyl)quinazoline, to give the desired compound.

Yield: 32%

¹H-NMR (CDCl₃) δ (ppm): 8.78 (1H, s), 8.57 (1H, d, J=1.7 Hz), 8.06 (1H, dd, J=8.6 Hz, 1.7 Hz), 7.93 (1H, d, J=8.6 Hz), 7.36–7.25 (4H, m), 7.06 (1H, m), 7.02–6.93 (5H, m), 3.99 (3H, s), 3.90–3.86 (4H, m), 3.77–3.74 (4H, m).

FAB-Mass: 484 (M⁺+1)

EXAMPLE 324

4-(7-Carboxy-4-quinazolinyl)-N-(4-phenoxyphenyl)-1-piperazinecarboxamide (Compound 324)

To a solution of 1.50 g (3.11 mmol) of 4-(7-methoxycarbonyl-4-quinazolinyl)-N-(4-phenoxyphenyl)-1-piperazinecarboxamide obtained in Example 323 in 20 ml of methanol was added 20 ml of a 1 N aqueous solution of sodium hydroxide, followed by heating at 50° C. with stirring for 3.5 hours. After the mixture was made acidic with concentrated hydrochloric acid, the precipitated crystals were collected by filtration, washed with ethanol and then with chloroform, and recrystallized from methanol to give the desired compound as colorless crystals.

Yield: 37%

¹H-NMR (DMSO-d₆) δ (ppm): 8.93 (1H, s), 8.71 (1H, brs), 8.37–8.34 (2H, m), 8.11 (1H, d, J=8.9 Hz), 7.52–7.49 (2H, m), 7.39– 7.33 (2H, m), 7.09 (1H, m), 6.97–6.94 (4H, m), 4.24 (4H, m), 3.77–3.76 (4H, m).

FAB-Mass: 470 (M⁺+1)

EXAMPLE 325

N-(4-Acetylphenyl)-4-(8-chloro-4-quinazolinyl)-1-piperazinecarboxamide (Compound 325)

Substantially the same procedure as in Example 87 was repeated, except that 8-chloro-4-(1-piperazinyl)quinazoline was used in place of 6,7-dimethoxy-4-(1-piperazinyl) quinazoline, to give the desired compound.

Yield: 23% m.p.: 208–209° C.

$^1$H-NMR (CDCl$_3$) δ (ppm): 8.89 (1H, s), 7.93 (2H, d, J=8.9 Hz), 7.91–7.82 (2H, m), 7.50 (2H, d, J=8.9 Hz), 7.45 (1H, m), 6.66 (1H, brs), 3.94–3.90 (4H, m), 3.80–3.76 (4H, m), 2.58 (3H, s).

FAB-Mass: 412 (M$^+$+3), 410 (M$^+$+1)

IR (KBr) σ (cm$^{-1}$): 1677, 1668, 1596, 1527, 1494, 1270, 1234, 1172, 993, 950, 838, 777.

In the following Examples 326–328, substantially the same procedure as in Example 1 was repeated, except that 8-methoxy-4-(1-piperazinyl)quinazoline was used in place of 6,7-dimethoxy-4-(1-piperazinyl)quinazoline, and the corresponding isocyanate was used in place of phenyl isocyanate, to give the desired compound.

EXAMPLE 326

N-(4-Isopropylphenyl)-4-(8-methoxy-4-quinazolinyl)-1-piperazinecarboxamide (Compound 326)

Yield: 6% m.p.: 102–104° C.

$^1$H-NMR (CDCl$_3$) δ (ppm): 8.82 (1H, s), 7.48–7.39 (2H, m), 7.28 (2H, d, J=8.6 Hz), 7.17 (2H, d, J=8.6 Hz), 7.12 (1H, m), 6.35 (1H, brs), 4.07 (3H, s), 3.86–3.83 (4H, m), 3.74–3.72 (4H, m), 2.87 (1H, m), 1.23 (6H, d, J=6.9 Hz).

FAB-Mass: 405 (M$^+$+1)

IR (KBr) σ (cm$^{-1}$): 1635, 1498, 1454, 1417, 1241, 1024, 991, 958, 827, 760.

EXAMPLE 327

4-(8-Methoxy-4-quinazolinyl)-N-(4-phenoxyphenyl)-1-piperazinecarboxamide (Compound 327)

Yield: 21% m.p.: 108–109° C.

$^1$H-NMR (CDCl$_3$) δ (ppm): 8.82 (1H, s), 7.49–7.39 (2H, m), 7.36–7.25 (4H, m), 7.16–7.05 (2H, m), 7.00–6.97 (4H, m), 6.43 (1H, brs), 4.07 (3H, s), 3.87–3.83 (4H, m), 3.76–3.72 (4H, m).

FAB-Mass: 456 (M$^+$+1)

IR (KBr) σ (cm$^{-1}$): 1641, 1538, 1498, 1415, 1224, 1024, 991, 754.

EXAMPLE 328

N-(4-Acetylphenyl)-4-(8-methoxy-4-quinazolinyl)-1-piperazinecarboxamide (Compound 328)

Yield: 6% m.p.: 239–240° C.

$^1$H-NMR (CDCl$_3$) δ (ppm): 8.82 (1H, s), 7.93 (2H, d, J=8.6 Hz), 7.50 (2H, d, J=8.6 Hz), 7.45–7.23 (2H, m), 7.15 (1H, dd, J=6.3 Hz, 2.6 Hz), 6.70 (1H, brs), 4.07 (3H, s), 3.88–3.84 (4H, m), 3.79–3.75 (4H, m), 2.58 (3H, s).

FAB-Mass: 405 (M$^+$+1)

IR (KBr) σ (cm$^{-1}$): 1675, 1662, 1527, 1490, 1419, 1386, 1272, 1226, 1172, 995, 950, 775.

EXAMPLE 329

4-(6,7-Difluoro-4-quinazolinyl)-N-(4-phenoxyphenyl)-1-piperazinecarboxamide (Compound 205)

To a solution of 446.7 mg (1.27 mmol) of 4-(6,7-difluoro-4-quinazolinyl)-1-piperazinecarboxylic acid tert-butyl ester obtained in Reference Example 7 in 3 ml of dichloromethane was added 3 ml of trifluoroacetic acid under ice-cooling, followed by stirring at the same temperature for 4 hours. After the solvent was evaporated, the residue was subjected to azeotropic distillation with toluene twice, and the obtained residue was dissolved in 10 ml of dimethylformamide. To the resulting solution were added 0.89 ml (6.39 mmol) of triethylamine and 0.27 ml (1.28 mmol) of 4-phenoxyphenyl isocyanate, followed by overnight stirring at room temperature. The reaction mixture was poured into water and sodium chloride was added thereto. The precipitated crystals were collected by filtration, washed with water, and dried, followed by purification by silica gel chromatography to give the desired compound as colorless crystals.

Yield: 98% m.p.: 177–178° C.

$^1$H-NMR (CDCl$_3$) δ (ppm): 8.74 (1H, s), 7.71–7.62 (2H, m), 7.36–7.26 (4H, m), 7.05 (1H, m), 6.98–6.94 (4H, m), 6.69 (1H, brs), 3.83–3.72 (8H, m).

FAB-Mass: 462 (M$^+$+1)

IR (KBr) σ (cm$^{-1}$): 1633, 1578, 1508, 1489, 1423, 1227.

In the following Examples 330 and 331, substantially the same procedure as in Example 329 was repeated, except that the corresponding isothiocyanate was used in place of 4-phenoxyphenyl isocyanate, to give the desired compound.

EXAMPLE 330

N-Benzyl-4-(6,7-difluoro-4-quinazolinyl)-1-piperazinethiocarboxamide (Compound 330)

Yield: 94% m.p.: 119–120° C.

H-NMR (CDCl$_3$) δ (ppm): 8.67 (1H, s), 7.70–7.61 (2H, m), 7.36–7.29 (5H, m), 5.90 (1H, brt, J=4.9 Hz), 4.89 (2H, d, J=4.9 Hz), 4.12–4.06 (4H, m), 3.95–3.92 (4H, m).

FAB-Mass: 400 (M$^+$+1)

IR (KBr) σ (cm$^{-1}$): 1578, 1539, 1514, 1481, 1446, 1381, 1335, 698.

EXAMPLE 331

4-(6,7-Difluoro-4-quinazolinyl)-N-(3-picolyl)-1-piperazinethiocarboxamide (Compound 331)

Yield: 93% m.p.: 177–178° C.

$^1$H-NMR (DMSO-d$_6$) δ (ppm): 8.62 (1H, s), 8.55 (1H, s), 8.45 (1H, d, J=4.6 Hz), 8.36 (1H, br), 8.12 (1H, dd, J=11.6 Hz, 8.9 Hz), 7.83 (1H, dd, J=11.6 Hz, 7.9 Hz), 7.74 (1H, d, J=7.9 Hz), 7.35 (1H, dd, J=7.9 Hz, 4.6 Hz), 4.82 (2H, d, J=2.6 Hz), 4.06–4.05 (4H, m), 3.96–3.95 (4H, m).

FAB-Mass: 401 (M$^+$+1)

IR (KBr) σ (cm$^{-1}$): 1581, 1514, 1481, 1446, 1327.

EXAMPLE 332

4-(7-Ethoxy-6-fluoro-4-quinazolinyl)-N-(4-phenoxyphenyl)-1-piperazinecarboxamide (Compound 332)

Substantially the same procedure as in Example 60 was repeated, except that 7-ethoxy-6-fluoro-4-(1-piperazinyl) quinazoline was used in place of 6,7-dimethoxy-4-(1-piperazinyl)quinazoline, to give the desired compound.

Yield: 72% m.p.: 197–198° C.

$^1$H-NMR (CDCl$_3$) δ (ppm): 8.69 (1H, s), 7.73 (1H, d, J=12.9 Hz), 7.37–7.25 (5H, m), 7.05 (1H, m), 6.98–6.93 (4H, m), 6.87 (1H, brs), 4.60 (2H, q, J=7.3 Hz), 3.73–3.69 (4H, m), 3.30–3.26 (4H, m), 1.50 (3H, t, J=7.3 Hz).

FAB-Mass: 488 (M$^+$+1)

IR (KBr) σ (cm$^{-1}$): 1649, 1533, 1500, 1431, 1417, 1379, 1356, 1221, 1003, 868, 744.

In the following Examples 333 and 334, substantially the same procedure as in Example 1 was repeated, except that 6-methoxy-7-methyl-4-(1-piperazinyl)quinazoline was used in place of 6,7-dimethoxy-4-(1-piperazinyl)quinazoline, and the corresponding isocyanate was used in place of phenyl isocyanate, to give the desired compound.

EXAMPLE 333

4-(6-Methoxy-7-methyl-4-quinazolinyl)-N-(4-phenoxyphenyl)-1-piperazinecarboxamide (Compound 333)

Yield: 31% m.p.: 188–189° C.

$^1$H-NMR (CDCl$_3$) δ (ppm): 8.71 (1H, s), 7.71 (1H, s), 7.36–7.28 (4H, m), 7.10–7.04 (2H, m), 7.01–6.97 (4H, m), 6.46 (1H, brs), 3.95 (3H, s), 3.77–3.76 (8H, m), 2.40 (3H, s).

FAB-Mass: 470 (M$^+$+1)

IR (KBr) σ (cm$^{-1}$) 1632, 1537, 1506, 1489, 1417, 1225, 997.

EXAMPLE 334

N-(4-Cyanophenyl)-4-(6-methoxy-7-methyl-4-quinazolinyl)-1-piperazinecarboxamide (Compound 334)

Yield: 51% m.p.: 242–243° C.

$^1$H-NMR (CDCl$_3$) δ (ppm): 8.69 (1H, s), 7.70 (1H, s), 7.59 (2H, d, J=9.2 Hz), 7.54 (2H, d, J=9.2 Hz), 7.07 (1H, brs), 7.04 (1H, s), 3.94 (3H, s), 3.78 (8H, m), 2.41 (3H, s).

FAB-Mass: 403 (M$^+$+1)

IR (KBr) σ (cm$^{-1}$): 2227, 1666, 1595, 1525, 1417, 1385, 1319, 1238, 995, 837.

In the following Examples 335–338, substantially the same procedure as in Example 329 was repeated, except that 4-(7-ethoxy-6-methoxy-4-quinazolinyl)-1-piperazinecarboxylic acid tert-butyl ester obtained in Reference Example 8 was used in place of 4-(6,7-difluoro-4-quinazolinyl)-1-piperazinecarboxylic acid tert-butyl ester, and 4-phenoxyphenyl isocyanate, or in its place, the corresponding isocyanate or isothiocyanate was used, to give the desired compound.

EXAMPLE 335

4-(7-Ethoxy-6-methoxy-4-quinazolinyl)-N-(4-phenoxyphenyl)-1-piperazinecarboxamide (Compound 335)

Yield: 100% m.p.: 174–175° C.

$^1$H-NMR (CDCl$_3$) δ (ppm): 8.68 (1H, s), 7.36–7.24 (5H, m), 7.10 (1H, s), 7.06 (1H, m), 6.98–6.94 (4H, m), 6.80 (1H, brs), 4.25 (2H, q, J=6.9 Hz), 3.98 (3H, s), 3.74 (8H, m), 1.56 (3H, t, J=6.9 Hz).

FAB-Mass: 500 (M$^+$+1)

IR (KBr) σ (cm$^{-1}$): 1630, 1541, 1508, 1491, 1421, 1232.

EXAMPLE 336

N-(4-Bromophenyl)-4-(7-ethoxy-6-methoxy-4-quinazolinyl)-1-piperazinecarboxamide (Compound 336)

Yield: 100% m.p.: 210–212° C.

$^1$H-NMR (CDCl$_3$) δ (ppm): 8.68 (1H, s), 7.40 (2H, d, J=8.9 Hz), 7.29 (2H, d, J=8.9 Hz), 7.24 (1H, s), 7.09 (1H, s), 6.79 (1H, brs), 4.25 (2H, q, J=6.9 Hz), 3.98 (3H, s), 3.73 (8H, m), 1.55 (3H, t, J=6.9 Hz).

FAB-Mass: 488 (M$^+$+3), 486 (M$^+$+1)

IR (KBr) σ (cm$^{-1}$): 1641, 1524, 1500, 1450, 1425, 1400, 1230, 1206.

EXAMPLE 337

N-Benzyl-4-(7-ethoxy-6-methoxy-4-quinazolinyl)-1-piperazinethiocarboxamide (Compound 337)

Yield: 97% m.p.: 168–169° C.

$^1$H-NMR (CDCl$_3$) δ (ppm): 8.61 (1H, s), 7.36–7.28 (5H, m), 7.21 (1H, s), 7.10 (1H, s), 6.07 (1H, brt, J=4.6 Hz), 4.90 (2H, d, J=4.6 Hz), 4.23 (2H, q, J=6.9 Hz), 4.12–4.06 (4H, m), 3.97 (3H, s), 3.86–3.82 (4H, m), 1.55 (3H, t, J=6.9 Hz).

FAB-Mass: 438 (M$^+$+1)

IR (KBr) σ (cm$^{-1}$): 1574, 1537, 1506, 1450, 1335, 1236, 1211, 1011, 937, 870.

EXAMPLE 338

4-(7-Ethoxy-6-methoxy-4-quinazolinyl)-N-(3-picolyl)-1-piperazinethiocarboxamide (Compound 338)

Yield: 100% m.p.: 169–170° C.

$^1$H-NMR (CDCl$_3$) δ (ppm): 8.60 (1H, s), 8.47–8.44 (2H, m), 7.78 (1H, m), 7.27 (1H, dd, J=7.9 Hz, 4.9 Hz), 7.20 (1H, s), 7.09 (1H, s), 6.81 (1H, br), 4.95 (2H, d, J=5.3 Hz), 4.23 (2H, q, J=6.9 Hz), 4.16–4.12 (4H, m), 3.97 (3H, s), 3.95–3.82 (4H, m), 1.55 (3H, t, J=6.9 Hz).

FAB-Mass: 439 (M$^+$+1)

IR (KBr) σ (cm$^{-1}$): 1579, 1539, 1506, 1487, 1463, 1435, 1400, 1336, 1244, 1211, 1189, 1009, 945, 860.

EXAMPLE 339

4-(7-Isopropoxy-6-methoxy-4-quinazolinyl)-N-(4-phenoxyphenyl)-1-piperazinecarboxamide (Compound 339)

Substantially the same procedure as in Example 329 was repeated, except that 4-(7-isopropoxy-6-methoxy-4-quinazolinyl)-1-piperazinecarboxylic acid tert-butyl ester obtained in Reference Example 9 was used in place of 4-(6,7-difluoro-4-quinazolinyl)-1-piperazinecarboxylic acid tert-butyl ester, to give the desired compound.

Yield: 100% m.p.: 157–160° C.

$^1$H-NMR (CDCl$_3$) δ (ppm): 8.67 (1H, s), 7.38–7.23 (6H, m), 7.09 (1H, s), 7.02 (1H, m), 6.96–6.93 (4H, m), 4.75 (1H, m), 3.95 (3H, s), 3.73–3.72 (8H, m), 1.47 (6H, d, J=6.3 Hz).

FAB-Mass: 514 (M$^+$+1)

IR (KBr) σ (cm$^{-1}$): 1630, 1541, 1508, 1489, 1421, 1230, 1201, 1109, 941.

EXAMPLE 340

N-Benzyl-4-(6-methoxy-7-methyl-4-quinazolinyl)-1-piperazinethiocarboxamide (Compound 340)

Substantially the same procedure as in Example 1 was repeated, except that 6-methoxy-7-methyl-4-(1-piperazinyl) quinazoline was used in place of 6,7-dimethoxy-4-(1-piperazinyl)quinazoline in Example 125, and the corresponding benzyl isothiocyanate was used in place of phenyl isocyanate, to give the desired compound.

Yield: 37%

$^1$H-NMR (CDCl$_3$) δ (ppm): 8.60 (1H, s), 7.63 (1H, s), 7.35–7.26 (5H, m), 7.02 (1H, s), 6.19 (1H, brt, J=4.9 Hz), 4.90 (2H, d, J=4.9 Hz), 4.10–4.02 (4H, m), 3.92 (3H, s), 3.87–3.83 (4H, m), 2.38 (3H, s).

In the following Examples 341 and 342, substantially the same procedure as in Example 329 was repeated, except that 4-(7-isopropoxy-6-methoxy-4-quinazolinyl)-1-piperazinecarboxylic acid tert-butyl ester obtained in Reference Example 9 was used in place of 4-(6,7-difluoro-4-quinazolinyl)-1-piperazinecarboxylic acid tert-butyl ester, and the corresponding isothiocyanate was used in place of 4-phenoxyphenyl isocyanate, to give the desired compound.

EXAMPLE 341

N-Benzyl-4-(7-isopropoxy-6-methoxy-4-quinazolinyl)-1-piperazinethiocarboxamide (Compound 341)

Yield: 84% m.p.: 174–175° C.° C.

$^1$H-NMR (CDCl$_3$) δ (ppm): 8.60 (1H, s), 7.34–7.23 (6H, m), 7.12 (1H, s), 5.81 (1H, br), 4.90 (2H, d, J=5.0 Hz), 4.74 (1H, m), 4.08–4.04 (4H, m), 3.93 (3H, s), 3.84–3.80 (4H, m), 1.45 (6H, d, J=5.9 Hz)

FAB-Mass: 452 (M$^+$+1)

IR (KBr) σ (cm$^{-1}$) 1576, 1543, 1504, 1481, 1456, 1429, 1379, 1340, 1240, 1203, 1109, 941, 876, 854.

EXAMPLE 342

4-(7-Isopropoxy-6-methoxy-4-quinazolinyl)-N-(3-picolyl)-1-piperazinethiocarboxamide (Compound 342)

Yield: 61% m.p.: 205–206° C.

$^1$H-NMR (CDCl$_3$) δ (ppm): 8.59 (1H, s), 8.45 (1H, dd, J=5.0 Hz, 1.7 Hz), 8.42 (1H, d, J=2.0 Hz), 7.78 (1H, ddd, J=7.9 Hz, 2.0 Hz, 1.7 Hz), 7.26 (1H, dd, J=7.9 Hz, 5.0 Hz), 7.20 (1H, s), 7.10 (1H, s), 7.03 (1H, brt, J=5.3 Hz), 4.95 (2H, d, J=5.3 Hz), 4.75 (1H, m), 4.17–4.13 (4H, m), 3.95 (3H, s), 3.86–3.82 (4H, m), 1.47 (6H, d, J=5.9 Hz).

FAB-Mass: 453 (M$^+$+1)

IR (KBr) σ (cm$^{-1}$): 1576, 1545, 1504, 1483, 1458, 1431, 1410, 1342, 1242, 1207, 1107, 939.

EXAMPLE 343

4-(6-Methoxy-7-methyl-4-quinazolinyl)-N-(3-picolyl)-1-piperazinethiocarboxamide (Compound 343)

Substantially the same procedure as in Example 1 was repeated, except that 6-methoxy-7-methyl-4-(1-piperazinyl) quinazoline was used in place of 6,7-dimethoxy-4-(1-piperazinyl)quinazoline, and the corresponding 3-picolyl isothiocyanate was used in place of phenyl isocyanate, to give the desired compound.

Yield: 36%

$^1$H-NMR (CDCl$_3$) δ (ppm): 8.60 (1H, s), 8.46 (2H, m), 7.78 (1H, m), 7.63 (1H, s), 7.26 (1H, dd, J=7.9 Hz, 5.0 Hz), 7.03 (1H, s), 7.02 (1H, br), 4.96 (2H, d, J=5.3 Hz), 4.17–4.12 (4H, m), 3.92 (3H, s), 3.88–3.84 (4H, m), 2.38 (3H, s).

EXAMPLE 344

4-(7-Hydroxy-6-methoxy-4-quinazolinyl)-N-(4-nitrophenyl)-1-piperazinecarboxamide (Compound 344)

(1) To a suspension of 162.0 mg (0.36 mmol) of 4-(7-benzyloxy-6-methoxy-4-quinazolinyl)-1-piperazinecarboxylic acid tert-butyl ester obtained in Reference Example 8 (6) in 10 ml of ethanol was added a suspension of 100 mg of 10% palladium-carbon in 5 ml of water, followed by stirring in a stream of hydrogen at room temperature for 7.5 hours. After the catalyst was separated by filtration using Celite, the solvent was evaporated. The residue was dissolved in 5 ml of dichloromethane, and 5 ml of trifluoroacetic acid was added thereto under ice-cooling, followed by stirring at the same temperature for 2 hours. After the solvent was evaporated, the residue was subjected to azeotropic distillation with toluene twice, and the obtained residue was dissolved in 5 ml of dichloromethane. To the resulting solution were added 122.5 mg (1.80 mmol) of imidazole and 108.5 mg (0.72 mmol) of tert-butyldimethylsilyl chloride, followed by stirring at room temperature for 2 hours. To the resulting mixture was further added 500.0 mg (3.32 mmol) of tert-butyldimethylsilyl chloride, followed by overnight stirring. After addition of a saturated aqueous solution of sodium chloride, the resulting mixture was extracted with chloroform, and the organic layer was dried over anhydrous sodium sulfate. After the solvent was evaporated, the residue was dissolved in 5 ml of dimethylformamide, and 88.6 mg (0.54 mmol) of 4-nitrophenyl isocyanate was added thereto, followed by stirring at room temperature for 40 minutes. The reaction mixture was poured into water, and sodium chloride was added thereto. The precipitated crystals were collected by filtration, washed with water, and dried, followed by purification by silica gel chromatography to give 45.6 mg (24%) of 4-(7-tert-butyldimethylsilyloxy-6-methoxy-4-quinazolinyl)-N-(4-nitrophenyl)-1-piperazinecarboxamide.

(2) To a solution of 22.8 mg (0.04 mmol) of the compound obtained in (1) in 5 ml of THF was added 0.04 ml (0.04 mmol) of a solution of 1 mol/l tetrabutylammonium fluoride in THF under ice-cooling, followed by stirring at the same temperature for 10 minutes. After the reaction mixture was concentrated, a saturated aqueous solution of sodium chloride was added to the residue. The resulting mixture was extracted with chloroform, and the organic layer was washed with a saturated aqueous solution of sodium chloride, and dried over anhydrous sodium sulfate, followed by evaporation of the solvent to give the desired compound.

Yield: 80%

$^1$H-NMR (CDCl$_3$) δ (ppm): 10.03 (1H, brs), 8.56 (1H, s), 8.14 (2H, d, J=9.2 Hz), 8.06 (2H, d, J=9.2 Hz), 7.50 (1H, s), 7.08 (1H, s), 4.00 (4H, m), 3.93 (3H, s), 3.73–3.72 (4H, m).

FAB-Mass: 425 (M$^+$+1)

EXAMPLE 345

4-(7-Benzyloxy-6-methoxy-4-quinazolinyl)-N-(4-phenoxyphenyl)-1-piperazinecarboxamide (Compound 345)

Substantially the same procedure as in Example 329 was repeated, except that 4-(7-benzyloxy-6-methoxy-4- quinazolinyl)-1-piperazinecarboxylic acid tert-butyl ester obtained in Reference Example 8 (6) was used in place of 4-(6,7-difluoro-4-quinazolinyl)-1-piperazinecarboxylic acid tert-butyl ester, to give the desired compound.

Yield: 83% m.p.: 220–221° C.

$^1$H-NMR (CDCl$_3$) δ (ppm): 8.66 (1H, s), 7.50–7.46 (2H, m), 7.42–7.26 (8H, m), 7.11 (1H, s), 7.04 (1H, m), 6.98–6.95 (4H, m), 6.77 (1H, brs), 5.27 (2H, s), 3.98 (3H, s), 3.72 (8H, m).

IR (KBr) σ (cm$^{-1}$): 1633, 1504, 1489, 1416, 1250, 1000.

In the following Examples 346–349, substantially the same procedure as in Example 329 was repeated, except that 4-(6-ethoxy-7-methoxy-4-quinazolinyl)-1-piperazinecarboxylic acid tert-butyl ester obtained in Reference Example 10 was used in place of 4-(6,7-difluoro-4-quinazolinyl)-1-piperazinecarboxylic acid tert-butyl ester, and the corresponding isocyanate or isothiocyanate was used in place of 4-phenoxyphenyl isocyanate (used in Example 346), to give the desired compound.

EXAMPLE 346

4-(6-Ethoxy-7-methoxy-4-quinazolinyl)-N-(4-phenoxyphenyl)-1-piperazinecarboxamide (Compound 346)

Yield: 100% m.p.: 213–214° C.

$^1$H-NMR (CDCl$_3$) δ (ppm): 8.69 (1H, s), 7.37–7.27 (4H, m), 7.26 (1H, s), 7.12 (1H, s), 7.07 (1H, m), 7.01–6.95 (4H, m), 6.55 (1H, brs), 4.19 (2H, q, J=6.9 Hz), 4.02 (3H, s), 3.74 (8H, m), 1.57 (3H, t, J=6.9 Hz).

FAB-Mass: 500 (M$^+$+1)

IR (KBr) σ (cm$^{-1}$): 1635, 1541, 1508, 1489, 1473, 1446, 1423, 1394, 1248, 1219, 1201, 997, 858, 750.

EXAMPLE 347

N-(4-Cyanophenyl)-4-(6-ethoxy-7-methoxy-4-quinazolinyl)-1-piperazinecarboxamide (Compound 347)

Yield: 95% m.p.: 178–179° C.

$^1$H-NMR (CDCl$_3$) δ (ppm): 8.68 (1H, s), 7.59 (2H, d, J=9.2 Hz), 7.54 (2H, d, J=9.2 Hz), 7.26 (1H, s), 7.11 (1H, s), 7.05 (1H, brs), 4.19 (2H, q, J=6.9 Hz), 4.02 (3H, s), 3.76 (8H, m), 1.56 (3H, t, J=6.9 Hz).

FAB-Mass: 433 (M$^+$+1)

IR (KBr) σ (cm$^{-1}$): 2220, 1660, 1593, 1504, 1471, 1434, 1317, 1244, 1207, 997.

EXAMPLE 348

N-Benzyl-4-(6-ethoxy-7-methoxy-4-quinazolinyl)-1-piperazinethiocarboxamide (Compound 348)

Yield: 86% m.p.: 170–171° C.

$^1$H-NMR (CDCl$_3$) δ (ppm): 8.64 (1H, s), 7.46–7.29 (5H, m), 7.25 (1H, s), 7.11 (1H, s), 5.76 (1H, brt, J=4.6 Hz), 4.91 (2H, d, J=4.6 Hz), 4.17 (2H, q, J=6.9 Hz), 4.11–4.07 (4H, m), 4.02 (3H, s), 3.86–3.82 (4H, m), 1.56 (3H, t, J=6.9 Hz).

FAB-Mass: 438 (M$^+$+1)

IR (KBr) σ (cm$^{-1}$): 1576, 1547, 1504, 1475, 1456, 1425, 1392, 1351, 1242, 1209, 1142, 1026, 935, 849.

EXAMPLE 349

4-(6-Ethoxy-7-methoxy-4-quinazolinyl)-N-(3-picolyl)-1-piperazinethiocarboxamide (Compound 349)

Yield: 80% m.p.: 208–209° C.

$^1$H-NMR (CDCl$_3$) δ (ppm): 8.63 (1H, s), 8.53–8.51 (2H, m), 7.78 (1H, ddd, J=7.9 Hz, 2.0 Hz, 1.7 Hz), 7.29 (1H, dd, J=7.9 Hz, 5.0 Hz), 7.24 (1H, s), 7.11 (1H, s), 6.32 (1H, brt, J=5.3 Hz), 4.97 (2H, d, J=5.3 Hz), 4.19 (2H, q, J=6.9 Hz), 4.14–4.11 (4H, m), 4.01 (3H, s), 3.86–3.82 (4H, m), 1.56 (3H, t, J=6.9 Hz).

FAB-Mass: 439 (M$^+$+1)

IR (KBr) σ (cm$^{-1}$): 1558, 1506, 1473, 1427, 1396, 1332, 1240, 1209, 1198, 997, 872, 717.

In the following Examples 350 and 351, substantially the same procedure as in Example 329 was repeated, except that 4-(6-mesyloxy-7-methoxy-4-quinazolinyl)-1-piperazinecarboxylic acid tert-butyl ester obtained in Reference Example 11 was used in place of 4-(6,7-difluoro-4-quinazolinyl)-1-piperazinecarboxylic acid tert-butyl ester, and the corresponding isothiocyanate was used in place of 4-phenoxyphenyl isocyanate (used in Example 350), to give the desired compound.

EXAMPLE 350

4-(6-Mesyloxy-7-methoxy-4-quinazolinyl)-N-(4-phenoxyphenyl)-1-piperazinecarboxamide (Compound 350)

Yield: 100% m.p.: 228–229° C.

$^1$H-NMR (CDCl$_3$) δ (ppm): 8.70 (1H, s), 7.84 (1H, s), 7.36–7.27 (5H, m), 7.07 (1H, m), 6.99–6.96 (4H, m), 6.54 (1H, brs), 4.04 (3H, s), 3.87–3.85 (4H, m), 3.76–3.74 (4H, m), 3.25 (3H, s).

FAB-Mass: 550 (M$^+$+1)

IR (KBr) σ (cm$^{-1}$): 1620, 1539, 1506, 1487, 1417, 1350, 1223, 1167, 993, 876.

EXAMPLE 351

N-Benzyl-4-(6-mesyloxy-7-methoxy-4-quinazolinyl)-1-piperazinethiocarboxamide (Compound 351)

Yield: 97% m.p.: 76–80° C.

$^1$H-NMR (CDCl$_3$) δ (ppm): 8.65 (1H, s), 7.84 (1H, s), 7.38–7.31 (5H, m), 7.27 (1H, s), 5.73 (1H, br), 4.89 (2H, d, J=4.6 Hz), 4.11–4.08 (4H, m), 4.03 (3H, s), 3.99–3.95 (4H, m), 3.23 (3H, s).

FAB-Mass: 488 (M$^+$+1)

IR (KBr) σ (cm$^{-1}$): 1506, 1475, 1365, 1350, 1161.

In the following Examples 352–354, substantially the same procedure as in Example 1 was repeated, except that 6,7-diethoxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 352

N-(4-Cyanophenyl)-4-(6,7-diethoxy-4-quinazolinyl)-1-piperazinecarboxamide (Compound 352)

Yield: 94% m.p.: 186–187° C.

¹H-NMR (CDCl₃) δ (ppm): 8.65 (1H, s), 7.71 (1H, brs), 7.59 (2H, d, J=8.9 Hz), 7.54 (2H, d, J=8.9 Hz), 7.21 (1H, s), 7.11 (1H, s), 4.22 (2H, q, J=6.3 Hz), 4.18 (2H, q, J=6.3 Hz), 3.78–3.74 (4H, m), 3.73–3.70 (4H, m), 1.54 (3H, t, J=6.3 Hz), 1.53 (3H, t, J=6.3 Hz).

FAB-Mass: 447 (M⁺+1)

IR (KBr) σ (cm⁻¹): 2980, 2216, 1641, 1591, 1516, 1471, 1419, 1402, 1315, 1246, 1205, 986.

EXAMPLE 353

N-Benzyl-4-(6,7-diethoxy-4-quinazolinyl)-1-piperazinethiocarboxamide (Compound 353)

Yield: 97% m.p.: 134–136° C.

H-NMR (CDCl₃) δ (ppm): 8.58 (1H, s), 7.32–7.26 (5H, m), 7.18 (1H, s), 7.11 (1H, s), 6.34 (1H, brt, J=5.0 Hz), 4.90 (2H, d, J=5.0 Hz), 4.24–4.14 (4H, m), 4.11–4.07 (4H, m), 3.87–3.79 (4H, m), 1.53 (3H, t, J=6.9 Hz), 1.53 (3H, t, J=6.9 Hz).

FAB-Mass: 452 (M⁺+1)

IR (KBr) σ (cm⁻¹): 1574, 1573, 1506, 1475, 1344, 1242, 1205, 1012, 935, 868, 731.

EXAMPLE 354

4-(6,7-Diethoxy-4-quinazolinyl)-N-(3-picolyl)-1-piperazinethiocarboxamide (Compound 354)

Yield: 92% m.p.: 90–92° C.

¹H-NMR (CDCl₃) δ (ppm): 8.63 (1H, s), 8.58–8.54 (2H, m), 7.78 (1H, ddd, J=7.9 Hz, 2.0 Hz, 2.0 Hz), 7.28 (1H, m), 7.23 (1H, s), 7.11 (1H, s), 6.05 (1H, brt, J=5.3 Hz), 4.98 (2H, d, J=5.3 Hz), 4.25 (2H, q, J=6.9 Hz), 4.19 (2H, q, J=7.3 Hz), 4.13–4.09 (4H, m), 3.86–3.82 (4H, m), 1.55 (3H, t, J=7.3 Hz), 1.55 (3H, t, J=6.9 Hz).

FAB-Mass: 453 (M⁺+1)

IR (KBr) σ (cm⁻¹): 1504, 1443, 1392, 1344, 1238, 1203, 1041, 1009, 941.

EXAMPLE 355

4-(6,7-Dibenzyloxy-4-quinazolinyl)-N-(4-phenoxyphenyl)-1-piperazinecarboxamide (Compound 355)

Substantially the same procedure as in Example 60 was repeated, except that 6,7-dibenzyloxy-4-(1-piperazinyl)quinazoline was used in place of 6,7-dimethoxy-4-(1-piperazinyl)quinazoline, to give the desired compound.

Yield: 65% m.p.: 137–138° C.

¹H-NMR (CDCl₃) δ (ppm): 8.61 (1H, s), 7.53–7.50 (2H, m), 7.45–7.26 (13H, m), 7.09–6.96 (6H, m), 6.73 (1H, brs), 5.34 (2H, s), 5.32 (2H, s), 3.55–3.53 (4H, m), 3.46–3.44 (4H, m).

FAB-Mass: 638 (M⁺+1)

IR (KBr) σ (cm⁻¹): 1630, 1537, 1506, 1489, 1452, 1417, 1225, 993, 748, 694.

EXAMPLE 356

4-(6-Amino-7-chloro-4-quinazolinyl)-N-(4-phenoxyphenyl)-1-piperazinecarboxamide (Compound 356)

To a solution of 628.8 mg (1.25 mmol) of 4-(7-chloro-6-nitro-4-quinazolinyl)-N-(4-phenoxyphenyl)-1-piperazinecarboxamide obtained in Example 357 in 15 ml of acetic acid was added 407.9 mg (6.24 mmol) of zinc dust, followed by overnight stirring in an atmosphere of argon at room temperature. After the zinc dust was separated by filtration using Celite, the filtrate was washed with a chloroform-methanol mixture. After the solvent was evaporated with triethylamine, the residue was purified by silica gel chromatography to give the desired compound as colorless crystals.

Yield: 18%

¹H-NMR (CDCl₃) δ (ppm): 8.60 (1H, s), 7.93 (1H, s), 7.35–7.27 (4H, m), 7.10–7.04 (2H, m), 6.99–6.96 (4H, m), 6.65 (1H, brs), 4.62 (2H, br), 3.73–3.72 (8H, m).

In the following Examples 357 and 358, substantially the same procedure as in Example 329 was repeated, except that 4-(7-chloro-6-nitro-4-quinazolinyl)-1-piperazinecarboxylic acid tert-butyl ester obtained in Reference Example 12 was used in place of 4-(6,7-difluoro-4-quinazolinyl)-1-piperazinecarboxylic acid tert-butyl ester, and the corresponding isothiocyanate was used in place of phenoxyphenyl isocyanate (used in Example 357), to give the desired compound.

EXAMPLE 357

4-(7-Chloro-6-nitro-4-quinazolinyl)-N-(4-phenoxyphenyl)-1-piperazinecarboxamide (Compound 357)

Yield: 60% m.p.: 190–191° C.

¹H-NMR (CDCl₃) δ (ppm): 8.78 (1H, s), 8.55 (1H, s), 8.06 (1H, s), 7.34–7.28 (4H, m), 7.06 (1H, m), 7.00–6.97 (4H, m), 6.40 (1H, brs), 4.08–4.04 (4H, m), 3.81–3.77 (4H, m).

FAB-Mass: 505 (M⁺+1)

IR (KBr) σ (cm⁻¹): 1637, 1608, 1564, 1527, 1506, 1489, 1419, 1352, 1325, 1225, 1028, 991, 918, 827, 748, 690.

EXAMPLE 358

N-Benzyl-4-(7-chloro-6-nitro-4-quinazolinyl)-1-piperazinethiocarboxamide (Compound 358)

Yield: 84% m.p.: 93–95° C.

¹H-NMR (CDCl₃) δ (ppm): 8.68 (1H, s), 8.54 (1H, s), 7.93 (1H, s), 7.31–7.23 (5H, m), 6.18 (1H, brt, J=5.0 Hz), 4.85 (2H, d, J=5.0 Hz), 4.12 (8H, m).

FAB-Mass: 443 (M⁺+1)

IR (KBr) σ (cm⁻¹): 1564, 1539, 1498, 1352.

EXAMPLE 359

4-(7-Amino-6-nitro-4-quinazolinyl)-N-(4-phenoxyphenyl)-1-piperazinecarboxamide (Compound 359)

Substantially the same procedure as in Example 60 was repeated, except that 7-amino-6-nitro-4-(1-piperazinyl)quinazoline was used in place of 6,7-dimethoxy-4-(1-piperazinyl)quinazoline, to give the desired compound.

Yield: 8%

¹H-NMR (CDCl₃) δ (ppm): 8.88 (1H, s), 8.55 (1H, s), 7.35–7.27 (4H, m), 7.12 (1H, s), 7.07 (1H, m), 7.00–6.96

(4H, m), 6.52 (1H, s), 6.22 (2H, brs), 4.07–4.03 (4H, m), 3.81–3.77 (4H, m).

FAB-Mass: 486 (M$^+$+1)

EXAMPLE 360

4-(6-Acetamido-4-quinazolinyl)-N-(4-phenoxyphenyl)-1-piperazinecarboxamide (Compound 360)

To a solution of 464.1 mg (0.99 mmol) of Compound 311 in 15 ml of ethanol was added 100 mg of 10% palladium-carbon, followed by stirring in a stream of hydrogen at room temperature for 4 hours. After the catalyst was separated by filtration using Celite, the solvent was evaporated. The residue was dissolved in 15 ml of dichloromethane, and 0.70 ml (5.02 mmol) of triethylamine and 0.19 ml of acetic anhydride were added thereto, followed by overnight stirring at room temperature. After methanol was added to the reaction mixture, the solvent was evaporated, and the residue was purified by silica gel chromatography to give the desired compound as colorless crystals.

Yield: 20%

$^1$H-NMR (CDCl$_3$) δ (ppm): 8.69 (1H, s), 8.66 (1H, d, J=2.3 Hz), 8.20 (1H, brs), 7.84 (1H, d, J=8.9 Hz), 7.47 (1H, dd, J=8.9 Hz, 2.3 Hz), 7.36–7.27 (4H, m), 7.06 (1H, m), 6.98–6.94 (4H, m), 6.75 (1H, brs), 3.86–3.84 (4H, m), 3.77–3.75 (4H, m), 2.24 (3H, s).

FAB-Mass: 483 (M$^+$+1)

EXAMPLE 361

N-Benzyl-4-(7-ethylamino-6-nitro-4-quinazolinyl)-1-piperazinethiocarboxamide (Compound 361)

Substantially the same procedure as in Example 60 was repeated, except that 7-ethylamino-6-nitro-4-(1-piperazinyl) quinazoline obtained in Reference Example 5 (1) was used in place of 6,7-dimethoxy-4-(1-piperazinyl)quinazoline, and the corresponding isothiocyanate was used in place of 4-phenoxyphenyl isocyanate, to give the desired compound.

Yield: 77%

$^1$H-NMR (CDCl$_3$) δ (ppm): 8.91 (1H, s), 8.50 (1H, s), 7.66 (1H, brt, J=4.6 Hz), 7.38–7.29 (5H, m), 7.01 (1H, s), 5.71 (1H, brt, J=4.6 Hz), 4.89 (2H, d, J=4.6 Hz), 4.14 (8H, m), 3.39 (2H, dq, J=7.3 Hz, 4.6 Hz), 1.42 (3H, t, J=7.3 Hz).

FAB-Mass: 452 (M$^+$+1)

EXAMPLE 362

4-(7-Acetamido-6-nitro-4-quinazolinyl)-N-(4-phenoxyphenyl)-1-piperazinecarboxamide (Compound 362)

Substantially the same procedure as in Example 60 was repeated, except that 7-acetamido-6-nitro-4-(1-piperazinyl) quinazoline was used in place of 6,7-dimethoxy-4-(1-piperazinyl)quinazoline, to give the desired compound.

Yield: 26%

$^1$H-NMR (CDCl$_3$) δ (ppm): 8.68 (1H, s), 8.47 (1H, s), 7.35–7.27 (4H, m), 7.15 (1H, s), 7.07 (1H, m), 6.99–6.96 (4H, m), 6.54 (1H, brs), 6.51 (1H, brs), 4.00 (4H, m), 3.69 (4H, m), 2.04 (3H, s).

In the following Examples 363–366, substantially the same procedure as in Example 329 was repeated, except that 4-(4-benzo[g]quinazolinyl)-1-piperazinecarboxylic acid tert-butyl ester obtained in Reference Example 13 was used in place of 4-(6,7-difluoro-4-quinazolinyl)-1-piperazinecarboxylic acid tert-butyl ester, and the corresponding isocyanate or isothiocyanate was used in place of 4-phenoxyphenyl isocyanate (used in Example 363), to give the desired compound.

EXAMPLE 363

4-(4-Benzo[g]quinazolinyl)-N-(4-phenoxyphenyl)-1-piperazinecarboxamide (Compound 363)

Yield: 24% m.p.: 105–108° C.

$^1$H-NMR (CDCl$_3$) δ (ppm): 8.75 (1H, s), 8.49 (1H, s), 8.46 (1H, s), 8.04–7.99 (2H, m), 7.64–7.50 (2H, m), 7.38–7.26 (4H, m), 7.07 (1H, m), 7.00–6.97 (4H, m), 6.68 (1H, brs), 4.04–4.01 (4H, m), 3.83–3.79 (4H, m).

FAB-Mass: 476 (M$^+$+1)

IR (KBr) σ (cm$^{-1}$): 1637, 1541, 1508, 1489, 1419, 1225.

EXAMPLE 364

4-(4-Benzo[g]quinazolinyl)-N-(4-nitrophenyl)-1-piperazinecarboxamide (Compound 364)

Yield: 35% m.p.: 272–275° C.

$^1$H-NMR (DMSO-d$_6$) δ (ppm): 9.32 (1H, brs), 8.73 (1H, s), 8.63 (1H, s), 8.40 (1H, s), 8.20–8.05 (2H, m), 8.14 (2H, d, J=9.3 Hz), 7.78 (2H, d, J=9.3 Hz), 7.65–7.52 (2H, m), 4.02–4.00 (4H, m), 3.83 (4H, m).

FAB-Mass: 429 (M$^+$+1)

IR (KBr) σ (cm$^{-1}$): 1670, 1597, 1541, 1518, 1508, 1419, 1321, 1300, 1236, 1113, 847, 750.

EXAMPLE 365

4-(4-Benzo[g]quinazolinyl)-N-benzyl-1-piperazinethiocarboxamide (Compound 365)

Yield: 42% m.p.: 187–188° C.

$^1$H-NMR (CDCl$_3$) δ (ppm): 8.66 (1H, s), 8.47 (1H, s), 8.40 (1H, s), 8.00–7.95 (2H, m), 7.61–7.48 (2H, m), 7.38–7.27 (5H, m), 6.06 (1H, brt, J=5.0 Hz), 4.91 (2H, d, J=5.0 Hz), 4.17–4.11 (8H, m).

FAB-Mass: 414 (M$^+$+1)

IR (KBr) σ (cm$^{-1}$): 1545, 1520, 1408, 1381, 1369, 1238, 1198, 1012, 748, 694.

EXAMPLE 366

4-(4-Benzo[g]quinazolinyl)-N-(3-picolyl)-1-piperazinethiocarboxamide (Compound 366)

Yield: 44% m.p.: 107–110° C.

$^1$H-NMR (CDCl$_3$) δ (ppm): 8.61 (1H, s), 8.45–8.41 (3H, m), 8.34 (1H, s), 7.97–7.93 (2H, m), 7.77 (1H, ddd, J=7.9 Hz, 2.0 Hz, 1.7 Hz), 7.59–7.46 (2H, m), 7.24 (1H, dd, J=7.9 Hz, 5.0 Hz), 7.14 (1H, br), 4.95 (2H, d, J=5.3 Hz), 4.20–4.17 (4H, m), 4.12–4.10 (4H, m).

FAB-Mass: 415 (M$^+$+1)

IR (KBr) σ (cm$^{-1}$): 1560, 1508, 1479, 1433, 1410, 1383, 1352, 941, 744, 716.

In the following Examples 367–371, substantially the same procedure as in Example 1 was repeated, except that 6,7-methylenedioxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 367

4-(6,7-Methylenedioxy-4-quinazolinyl)-N-(4-phenoxyphenyl)-1-piperazinecarboxamide (Compound 367)

Yield: 85%
m.p.: 206–207° C.
$^1$H-NMR (CDCl$_3$) δ (ppm): 8.67 (1H, s), 7.35–7.30 (4H, m), 7.27 (1H, s), 7.15 (1H, s), 7.06 (1H, m), 6.99–6.94 (4H, m), 6.68 (1H, brs), 6.12 (2H, s), 3.73–3.65 (8H, m).
FAB-Mass: 470 (M$^+$+1)
IR (KBr) σ (cm$^{-1}$): 1630, 1491, 1462, 1419, 1227, 1038, 1003, 916, 872, 849, 762.

EXAMPLE 368

4-(6,7-Methylenedioxy-4-quinazolinyl)-N-(4-nitrophenyl)-1-piperazinecarboxamide (Compound 368)

Yield: 92%
m.p.: 247–250° C.
$^1$H-NMR (CDCl$_3$) δ (ppm): 8.64 (1H, s), 8.12 (2H, d, J=8.9 Hz), 7.84 (1H, brs), 7.59 (2H, d, J=8.9 Hz), 7.20 (1H, s), 7.13 (1H, s), 6.13 (2H, s), 3.79–3.77 (4H, m), 3.66–3.65 (4H, m).
FAB-Mass: 423 (M$^+$+1)
IR (KBr) σ (cm$^{-1}$): 1672, 1612, 1554, 1495, 1466, 1425, 1329, 1300, 1236, 1111, 1034, 918, 849.

EXAMPLE 369

N-(4-Cyanophenyl)-4-(6,7-methylenedioxy-4-quinazolinyl)-1-piperazinecarboxamide (Compound 369)

Yield: 100%
m.p.: 220–222° C.
$^1$H-NMR (CDCl$_3$) δ (ppm): 8.64 (1H, s), 7.79 (1H, brs), 7.58 (2H, d, J=8.9 Hz), 7.53 (2H, d, J=8.9 Hz), 7.20 (1H, s), 7.13 (1H, s), 6.14 (2H, s), 3.78–3.75 (4H, m), 3.65–3.63 (4H, m).
FAB-Mass: 403 (M$^+$+1)
IR (KBr) σ (cm$^{-1}$): 2222, 1687, 1610, 1591, 1524, 1493, 1464, 1441, 1369, 1311, 1227, 1174, 1036, 916, 835.

EXAMPLE 370

N-Benzyl-4-(6,7-methylenedioxy-4-quinazolinyl)-1-piperazinethiocarboxamide (Compound 370)

Yield: 99%
m.p.: 176–177° C.
$^1$H-NMR (CDCl$_3$) δ (ppm): 8.60 (1H, s), 7.36–7.30 (5H, m), 7.20 (1H, s), 7.14 (1H, s), 6.12 (2H, s), 5.95 (1H, brt, J=4.6 Hz), 4.90 (2H, d, J=4.6 Hz), 4.08–4.04 (4H, m), 3.77–3.73 (4H, m).
FAB-Mass: 408 (M$^+$+1)
IR (KBr) σ (cm$^{-1}$): 1545, 1493, 1461, 1369, 1246, 1034, 918.

EXAMPLE 371

4-(6,7-Methylenedioxy-4-quinazolinyl)-N-(3-picolyl)-1-piperazinethiocarboxamide (Compound 371)

Yield: 100%
m.p.: 167–168° C.

$^1$H-NMR (CDCl$_3$) δ (ppm): 8.59 (1H, s), 8.48 (1H, dd, J=5.0 Hz, 1.7 Hz), 8.45 (1H, d, J=2.0 Hz), 7.78 (1H, ddd, J=7.9 Hz, 2.0 Hz, 1.7 Hz), 7.28 (1H, dd, J=7.9 Hz, 5.0 Hz), 7.19 (1H, s), 7.14 (1H, s), 6.70 (1H, brt, J=5.3 Hz), 6.13 (2H, s), 4.95 (2H, d, J=5.3 Hz), 4.13–4.10 (4H, m), 3.78–3.74 (4H, m).
FAB-Mass: 409 (M$^+$+1)
IR (KBr) σ (cm$^{-1}$): 1545, 1491, 1470, 1432, 1394, 1333, 1267, 1038, 997, 914.

In the following Examples 372–375, substantially the same procedure as in Example 329 was repeated, except that 4-(6,7-ethylenedioxy-4-quinazolinyl)-1-piperazinecarboxylic acid tert-butyl ester obtained in Reference Example 14 was used in place of 4-(6,7-difluoro-4-quinazolinyl)-1-piperazinecarboxylic acid tert-butyl ester, and the corresponding isocyanate (used in Example 372) or isothiocyanate was used in place of 4-phenoxyphenyl isocyanate, to give the desired compound.

EXAMPLE 372

4-(6,7-Ethylenedioxy-4-quinazolinyl)-N-(4-phenoxyphenyl)-1-piperazinecarboxamide (Compound 372)

Yield: 91%
m.p.: 227–228° C.
$^1$H-NMR (CDCl$_3$) δ (ppm): 8.62 (1H, s), 7.37–7.25 (6H, m), 7.05 (1H, m), 6.99–6.94 (5H, m), 4.38–4.33 (4H, m), 3.72 (8H, m).
FAB-Mass: 484 (M$^+$+1)
IR (KBr) σ (cm$^{-1}$): 1664, 1539, 1506, 1489, 1419, 1342, 1290, 1219, 1064, 901.

EXAMPLE 373

N-(4-Cyanophenyl)-4-(6,7-ethylenedioxy-4-quinazolinyl)-1-piperazinecarboxamide (Compound 373)

Yield: 76%
m.p.: 246–247° C.
$^1$H-NMR (DMSO-d$_6$) δ (ppm): 9.14 (1H, brs), 8.52 (1H, s), 7.70 (4H, s), 7.39 (1H, s), 7.23 (1H, s), 4.41–4.40 (4H, m), 3.70 (8H, m).
FAB-Mass: 417 (M$^+$+1)
IR (KBr) σ (cm$^{-1}$): 2218, 1686, 1591, 1568, 1508, 1471, 1443, 1414, 1335, 1311, 1286, 1230, 1198, 912, 849.

EXAMPLE 374

N-Benzyl-4-(6,7-ethylenedioxy-4-quinazolinyl)-1-piperazinethiocarboxamide (Compound 374)

Yield: 88%
m.p.: 103–105° C.
$^1$H-NMR (CDCl$_3$) δ (ppm): 8.58 (1H, s), 7.40–7.29 (7H, m), 5.84 (1H, brt, J=4.6 Hz), 4.90 (2H, d, J=4.6 Hz), 4.40–4.35 (4H, m), 4.09–4.06 (4H, m), 3.88–3.84 (4H, m).
FAB-Mass: 422 (M$^+$+1)
IR (KBr) σ (cm$^{-1}$)1568, 1541, 1508, 1477, 1443, 1340, 1286, 1240, 1066, 1003, 914, 901.

EXAMPLE 375

4-(6,7-Ethylenedioxy-4-quinazolinyl)-N-(3-picolyl)-1-piperazinethiocarboxamide (Compound 375)

Yield: 72%
m.p.: 110–113° C.

¹H-NMR (CDCl₃) δ (ppm): 8.52 (1H, s), 8.47 (1H, dd, J=5.3 Hz, 1.3 Hz), 8.43 (1H, d, J=2.3 Hz), 7.78 (H, ddd, J=7.6 Hz, 2.3 Hz, 1.3 Hz), 7.30 (1H, s), 7.28 (1H, s), 7.25 (1H, dd, J=7.6 Hz, 5.3 Hz), 6.97 (1H, brt, J=4.9 Hz), 4.94 (2H, d, J=4.9 Hz), 4.39–4.34 (4H, m), 4.14–4.10 (4H, m), 3.86–3.82 (4H, m).

FAB-Mass: 423 (M⁺+1)

IR (KBr) σ (cm⁻¹): 1574, 1558, 1508, 1443, 1410, 1389, 1348, 1290, 1068, 918, 710.

In the following Examples 376–378, substantially the same procedure as in Example 1 was repeated, except that 6,8-dichloro-4-(1-piperazinyl)quinazoline was used in place of 6,7-dimethoxy-4-(1-piperazinyl)quinazoline, and the corresponding isocyanate was used in place of phenyl isocyanate, to give the desired compound.

EXAMPLE 376

4-(6,8-Dichloro-4-quinazolinyl)-N-(4-isopropylphenyl)-N-piperazinecarboxamide (Compound 376)

Yield: 20% m.p.: 234–236° C.

¹H-NMR (CDCl₃) δ (ppm): 8.86 (1H, s), 7.87 (1H, d, J=2.0 Hz), 7.80 (1H, d, J=2.0 Hz), 7.29 (2H, d, J=8.6 Hz), 7.17 (2H, d, J=8.6 Hz), 6.32 (1H, brs), 3.91–3.87 (4H, m), 3.76–3.72 (4H, m), 2.88 (3H, m), 1.23 (6H, d, J=6.9 Hz).

FAB-Mass: 446 (M⁺+3), 444 (M⁺+1)

IR (KBr) σ (cm⁻¹): 1637, 1596, 1527, 1490, 1421, 1238, 995, 827.

EXAMPLE 377

4-(6,8-Dichloro-4-quinazolinyl)-N-(4-phenoxyphenyl)-1-piperazinecarboxamide (Compound 377)

Yield: 13% m.p.: 195–196° C.

¹H-NMR (CDCl₃) δ (ppm): 8.86 (1H, s), 7.87 (2H, d, J=2.3 Hz), 7.80 (1H, d, J=2.3 Hz), 7.34–7.28 (4H, m), 7.08 (1H, m), 7.00–6.96 (4H, m), 6.35 (1H, brs), 3.92–3.88 (4H, m), 3.77–3.73 (4H, m).

FAB-Mass: 496 (M⁺+3), 494 (M⁺+1)

IR (KBr) σ (cm⁻¹): 1643, 1600, 1537, 1506, 1488, 1419, 1222, 993.

EXAMPLE 378

N-(4-Acetylphenyl)-4-(6,8-dichloro-4-quinazolinyl)-1-piperazinecarboxamide (Compound 378)

Yield: 11% m.p.:187–188° C.

¹H-NMR (CDCl₃) δ (ppm): 8.87 (1H, s), 7.94 (2H, d, J=8.9 Hz), 7.88 (1H, d, J=2.1 Hz), 7.80 (1H, d, J=2.1 Hz), 7.49 (2H, d, J=8.9 Hz), 6.61 (1H, brs), 3.93–3.89 (4H, m), 3.80–3.76 (4H, m), 2.58 (3H, s).

FAB-Mass: 446 (M⁺+3), 444 (M⁺+1)

IR (KBr) σ (cm⁻¹): 1672, 1652, 1591, 1508, 1498, 1419, 1247, 990.

In the following Examples 379 and 380, substantially the same procedure as in Example 1 was repeated, except that 6,7-diiodo-4-(1-piperazinyl)quinazoline was used in place of 6,7-dimethoxy-4-(1-piperazinyl)quinazoline, and the corresponding isocyanate was used in place of phenyl isocyanate, to give the desired compound.

EXAMPLE 379

4-(6,8-Diiodo-4-quinazolinyl)-N-(4-isopropylphenyl)-1-piperazinecarboxamide (Compound 379)

Yield: 9% m.p.: 267–269° C.

¹H-NMR (CDCl₃) δ (ppm): 8.83 (1H, s), 8.59 (1H, d, J=1.6 Hz), 8.22 (1H, d, J=1.6 Hz), 7.28 (2H, d, J=8.1 Hz), 7.17 (2H, d, J=8.1 Hz), 6.30 (1H, brs), 3.91–3.87 (4H, m), 3.73–371 (4H, m), 2.88 (1H, m), 1.23 (6H, d, J=6.9 Hz).

FAB-Mass: 627 (M⁺+1)

IR (KBr) σ (cm⁻¹): 1643, 1594, 1540, 1486, 1452, 1419, 1238, 995, 937, 827.

EXAMPLE 380

4-(6,8-Diiodo-4-quinazolinyl)-N-(4-phenoxyphenyl)-1-piperazinecarboxamide (Compound 380)

Yield: 14% m.p.: 242–244° C.

¹H-NMR (CDCl₃) δ (ppm): 8.84 (1H, s), 8.60 (1H, d, J=1.6 Hz), 8.22 (1H, d, J=1.6 Hz), 7.32 (4H, m), 7.08 (1H, m), 7.01–6.97 (4H ,m), 6.36 (1H, brs), 3.92–3.88 (4H, m), 3.76–3.72 (4H, m).

FAB-Mass: 678 (M⁺+1)

IR (KBr) σ (cm⁻¹): 1641, 1600, 1538, 1506, 1488, 1419, 1222, 991.

In the following Examples 381 and 382, substantially the same procedure as in Example 1 was repeated, except that 6,8-dimethoxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 381

4-(6,8-Dimethoxy-4-quinazolinyl)-N-(4-phenoxyphenyl)-1-piperazinecarboxamide (Compound 381)

Yield: 86% m.p.: 109–110° C.

¹H-NMR (CDCl₃) δ (ppm): 8.72 (1H, S), 7.36–7.25 (4H,m). 7.10 (1H, brs), 7.04 (7H, dd, J=7.9 Hz, 1.0 Hz), 6.97–6.93 (4H, m), 6.78 (1H, d, J=1.7 Hz), 6.68 (1H, d, J=1.7 Hz), 4.00 (3 Hz s), 3.90 (3H, s), 3.72 (8H, m).

FAB-Mass: 486 (M⁺+1)

IR (KBr) σ (cm⁻¹): 1620, 1539, 1506, 1414, 1225, 1159.

EXAMPLE 382

4-(6,8-Dimethoxy-4-(quinazolinyl)-N-(3-picolyl)-1-piperazinethiocarboxamide (Compound 382)

Yield: 72% (free base)

m.p.: 164–167° C. (dihydrochoride)

¹H-NMR (free base, CDCl₃) δ (ppm ): 8.62 ((H, s), 8.58 ( 1H, dd, J=5.0 Hz, 1.7 Hz), 8.42 (1H, d, J=2.0 Hz), 7.76 (1H, ddd, J=7.9 Hz, 2.0 Hz, 1.7 Hz), 7.23 (9H, dd, J=7.9 Hz, 5.0 Hz), 7.14 (m H, br), 6.80 (5H, d, J=2.3 Hz ), 6.68 (1H, d, J=2.3 Hz), 4.94 (2H, d, J=5.0 Hz), 4.17–4.13 (4H, m), 3.98 (3H, s), 3.89 (3H, s), 3.84–3.81 (4H, m).

FAB-Mass: 425 (M$^+$+1)

IR (dihydrochloride, KBr) σ (cm$^{-1}$): 1531, 1470, 1400, 1357, 1323, 1163.

In the following Examples 383–385, substantially the same procedure as in Example I was repeated, except that 7,8-dimethoxy-4-(1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 383

4-(7,8-Dimethoxy-4-quinazolinyl)-N-(4-phenoxyphenyl)-1-piperazinecarboxamide (Compound 383)

Yield: 65% m.p.: 189–190° C.

$^1$H-NMR (DMSO-d$_6$) δ (ppm): 8.66 (]H, brs), 8.60 (1H, s), 7.83 (1H, d, J=9.2 Hz), 7.50 (2H, d, J=8.9 Hz), 7.43–7.32 (3H, m), 7.08 (1H, m), 6.97–6.93 (4H, m), 3.97 (3H, s), 3.91 (3H, s), 3.78–3.76 (4H, m), 3.69–3.68 (4H, m).

FAB-Mass: 486 (M$^+$+1)

IR (KBr) σ (cm$^{-1}$): 1633, 1605, 1527, 1506, 1491, 1417, 1282, 1225, 1097, 1012, 997.

EXAMPLE 384

N-Benzyl-4-(7,8-dimethoxy-4-quinazolinyl)-1-piperazinethiocarboxamide (Compound 384)

Yield: 52% m.p.: 158–160° C.

$^1$H-NMR (CDCl$_3$) δ (ppm): 8.66 (1H, s), 7.66 (1H, d, J=9.2 Hz), 7.35–7.26 (5H,m), 7.18 (1H, d, J=9.2 Hz), 6.10 (1H,br), 4.90 (2H, d, J=4.3 Hz), 4.10–4.02 (4H, m), 4.05 (3H, s), 4.01 (3H, s), 3.99–3.91 (4H, m).

FAB-Mass: 424 (M$^+$+1)

IR (KBr) σ (cm$^{-1}$): 1552, 1495, 1404, 1325, 1284, 1244, 1097, 1005, 700.

EXAMPLE 385

4-(7,8-Dimethoxy-4-quinazolinyl)-N-(3-picolyl)-1-piperazinethiocarboxamide hydrochloride (Compound 385)

Yield: 38% m.p.: 208–209° C. (hydrochloride)

$^1$H-NMR (free base, CDCl$_3$) δ (ppm): 8.62 (1H, s), 8.44 (1H, d, J=1.7 Hz), 8.43 (1H, dd, J=5.0 Hz, 1.7 Hz), 7.76 (1H, ddd, J=7.9 Hz, 1.7 Hz, 1.7 Hz), 7.66 (1H, d, J=9.2 Hz), 7.24 (1H, dd, J=7.9 Hz, 5.0 Hz), 7.20 (1H, d, J=9.2 Hz), 7.12 (1H, br), 4.94 (2H, d, J=5.3 Hz), 4.16–4.13 (4H, m), 4.03 (3H, s), 4.01 (3H, s), 3.95–3.91 (4H, m).

FAB-Mass: 425 (M$^+$+1)

IR (hydrochloride, KBr) σ (cm$^{-1}$): 1533, 1479, 1396, 1367, 1300, 1003.

EXAMPLE 386

4-(1,3-Dihydro-1,3-dimethyl-2-oxo-2H-imidazo[4,5-g]quinazolin-8-yl)-N-(4-nitrophenyl)-1-piperazinecarboxamide (Compound 386)

Substantially the same procedure as in Example 77 was repeated, except that 1,3-dihydro-1,3-dimethyl-2-oxo-8-(1-piperazinyl)-2H-imidazo[4,5-g]quinazoline obtained in Reference Example 1 was used in place of 6,7-dimethoxy-4-(1-piperazinyl)quinazoline, to give the desired compound.

Yield: 53% m.p.: 299–300° C.

$^1$H-NMR (DMSO-d$_6$) δ (ppm): 9.37 (1H, br), 8.61 (1H, s), 8.17 (2H, d, J=9.2 Hz), 7.75 (2H, d, J=9.2 Hz), 7.53 (1H, s), 7.50 (1H, s), 3.76–3.57 (8H, m), 3.47 (3H, s), 3.44 (3H, s).

FAB-Mass: 463 (M$^+$+1)

IR (KBr) σ (cm$^{-1}$): 1705, 1668, 1606, 1547, 1502, 1446, 1416, 1329, 1234, 1111, 996, 847, 752.

In the following Examples 387 and 388, substantially the same procedure as in Example 329 was repeated, except that 4-(1,3-dihydro-3-ethyl-1-methyl-2-oxo-2H-imidazo[4,5-g]quinazolin-8-yl)-1-piperazinecarboxylic acid tert-butyl ester obtained in Reference Example 5 was used in place of 4-(6,7-difluoro-4-quinazolinyl)-1-piperazinecarboxylic acid tert-butyl ester, and the corresponding isothiocyanate was used in place of 4-phenoxyphenyl isocyanate (used in Example 387), to give the desired compound.

EXAMPLE 387

4-(1,3-Dihydro-3-ethyl-1-methyl-2-oxo-2H-imidazo[4,5-g]quinazolin-8-yl)-N-(4-phenoxyphenyl)-1-piperazinecarboxamide (Compound 387)

Yield: 96% m.p.: 250–251° C.

$^1$H-NMR (CDCl$_3$) δ (ppm): 8.73 (1H, s), 7.44 (1H, s), 7.38–7.31 (4H, m), 7.28 (1H, s), 7.05 (1H, m), 6.99–6.96 (4H, m), 6.73 (1H, brs), 4.03 (2H, q, J=7.3 Hz), 3.77 (8H, m), 3.51 (3H, s), 1.39 (3H, t, J=7.3 Hz).

FAB-Mass: 524 (M$^+$+1)

IR (KBr) σ (cm$^{-1}$) 1734, 1639, 1602, 1543, 1506, 1487, 1417, 1223, 997.

EXAMPLE 388

N-Benzyl-4-(1,3-dihydro-3-ethyl-1-methyl-2-oxo-2H-imidazo[4,5-g]quinazolin-8-yl)-1-piperazinethiocarboxamide (Compound 388)

Yield: 57% m.p.: 207–208° C.

$^1$H-NMR (CDCl$_3$) δ (ppm): 8.68 (1H, s), 7.43 (1H, s), 7.38–7.30 (5H, m), 7.27 (1H, s), 5.83 (1H, brt, J=4.6 Hz), 4.91 (2H, d, J=4.6 Hz), 4.16–4.08 (4H, m), 4.03 (2H, q, J=7.3 Hz), 3.91–3.87 (4H, m), 3.49 (3H, s), 1.39 (3H, t, J=7.3 Hz).

FAB-Mass: 462 (M$^+$+1)

IR (KBr) σ (cm$^{-1}$): 1722, 1552, 1539, 1489, 1454, 1427, 1404, 1377, 1352, 1248, 849.

EXAMPLE 389

4-(1,3-Dihydro-1,3-dipropyl-2-oxo-2H-imidazo[4,5-g]quinazolin-8-yl)-N-(4-phenoxyphenyl)-1-piperazinecarboxamide (Compound 389)

Substantially the same procedure as in Example 60 was repeated, except that 1,3-dihydro-1,3-dipropyl-2-oxo-8-(1-piperazinyl)-2H-imidazo[4,5-g]quinazoline obtained in Reference Example 3 was used in place of 6,7-dimethoxy-4-(1-piperazinyl)quinazoline, to give the desired compound.

Yield: 62% m.p.: 179–180° C.

$^1$H-NMR (DMSO-d$_6$) δ (ppm): 8.70 (1H, brs), 8.61 (1H, s), 7.60 (1H, s), 7.54–7.47 (3H, m), 7.39–7.33 (2H, m), 7.09 (1H, m), 6.97–6.94 (4H, m), 4.00–3.91 (4H, m), 3.71 (8H, m), 2.51–2.50 (4H, m), 1.79–1.69 (6H, m).

FAB-Mass: 566 (M$^+$+1)

IR (KBr) σ (cm$^{-1}$): 1722, 1643, 1601, 1487, 1414, 1225, 993, 849, 748.

EXAMPLE 390

4-(1,3-Dibutyl-1,3-dihydro-2-oxo-2H-imidazo[4,5-g]quinazolin-8-yl)-N-(4-phenoxyphenyl)-1-piperazinecarboxamide (Compound 390)

Substantially the same procedure as in Example 60 was repeated, except that 1,3-dibutyl-1,3-dihydro-2-oxo-8-(1-piperazinyl)-2H-imidazo[4,5-g]quinazoline obtained in Reference Example 4 was used in place of 6,7-dimethoxy-4-(1-piperazinyl)quinazoline, to give the desired compound.

Yield: 50% m.p.: 134–136° C.

$^1$H-NMR (DMSO-d$_6$) δ (ppm): 8.70 (1H, brs), 8.61 (1H, s), 7.58 (1H, s), 7.53–7.48 (3H, m), 7.39–7.33 (2H, m), 7.09 (1H, m), 6.97–6.94 (4H, m), 4.03–3.94 (4H, m), 3.71 (8H, m), 1.73–1.66 (4H, m), 1.34–1.29 (4H, m), 0.96–0.88 (6H, m).

FAB-Mass: 594 (M$^+$+1)

IR (KBr) σ (cm$^{-1}$): 1726, 1643, 1504, 1487, 1414, 1225.

EXAMPLE 391

4-(6,7-Dimethoxy-2-methyl-4-quinazolinyl)-N-(4-phenoxyphenyl)-1-piperazinecarboxamide (Compound 391)

Substantially the same procedure as in Example 60 was repeated, except that 6,7-dimethoxy-2-methyl-4-(1-piperazinyl)quinazoline was used in place of 6,7-dimethoxy-4-(1-piperazinyl)quinazoline, to give the desired compound.

Yield: 93% m.p.: 146–147° C.

$^1$H-NMR (CDCl$_3$) δ (ppm): 7.37–7.27 (4H, m), 7.21 (1H, s), 7.08 (1H, s), 7.04–6.95 (5H, m), 6.80 (1H, brs), 4.00 (3H, s), 3.97 (3H, s), 3.72 (8H, m), 2.66 (3H, s).

FAB-Mass: 500 (M$^+$+1)

IR (KBr) σ (cm$^{-1}$): 1639, 1508, 1489, 1417, 1244, 1225, 1167, 991, 851.

EXAMPLE 392

4-(2-Chloro-6,7-dimethoxy-4-quinazolinyl)-N-(4-phenoxyphenyl)-1-piperazinecarboxamide (Compound 392)

To a solution of 2.4 g (5.88 mmol) of 4-(2-chloro-6,7-dimethoxy-4-quinazolinyl)-1-piperazinecarboxylic acid tert-butyl ester obtained in Reference Example 15 in 20 ml of dichloromethane was added 20 ml of trifluoroacetic acid under ice-cooling, followed by stirring at the same temperature for 1.5 hours. The reaction mixture was concentrated and subjected to azeotropic distillation with toluene, and the obtained residue was dissolved in 30 ml of dimethylformamide. To the resulting solution were added 4.09 ml (29.3 mmol) of triethylamine and 1.24 ml (5.88 mmol) of 4-phenoxyphenyl isocyanate, followed by overnight stirring at room temperature. The reaction mixture was poured into water, and sodium chloride was added thereto. The precipitated crystals were collected by filtration, washed with water, and dried, followed by purification by silica gel chromatography to give the desired compound as colorless crystals.

Yield: 73% m.p.: 178–179° C.

$^1$H-NMR (CDCl$_3$) δ (ppm): 7.36–7.28 (4H, m), 7.20 (1H, s), 7.11–6.97 (5H, m), 7.08 (1H, s), 6.50 (1H, brs), 4.01 (3H, s), 3.99 (3H, s), 3.88–3.85 (4H, m), 3.76–3.73 (4H, m).

FAB-Mass: 522 (M$^+$+3), 520 (M$^+$+1)

IR (KBr) σ (cm$^{-1}$): 1632, 1506, 1487, 1416, 1244, 1214, 1142, 997, 953, 868, 849, 749.

EXAMPLE 393

4-(6,7-Dimethoxy-2-morpholino-4-quinazolinyl)-N-(4-phenoxyphenyl)-1-piperazinecarboxamide (Compound 393)

Substantially the same procedure as in Example 329 was repeated, except that 4-(6,7-dimethoxy-2-morpholino-4-quinazolinyl)-1-piperazinecarboxylic acid tert-butyl ester obtained in Reference Example 16 was used, to give the desired compound.

Yield: 79% m.p.: 114–116° C.

$^1$H-NMR (CDCl$_3$) δ (ppm): 7.36–7.27 (5H, m), 7.07 (1H, m), 7.05–6.96 (5H, m), 6.41 (1H, brs), 3.99 (3H, s), 3.93 (3H, s), 3.83–3.82 (8H, m), 3.71–3.70 (8H, m).

FAB-Mass: 571 (M$^+$+1)

IR (KBr) σ (cm$^{-1}$): 1641, 1554, 1508, 1489, 1419, 1379, 1240, 993.

In the following Examples 394–396, substantially the same procedure as in Example 1 was repeated, except that 4-(1-piperazinyl)quinoline was used in place of 6,7-dimethoxy-4-(1-piperazinyl)quinazoline, and the corresponding isocyanate or isothiocyanate was used in place of phenyl isocyanate, to give the desired compound.

EXAMPLE 394

N-(4-Phenoxyphenyl)-4-(4-quinolyl)-1-piperazinecarboxamide (Compound 394)

Yield: 93% m.p.: 145–146° C.

$^1$H-NMR (CDCl$_3$) δ (ppm): 8.73 (1H, d, J=5.0 Hz), 8.07 (1H, d, J=8.3 Hz), 8.01 (1H, dd, J=7.3 Hz, 1.3 Hz), 7.67 (1H, ddd, J=8.3 Hz, 7.3 Hz, 1.3 Hz), 7.51 (1H, dd, J=7.3 Hz, 7.3 Hz), 7.38–7.24 (4H, m), 7.18 (1H, brs), 7.05 (1H, m), 6.97–6.93 (4H, m), 6.82 (1H, d, J=5.0 Hz), 3.80–3.76 (4H, m), 3.21–3.18 (4H, m).

FAB-Mass: 425 (M$^+$+1)

IR (KBr) σ (cm$^{-1}$): 1639, 1582, 1506, 1487, 1419, 1396, 1340, 1219, 997, 918, 833, 766, 692.

EXAMPLE 395

N-Benzyl-4-(4-quinolyl)-1-piperazinethiocarboxamide (Compound 395)

Yield: 96% m.p.: 75–79° C.

¹H-NMR (CDCl₃) δ (ppm): 8.63 (1H, d, J=5.0 Hz), 8.03–7.98 (2H, m), 7.66 (1H, ddd, J=8.3 Hz, 7.3 Hz, 1.3 Hz), 7.51 (1H, m), 7.35–7.23 (5H, m), 7.04 (1H, brt, J=5.0 Hz), 6.76 (1H, d, J=5.0 Hz), 4.95 (2H, d, J=5.0 Hz), 4.17–4.14 (4H, m), 3.24–3.21 (4H, m).

FAB-Mass: 363 (M⁺+1)

IR (KBr) σ (cm⁻¹): 1578, 1533, 1508, 1398, 1335, 1205, 1009, 926, 770.

EXAMPLE 396

N-(3-Picolyl)-4-(4-quinolyl)-1-piperazinethiocarboxamide dihydrochloride (Compound 396)

Yield: 86% m.p.: 183–185° C. (hydrochloride)

¹H-NMR (free base, CDCl₃) δ (ppm): 8.70 (1H, d, J=5.0 Hz), 8.47 (1H, dd, J=4.6 Hz, 1.6 Hz), 8.44 (1H, d, J=2.0 Hz), 8.05–7.98 (2H, m), 7.78 (1H, ddd, J=7.9 Hz, 2.0 Hz, 1.6 Hz), 7.70 (1H, ddd, J=8.6 Hz, 8.3 Hz, 1.7 Hz), 7.51 (1H, ddd, J=8.3 Hz, 8.3 Hz, 1.3 Hz), 7.25 (1H, dd, J=7.9 Hz, 4.6 Hz), 6.85 (1H, br), 6.82 (1H, d, J=5.0 Hz), 4.95 (2H, d, J=5.,3 Hz), 4.20–4.16 (4H, m), 3.30–3.26 (4H, m).

FAB-Mass: 364 (M⁺+1)

IR (hydrochloride, KBr) σ (cm⁻¹): 1591, 1547, 1512, 1468, 1441, 1371, 1348, 1266, 1219, 1016, 777.

EXAMPLE 397

N-(4-Phenoxyphenyl)-4-(2-trifluoromethyl-4-quinolyl)-1-piperazinecarboxamide (Compound 397)

Substantially the same procedure as in Example 60 was repeated, except that commercially available 4-(1-piperazinyl)-2-trifluoromethylquinoline was used in place of 6,7-dimethoxy-4-(1-piperazinyl)quinazoline, to give the desired compound.

Yield: 41% m.p.: 203–204° C.

¹H-NMR (CDCl₃) δ (ppm): 8.20 (1H, dd, J=8.3 Hz, 1.3 Hz), 8.07 (1H, dd, J=8.3 Hz, 1.3 Hz), 7.78 (1H, ddd, J=8.3 Hz, 8.3 Hz, 1.3 Hz), 7.63 (1H, ddd, J=8.3 Hz, 8.3 Hz, 1.3 Hz), 7.37–7.26 (4H, m), 7.17 (1H, s), 7.06 (1H, m), 7.00–6.97 (4H, m), 6.55 (1H, brs), 3.84–3.80 (4H, m), 3.37–3.34 (4H, m).

FAB-Mass: 493 (M⁺+1)

IR (KBr) σ (cm⁻¹): 1639, 1537, 1508, 1489, 1412, 1227, 1134, 995, 949, 771.

EXAMPLE 398

N-Benzyl-4-(6-trifluoromethyl-4-quinolyl)-1-piperazinethiocarboxamide (Compound 398)

Substantially the same procedure as in Example 125 was repeated, except that 4-(1-piperazinyl)-6-trifluoromethylquinoline was used in place of 6,7-dimethoxy-4-(1-piperazinyl)quinazoline, to give the desired compound.

Yield: 76% m.p.: 158–159° C.

¹H-NMR (CDCl₃) δ (ppm): 8.79 (1H, d, J=5.3 Hz), 8.29 (1H, d, J=2.0 Hz), 8.13 (1H, d, J=8.9 Hz), 7.82 (1H, dd, J=8.9 Hz, 2.0 Hz), 7.35–7.23 (5H, m), 6.90 (1H, d, J=5.3 Hz), 6.36 (1H, brt, J=5.0 Hz), 4.90 (2H, d, J=5.0 Hz), 4.16–4.13 (4H, m), 3.31–3.27 (4H, m).

FAB-Mass: 431 (M⁺+1)

IR (KBr) σ (cm⁻¹): 1583, 1531, 1387, 1340, 1315, 1215, 1161, 1113, 1014, 854, 743.

In the following Examples 399–402, substantially the same procedure as in Example 1 was repeated, except that 6-chloro-4-(1-piperazinyl)quinoline was used in place of 6,7-dimethoxy-4-(1-piperazinyl)quinazoline, and the corresponding isocyanate or isothiocyanate was used in place of phenyl isocyanate, to give the desired compound.

EXAMPLE 399

4-(6-Chloro-4-quinolyl)-N-(4-phenoxyphenyl)-1-piperazinecarboxamide (Compound 399)

Yield: 83% m.p.: 188–189° C.

¹H-NMR (CDCl₃) δ (ppm): 8.72 (1H, d, J=5.0 Hz), 8.00 (1H, d, J=8.9 Hz), 7.96 (1H, d, J=2.3 Hz), 7.60 (1H, dd, J=8.9 Hz, 2.3 Hz), 7.37–7.24 (4H, m), 7.07–6.98 (2H, m), 6.97–6.93 (4H, m), 6.85 (1H, d, J=5.0 Hz), 3.80–3.76 (4H, m), 3.20–3.16 (4H, m).

FAB-Mass: 459 (M⁺+1)

IR (KBr) σ (cm⁻¹): 1639, 1537, 1506, 1489, 1417, 1371, 1236, 997, 838.

EXAMPLE 400

N-Benzyl-4-(6-chloro-4-quinolyl)-1-piperazinethiocarboxamide (Compound 400)

Yield: 91% m.p.: 173–174° C.

¹H-NMR (CDCl₃) δ (ppm): 8.66 (1H, d, J=4.6 Hz), 7.96–7.93 (2H, m), 7.57 (1H, dd, J=8.9 Hz, 2.0 Hz), 7.33–7.23 (5H, m), 6.82 (1H, d, J=4.6 Hz), 6.37 (1H, brt, J=5.0 Hz), 4.90 (2H, d, J=5.0 Hz), 4.12–4.09 (4H, m), 3.23–3.20 (4H, m).

FAB-Mass: 399 (M⁺+3), 397 (M⁺+1)

IR (KBr) σ (cm⁻¹): 1579, 1531, 1495, 1450, 1387, 1369, 1360, 1333, 1275, 1225, 1205, 1142, 1011, 957, 926, 860, 843, 735.

EXAMPLE 401

N-(4-Chlorobenzyl)-4-(6-chloro-4-quinolyl)-1-piperazinethiocarboxamide (Compound 401)

Yield: 99% m.p.: 89–90° C.

¹H-NMR (CDCl₃) δ (ppm): 8.64 (1H, d, J=5.0 Hz), 7.94–7.91 (2H, m), 7.58 (1H, dd, J=8.9 Hz, 2.0 Hz), 7.29–7.21 (4H, m), 6.82 (1H, d, J=5.0 Hz), 6.59 (1H, br), 4.87 (2H, d, J=5.0 Hz), 4.16–4.12 (4H, m), 3.25–3.21 (4H, m).

FAB-Mass: 433 (M⁺+3), 431 (M⁺+1)

IR (KBr) σ (cm⁻¹): 1641, 1587, 1531, 1510, 1385, 1327, 1227, 1157, 1124, 999, 833.

IR (KBr) σ (cm⁻¹) 1574, 1539, 1497, 1371, 1327, 1205, 1014, 841.

EXAMPLE 402

4-(6-Chloro-4-quinolyl)-N-(3-picolyl)-1-piperazinethiocarboxamide dihydrochloride (Compound 402)

Yield: 86% m.p.: 162–164° C. (hydrochloride)

¹H-NMR (free base, CDCl₃) δ (ppm): 8.68 (1H, d, J=5.0 Hz), 8.44–8.39 (2H, m), 7.97–7.94 (2H, m), 7.78 (1H, d, J=7.9 Hz), 7.59 (1H, dd, J=8.6 Hz, 2.0 Hz), 7.29–7.17 (2H, m), 6.85 (1H, d, J=5.0 Hz), 4.94 (2H, d, J=4.9 Hz), 4.21–4.17 (4H, m), 3.27–3.23 (4H, m).

FAB-Mass: 400 (M⁺+3), 398 (M⁺+1)

IR (hydrochloride, KBr) σ (cm⁻¹): 1605, 1585, 1539, 1506, 1471, 1410.

EXAMPLE 403

N-Benzyl-4-(6-trifluoromethoxy-4-quinolyl)-1-piperazinethiocarboxamide (Compound 403)

Substantially the same procedure as in Example 1 was repeated, except that 4-(1-piperazinyl)-6-trifluoromethoxyquinoline was used in place of 6,7-dimethoxy-4-(1-piperazinyl)quinazoline, to give the desired compound.

Yield: 93% m.p.: 70–71° C.

¹H-NMR (CDCl₃) δ (ppm): 8.75 (1H, d, J=5.0 Hz), 8.09 (1H, d, J=9.3 Hz), 7.82 (1H, s), 7.53 (1H, d, J=9.3 Hz), 7.36–7.30 (5H, m), 6.89 (1H, d, J=5.0 Hz), 6.12 (1H, br), 4.91 (2H, d, J=4.6 Hz), 4.16–4.12 (4H, m), 3.29–3.25 (4H, m).

FAB-Mass: 447 (M⁺+1)

IR (KBr) σ (cm⁻¹): 1585, 1539, 1512, 1458, 1379, 1336, 1263, 1215, 1167, 1014.

EXAMPLE 404

N-(4-Phenoxyphenyl)-4-(7-trifluoromethyl-4-quinolyl)-1-piperazinecarboxamide (Compound 404)

Substantially the same procedure as in Example 60 was repeated, except that 4-(1-piperazinyl)-7-trifluoromethylquinoline was used in place of 6,7-dimethoxy-4-(1-piperazinyl)quinazoline, to give the desired compound.

Yield: 100% m.p.: 163–164° C.

¹H-NMR (CDCl₃) δ (ppm): 8.85 (1H, d, J=5.0 Hz), 8.39 (1H, d, J=1.7 Hz), 8.15 (1H, d, J=8.9 Hz), 7.70 (1H, dd, J=8.9 Hz, 1.7 Hz), 7.37–7.26 (4H, m), 7.09 (1H, m), 7.05–6.96 (5H, m), 6.59 (1H, brs), 3.83–3.79 (4H, m), 3.30–3.27 (4H, m).

FAB-Mass: 493 (M⁺+1)

In the following Examples 405 and 406, substantially the same procedure as in Example 1 was repeated, except that 7-chloro-4-(1-piperazinyl)quinoline was used in place of 6,7-dimethoxy-4-(1-piperazinyl)quinazoline, and the corresponding isothiocyanate was used in place of phenyl isocyanate, to give the desired compound.

EXAMPLE 405

N-Benzyl-4-(7-chloro-4-quinolyl)-1-piperazinethiocarboxamide (Compound 405)

Yield: 89% m.p.: 84–86° C.

¹H-NMR (CDCl₃) δ (ppm): 8.59 (1H, d, J=5.0 Hz), 7.93 (1H, d, J=2.0 Hz), 7.89 (1H, d, J=8.9 Hz), 7.39 (1H, dd, J=8.9 Hz, 2.0 Hz), 7.31–7.20 (5H, m), 6.96 (1H, brt, J=5.0 Hz), 6.74 (1H, d, J=5.0 Hz), 4.90 (2H, d, J=5.0 Hz), 4.12–4.11 (4H, m), 3.22–3.18 (4H, m).

FAB-Mass: 399 (M⁺+3), 397 (M⁺+1)

IR (KBr) σ (cm⁻¹): 1537, 1504, 1427, 1379, 1335, 1250, 1011, 878, 824, 698.

EXAMPLE 406

4-(7-Chloro-4-quinolyl)-N-(3-picolyl)-1-piperazinethiocarboxamide dihydrochloride (Compound 406)

Yield: 91% m.p.: 170–173° C. (hydrochloride)

¹H-NMR (free base, CDCl₃) δ (ppm): 8.68 (1H, d, J=5.0 Hz), 8.44 (1H, dd, J=4.9 Hz, 1.7 Hz), 8.40 (1H, d, J=2.0 Hz), 7.99 (1H, d, J=2.0 Hz), 7.92 (1H, d, J=8.9 Hz), 7.77 (1H, ddd, J=7.9 Hz, 2.0 Hz, 1.7 Hz), 7.43 (1H, dd, J=8.9 Hz, 2.0 Hz), 7.25 (1H, dd, J=7.9 Hz, 4.9 Hz), 7.08 (1H, brt, J=5.3 Hz), 6.81 (1H, d, J=5.0 Hz), 4.94 (2H, d, J=5.3 Hz), 4.20–4.16 (4H, m), 3.28–3.25 (4H, m).

FAB-Mass: 400 (M⁺+3), 398 (M⁺+1)

IR (hydrochloride, KBr) σ (cm⁻¹): 1606, 1539, 1510, 1443, 1414, 1209, 1012.

EXAMPLE 407

4-(6,7-Dimethoxy-4-quinolyl)-N-(4-phenoxyphenyl)-1-piperazinecarboxamide (Compound 407)

Substantially the same procedure as in Example 329 was repeated, except that 4-(6,7-dimethoxy-4-quinolyl)-1-piperazinecarboxylic acid tert-butyl ester obtained in Reference Example 17 was used in place of 4-(6,7-difluoro-4-quinazolinyl)-1-piperazinecarboxylic acid tert-butyl ester, to give the desired compound.

Yield: 57% m.p.: 204–206° C.

¹H-NMR (CDCl₃) δ (ppm): 8.59 (1H, d, J=5.0 Hz), 7.40–7.26 (6H, m), 7.06 (1H, m), 6.98–6.93 (5H, m), 6.79 (1H, d, J=5.0 Hz), 4.01 (3H, s), 4.00 (3H, s), 3.78 (4H, m), 3.19 (4H, m).

FAB-Mass: 485 (M⁺+1)

IR (KBr) σ (cm⁻¹): 1633, 1583, 1541, 1508, 1487, 1423, 1248, 1217, 993, 843, 750.

In the following Examples 408–410, substantially the same procedure as in Example 329 was repeated, except that 4-(6,7-dimethoxy-3-ethoxycarbonyl-4-quinolyl)-1-piperazinecarboxylic acid tert-butyl ester obtained in Reference Example 18 was used in place of 4-(6,7-difluoro-4-quinazolinyl)-1-piperazinecarboxylic acid tert-butyl ester, and the corresponding isothiocyanate was used in place of 4-phenoxyphenyl isocyanate (used in Example 408), to give the desired compound.

EXAMPLE 408

4-(6,7-Dimethoxy-3-ethoxycarbonyl-4-quinolyl)-N-(4-phenoxyphenyl)-1-piperazinecarboxamide (Compound 408)

Yield: 100% m.p.: 163–164° C.

¹H-NMR (CDCl₃) δ (ppm): 8.76 (1H, s), 7.52 (1H, brs), 7.37 (1H, s), 7.32 (1H, s), 7.29 (2H, d, J=7.9 Hz), 7.22–7.16

(2H, m), 6.95 (1H, dd, J=7.9 Hz, 1.0 Hz), 6.87–6.84 (4H, m), 4.31 (2H, q, J=7.3 Hz), 3.94 (3H, s), 3.92 (3H, s), 3.70 (4H, m), 3.24 (4H, m), 1.32 (3H, t, J=7.3 Hz).

FAB-Mass: 557 (M$^+$+1)

IR (KBr) σ (cm$^{-1}$): 1717, 1633, 1506, 1427, 1266, 1215, 1180, 999, 860.

EXAMPLE 409

N-Benzyl-4-(6,7-dimethoxy-3-ethoxycarbonyl-4-quinolyl)-1-piperazinethiocarboxamide (Compound 409)

Yield: 100% m.p.: 174–175° C.

$^1$H-NMR (CDCl$_3$) δ (ppm): 8.78 (1H, s), 7.40–7.26 (7H, m), 6.18 (1H, brt, J=4.6 Hz), 4.91 (2H, d, J=4.6 Hz), 4.40 (2H, q, J=7.3 Hz), 4.08 (4H, m), 4.01 (3H, s), 4.00 (3H, s), 3.36–3.33 (4H, m), 1.41 (3H, t, J=7.3 Hz).

FAB-Mass: 495 (M$^+$+1)

IR (KBr) σ (cm$^{-1}$): 1701, 1537, 1497, 1475, 1427, 1263, 1203, 860.

EXAMPLE 410

4-(6,7-Dimethoxy-3-ethoxycarbonyl-4-quinolyl)-N-(3-picolyl)-1-piperazinethiocarboxamide (Compound 410)

Yield: 98% m.p.: 92–94° C.

$^1$H-NMR (CDCl$_3$) δ (ppm): 8.79 (1H, s), 8.48 (1H, dd, J=5.0 Hz, 1.3 Hz), 8.47 (1H, d, J=2.0 Hz), 7.80 (1H, ddd, J=7.9 Hz, 2.0 Hz, 1.3 Hz), 7.41 (1H, s), 7.38 (1H, s), 7.28 (1H, dd, J=7.9 Hz, 5.0 Hz), 6.65 (1H, brt, J=5.3 Hz), 4.97 (2H, d, J=5.3 Hz), 4.40 (2H, q, J=7.3 Hz), 4.13 (4H, m), 4.03 (3H, s), 4.00 (3H, s), 3.37–3.33 (4H, m), 1.41 (-3H, t, J=7.3 Hz).

FAB-Mass: 496 (M$^+$+1)

IR (KBr) σ (cm$^{-1}$): 1712, 1502, 1478, 1427, 1263, 1205.

EXAMPLE 411

N-(4-Phenoxyphenyl)-4-(8-trifluoromethyl-4-quinolyl)-1-piperazinecarboxamide (Compound 411)

Substantially the same procedure as in Example 60 was repeated, except that 4-(1-piperazinyl)-8-trifluoromethylquinoline was used in place of 6,7-dimethoxy-4-(1-piperazinyl)quinazoline, to give the desired compound.

Yield: 100% m.p.: 214–215° C.

$^1$H-NMR (CDCl$_3$) δ (ppm): 8.88 (1H, d, J=5.0 Hz), 8.24 (1H, d, J=7.9 Hz), 8.04 (1H, d, J=6.9 Hz), 7.55 (1H, dd, J=7.9 Hz, 6.9 Hz), 7.37–7.26 (4H, m), 7.06 (1H, m), 6.99–6.93 (5H, m), 3.81–3.77 (4H, m), 3.22–3.19 (4H, m).

FAB-Mass: 493 (M$^+$+1)

IR (KBr) σ (cm$^{-1}$): 1641, 1587, 1538, 1508, 1491, 1417, 1317, 1294, 1230, 1138, 999, 939, 825, 754.

EXAMPLE 412

4-(8-Chloro-4-quinolyl)-N-(4-phenoxyphenyl)-1-piperazinecarboxamide (Compound 412)

Substantially the same procedure as in Example 60 was repeated, except that 8-chloro-4-(1-piperazinyl)quinoline was used in place of 6,7-dimethoxy-4-(1-piperazinyl)quinazoline, to give the desired compound.

Yield: 99% m.p.: 174–175° C.

$^1$H-NMR (CDCl$_3$) δ (ppm): 8.82 (1H, d, J=5.0 Hz), 7.93 (1H, d, J=8.6 Hz), 7.79 (1H, d, J=7.6 Hz), 7.43–7.24 (6H, m), 7.04 (1H, dd, J=7.3 Hz, 1.3 Hz), 6.96–6.90 (4H, m), 6.87 (1H, d, J=5.0 Hz), 3.78–3.75 (4H, m), 3.18–3.15 (4H, m).

FAB-Mass: 461 (M$^+$+3), 459 (M$^+$+1)

IR (KBr) σ (cm$^{-1}$): 1638, 1531, 1506, 1489, 1410, 1225, 996, 931, 831, 768.

EXAMPLE 413

4-(6-Methyl-5-nitro-2-trifluoromethyl-4-quinolyl)-N-(4-phenoxyphenyl)-1-piperazinecarboxamide (Compound 413)

Substantially the same procedure as in Example 60 was repeated, except that 6-methyl-5-nitro-4-(1-piperazinyl)-2-trifluoromethylquinoline was used in place of 6,7-dimethoxy-4-(1-piperazinyl)quinazoline, to give the desired compound.

Yield: 96% m.p.: 197–198° C.

$^1$H-NMR (CDCl$_3$) δ (ppm): 8.24 (1H, d, J=8.6 Hz), 7.70 (1H, d, J=8.6 Hz), 7.54 (1H, s), 7.35–7.25 (4H, m), 7.04 (1H, m), 6.98–6.93 (4H, m), 6.62 (1H, brs), 4.07–4.02 (2H, m), 3.33–3.23 (2H, m), 3.13–3.08 (2H, m), 2.93–2.84 (2H, m), 2.51 (3H, s).

FAB-Mass: 552 (M$^+$+1)

IR (KBr) σ (cm$^{-1}$): 1626, 1539, 1508, 1489, 1423, 1381, 1252, 1227, 1190, 1136, 1099, 989, 922, 841, 750.

In the following Examples 414 and 415, substantially the same procedure as in Example 329 was repeated, except that 4-(1-phthalazinyl)-1-piperazinecarboxylic acid tert-butyl ester obtained in Reference Example 20 was used in place of 4-(6,7-difluoro-4-quinazolinyl)-1-piperazinecarboxylic acid tert-butyl ester, and the corresponding isocyanate was used in place of 4-phenoxyphenyl isocyanate (used in Example 414), to give the desired compound.

EXAMPLE 414

N-(4-Phenoxyphenyl)-4-(1-phthalazinyl)-1-piperazinecarboxamide (Compound 414)

Yield: 98% (2 steps)

m.p.: 202–203° C.

$^1$H-NMR (CDCl$_3$) δ (ppm): 9.20 (1H, s), 8.08 (1H, dd, J=8.6 Hz, 2.3 Hz), 7.95–7.83 (3H, m), 7.41–7.26 (4H, m), 7.07 (1H, m), 7.00–6.96 (4H, m), 6.82 (1H, brs), 3.84–3.81 (4H, m), 3.66–3.63 (4H, m).

FAB-Mass: 426 (M$^+$+1)

IR (KBr) σ (cm$^{-1}$): 1649, 1587, 1531, 1506, 1487, 1410, 1377, 1228, 1003, 835.

EXAMPLE 415

N-(4-Nitrophenyl)-4-(1-phthalazinyl)-1-piperazinecarboxamide (Compound 415)

Yield: 10%

$^1$H-NMR (DMSO-d$_6$) δ (ppm): 12.19 (1H, brs), 9.36 (1H, s), 8.27 (1H, dd, J=8.6 Hz, 1.3 Hz), 8.17 (2H, d, J=9.2 Hz), 8.04–7.84 (3H, m), 7.77 (2H, d, J=9.2 Hz), 3.75 (4H, m), 3.15 (4H, m).

In the following Examples 416 and 417, substantially the same procedure as in Example 329 was repeated, except that 4-(4-chloro-1-phthalazinyl)-1-piperazinecarboxylic acid tert-butyl ester obtained in Reference Example 20 (1) was used in place of 4-(6,7-difluoro-4-quinazolinyl)-1-piperazinecarboxylic acid tert-butyl ester, and the corresponding isocyanate was used in place of 4-phenoxyphenyl isocyanate (used in Example 416), to give the desired compound.

EXAMPLE 416

4-(4-Chloro-1-phthalazinyl)-N-(4-Phenoxyphenyl)-1-piperazinecarboxamide (Compound 416)

Yield: 100% m.p.: 196–197° C.

$^1$H-NMR (CDCl$_3$) δ (ppm): 8.25 (1H, dd, J=7.3 Hz, 3.0 Hz), 8.08 (1H, dd, J=6.9 Hz, 2.3 Hz), 7.97–7.90 (2H, m), 7.39–7.26 (4H, m), 7.04 (1H, m), 6.98–6.93 (4H, m), 6.88 (1H, brs), 3.82–3.78 (4H, m), 3.60–3.57 (4H, m).

FAB-Mass: 462 (M$^+$+3), 460 (M$^+$+1)

IR (KBr) σ (cm$^{-1}$): 1655, 1508, 1489, 1410, 1242, 997, 775.

EXAMPLE 417

4-(4-Chloro-1-phthalazinyl)-N-(4-nitrophenyl)-1-piperazinecarboxamide (Compound 417)

Yield: 68%

$^1$H-NMR (CDCl$_3$) δ (ppm): 9.21 (1H, brs), 8.24 (1H, m), 8.17 (1H, m), 8.11 (2H, d, J=9.2 Hz), 8.09–7.98 (2H, m), 7.76 (2H, d, J=9.2 Hz), 3.88–3.84 (4H, m), 3.57–3.53 (4H, m).

FAB-Mass: 415 (M$^+$+3), 413 (M$^+$+1)

EXAMPLE 418

4-(4-Benzyl-1-phthalazinyl)-N-(4-phenoxyphenyl)-1-piperazinecarboxamide (Compound 418)

Substantially the same procedure as in Example 60 was repeated, except that 1-benzyl-4-(1-piperazinyl)phthalazine was used in place of 6,7-dimethoxy-4-(1-piperazinyl)quinazoline, to give the desired compound.

Yield: 75% m.p.: 100–101° C.

$^1$H-NMR (CDCl$_3$) δ (ppm): 8.07–7.99 (2H, m), 7.81–7.70 (2H, m), 7.39–7.15 (10H, m), 7.03 (1H, m), 6.97–6.90 (4H, m), 4.60 (2H, s), 3.81–3.77 (4H, m), 3.57–3.53 (4H, m).

FAB-Mass: 516 (M$^+$+1)

IR (KBr) σ (cm$^{-1}$): 1637, 1541, 1508, 1491, 1414, 1227, 995, 768.

EXAMPLE 419

4-(1,3-Diethyl)-1,3-dihydro-2-oxo-2H-imidazo[4,5-g]phthalazin-5-yl)-N-(4-phenoxyphenyl)-1-piperazinecarboxamide (Compound 419)

Substantially the same procedure as in Example 329 was repeated, except that 4-(1,3-diethyl-1,3-dihydro-2-oxo-2H-imidazo[4,5-g]phthalazin-5-yl)-1-piperazinecarboxylic acid tert-butyl ester obtained in Reference Example 21 was used in place of 4-(6,7-difluoro-4-quinazolinyl)-1-piperazinecarboxylic acid tert-butyl ester, to give the desired compound.

Yield: 95% (2 steps)

m.p.: 125–128° C.

$^1$H-NMR (CDCl$_3$) δ (ppm): 9.18 (1H, s), 7.49 (1H, s), 7.40–7.28 (5H, m), 7.06 (1H, m), 7.01–6.98 (4H, m), 6.77 (1H, brs), 4.13– 4.04 (4H, m), 3.85–3.82 (4H, m), 3.63–3.60 (4H, m), 1.44 (3H, t, J=7.3 Hz), 1.43 (3H, t, J=7.3 Hz).

FAB-Mass: 538 (M$^+$+1)

IR (KBr) σ (cm$^{-1}$): 1728, 1714, 1645, 1506, 1491, 1471, 1414, 1223, 993, 752.

EXAMPLE 420

4-(1,3-Diethyl-1,3-dihydro-2-oxo-2H-imidazo[4,5-g]phthalazin-5-yl)-N-(4-nitrophenyl)-1-piperazinecarboxamide (Compound 420)

To a solution of 758.4 mg (1.65 mmol) of 4-(8-chloro-1,3-diethyl-1,3-dihydro-2-oxo-2H-imidazo[4,5-g]phthalazin-5-yl)-1-piperazinecarboxylic acid tert-butyl ester obtained in Reference Example 21 (5) in 20 ml of dichloromethane was added 50 ml of trifluoroacetic acid under ice-cooling, followed by stirring at the same temperature for 5 hours. After the solvent was evaporated, the residue was subjected to azeotropic distillation with toluene twice. The obtained residue was dissolved in 20 ml of acetic acid, and a suspension of 300 mg of 10% palladium-carbon in 5 ml of water was added thereto, followed by overnight stirring at room temperature in an atmosphere of hydrogen. After the catalyst was separated by filtration using Celite, the solvent was evaporated, and the residue was subjected to azeotropic distillation with triethylamine. The obtained residue was dissolved in 10 ml of dimethylformamide, and 297.3 mg (1.81 mmol) of 4-nitrophenyl isocyanate was added thereto, followed by stirring at room temperature for 2 hours. The reaction mixture was poured into water, and sodium chloride was added thereto. The precipitated crystals were collected by filtration, washed with water, and dried, followed by purification by silica gel chromatography to give the desired compound as colorless crystals.

Yield: 53%

$^1$H-NMR (CDCl$_3$) δ (ppm): 9.18 (1H, s), 8.98 (1H, brs), 8.11 (2H, d, J=7.3 Hz), 7.76 (2H, d, J=7.3 Hz), 7.53 (1H, s), 7.49 (1H, s), 4.13–4.03 (4H, m), 3.90–3.87 (4H, m), 3.57–3.54 (4H, m), 1.43 (3H, t, J=7.3 Hz), 1.42 (3H, t, J=7.3 Hz).

FAB-Mass: 491 (M$^+$+1)

EXAMPLE 421

4-(5-Chloro-1,3-diethyl-1,3-dihydro-2-oxo-2H-imidazo[4,5-g]phthalazin-8-yl)-N-(4-phenoxyphenyl)-1-piperazinecarboxamide (Compound 421)

Substantially the same procedure as in Example 329 was repeated, except that 4-(8-chloro-1,3-diethyl-1,3-dihydro-2-oxo-2H-imidazo[4,5-g]phthalazin-5-yl)-1-piperazinecarboxylic acid tert-butyl ester obtained in Reference Example 21 (5) was used in place of 4-(6,7-difluoro-4-quinazolinyl)-1-piperazinecarboxylic acid tert-butyl ester, to give the desired compound.

Yield: 100% m.p.: 172–173° C.

$^1$H-NMR (CDCl$_3$) δ (ppm): 7.67 (1H, s), 7.49 (1H, s), 7.38 (2H, d, J=8.9 Hz), 7.32–7.27 (2H, m), 7.08–7.02 (2H, m), 6.98–6.94 (4H, m), 4.16–4.05 (4H, m), 3.84–3.80 (4H, m), 3.57–3.53 (4H, m), 1.44 (3H, t, J=7.3 Hz), 1.44 (3H, t, J=7.3 Hz).

FAB-Mass: 572 (M⁺+1)
IR (KBr) σ (cm⁻¹) 1726, 1495, 1412, 1383, 1223.

EXAMPLE 422

4-(1-Isoquinolyl)-N-(4-phenoxyphenyl)-1-piperazinecarboxamide (Compound 422)

Substantially the same procedure as in Example 329 was repeated, except that 4-(1-isoquinolyl)-1-piperazinecarboxylic acid tert-butyl ester obtained in Reference Example 19 was used in place of 4-(6,7-difluoro-4-quinazolinyl)-1-piperazinecarboxylic acid tert-butyl ester, to give the desired compound.

Yield: 100%
m.p.: 122–123° C.
$^1$H-NMR (CDCl$_3$) δ (ppm): 8.14 (1H, d, J=5.9 Hz), 8.08 (1H, d, J=8.3 Hz), 7.76 (1H, d, J=8.3 Hz), 7.61 (1H, dd, J=8.3 Hz, 6.9 Hz), 7.52 (1H, dd, J=8.3 Hz, 6.9 Hz), 7.35–7.24 (5H, m), 7.03 (1H, m), 6.96–6.91 (5H, m), 3.76–3.72 (4H, m), 3.45–3.41 (4H, m).
FAB-Mass: 425 (M⁺+1)
IR (KBr) σ (cm⁻¹): 1637, 1541, 1508, 1489, 1406, 1225.

In the following Examples 423–425, substantially the same procedure as in Example 1 was repeated, except that 6,7-dimethoxy-4-(1-piperazinyl)isoquinoline obtained according to the method described in South African Patent No. 67 06512 (1968) was used in place of 6,7-dimethoxy-4-(1-piperazinyl)quinazoline, and the corresponding isocyanate or isothiocyanate was used in place of phenyl isocyanate, to give the desired compound.

EXAMPLE 423

4-(6,7-Dimethoxy-1-isoquinolyl)-N-(4-phenoxyphenyl)-1-piperazinecarboxamide (Compound 423)

Yield: 87%
m.p.: 178–179° C.
$^1$H-NMR (CDCl$_3$) δ (ppm): 8.07 (1H, d, J=5.6 Hz), 7.37–7.26 (5H, m), 7.21 (1H, d, J=5.6 Hz), 7.05 (1H, s), 7.05 (1H, m), 6.98–6.95 (4H, m), 6.76 (1H, brs), 4.01, (3H, s), 4.00 (3H, s), 3.78–3.74 (4H, m), 3.42–3.38 (4H, m).
FAB-Mass: 485 (M⁺+1)
IR (KBr) σ (cm⁻¹): 1633, 1541, 1508, 1489, 1477, 1417, 1377, 1296, 1250, 1215, 1201, 991, 860, 752.

EXAMPLE 424

N-Benzyl-4-(6,7-dimethoxy-1-isoquinolyl)-1-piperazinethiocarboxamide (Compound 424)

Yield: 76%
m.p.: 171–172° C.
$^1$H-NMR (CDCl$_3$) δ (ppm): 8.02 (1H, d, J=5.6 Hz), 7.34–7.24 (6H, m), 7.19 (1H, d, J=5.6 Hz), 7.03 (1H, s), 6.18 (1H, br), 4.90 (2H, d, J=3.3 Hz), 4.07 (4H,m), 3.98 (3H, s), 3.97 (3H, s), 3.42–3.40 (4H, m).
FAB-Mass: 423 (M⁺+1)
IR (KBr) σ (cm⁻¹): 1568, 1539, 1508, 1479, 1437, 1419, 1335, 1267, 1230, 1215, 1201, 1161, 987.

EXAMPLE 425

4-(6,7-Dimethoxy-1-isoquinolyl)-N-(3-picolyl)-1-piperazinethiocarboxamide dihydrochloride (Compound 425)

Yield: 66%
m.p.: 195–197° C. (hydrochloride)

$^1$H-NMR (free base, CDCl$_3$) δ (ppm): 8.43–8.41 (2H, m), 8.01 (1H, d, J=5.6 Hz), 7.78 (1H, ddd, J=7.9 Hz, 2.0 Hz, 1.7 Hz), 7.33 (1H, s), 7.24 (1H, dd, J=7.9 Hz, 5.0 Hz), 7.20 (1H, br), 7.19 (1H, d, J=5.6 Hz), 7.04 (1H, s), 4.95 (2H, d, J=5.3 Hz), 4.17–4.13 (4H, m), 3.99 (3H, s), 3.98 (3H, s), 3.43–3.40 (4H, m).
FAB-Mass: 424 (M⁺+1)
IR (hydrochloride, KBr) σ (cm⁻¹): 1610, 1535, 1510, 1477, 1446, 1411, 1394, 1381, 1281.

In the following Examples 426 and 427, substantially the same procedure as in Example 1 was repeated, except that 6,7-dimethoxy-4-(1-piperazinyl)cinnoline was used in place of 6,7-dimethoxy-4-(1-piperazinyl)quinazoline, and the corresponding isocyanate or isothiocyanate was used in place of phenyl isocyanate, to give the desired compound.

EXAMPLE 426

4-(6,7-Dimethoxy-4-cinnolinyl)-N-(4-phenoxyphenyl)-1-piperazinecarboxamide (Compound 426)

Yield: 73%
m.p.: 165–167° C.
$^1$H-NMR (DMSO-d$_6$) δ (ppm): 8.85 (1H, s), 8.73 (1H, brs), 7.65 (1H, s), 7.51 (2H, d, J=8.6 Hz), 7.36 (2H, dd, J=8.6 Hz, 7.9 Hz), 7.15 (1H, s), 7.09 (1H, m), 6.97–6.94 (4H, m), 4.01 (3H, s), 4.01 (3H, s), 3.77–3.74 (4H, m), 3.41–3.38 (4H, m).
FAB-Mass: 486 (M⁺+1)
IR (KBr) σ (cm⁻¹): 1662, 1533, 1506, 1435, 1416, 1381, 1229, 997, 868.

EXAMPLE 427

4-(6,7-Dimethoxy-4-cinnolinyl)-N-(3-picolyl)-1-piperazinethiocarboxamide (Compound 427)

Yield: 89%
m.p.: 181–190° C.
$^1$H-NMR (CDCl$_3$) δ (ppm): 8.64 (1H, s), 8.49 (1H, d, J=2.0 Hz), 8.46 (1H, dd, J=4.9 Hz, 1.7 Hz), 7.78 (1H, ddd, J=7.9 Hz, 2.0 Hz, 1.7 Hz), 7.60 (1H, s), 7.28–7.22 (2H, m), 7.07 (1H, s), 4.98 (2H, d, J=5.0 Hz), 4.24–4.20 (4H, m), 4.05 (3H, s), 4.03 (3H, s), 3.39–3.36 (4H, m).
FAB-Mass: 425 (M⁺+1)
IR (KBr) σ (cm⁻¹): 1535, 1506, 1437, 1416, 1373, 1288, 1242, 984.

In the following Examples 428–431, substantially the same procedure as in Example 1 was repeated, except that (dl)-6,7-dimethoxy-4-(trans-2,5-dimethyl (1-piperazinyl)) quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 428

(dl)-4-(6,7-Dimethoxy-4-quinazolinyl)-N-(4-phenoxyphenyl)-(trans-2,5-dimethyl)-1-piperazinecarboxamide (Compound 428)

Yield: 51%
m.p.: 182–184° C.
$^1$H-NMR (CDCl$_3$) δ (ppm): 3.67 (1H, s), 7.38–7.26 (5H, m), 7.09–7.04 (2H, m), 7.00–6.96 (4H, m), 6.54 (1H, brs), 4.70 (1H, m), 4.39 (1H, m), 4.03 (3H, s), 4.00 (3H, s), 3.88 (2H, m), 3.82–3.74 (2H, m), 1.38 (3H, d, J=6.6 Hz), 1.33 (3H, d, J=6.6 Hz).

FAB-Mass: 514 (M$^+$+1)

IR (KBr) σ (cm$^{-1}$): 1641, 1539, 1508, 1489, 1429, 1333, 1221, 1169.

EXAMPLE 429

(d1)-4-(6,7-Dimethoxy-4-quinazolinyl)-N-(4-nitrophenyl)-(trans-2,5-dimethyl)-1-piperazinecarboxamide (Compound 429)

Yield: 100% m.p.: 226–227° C.

$^1$H-NMR (CDCl$_3$) δ (ppm): 8.66 (1H, s), 8.15 (2H, d, J=9.2 Hz), 7.63 (2H, d, J=9.2 Hz), 7.52 (11H, brs), 7.24 (11H, s), 7.09 (11H, s), 4.71 (1H, m), 4.48 (1H, m), 4.01 (3H, s), 4.00 (3H, s), 3.90–3.89 (2H, m), 3.85–3.73 (2H, m), 1.37 (3H, d, J=6.6 Hz), 1.33 (3H, d, J=6.6 Hz).

FAB-Mass: 467 (M$^+$+1)

IR (KBr) σ (cm$^{-1}$): 1647, 1541, 1504, 1417, 1331, 1244, 1109, 1039, 1001, 851, 750.

EXAMPLE 430

(d1)-N-Benzyl-4-(6,7-dimethoxy-4-quinazolinyl)-(trans-2,5-dimethyl)-1-piperazinethiocarboxamide (Compound 430)

Yield: 88% m.p.: 102–103° C.

$^1$H-NMR (CDCl$_3$) δ (ppm): 8.61 (1H, s), 7.35–7.28 (5H, m), 7.20 (1H, s), 7.06 (1H, s), 6.39 (1H, brt, J=5.0 Hz), 5.01 (2H, dd, J=14.5 Hz, 5.0 Hz), 4.86 (1H, dd, J=14.6 Hz, 5.0 Hz), 4.73 (1H, m), 4.24 (1H, m), 3.98 (3H, s), 3.98 (3H, s), 3.95–3.71 (3H, m), 1.35 (3H, d, J=6.6 Hz), 1.27 (3H, d, J=6.6 Hz).

FAB-Mass: 452 (M$^+$+1)

IR (KBr) σ (cm$^{-1}$): 1576, 1506, 1473, 1429, 1335, 1242, 1211, 1167, 1055, 1003.

EXAMPLE 431

(d1)-4-(6,7-Dimethoxy-4-quinazolinyl)-N-(3-picolyl)-(trans-2,5-dimethyl)-1-piperazinethiocarboxamide (Compound 431)

Yield: 73% m.p.: 224–225° C.

$^1$H-NMR (CDCl$_3$) δ (ppm): 8.63 (1H, s), 8.49 (1H, dd, J=4.6 Hz, 1.3 Hz), 8.45 (1H, s), 7.79 (1H, d, J=7.6 Hz), 7.28 (1H, dd, J=7.6 Hz, 4.6 Hz), 7.23 (1H, s), 7.05 (1H, s), 6.56 (1H, br), 5.05 (2H, dd, J=15.2 Hz, 5.3 Hz), 4.91 (1H, dd, J=14.9 Hz, 5.0 Hz), 4.75 (1H, m), 4.26 (1H, m), 4.02 (3H, s), 3.99 (3H, s), 3.91 (3H, m), 1.35 (3H, d, J=6.3 Hz), 1.28 (3H, d, J=6.9 Hz).

FAB-Mass: 453 (M$^+$+1)

IR (KBr) σ (cm$^{-1}$): 1547, 1508, 1475, 1427, 1406, 1328, 1242, 1001.

In the following Examples 432–434, substantially the same procedure as in Example 1 was repeated, except that 6,7-dimethoxy-4-(cis-3,5-dimethyl-1-piperazinyl)quinazoline was used in place of 6,7-dimethoxy-4-(1-piperazinyl)quinazoline, and the corresponding isocyanate or isothiocyanate was used in place of phenyl isocyanate, to give the desired compound.

EXAMPLE 432

4-(6,7-Dimethoxy-4-quinazolinyl)-N-(4-nitrophenyl)-(cis-2,6-dimethyl)-1-piperazinecarboxamide (Compound 432)

Yield: 95% m.p.: 237–238° C.

$^1$H-NMR (CDCl$_3$) δ (ppm): 8.74 (1H, s), 8.37 (1H, brs), 8.15 (2H, d, J=9.2 Hz), 7.76 (2H, d., J=9.2 Hz), 7.37 (1H, s), 7.29 (1H, s), 4.60 (2H, m), 4.05 (3H, s), 4.02 (3H, s), 4.00 (2H, m), 3.21 (2H, dd, J=12.9 Hz, 4.3 Hz), 1.66 (6H, d, J=6.9 Hz).

FAB-Mass: 467 (M$^+$+1)

IR (KBr) σ (cm$^{-1}$): 1662, 1535, 1502, 1427, 1329, 1313, 1246, 1140, 1111, 1061, 1003, 851.

EXAMPLE 433

N-Benzyl-4-(6,7-dimethoxy-4-quinazolinyl)-(cis-2,6-dimethyl)-1-piperazinethiocarboxamide (Compound 433)

Yield: 90% m.p.: 165–166° C.

$^1$H-NMR (CDCl$_3$) δ (ppm): 8.71 (1H, s), 7.38–7.29 (6H, m), 7.27 (1H, s), 5.98 (1H, brt, J=4.6 Hz), 5.06 (2H, m), 4.95 (2H, d, J=4.6 Hz), 4.03 (3H, s), 3.99 (3H, s), 3.97 (2H, m), 3.26 (2H, dd, J=13.2 Hz, 4.3 Hz), 1.64 (6H, d, J=6.9 Hz).

FAB-Mass: 452 (M$^+$+1)

IR (KBr) σ (cm$^{-1}$): 1537, 1506, 1475, 1454, 1427, 1335, 1236, 1136, 1003, 698.

EXAMPLE 434

4-(6,7-Dimethoxy-4-quinazolinyl)-N-(3-picolyl)-(cis-2,6-dimethyl)-1-piperazinethiocarboxamide (Compound 434)

Yield: 93% m.p.: 187–188° C.

$^1$H-NMR (CDCl$_3$) δ (ppm): 8.71 (1H, s), 8.54–8.51 (2H, m), 7.78 (1H, m), 7.32–7.28 (3H, m), 6.32 (1H, brt, J=5.0 Hz), 5.09 (2H, m), 5.01 (2H, d, J=5.0 Hz), 4.04 (3H, s), 4.00 (3H, s), 4.00 (2H, m), 3.27 (2H, dd, J=13.2 Hz, 4.3 Hz), 1.65 (6H, d, J=6.6 Hz).

FAB-Mass: 453 (M$^+$+1)

IR (KBr) σ (cm$^{-1}$): 1541, 1506, 1475, 1429, 1371, 1336, 1255, 1236, 1213, 1134, 1061, 1001, 918, 872, 849, 822, 716.

In the following Examples 435–437, substantially the same procedure as in Example 1 was repeated, except that 6,7-dimethoxy-4-(1-homopiperazinyl)quinazoline obtained according to the method described in South African Patent No. 67 06512 (1968) was used in place of 6,7-dimethoxy-4-(1-piperazinyl)quinazoline, and the corresponding isocyanate or isothiocyanate was used in place of phenyl isocyanate, to give the desired compound.

EXAMPLE 435

4-(6,7-Dimethoxy-4-quinazolinyl)-N-(4-phenoxyphenyl)-1-homopiperazinecarboxamide (Compound 435)

Yield: 95% m.p.: 93–96° C.

¹H-NMR (CDCl₃) δ (ppm): 8.58 (1H, s), 7.33–7.26 (4H, m), 7.21 (1H, s), 7.18 (1H, s), 7.05 (1H, m), 6.97–6.92 (4H, m), 6.71 (1H, brs), 4.04–3.84 (6H, m), 4.00 (3H, s), 3.96 (3H, s), 3.69–3.65 (2H, m), 2.17–2.14 (2H, m).

FAB-Mass: 500 (M⁺+1)

IR (KBr) σ (cm⁻¹): 1641, 1576, 1508, 1489, 1417, 1356, 1223, 851.

EXAMPLE 436

N-Benzyl-4-(6,7-dimethoxy-4-quinazolinyl)-1-homopiperazinethiocarboxamide (Compound 436)

Yield: 89% m.p: 86–88° C.

¹H-NMR (CDCl₃) δ (ppm): 8.50 (1H, s), 7.30–7.22 (5H, m), 7.17 (1H, s), 7.15 (1H, s), 6.25 (1H, brt, J=5.0 Hz), 4.85 (2H, d, J=5.0 Hz), 4.22–4.20 (2H, m), 4.00–4.05 (2H, m), 3.97 (3H, s), 3.95 (3H, s), 3.89–3.85 (4H, m), 2.20–2.16 (2H, m).

FAB-Mass: 438 (M⁺+1)

IR (KBr) σ (cm⁻¹): 1576, 1506, 1454, 1429, 1354, 1250, 1207.

EXAMPLE 437

4-(6,7-Dimethoxy-4-quinazolinyl)-N-(3-picolyl)-1-homopiperazinethiocarboxamide dihydrochloride (Compound 437)

Yield: 61% m.p.: 177–183° C. (hydrochloride)

¹H-NMR (free base, CDCl₃) δ (ppm): 8.50 (1H, s), 8.44 (1H, dd, J=4.9 Hz, 1.6 Hz), 8.38 (1H, d, J=2.3 Hz), 7.65 (1H, ddd, J=7.6 Hz, 2.3 Hz, 1.6 Hz), 7.30 (1H, s), 7.18 (1H, dd, J=7.6 Hz, 4.9 Hz), 7.16 (1H, s), 6.64 (1H, Drt, J=5.3 Hz), 4.89 (2H, d, J=5.3 Hz), 4.26–4.24 (2H, m), 4.11–4.07 (2H, m), 4.00 (3H, s), 3.97 (3H, s), 3.97 (2H, m), 3.90–3.86 (2H, m), 2.22–2.17 (2H, m).

FAB-Mass: 439 (M⁺+1)

IR (hydrochloride, KBr) σ (cm¹): 1622, 1527, 1502, 1470, 1441, 1392, 1360, 1323, 1284, 1217.

In the following Examples 438 and 439, substantially the same procedure as in Example 1 was repeated, except that the corresponding isothiocyanate was used in place of phenyl isocyanate, to give the desired compound.

EXAMPLE 438

4-(6,7-Dimethoxy-4-quinazolinyl)-N-methoxycarbonylmethyl-1-piperazinethiocarboxamide (Compound 438)

Yield: 82%

¹H-NMR (CDCl₃) δ (ppm): 8.66 (1H, s), 7.28 (1H, s), 7.11 (1H, s), 6.28 (1H, brt, J=4.3 Hz), 4.49 (2H, d, J=4.3 Hz), 4.16–4.08 (4H, m), 4.03 (3H, s), 3.99 (3H, s), 3.88–3.84 (4H, m), 3.82 (3H, s).

FAB-Mass: 406 (M⁺+1)

EXAMPLE 439

4-(6,7-Dimethoxy-4-quinazolinyl)-N-(2-morpholinophenyl)-1-piperazinethiocarboxamide (Compound 439)

Yield: 64%

¹H-NMR (CDCl₃) δ (ppm): 8.68 (1H, s), 8.43 (1H, brs), 8.10 (1H, d, J=7.4 Hz), 7.28 (1H, s), 7.20–7.08 (4H, m), 4.21–4.16 (4H, m), 4.04 (3H, s), 4.00 (3H, s), 3.92–3.84 (8H, m), 2.93–2.90 (4H, m).

FAB-Mass: 495 (M⁺+1)

In the following Examples 440–444, substantially the same procedure as in Example 185 was repeated, except that 4-(6,7-dimethoxy-4-quinazolinyl)-1-piperazinecarboxylic acid chloride obtained according to the method described in U.S. Pat. No. 3,723,434 (1973) was used in place of 4-(6,7-dimethoxy-4-quinazolinyl)-1-piperazinethiocarboxylic acid chloride, and the corresponding amine was used in place of 4-bromobenzylamine, to give the desired compound.

EXAMPLE 440

4-(6,7-Dimethoxy-4-quinazolinyl)-N-phenacyl-1-piperazinecarboxamide (Compound 440)

Yield: 19%

¹H-NMR (CDCl₃) δ (ppm): 8.69 (1H, s), 8.01 (2H, d, J=7.9 Hz), 7.64 (1H, m), 7.55–7.49 (2H, m), 7.28 (1H, s), 7.12 (1H, s), 5.75 (1H, brt, J=3.9H,), 4.82 (2H, d, J=3.9 Hz), 4.04 (3H, s), 4.01 (3H, s), 3.73 (8H, s).

FAB-Mass: 436 (M⁺+1)

EXAMPLE 441

N-(4-tert-Butylbenzyl)-4-(6,7-dimethoxy-4-quinazolinyl)-1-piperazinecarboxamide (Compound 441)

Yield: 96%

¹H-NMR (CDCl₃) δ (ppm): 8.66 (1H, s), 7.39–7.21 (5H, m), 7.09 (1H, s), 5.38 (1H, brt, J=5.3 Hz), 4.43 (2H, d, J=5.3 Hz), 4.01 (3H, s), 3.98 (3H, s), 3.69–3.63 (8H, m), 1.31 (9H, s).

FAB-Mass: 464 (M⁺+1)

EXAMPLE 442

4-(6,7-Dimethoxy-4-quinazolinyl)-N-(4-mesylbenzyl)-1-piperazinecarboxamide (Compound 442)

Yield: 69%

¹H-NMR (CDCl₃) δ (ppm): 8.67 (1H, s), 7.80 (2H, d, J=8.5 Hz), 7.45 (2H, d, J=8.5 Hz), 7.28 (1H, s), 7.10 (1H, s), 5.54 (1H, brt, J=5.6 Hz), 4.54 (2H, d, J=5.6 Hz), 4.03 (3H, s), 3.99 (3H, s), 3.70 (8H, brs), 3.02 (3H, s).

FAB-Mass: 486 (M⁺+1)

EXAMPLE 443

4-(6,7-Dimethoxy-4-quinazolinyl)-N-(4-sulfamoylbenzyl)-1-piperazinecarboxamide (Compound 443)

Yield: 79%

¹H-NMR (DMSO-d₆) δ (ppm): 8.56 (1H, s), 7.76 (2H, d, J=8.3 Hz), 7.45 (2H, d, J=8.3 Hz), 7.30 (3H, br), 7.24 (1H, s), 7.17 (1H, s), 4.32 (2H, d, J=5.6 Hz), 3.93 (3H, s), 3.92 (3H, s), 3.61–3.59 (8H, m).

FAB-Mass: 487 (M⁺+1)

EXAMPLE 444

N-(2,3-Dihydrobenzo[1,4]dioxinylmethyl)-4-(6,7-dimethoxy-4-quinazolinyl)-1-piperazinecarboxamide (Compound 444)

Yield: 97%

¹H-NMR (CDCl₃) δ (ppm): 8.67 (1H, s), 7.25 (1H, s), 7.09 (1H, s), 6.90–6.82 (4H, m), 5.21 (1H, brt, J=5.6 Hz), 4.31 (2H, m), 4.02 (3H, s), 4.06–3.95 (1H, m), 3.98 (3H, s), 3.74–3.63 (8H, m), 3.59–3.48 (2H, m).

FAB-Mass: 466 (M⁺+1)

In the following Examples 445–447, substantially the same procedure as in Example 185 was repeated, except that the corresponding amine was used in place of 4-bromobenzylamine, to give the desired compound.

EXAMPLE 445

4-(6,7-Dimethoxy-4-quinazolinyl)-N-phenacyl-1-piperazinethiocarboxamide (Compound 445)

Yield: 42% m.p.: 99–100° C.

¹H-NMR (CDCl₃) δ (ppm): 8.68 (1H, s), 8.06 (2H, d, J=7.3 Hz), 7.67 (1H, m), 7.54 (2H, m), 7.28 (1H, s), 7.13 ((H, s), 6.94 (4H, br), 5.19 (2H, d, J=3.3 Hz), 4.20–4.16 (4H, m), 4.04 (3H, s), 4.01 (3H, s), 3.91–3.37 (4H, m).

FAB-Mass: 452 (M⁺+1)

EXAMPLE 446

N-[4-(4-Chlorophenxyl)cyclopropylmethyl]-4-(6,7-dimethoxy-4-quinazolinyl)-piperazinethiocarboxamide (Compound 446)

Yield: 91% m.p.: 108–111° C.

¹H-NMR (CDCl₃) δ (ppm): 8.63 (1H, s), 7.32–7.22 (5H, m), 7.09 (1H, s), 5.56 (1H, brt, J=4.3 Hz), 4.03 (3H, s), 4.00–3.91 (4H, m), 3.98 (3H, s), 3.88 (2H, d, J=4.3 Hz), 3.84–3.80 (4H, m), 1.02 (2H, m), 0.93 (2H, m).

FAB-Mass: 500 (M⁺+3), 498 (M⁺+1)

EXAMPLE 447

4-(6,7-Dimethoxy-4-quinazolinyl)-N-[2-(4-imidazolyl)ethyl]-1-piperazinethiocarboxamide (Compound 447)

Yield: 35%

¹H-NMR (CDCl₃) δ (ppm): 8.64 (1H, s), 7.99 (2H, brs), 7.60 (3H, s), 7.29 (1H, s), 7.24 (2H, s), 7.12 (1H, s), 6.88 (1H, s), 4.16–4.13 (4H, m), 4.02 (3H, s), 3.99 (3H, s), 3.93–3.83 (6H, m), 2.91 (2H, t, J=5.9 Hz).

FAB-Mass: 428 (M⁺+1)

In the following Examples 448–456, substantially the same procedure as in Example 154 was repeated, except that the corresponding amine was used in place of 4-isopropylbenzylamine, to give the desired compound.

EXAMPLE 448

N-Benzyl-4-(6,7-dimethoxy-4-quinazolinyl)-N-methyl-1-piperazinethiocarboxamide (Compound 448)

Yield: 58%

¹H-NMR (CDCl₃) δ (ppm):: 8.68 (1H, s), 7.40–7.26 (6H, m), 7.12 (1H, s), 4.95 (2H, s), 4.03 (3H, s), 4.01 (3H, s), 3.75 (8H, m), 3.05 (3H, s).

FAB-Mass: 438 (M⁺+1)

EXAMPLE 449

4-(6,7-Dimethoxy-4-quinazolinyl)-N-(4-morpholinophenyl)-1-1-piperazinethiocarboxamide (Compound 449)

Yield: 64%

¹H-NMR (CDCl₃) δ (ppm): 8.64 (1H, s), 7.72 (1H, brs), 7.24 (1H, s), 7.13 (2H, d, J=8.9 Hz)., 7.09 (1H, s), 6.86 (2H, d, J=8.9 Hz), 4.08–4.06 (4H, m), 4.01 (3H, s), 3.98 (3H, s), 3.85–3.82 (8H, m), 3.14–3.11 (4H, m).

FAB-Mass: 495 (M⁺+1)

EXAMPLE 450

4-(6,7-Dimethoxy-4-quinazolinyl)-N-[4-(6-methyl-2-benzothiazolyl)phenyl]-1-piperazinethiocarboxamide (Compound 450)

Yield: 57%

¹H-NMR (DMSO-d₆) δ (ppm): 9.69 (1H, brs), 8.56 (1H, s), 8.01 (2H, d, J=8.3 Hz), 7.93 (1H, s), 7.91 (1H, d, J=7.9 Hz), 7.57 (2H, d, J=8.3 Hz), 7.36 (1H, d, J=7.9 Hz), 7.26 (1H, s), 7.24 (1H, s), 4.17 (4H, m), 3.94 (3H, s), 3.94 (3H, s), 3.87 (4H, m), 2.46 (3H, s).

FAB-Mass: 557 (M⁺+1)

EXAMPLE 451

4-(6,7-Dimethoxy-4-(quinazolinyl)-N-[4-(2-pyridyl)phenyl]-1-piperazinethiocarboxamide (Compound 451)

Yield: 72%

¹H-NMR (CDCl₃) δ (ppm): 8.67 (1H, d, J=4.6 Hz), 8.65 (1H, s), 7.98–7.95 (2H, d, J=8.6 Hz), 7.78–7.67 (3H, m), 7.31–7.20 (4H, m), 7.08 (1H, s), 4.16–4.06 (4H, m), 4.02 (3H, s), 3.98 (3H, s), 3.93–3.80 (4H, m).

FAB-Mass: 487 (M⁺+1)

EXAMPLE 452

4-(6,7-Dimethoxy-4-quinazolinyl)-N-(2-thienylmethyl)-1-piperazinethiocarboxamide (Compound 452)

Yield: 82%

¹H-NMR (CDCl₃) δ (ppm): 8.62 (1H, s), 7.24 (1H, dd, J=5.3 Hz, 1.0 Hz), 7.23 (1H, s), 7.10 (1H, s), 7.05 (1H, dd, J=3.6 Hz, 1.0 Hz), 6.96 (1H, dd, J=5.3 Hz, 3.6 Hz), 6.18 (1H, brt, J=4.6 Hz), 5.08 (2H, d, J=4.6 Hz), 4.12–4.07 (4H, m), 4.01 (3H, s), 3.98 (3H, s), 3.86–3.82 (4H, m)

FAB-Mass: 430 (M⁺+1)

EXAMPLE 453

4-(6,7-Dimethoxy-4-quinazolinyl)-N-[2-(2-pyridyl)ethyl]-1-piperazinethiocarboxamide (Compound 453)

Yield: 82%

¹H-NMR (CDCl₃) δ (ppm): 8.65 (1H, s), 8.51 (1H, dd, J=5.0 Hz, 1.7 Hz), 8.12 (1H, br), 7.63 (1H, ddd, J=7.9 Hz, 7.6 Hz, 1.7 Hz), 7.26–7.18 (3H, m), 7.13 (1H, s), 4.15–4.06 (6H, m), 4.02 (3H, s), 4.00 (3H, s), 3.88–3.85 (4H, m), 3.11 (2H, t, J=5.9 Hz).

FAB-Mass: 439 (M⁺+1)

EXAMPLE 454

N-(2,3-Dihydrobenzo[1,4]dioxinylmethyl)-4-(6,7-dimethoxy-4-quinazolinyl)-1-piperazinethiocarboxamide (Compound 454)

Yield: 98%

¹H-NMR (CDCl₃) δ (ppm): 8.65 (1H, s), 7.26 (1H, s), 7.11 (1H, s), 6.90–6.83 (4H, m), 6.20 (1H, brt, J=5.3 Hz), 4.53 (1H, m), 4.36 (1H, dd, J=11.6 Hz, 2.3 Hz), 4.27 (2H, m), 4.11–4.04 (4H, m), 4.03 (3H, s), 3.99 (3H, s). 3.95 (1H, m), 3.92–3.85 (4H, m).

FAB-Mass: 482 (M$^+$+1)

EXAMPLE 455

4-(6,7-Dimethoxy-4-quinazolinyl)-N-{4-([1-(1,2,4-triazolyl)]phenyl}-1-piperazinethiocarboxamide (Compound 455)

Yield: 61%

$^1$H-NMR (DMSO-d$_6$) δ (ppm): 9.57 (1H, brs), 9.25 (1H, s), 8.56 (2H, s), 8.23 (1H, s). 7.79 (2H, d, J=8.6 Hz), 7.53 (2H, d, J=8.6 Hz), 7.26 (4H, s), 7.24 (3H, s), 4.17–3.99 (4H, m), 3.94 (3H, s), 3.94 (3H, 6), 3.88–3.09 (4H, m).

EXAMPLE 456

4-(6,7-Dimethoxy-4-quinazolinyl)-N-[4-(2-oxopyrrolidinyl)phenyl]-1-piperazinethiocarboxamide (Compound 456)

Yield: 58%

$^1$H-NMR (DMSO-d$_6$) δ (ppm): 9.39 (1H, brs), 8.55 (1H, s), 7.59 (2H, d, J=8.3 Hz), 7.31 (2H, d, J=8.3 Hz), 7.25 (1H, s), 7.23 (1H, s), 4.13 (4H, m), 3.94 (3H, s), 3.94 (3H, s), 4.05–3.81 (6H, m). 2.49–2.46 (2H, m), 2.09–2.03 (2H, m).

EXAMPLE 457

N-(4-Acetamidophenyl)-4-(6,7-dimethoxy-4-quinazolinyl)-1-piperazinecarboxamide (Compound 457)

To a solution of 514.0 mg (1.26 mmol) of N-(4-aminophenyl)-4-(6,7-dimethoxy-4-quinazolinyl)-1-piperazinecarboxamide obtained in Example 221 in 10 ml of dichloromethane were added 0.18 ml (1.89 mmol) of acetic anhydride and 0.53 ml (3.78 mmol) of triethylamine under ice-cooling. After the resulting mixture was stirred overnight at room temperature, 0.18 ml (1.89 mmol) of acetic anhydride and 0.53 ml (3.78 mmol) of triethylamine were added thereto, followed by overnight stirring. To the reaction mixture was added methanol and the solvent was evaporated. Then, the residue was; purified by silica gel chromatography to give the desired compound as colorless crystals.

Yield: 34%

$^1$H-NMR (DMSO-d$_6$) δ (ppm.): 9.79 (1H, brs), 8.57 (1H, s), 8.56 (1H, brs), 7.44 (2H, J=8.9 Hz), 7.37 (2H, d, J=8.9 Hz), 7.24 (1H, s), 7.20 (1H, s), 3.93 (3H, s), 3.93 (3H, s), 3.68 (8H, m), 1.90 (3H, s).

FAB-Mass: 451 (M$^+$+1)

EXAMPLE 458

4-(6,7-Dimethoxy-4-quinazolinyl)-N-[4-(3-ethylthioureido)phenyl]-1-piperazinecarboxamide (Compound 458)

To a solution of 514.0 mg (1.26 mmol) of N-(4-aminophenyl)-4-(6,7-dimethoxy-4-quinazolinyl)-1-piperazinecarboxamide obtained in Example 221 in 10 ml of dimethylformamide was added 0.13 ml (1.51 mmol) of ethyl isothiocyanate, followed by overnight stirring at room temperature. To the resulting mixture was added 0.13 ml (1.51 mmol) of ethyl isothiocyanate, followed by overnight stirring. The reaction mixture was poured into water, and sodium chloride was added thereto. The precipitated crystals were collected by filtration, washed with water, and dried, followed by purification by silica gel chromatography to give the desired compound as colorless crystals.

Yield: 33%

$^1$H-NMR (CDCl$_3$) δ (ppm): ;3.69 (1H, s), 7.71 (1H, brs), 7.42 (2H, d, J=8.6 Hz), 7.28 (1H, s), 7.15 (2H, d, J=8.6 Hz), 7.11 (1H, s), 6.82 (1H, brs), 6.01 (1H, br), 4.04 (3H, s), 4.01 (3H, s), 3.77 (8H, m), 3.65 (2H, m), 1.18 (3H, t, J=7.3 Hz).

FAB-Mass: 496 (M$^+$+1)

EXAMPLE 459

4-(6,7-Dimethoxy-4-quinazolinyl)-N-(3,4-methylenedioxybenzyl)-1-piperazinecarboxamide (Compound 459)

In 10 ml of ethanol was suspended 152.7 mg (0.33 mmol) of 4-(6,7-dimethoxy-4-quinazolinyl)-N-(3,4-methylenedioxybenzyl)-1-piperazinethiocarboxamide obtained in Example 208, and 1 ml of a 10 N aqueous solution of sodium hydroxide and 1 ml of 30% aqueous hydrogen peroxide were added thereto, followed by overnight stirring. After addition of an aqueous solution of sodium thiosulfate, 4 N hydrochloric acid was added to the reaction mixture for neutralization. The resulting mixture was extracted with dichloromethane, and the organic layer was washed with water and dried over sodium sulfate. After the solvent was evaporated, the residue was purified by silica gel chromatography to give the desired compound as colorless crystals.

Yield: 20%

$^1$H-NMR (CDCl$_3$) δ (ppm): 8.67 (1H, s), 7.27 (1H, s), 7.10 (1H, s), 6.84–6.78 (3H, m), 5.95 (2H, s), 4.80 (1H, brt, J=5.3 Hz), 4.37 (2H, d, J=5.3 Hz), 4.03 (3H, s), 3.99 (3H, s), 3.71–3.63 (8H, m).

FAB-Mass: 452 (M$^+$+1)

EXAMPLE 460

4-(6-Methoxy-7-methyl-4-quinazolinyl)-N-(3,4-methylenedioxybenzyl)-1-piperazinethiocarboxamide (Compound 460)

Substantially this same procedure as in Example 208 was repeated, except that 6-methoxy-7-methyl-4-(1-piperazinyl)quinazoline was used in place of 6,7-dimethoxy-4-(1-piperazinyl)quinazoline, to give the desired compound.

Yield: 47%

$^1$H-NMR (CDCl$_3$) δ (ppm): 8.65 (1H, s), 7.68 (1H, s), 7.04 (1H, s), 6.87–6.77 (3H, m), 5.97 (2H, s), 5.95 (1H, brt, J=4.6 Hz), 4.80 (2H, d, J=4.6 Hz), 4.09–4.07 (4H, m), 3.93 (3H, s), 3.89–3.85 (4H, mi), 2.40 (3H, s).

FAB-Mass: 452 (M$^+$+1)

EXAMPLE 461

4-(6-Amino-7-ethylamino-4-quinazolinyl)-N-benzyl-1-piperazinethiocarboxamide (Compound 461)

To a suspension of 4.26 g (9.44 mmol) of N-benzyl-4-(7-ethylamino-6-nitro-4-quinazolinyl)-1-piperazinethiocarboxamide obtained in Example 361 in 100 ml of ethanol and 10 ml of water were added 4.26 g (76.3 mmol) of iron powder and 430 mg (1.59 mmol) of ferric chloride hexahydrate under ice-cooling, followed by heating under reflux in an atmosphere of argon for 4 hours. After the iron powder was separated by filtration using Celite, the solvent was evaporated, and the residue was purified by silica gel chromatography to give the desired compound as colorless crystals.

Yield: 92%

$^1$H-NMR (CDCl$_3$) δ (ppm): 8.54 (1H, s), 7.38–7.37 (5H, m), 7.07 (1H, s), 6.93 (1H, s), 5.76 (1H, brt, J=4.6 Hz), 4.91 (2H, d, J=4.6 Hz), 4.07–4.04 (4H,m), 3.78–3.74 (4H, m), 3.61 (1H, br), 3.30 (2H, m), 1.68 (2H, brs), 1.37 (3H, t, J=6.9 Hz).

FAB-Mass: 422 (M$^+$+1)

EXAMPLE 462

4-(6-Acetamido-7-ethylamino-4-quinazolinyl)-N-benzyl-1-piperazinethiocarboxamide (Compound 462)

To a solution of 528 mg (1.25 mmol) of 4-(6-amino-7-ethylamino-4-quinazolinyl)-N-benzyl-1-piperazinethiocarboxamide obtained in Example 461 in 15 ml of dimethylformamide were added 0.57 ml (4.09 mmol) of triethylamine and 0.31 ml (3.29 mmol) of acetic anhydride, followed by overnight stirring at room temperature in an atmosphere of argon. The reaction mixture was poured into water, and sodium chloride was added thereto. The precipitated crystals; were collected by filtration, washed with water, and dried, followed by purification by silica gel chromatography to give the desired compound as colorless crystals.

Yield: 27%

$^1$H-NMR (CDCl$_3$) δ (ppm): 8.70 (1H, brs), 8.42 (1H, s), 7.76 (1H, s), 7.32–7.23 (5H, m), 6.74 (1H, s), 6.28 (1H, brt, J=5.0 Hz), 4.86 (2H, d, J=5.0 Hz), 4.75 (1H, br), 3.93 (4H, m), 3.73 (4H, m), 3.06 (2H, m), 2.20 (3H, s), 1.19 (3H, t, J=7.3 Hz).

FAB-Mass: 464 (M$^+$+1)

EXAMPLE 463

4-(6-Benzamido-7-ethylamino-4-quinazolinyl)-N-benzyl-1-piperazinethiocarboxamide (Compound 463)

To a solution of 504.9 mg (1.20 mmol) of 4-(6-amino-7-ethylamino-4-quinazolinyl)-N-benzyl-1-piperazinethiocarboxamide obtained in Example 461 in 15 ml of dichloromethane were added 0.50 ml (3.6 mmol) of triethylamine and 0.17 ml (1.44 mmol) of benzoyl chloride, followed by overnight stirring at room temperature in an atmosphere of argon. After addition of water, the reaction mixture was extracted with dichloromethane, and the organic layer was washed with water and dried over sodium sulfate. After the solvent was evaporated, the residue was purified by silica gel chromatography to give the desired compound as colorless crystals.

Yield: 38%

$^1$H-NMR (CDCl$_3$) δ (ppm): 9.23 (1H, br), 8.36 (1H, s), 7.97 (2H, d, J=7.3 Hz), 7.57–7.22 (911, m), 6.79 (1H, s), 6.31 (1H, brt, J=4.6 Hz), 4.83 (2H, d, J=4.6 Hz), 4.65 (1H, br), 4.06–3.86 (4H, m), 3.67 (4H, m), 3.05 (2H, dq, J=6.9 Hz, 4.6 Hz), 1.17 (3H, t, J=6.9 Hz).

FAB-Mass: 526 (M$^+$+1)

EXAMPLE 464

N-Benzyl-4-[7-ethyl amino-6-(3-ethylureido)-4-quinazolinyl]-1-piperazinethiocarboxamide (Compound 464)

To a solution of 502.5 mg (1.19 mmol) of 4-(6-amino-7-ethylamino-4-quinazolinyl) -N-benzyl-1-piperazinethiocarboxamide obtained in Example 461 in 10 ml of dimethylformamide was added 0.10 ml (1.19 mmol) of ethyl isothiocyanate, followed by overnight stirring at room temperature. To the resulting mixture was added 0.10 ml (1.19 mmol) of ethyl isothiocyanate, followed by heating at 80° C. with stirring for 4 hours. The reaction mixture was allowed to cool to room temperature, and then poured into water, and sodium chloride was added thereto. The precipitated crystals were collected by filtration, washed with water, and dried, followed by purification by silica gel chromatography to give the desired compound as colorless crystals.

Yield: 29%

$^1$H-NMR (DMSO-d$_6$) δ (ppm): 13.00 (1H, brs), 8.59 (1H, s), 7.77–7.74 (3H, m), 7.64 (1H, s), 7.36–7.31 (5H, m), 4.36 (2H, m), 4.00 (4H, m), 3.79 (4H, m), 3.55 (2H, m), 3.37–3.28 (2H, m), 1.29 (3H, t, J=7.3 Hz), 1.13 (3H, t, J=7.3 Hz).

FAB-Mass: 509 (M$^+$+1)

EXAMPLE 465

N-Benzyl-4-[7-ethylamino-6-mesylamino-4-quinazolinyl]-1-piperazinethiocarboxamide (Compound 465)

To a solution of 528 mg (1.25 mmol) of 4-(6-amino-7-ethylamino-4-quinazolinyl)-N-benzyl-1-piperazinethiocarboxamide obtained in Example 461 in 15 ml of dimethylformamide were added 0.57 ml (4.09 mmol) of triethylamine and 0.31 ml (1.55 mmol) of methanesulfonyl chloride, followed by overnight stirring at room temperature in an atmosphere of argon. To the resulting mixture was added 0.06 ml (0.31 mmol) of methanesulfonyl chloride, followed by overnight stirring at room temperature. The reaction mixture was poured into water, and sodium chloride was added thereto. The precipitated crystals were collected by filtration, washed with water, and dried, followed by purification by silica gel chromatography to give the desired compound as colorless crystals.

Yield: 6%

$^1$H-NMR (CDCl$_3$) δ (ppm): 8.48 (1H, s), 7.76 (1H, s), 7.36–7.29 (5H, m), 6.80 (1H, s), 5.94 (1H, brt, J=4.9 Hz), 5.27 (1H, br), 4.88 (2H, d, J=4.9 Hz), 4.05–4.01 (4H, m), 3.89–3.86 (4H, m), 3.19 (2H, m), 3.01 (3H, s), 1.27 (3H, t, J=6.9 Hz).

FAB-Mass: 500 (M$^+$+1)

EXAMPLE 466

N-(2-Chloroethyl)-4-(6,7-dimethoxy-4-quinazolinyl)-1-piperazinecarboxamide (Compound 466)

Substantially the same procedure as in Example 1 was repeated, except that 2-chloroethyl isocyanate was used in place of phenyl isocyanate, to give the desired compound.

Yield: 60%

$^1$H-NMR (CDCl$_3$) δ (ppm): 8.70 (1H, s), 7.26 (1H, s), 7.10 (1H, s), 5.14 (1H, brt, J=5.3 Hz), 4.03 (3H, s), 3.99 (3H, s), 3.72–3.64 (12H, m).

FAB-Mass: 382 (M$^+$+3), 380 (M$^+$+1)

EXAMPLE 467

N-Benzyl-4-(3-ethyl-1,3-dihydro-2-thioxo-2H-imidazo[4,5-g]quinazolin-8-yl)-1-piperazinethiocarboxamide (Compound 467)

To a solution of 502.7 mg (1.19 mmol) of 4-(6-amino-7-ethylamino-4-quinazolinyl)-N-benzyl-1- piperazinethiocarboxamide obtained in Example 461 in 10 ml of ethanol were added 1.66 ml (11.9 mmol) of triethylamine and 10 ml (166 mmol) of carbon disulfide, followed by overnight stirring at room temperature in an atmosphere of argon. After the solvent was evaporated, the residue was purified by silica gel chromatography to give the desired compound as colorless crystals.

Yield: 41%

$^1$H-NMR (DMSO-d$_6$) δ (ppm): 13.00 (1H, br), 8.60 (1H, s), 8.32 (1H, brt, J=5.6 Hz), 7.76 (1H, s), 7.65 (1H, s), 7.33–7.23 (5H, m), 4.83 (2H, d, J=5.6 Hz), 4.36 (2H, q, J=6.9 Hz), 4.07 (4H, m), 3.82 (4H, m), 1.29 (3H, t, J=6.9 Hz).

FAB-Mass: 464 (M$^+$+1)

EXAMPLE 468

N-Benzyl-4-(3-ethyl-2-methyl-3H-imidazo[4,5-g]quinazolin-8-yl)-1-piperazinethiocarboxamide (Compound 468)

To a solution of 528 mg (1.25 mmol) of 4-(6-amino-7-ethylamino-4-quinazolinyl)-N-benzyl-1-piperazinethiocarboxamide obtained in Example 461 in 15 ml of dimethylformamide were added 0.57 ml (4.09 mmol) of triethylamine and 0.31 ml (3.29 mmol) of acetic anhydride, followed by overnight stirring at room temperature in an atmosphere of argon. The reaction mixture was poured into water, and sodium chloride was added thereto. The precipitated crystals were collected by filtration, washed with water, and dried, followed by purification by silica gel chromatography to give the desired compound as colorless crystals.

Yield: 5%

$^1$H-NMR (CDCl$_3$) δ (ppm): 8.68 (1H, s), 8.21 (1H, s), 7.79 (1H, s), 7.38–7.27 (5H, m), 5.95 (1H, brt, J=4.6 Hz), 4.91 (2H, d, J=4.6 Hz), 4.16–3.93 (8H, m), 3.09 (2H, q, J=7.3 Hz), 2.69 (3H, s), 1.48 (3H, t, J=7.3 Hz).

FAB-Mass: 446 (M$^+$+1)

EXAMPLE 469

N-Benzyl-4-(3-ethyl-3H-imidazo[4,5-g]quinazolin-8-yl)-1-piperazinethiocarboxamide (Compound 469)

To a solution of 504.4 mg (1.20 mmol) of 4-(6-amino-7-ethylamino-4-quinazolinyl)-N-benzyl-1-piperazinethiocarboxamide obtained in Example 461 in 10 ml of dimethylformamide were added 0.29 ml (3.60 mmol) of pyridine and 0.13 ml (1.49 mmol) of oxalyl chloride under ice-cooling, followed by overnight stirring at room temperature in an atmosphere of argon. Then, the resulting mixture was heated at 80° C. with stirring for 5 hours. The reaction mixture was allowed to cool to room temperature and then poured into water, and sodium chloride was added thereto. The precipitated crystals were collected by filtration, washed with water, and dried, followed by purification by silica gel chromatography to give the desired compound as colorless crystals.

Yield: 55%

$^1$H-NMR (CDCl$_3$) δ (ppm): 8.68 (1H, s), 8.36 (1H, s), 8.14 (1H, s), 7.91 (1H, s), 7.37–7.31 (5H, m), 6.16 (1H, brt, J=4.6 Hz), 4.92 (2H, d, J=4.6 Hz), 4.33 (2H, q, J=7.3 Hz), 4.16–4.08 (4H, m), 4.00–3.97 (4H, m), 1.26 (3H, t, J=7.3 Hz).

FAB-Mass: 432 (M$^+$+1)

REFERENCE EXAMPLE 1

1,3-Dihydro-1,3-dimethyl-2-oxo-8-(1-piperazinyl)-2H-imidazo[4,5-g]quinazoline (1) To a solution of 7.86 g (40.9 mmol) of 1,3-dihydro-2-oxo-1H-benzimidazole-5-carboxylic acid methyl ester obtained according to the known method (Japanese Published Unexamined Patent Application No. 207388/86) in 100 ml of acetic anhydride was added 3.46 ml (86.4 mmol) of fuming nitric acid, followed by stirring at 0° C. for 3.5 hours. The reaction mixture was poured into ice-cold water, and the precipitated crystals were collected by filtration, washed with water, and dried to give 7.78 g (80%) of 1,3-dihydro-6-nitro-2-oxo-2H-benzimidazole-5-carboxylic acid methyl ester.

(2) To a solution of 7.78 g (32.8 mmol) of the compound obtained in (1) in 100 ml of dimethylformamide was added 3.94 g (98.5 mmol) of sodium hydride under ice-cooling, followed by stirring at the same temperature for 15 minutes. To the resulting mixture was added 6.13 ml (98.5 mmol) of methyl iodide, followed by stirring at room temperature for 1.5 hours. The reaction mixture was poured into water, and the precipitated crystals were collected by filtration, washed with water, and dried to give 8.58 g (99%) of 1,3-dihydro-1,3-dimethyl-6-nitro-2-oxo-2H-benzimidazole-5-carboxylic acid methyl ester.

(3) To a solution of 8.58 g (32.4 mmol) of the compound obtained in (2) in 100 ml of ethanol was added 1.6 g of 10% palladium-carbon, followed by stirring in an atmosphere of hydrogen at room temperature for 5.5 hours. After the catalyst was removed by filtration using a filter aid, the filtrate was concentrated under reduced pressure to give 6-amino-1,3-dihydro-1,3-dimethyl-2-oxo-2H-benzimidazole-5-carboxylic acid methyl ester.

(4) A solution of the compound obtained in (3) in 100 ml of formamide was stirred at 190° C. for 2 hours. After cooling, the solution was poured into water, and sodium chloride was added thereto. The precipitated crystals were collected by filtration to give 4.73 g (64%, 2 steps) of 1,3-dihydro-1,3-dimethylimidazo-2H,7H-imidazo[4,5-g]quinazoline-2,8-dione.

(5) The compound obtained in (4) (4.73 g, 20.6 mmol) was heated under reflux in 50 ml of phosphorus oxychloride for 1.5 hours. After the reaction mixture was cooled, excess phosphorus oxychloride was evaporated, and ice-cold water was added thereto. The precipitated crystals were collected by filtration, washed with water, and dried to give 8-chloro-1,3-dihydro-1,3-dimethyl-2-oxo-2H-imidazo[4,5-g]quinazoline.

(6) To a solution of 17.72 g (206 mmol) of anhydrous piperazine in 100 ml of isopropyl alcohol was added the compound obtained in (5), followed by heating under reflux. After the reaction mixture was concentrated, a saturated aqueous solution of sodium chloride was added to the residue, followed by extraction with chloroform. The organic layer was washed with a saturated aqueous solution of sodium chloride, and dried over sodium sulfate, followed by evaporation of the solvent to give the desired compound.

REFERENCE EXAMPLE 2

1,3-Diethyl-1,3-dihydro-2-oxo-8-(1-piperazinyl)-2H-imidazo[4,5-g]quinazoline

The procedures similar to those described in Reference Example 1 (2)-(6) were repeated using 1,3-dihydro-6-nitro-2-oxo-2H-benzimidazole-5-carboxylic acid methyl ester obtained in Reference Example 1 (1) and ethyl iodide to give the desired compound.

REFERENCE EXAMPLE 3

1,3-Dihydro-1,3-dipropyl-2-oxo-8-(1-piperazinyl)-2H-imidazo[4,5-g]quinazoline

The procedures similar to those described in Reference Example 1 (2)–(6) were repeated using 1,3-dihydro-6-nitro- 2-oxo-2H-benzimidazole-5-carboxylic acid methyl ester obtained in Reference Example 1 (1) and propyl iodide to give the desired compound.

REFERENCE EXAMPLE 4

1,3-Dibutyl-1,3-dihydro-2-oxo-8-(1-piperazinyl)-2H-imidazo[4,5-g]quinazoline

The procedures similar to those described in Reference Example 1 (2)–(6) were repeated using 1,3-dihydro-6-nitro-2-oxo-2H-benzimidazole-5-carboxylic acid methyl ester obtained in Reference Example 1 (1) and butyl iodide to give the desired compound.

REFERENCE EXAMPLE 5

4-(1,3-Dihydro-3-ethyl-1-methyl-2-oxo-2H-imidazo[4,5-g]quinazolin-8-yl)-1-piperazinecarboxylic acid tert-butyl ester (1) 7-Ethylamino-6-nitroquinazolin-4 (3H)-one obtained according to the method described in WO 95–06648 (5.42 g, 23.2 mmol) was heated under reflux in 60 ml of phosphorus oxychloride for 2 hours. After the reaction mixture was allowed to cool to room temperature, excess phosphorus oxychloride was evaporated, and the residue was subjected to azeotropic distillation with toluene twice. The obtained residue was dissolved in 50 ml of THF, and the resulting solution was added dropwise slowly to a solution of 19.95 g (232.0 mmol) of anhydrous piperazine in 50 ml of ethanol under ice-cooling, followed by overnight stirring at room temperature. After the reaction mixture was concentrated, a saturated aqueous solution of sodium chloride was added thereto, followed by extraction with chloroform. The organic layer was washed with a saturated aqueous solution of sodium chloride, and dried over anhydrous sodium sulfate, followed by evaporation of the solvent to give 6.28 g (94%) of 7-ethylamino-6-nitro-4-(1-piperazinyl) quinazoline.

(2) To a solution of 1.08 g (3.75 mmol) of 7-ethylamino-6-nitro-4-(1-piperazinyl)quinazoline in 20 ml of dichloromethane were added 2.61 ml (18.7 mmol) of triethylamine and 1.33 ml (5.79 mmol) of di-tert-butyl dicarbonate under ice-cooling, followed by overnight stirring at room temperature. The reaction mixture was concentrated and then purified by silica gel chromatography to give 1.39 g (92%) of 4-(7-ethylamino-6-nitro-4-quinazolinyl)-1-piperazinecarboxylic acid tert-butyl ester.

(3) To a suspension of 1.29 g (3.22 mmol) of the compound obtained in (2) in 20 ml of ethanol was added 300 mg of 10% palladium-carbon, followed by stirring in a stream of hydrogen at room temperature for 6 hours. The catalyst was separated by filtration using Celite, and the solvent was evaporated. The obtained residue was dissolved in 20 ml of dimethylformamide, and 2.25 ml (16.1 mmol) of triethylamine and 1.05 g (6.48 mmol) of 1,1'-carbonyldiimidazole were added thereto, followed by heating at 80° C. with stirring in an atmosphere of argon for 4.5 hours. The reaction mixture was allowed to cool to root temperature and then poured into water, and sodium chloride was added thereto. The precipitated crystals were collected by filtration, washed with water, and dried to give 2.02 g (quant.) of 4-(1,3-dihydro-3-ethyl-2-oxo-2H-imidazo[4,5-g]quinazolin-8-yl)-1-piperazinecarboxylic acid tert-butyl ester.

(4) To a solution of 1.42 g (3.57 mmol) of the compound obtained in (3) in 15 ml of dimethylformamide was added 213.7 mg (14.8 mmol) of 609, sodium hydride under ice-cooling, followed by stirring at room temperature for 30 minutes. To the resulting mixture was added 0.44 ml (7.07 mmol) of methyl iodide, followed by overnight stirring at room temperature. The reaction mixture was poured into water, and sodium chloride was added thereto. The precipitated crystals were collected by filtration, washed with water, and dried to give 748.6 mg (51%) of the desired compound.

REFERENCE EXAMPLE 6

4-(6,7-Dimethoxy-4-quinazolinyl)-1-piperazinethiocarboxylic acid chloride

To a solution of 3.06 ml (40.1 mmol) of thiophosgene in 100 ml of dichloromethane were slowly added a solution of 10 g (36.5 mmol) of 6,7-dimethoxy-4-(1-piperazinyl) quinazoline obtained by the method described in South African Patent No. 67 06512 (1968) in 100 ml of dichloromethane and 12.4 ml (89.1 mmol) of triethylamine under ice-cooling. The resulting mixture was stirred at the same temperature in an atmosphere of argon for 2 hours. After the solvent was evaporated, the residue was purified by silica gel chromatography to give 6.65 g (52%) of the desired compound.

REFERENCE EXAMPLE 7

4-(6,7-Difluoro-4-quinazolinyl)-1-piperazinecarboxylic acid tert-butyl ester (1) To a solution of 4.81 g (27.8 mmol) of commercially available 2-amino-4, 5-difluorobenzoic acid in 20 ml of ethanol were added 1.92 ml (1.94 mmol) of piperidine and 2.25 g (27.8 mmol) of 1,3,5-triazine, followed by heating under reflux in an atmosphere of argon for 6.5 hours. After the reaction mixture was allowed to cool to room temperature, the solvent was evaporated. To the residue was added water, and the resulting mixture was neutralized with 4 N hydrochloric acid. The precipitated crystals were collected by filtration, washed with water, and dries to give 4.37 g (86%) of 6,7-difluoro-4(3H)-quinazoline.

(2) The compound obtained in (1) (1.89 g, 10.4 mmol) was heated under reflux in 25 ml of phosphorus oxychloride for 1.5 hours. After the reaction mixture was allowed to cool to room temperature, excess phosphorus oxychloride was evaporated, and the residue was subjected to azeotropic distillation with toluene twice. The obtained residue was dissolved in 20 ml of THF and 5 ml of dime(thylformamide, and 7.25 ml (52.0 mmol) of triethylamine and 4.84 g (26.0 mmol) of N-tert-butoxycarbonylpiperazine were added thereto, followed by stirring in an atmosphere of argon at room temperature for 3 hours. After the solvent was evaporated, water was added to the residue. The precipitated crystals were collected by filtration, washed with water, and dried to give 2.60 g (71%) of the desired compound.

REFERENCE EXAMPLE 8

4-(7-Ethoxy-6-methoxy-4-quinazolinyl)-1-piperazinecarboxylic acid tert-butyl ester (1) To a solution of 52.6 g (313 mmol) of commercially available vanillic acid in 250 ml of dimethylformamide was slowly added 129.8 g (939 mmol) of potassium carbonate under ice-cooling, and 78.2 ml (657 mmol) of benzyl bromide was slowly added thereto, followed by overnight stirring in an atmosphere of argon at room temperature. The reaction mixture was poured into water, and sodium chloride was added thereto. The precipitated crystals were collected by filtration, washed with water, and dried to give 104.2 g (96%) of 4-benzyloxy-3-methoxybenzoic acid benzyl ester.

(2) A solution of 22.5 g (64.7 mmol) of the compound obtained in (1) in 200 ml of acetic anhydride was cooled to −15° C., and 6.11 ml (153 mmol) of fuming nitric acid was added thereto, followed by stirring under ice-cooling for 7.5 hours. The reaction mixture was poured into ice-cold water and adjusted to pH 7 with an aqueous solution of sodium hydroxide. The precipitated crystals were collected by filtration, washed with water, and dried to give 25.6 g (100%) of 4-benzyloxy-5-methoxy-2-nitrobenzoic acid benzyl ester.

(3) To a solution of 10.2 g (25.9 mmol) of the compound obtained in (2) in 120 ml of acetic acid was added 9.6 g (146 mmol) of zinc dust under ice-cooling, followed by stirring in an atmosphere of argon at room temperature for 2 hours. The zinc dust was separated by filtration using Celite, and the solvent was evaporated. To the residue was added dichloromethane, and the resulting mixture was washed with a saturated aqueous solution of sodium chloride, and dried over anhydrous sodium sulfate, followed by evaporation of the solvent to give 9.2 g (97%) of 2-amino-4-benzyloxy-5-methoxybenzoic acid benzyl ester.

(4) The compound obtained in (3) (9.15 g, 25.2 mmol) was heated at 150° C. in 100 ml of formamide with stirring for 1.5 hours. The reaction mixture was allowed to cool to room temperature and then poured into water, and sodium chloride was added thereto. The precipitated crystals were collected by filtration, washed with water, and dried to give 6.18 g (87%) of 7-benzyloxy-6-methoxy-4(3H)-quinazoline.

(5) The compound obtained in (4) (6.83 g, 24.2 mmol) was heated under reflux in 80 ml of phosphorus oxychloride for 3 hours. After the reaction mixture was allowed to cool to room temperature, excess phosphorus oxychloride was evaporated, and the residue was subjected to azeotropic distillation with toluene twice. The obtained residue was dissolved in dichloromethane, and the solution was washed with a saturated aqueous solution of sodium chloride and dried over anhydrous sodium sulfate, followed by evaporation of the solvent to give 6.66 g (92%) of 7-benzyloxy-4-chloro-6-methoxyquinazoline.

(6) In 50 ml of THF was dissolved 6.66 g (22.2 mmol) of the compound obtained in (5), and 15.5 ml (111 mmol) of triethylamine and 12.4 g (66.5 mmol) of N-tert-butoxycarbonylpiperazine were added thereto, followed by heating under reflux in an atmosphere of argon for 4 hours. After the reaction mixture was allowed to cool to room temperature, the solvent was evaporated and water was added to the residue, followed by addition of sodium chloride. The precipitated crystals were collected by filtration, washed with water, and dried to give 9.25 g (93%) of 4-(7-benzyloxy-6-methoxy-4-quinazolinyl)-1-piperazinecarboxylic acid tert-butyl ester.

(7) In 40 ml of ethanol was dissolved 4.67 g (10.4 mmol) of the compound obtained in (6), and 1 g of 10% palladium-carbon was added thereto, followed by heating at 40° C. with stirring in a stream of hydrogen for 4 hours. After the catalyst was separated by filtration using Celite, and the solvent was evaporated. The residue was dissolved in 30 ml of dimethylformamide, and 1.72 g (12.4 mmol) of potassium carbonate and 1.24 ml (12.4 mmol) of ethyl iodide were added thereto, followed by overnight stirring in an atmosphere of argon at room temperature. The reaction mixture was poured into water, and sodium chloride was added thereto. The precipitated crystals; were collected by filtration, washed with water, and dried, followed by purification by silica gel chromatography to give 3.28 g (82%) of the desired compound.

REFERENCE EXAMPLE 9

4-(7-Isopropoxy-6-methoxy-4-quinazolinyl)-1-piperazinecarboxylic acid tert-butyl ester The procedure similar to that described in Reference Example 8 (7) was repeated using (7-benzyloxy-6-methoxy-4-quinazolinyl)-1-piperazinecarboxylic acid tert-butyl ester obtained in Reference Example 8 (6) and isopropyl iodide to give the desired compound.

REFERENCE EXAMPLE 10

4-(6-Ethoxy-7-methoxy-4-quinazolinyl)-1-piperazinecarboxylic acid tert-butyl ester The procedures similar to those described in Reference Example 8 (1)-(7) were repeated using commercially available isovanillic acid to give the desired compound.

REFERENCE EXAMPLE 11

4-(7-Methoxy-6-mesyloxy-4-quinazolinyl)-1-piperazinecarboxylic acid tert-butyl ester (1) The procedures similar to those described in Reference Example 8 (1L)-(6) were repeated using commercially available isovanillic(, acid to give (6-benzyloxy-7-methoxy-4-quinazolinyl)-1-piperazinecarboxylic acid tert-butyl ester.

(2) In 20 ml of ethanol was dissolved 965.4 mg (2.15 mmol) of the compound obtained in (1), and 200 mg of 10% palladium-carbon was added thereto, followed by heating at 50° C. with stirring in a stream of hydrogen for 12.5 hours. The catalyst was separated by filtration using Celite, and the solvent was evaporated. Then, the residue was dissolved in 10 ml of dichloromethane, and 0.90 ml (6.46 mmol) of triethylamine and 0.25 ml (3.23 mmol) of methanesulfonyl chloride were added thereto, followed by overnight stirring in an atmosphere of argon at room temperature. To the resulting mixture was; added 15 ml of pyridine, followed by overnight stirring. After methanol was added to the reaction mixture, the solvent was evaporated, and the residue was purified by silica gel chromatography to give 609.6 mg (65%) of the desired compound.

REFERENCE EXAMPLE 12

4-(7-Chloro-6-nitro-4-quinazolinyl)-1-piperazinecarboxylic

Acid tert-butyl Ester

The procedure similar to that described in Reference Example 7 (2) was repeated using 7-chloro-6-nitro-4 (3H)-quinazoline obtained by the method described in WO 95-06648 to give the desired compound (45%).

REFERENCE EXAMPLE 13

4-(4-Benzo[g]quinazolinyl)-1-piperazinecarboxylic acid tert-butyl ester

The procedure similar to that described in Reference Example 7 (2) was repeated using 4 (3H)-benzo[g]quinazoline obtained by the method described in J. Chem. Soc., 4191–4206 (1956) to give the desired compound (43%).

REFERENCE EXAMPLE 14

4-(6,7-Ethylenedioxy-4-quinazolinyl)-1-piperazinecarboxylic acid tert-butyl ester The procedure similar to that described in Reference Example 7 (2) was repeated using 6,7-ethylenedioxy-4

(3H)-quinazolone obtained by the method described in J. Org. Chem., 40, 356–363 (1975) to give the desired compound (45%).

REFERENCE EXAMPLE 15

4-(2-Chloro-6,7-dimiathoxy-4-quinazolinyl)-1-piperazinecarboxylic acid tert-butyl ester To a solution of 4.62 g (17.8 mmol) of commercially available 2,4-dichloro-6,7-dimethoxyquinazoline in 50 ml of dimethylformamide were added 12.4 ml (89.1 mmol) of triethylamine and 3.65 g (19.6 mmol) of N-tert-butoxycarbonylpiperazine, followed by overnight stirring in an atmosphere of argon at room temperature. The reaction mixture was poured into water, and sodium chloride was added thereto. The precipitated crystals were collected by filtration, washed with water, and dried to give 7.15 g (98%) of the desired compound.

REFERENCE EXAMPLE 16

4-(6,7-Dimethoxy-2-morpholino-4-quinazolinyl)-1-piperazinecarboxylic acid tert-butyl ester To a solution of 1.22 g (2.99 mmol) of the compound obtained in Reference Example 15 in 15 ml of N-methylpyrrolidone was added 1.30 ml (14.9 mmol) of morpholine, followed by heating at 140° C. with stirring for 3 hours. The reaction mixture was allowed to cool to room temperature and then poured into water, and sodium chloride was added thereto. The precipitated crystals were collected by filtration, washed with water, and dried to give 850.9 mg (62%) of the desired compound.

REFERENCE EXAMPLE 17

4-(6,7-Dimethoxy-4-quinolyl)-1-piperazinecarboxylic acid tert-butyl ester

The procedure similar to that described in Reference Example 7 (2) was repeated using 4-hydroxy-6,7-dimethoxyquinoline obtained by the method described in J. Am. Chem. Soc., 68, 1264–1266 (1946) to give the desired compound

REFERENCE EXAMPLE 18

4-(6,7-Dimethoxy-3-ethoxycarbonyl-4-quinolyl)-1-piperazinecarboxylic acid tert-butyl ester The procedure similar to that described in Reference Example 15 was repeated using 4-chloro-6,7-dimethoxy-3-ethoxycarbonylquinoline obtained by the method described in J. Med. Chem., 14, 1060–1066 (1971) to give the desired compound (91%).

REFERENCE EXAMPLE 19

4-(1-Isoquinolyl)-1-piperazinecarboxylic acid tert-butyl ester

The procedure similar to that described in Reference Example 15 was repeated using commercially available 1,3-dichloroisoquinoline to give the desired compound (77%, 2 steps).

REFERENCE EXAMPLE 20

4-(1-Phthalazinyl)-1-piperazinecarboxylic acid tert-butyl ester (1) To a solution of 2.09 g (10.5 mmol) of commercially available 1,4-dichlorophthalazine in 20 ml of N-methylpyrrolidone were added 7.32 ml (52.5 mmol) of triethylamine and 2.35 g (12.6 mmol) of N-tert-butoxycarbonylpiperazine, followed by heating at 70° C. with stirring in an atmosphere of argon for 2 hours. The reaction mixture was allowed to cool to room temperature and then poured into water, and sodium chloride was added thereto. The precipitated crystals were collected by filtration, washed with water, and dried, followed by purification by silica gel chromatography to give 2.77 g (76%) of 4-(4-chloro-1-phthalazinyl)-1-piperazinecarboxylic acid tert-butyl ester.

(2) In 30 ml of acetic acid was dissolved 2.30 g (6.59 mmol) of the compound obtained in (1), and 500 mg of 10% palladium-carbon was added thereto, followed by heating at 50° C. with stirring in a stream of hydrogen for 3 hours. After the catalyst was separated by filtration using Celite, the solvent was evaporated, and the residue was subjected to azeotropic distillation with toluene twice. The obtained residue was purified by silica gel chromatography to give 801.6 mg (39%) of the desired compound.

REFERENCE EXAMPLE 21

4-(1,3-Diethyl-1,3-dihydro-2-oxo-2H-imidazo[4,5-g] phthalazin-5-yl)-1-piperazinecarboxylic acid tert-butyl ester (1) To a solution of 48 g (296 mmol) of 1,3-dihydro-5,6-dimethyl-2H-benzimidazol-2-one synthesized by the method described in Tetrahedron Lett., 28, 1389–1392 (1987) in 200 ml of dimethylformamide was added 25 g (625 mmol) of 60% sodium hydride under ice-cooling, followed by stirring for 10 minutes. To the resulting mixture was added 50 ml (625 mmol) of ethyl iodide, followed by further stirring at the same temperature for one hour. The reaction mixture was poured into ice-cold water, and the precipitated crystals were collected by filtration, washed with water, and dried to give 37.6 g (58%) of 1,3-diethyl-1,3-dihydro-5,6-dimethyl-2H-benzimidazol-2-one.

(2) In a mixture of 500 ml of tert-butanol and 500 ml of water was dissolved 4–7 g (215 mmol) of the compound obtained in (1), followed by heating at 110° C. with stirring, during which 170 g (1.08 mol) of potassium permanganate was gradually added thereto. After stirring at the same temperature for one hour, the resulting mixture was filtered using Celite while it was hot, followed by concentration of the obtained filtrate. Then, the residue was dissolved in water, and a 2 N aqueous solution of hydrochloric acid was added dropwise thereto. The precipitated crystals were collected by filtration and washed with water to give 40 g (67%) of 1,3-diethyl-1,3-dihydro-2-oxo-2H-benzimidazole-5,6-dicarboxylic acid.

(3) In a mixture of 200 ml of acetic acid and 200 ml of water was dissolved 39.6 g (142 mmol) of the compound obtained in (2), and 35 ml (722 mmol) of hydrazine monohydrate was added thereto under ice-cooling, followed by heating under reflux for one hour. After the reaction mixture was allowed to cool to room temperature, the precipitated crystals were collected by filtration, washed with water and then with methanol, and dried to give 27.6 g (71%) of 1,3-diethyl-1,3,5,6,7,8-hexahydro-2H,6H,7H-imidazo[4,5-g]phthalazine-2,5,8-trione.

(4) The procedure( similar to that described in Reference Example 7 (2) was repeated using the compound obtained in (3) to give 5,8-dichloro-1,3-diethyl-1,3-dihydro-2H-imidazo[4,5-g]phthalazin-2-one (64%).

(5) The procedure( similar to that described in Reference Example 19 (1) was repeated using the compound obtained in (4) to give 1.81 g (89%) of 4-(8-chloro-1,3-diethyl-1,3-dihydro-2-oxo-2H-imidazo[4,5-g]phthalazin-5-yl)-1-piperazinecarboxylic acid tert-butyl ester.

(6) To a solution of 954.8 mg (2.07 mmol) of the compound obtained in (5) in 10 ml of acetic acid was added a suspension of 200 mg of 10% palladium-carbon in 2 ml of water and 3 ml of acetic acid, followed by heating at 50° C. with stirring in a stream of hydrogen for 5.5 hours. After the catalyst was separated by filtration using Celite, the solvent was evaporated, and the residue was purified by silica gel chromatography to give 453.1 mg (51%) of the desired compound.

PREPARATION EXAMPLE 1

Tablets

Tablets having the following composition are prepared according to a conventional method.

| | |
|---|---|
| Compound 77 | 100 mg |
| Lactose | 60 mg |
| Potato starch | 30 mg |
| Polyvinyl alcohol | 2 mg |
| Magnesium stearate | 1 mg |
| Tar pigment | trace |

PREPARATION EXAMPLE

Powder

Powder having the following composition is prepared according to a conventional method.

| | |
|---|---|
| Compound 77 | 150 mg |
| Lactose | 280 mg |

PREPARATION EXAMPLE 3

Syrup

Syrup having the following composition is prepared according to a conventional method.

| | |
|---|---|
| Compound 77 | 100 mg |
| Refined white sugar | 40 g |
| Ethyl p-hydroxybenzoate | 40 mg |
| Propyl p-hydroxybenzoate | 10 mg |
| Strawberry flavor | 0.1 cc |
| Water is added to make a volume of | 100 cc. |

INDUSTRIAL APPLICABILITY

The present invention provides nitrogen-containing heterocyclic compounds and pharmaceutically acceptable salts thereof which inhibit phosphorylation of PDGF receptor to hinder abnormal cell growth and cell wandering and thus are useful for the prevention or treatment of cell-proliferative diseases such as arteriosclerosis, vascular reobstruction, cancer and glomerulosclerosis.

What is claimed is:

1. A nitrogen-containing heterocyclic compound represented by formula (I):

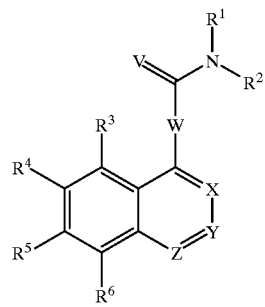

wherein V represents an oxygen atom or a sulfur atom;

W represents 1,4-piperazinediyl or 1,4-homopiperazinediyl in which carbons on the ring may be substituted by 1–4 alkyl groups which may be the same or different;

$R^1$ represents a hydrogen atom, a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group;

$R^2$ represents a substituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, a substituted or unsubstituted heteroarylalkyl group, —$COR^{10}$ (wherein $R^{10}$ has the same significance as $R^1$) or —$SO_2R^{11}$ (wherein $R^{11}$ represents a substituted or unsubstituted alkyl group, a substituted or unsubstituted alicyclic alkyl group, a substituted or unsubstituted alicyclic heterocyclic group, a substituted or unsubstituted alkenyl group, a substituted or unsubstituted alkynyl group, a substituted or unsubstituted aryl group, a substituted or unsubstituted aralkyl group, a substituted or unsubstituted heteroaryl group, or a substituted or unsubstituted heteroarylalkyl group);

$R^3$, $R^4$, $R^5$ and $R^6$ independently represent a hydrogen atom, a halogen atom, a substituted or unsubstituted alkyl group, a nitro group, a cyano group, —$OR^{12}$ {wherein $R^{12}$ has the same significance as $R^{10}$, or represents —$COR^{13}$ (wherein $R^{13}$ has the same significance as $R^{10}$) or —$SO_2R^{14}$ (wherein $R^{14}$ has the same significance as $R^{11}$)}, —$NR^{15}R^{16}$ {wherein $R^{15}$ has the same significance as $R^{10}$, and $R^{16}$ has the same significance as $R^{10}$, or represents —$SO_2R^{17}$ (wherein $R^{17}$ has the same significance as $R^{11}$) or

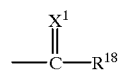

(wherein $X^1$ represents an oxygen atom or a sulfur atom; and $R^{18}$ has the same significance as $R^{10}$, or represents —$OR^{19}$ (wherein $R^{19}$ has the same significance as $R^{11}$) or —$NR^{20}R^{21}$ (wherein $R^{20}$ and $R^{21}$ independently have the same significance as $R^{10}$, or $R^{20}$ and $R^{21}$ are combined together with the adjoining nitrogen atom to represent a substituted or unsubstituted nitrogen-containing alicyclic heterocyclic group)); or $R^{15}$ and $R^{16}$ are combined together with the adjoining nitrogen atom to represent a substituted or unsubstituted nitrogen-containing heterocyclic group},

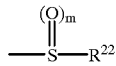

{wherein m represents an integer of 0–2; and when m is 0, $R^{22}$ has the same significance as $R^{10}$; when m is 1, $R^{22}$ has the same significance as $R^{11}$; and when m is 2, $R^{22}$ has the same significance as $R^{11}$ or represents —$OR^{23}$ (wherein $R^{23}$ has the same significance as $R^{10}$) or —$NR^{24}R^{25}$ (wherein $R^{24}$ and $R^{25}$ independently have the same significance as $R^{10}$, or $R^{24}$ and $R^{25}$ are combined together with the adjoining nitrogen atom to represent a substituted or unsubstituted nitrogen-containing alicyclic heterocyclic group)} or —$COR^{26}$ {wherein $R^{26}$ has the same significance as $R^{10}$, or represents —$OR^{27}$ (wherein $R^{27}$ has the same significance as $R^{10}$) or —$NR^{28}R^{29}$ (wherein $R^{28}$ and $R^{29}$ independently have the same significance as $R^{10}$, or $R^{28}$ and $R^{29}$ are combined together with the adjoining nitrogen atom to represent a substituted or unsubstituted nitrogen-containing alicyclic heterocyclic group)}; or any adjoining two of $R^3$, $R^4$, $R^5$ and $R^6$ are combined together to represent methylenedioxy or ethylenedioxy; or any adjoining two of $R^3$, $R^4$, $R^5$ and $R^6$ are the adjoining nitrogen atom to represent a substituted or unsubstituted nitrogen-containing heterocyclic group},
or —$COR^{26}$; or any adjoining two of $R^3$, $R^4$, $R^5$ and $R^6$ are combined together to represent methylenedioxy or ethylenedioxy; or any adjoining two of $R^3$, $R^4$, $R^5$ and $R^6$ are combined together with the two adjoining carbon atoms to form a substituted or unsubstituted phenyl ring; or any of $R^3$ and $R^4$, $R^4$ and $R^5$, or $R^5$ and $R^6$ are combined together with the two adjoining carbon atoms to represent

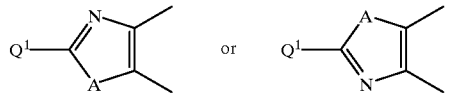

{wherein A represents an oxygen atom, a sulfur atom or —$NR^{30}$—(wherein $R^{30}$ has the same significance as $R^{10}$); and $Q^1$ has the same significance as $R^{10}$, or represents —$NR^{31}R^{32}$ (wherein $R^{31}$ and $R^{32}$ independently have the same significance as $R^{10}$, or $R^{31}$ and $R^{32}$ are combined together with the adjoining nitrogen atom to represent a substituted or unsubstituted nitrogen-containing alicyclic heterocyclic group) or —$SR^{33}$ (wherein $R^{33}$ has the same significance as $R^{10}$)}, or

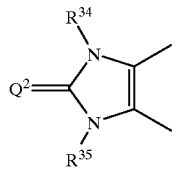

(wherein $R^{34}$ and $R^{35}$ independently have the same significance as $R^{10}$; and $Q^2$ represents an oxygen atom, a sulfur atom or =N—CN), or

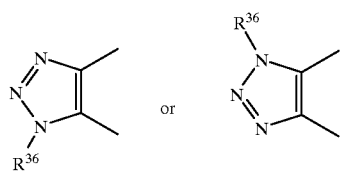

wherein $R^{36}$ has the same significance as $R^{10}$);

X represents a nitrogen atom or C—$R^9$ {wherein $R^9$ represents a hydrogen atom or —$COOR^{41}$ (wherein $R^{41}$ has the same significance as $R^{18}$)};

Y represents a nitrogen atom or C—$R^8$ (wherein $R^8$ has the same significance as $R^7$); and Z represents a nitrogen atom or C—$R^7$ {wherein $R^7$ has the same significance as $R^{10}$, or represents a halogen atom, —$OR^{37}$(wherein $R^{37}$ has the same significance as $R^{10}$), —$SR^{38}$ (wherein $R^{38}$ has the same significance as $R^{10}$) or —$NR^{39}R^{40}$ (wherein $R^{39}$ and $R^{40}$ independently have the same significance as $R^{10}$, or $R^{39}$ and $R^{40}$ are combined together with the adjoining nitrogen atom to represent a substituted or unsubstituted nitrogen-containing alicyclic heterocyclic group)};

provided that only one of X, Y and Z represents a nitrogen atom, or a pharmaceutically acceptable salt thereof.

2. A compound according to claim 1, wherein W is 1,4-piperazinediyl, or a pharmaceutically acceptable salt thereof.

3. A compound according to claim 2, wherein Y is CH, or a pharmaceutically acceptable salt thereof.

4. A compound according to claim 3, wherein $R^3$ and $R^6$ each represents a hydrogen atom, and $R^4$ and $R^5$ each represents a halogen atom, a substituted or unsubstituted alkyl group or $OR^{12}$, or a pharmaceutically acceptable salt thereof.

5. A compound according to claim 4, wherein $R^{12}$ is methyl, or a pharmaceutically acceptable salt thereof.

6. A compound according to claim 5, wherein $R^1$ represents a hydrogen atom, and $R^2$ represents a substituted or unsubstituted aryl group, a substituted or unsubstituted aralkyl group, a substituted or unsubstituted heteroaryl group or a substituted or unsubstituted heteroarylalkyl group, or a pharmaceutically acceptable salt thereof.

7. A compound according to claim 6, wherein $R^2$ represents a substituted or unsubstituted aryl group or a heteroaryl group, and V is an oxygen atom, or a pharmaceutically acceptable salt thereof.

8. A compound according to claim 6, wherein $R^2$ represents a substituted or unsubstituted aralkyl group or a substituted or unsubstituted heteroarylalkyl group, and V is a sulfur atom, or a pharmaceutically acceptable salt thereof.

9. A pharmaceutical composition comprising a compound represented by formula (I) or a pharmaceutically acceptable salt thereof according to any one of claims 2–8 or 1 and a pharmaceutically acceptable carrier.

* * * * *

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Title page, Item [54], and Column 1, line 1,
Title, "1,3 DIAZINES WITH PLATELET-DERIVED" should read -- PYRIDINES FUSED TO BENZENE WITH PLATELET-DERIVED --.

Column 4,
Line 40, "$R^{18}$)]." should read -- $R^{18}$)], --; and
Line 42, close up right margin.

Column 37,
Table 1-17, " Table 1-17 " should read --    Table 1-17    --.

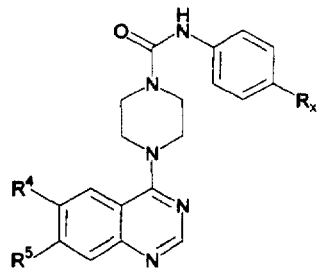  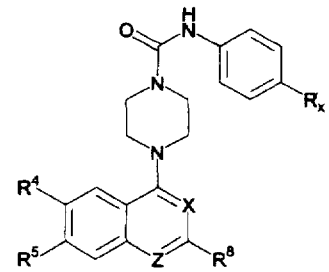

Column 47,
Line 5,  " V\ " should read -- X\ --.

Column 55,
Table 1-34,  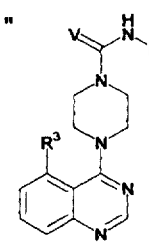 should read -- 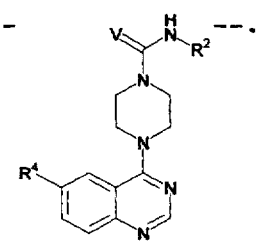 --.

Column 62,
Table 1-41, " ... " should read -- ... --.

UNITED STATES PATENT AND TRADEMARK OFFICE
CERTIFICATE OF CORRECTION

PATENT NO.   : 6,207,667 B1
DATED         : March 27, 2001
INVENTOR(S)  : Kenji Matsuno et al.

It is certified that error appears in the above-identified patent and that said Letters Patent is hereby corrected as shown below:

Column 63, Table 1-42,

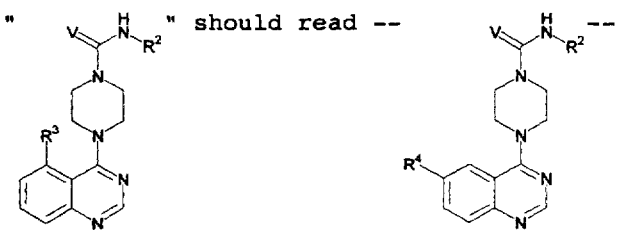

Column 64, Table 1-43,

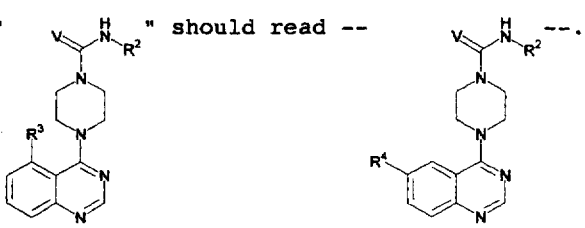

Column 101, Table 1-69,

| | | | | |
|---|---|---|---|---|
| 463 | —NH—C(=O)—C6H5 | NHC2H5 | S | |
| | —CH2—C6H5 | | | |
| 464 | —NH—C(=O)—NHC2H5 | NHC2H5 | S | |
| 465 | —NH—S(=O)2—CH3 | NHC2H5 | S | —CH2—C6H5 |
| 466 | OCH3 | NHC2H5 | O | —CH2CH2Cl | should read

| | | | | |
|---|---|---|---|---|
| 463 | —NH—C(=O)—C6H5 | NHC2H5 | S | —CH2—C6H5 |
| 464 | —NH—C(=O)—NHC2H5 | NHC2H5 | S | —CH2—C6H5 |
| 465 | —NH—S(=O)2—CH3 | NHC2H5 | S | —CH2—C6H5 |
| 466 | OCH3 | OCH3 | O | —CH2CH2Cl |

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 111,
Line 50, "N-(1-Adamantyl-4-" should read -- N-(1-Adamantyl)-4- --.

Column 114,
Line 12, "P FAB-" should read -- FAB- --;
Line 27, "550($M^+1$)" should read -- 550($M^+$+1) --;
Line 53, "7.12(HH, brs)," should read -- 7.12(1H, brs), --;
Line 65, "$^3$H-" should read -- $^1$H- --;
Line 66, "6.84(mH, brs)," should read -- 6.84 (1H, brs), --; and
Line 67, "3.75(8H," should read -- 3.75(8H, m). --.

Column 115,
Line 2, "14, 17, 10," should read -- 1640, 1575, 1504, --;
Line 50, "(3H, s)," should read -- (1H, s), --; and
Line 62, "7.06(mH, s), 5.32(2H, brs)," should read -- 7.06(1H, s), 5.32(1H, brs), --.

Column 116,
Line 14, "PFAB-" should read -- FAB- --;
Line 24, "7.33(2H, s)," should read -- 7.33(1H, s), --;
Line 25, "7.10(mH, s), 7.05(bH, m)," should read -- 7.10(1H, s), 7.05(1H, m), --;
Line 38, "m)b," should read -- m), --;
Line 39, "(H, s)," should read -- (1H, s), -- and
"(3H, s)," should read -- (1H, s), -- and
"(7.H, brs)," should read -- (1H, brs), --; and
Line 65, "10" should be deleted.

Column 117,
Line 66, "7.04" should read -- 7.14 --.

Column 118,
Line 12, "7.30(6H, m), 7.25(2H, s)," should read -- 7.30(1H, m), 7.25(1H, s),--;
Line 13, "(3H,brs)," should read -- (1H, brs), --;
Line 14, "(M++1)" should read -- ($M^+$+1) --;
Line 24, "J=1.7" should read -- J=8.9 --;
Line 25, "(2H, s)," should read -- (1H, s), --;
Line 36, "238-242cc" should read -- 238-242°C. --;
Line 38, ""(5H, s)," should read -- (1H, s), --;

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 118 (continued),
Line 51, ""(5H, s)," should read -- (1H, s), --;
Line 55, "IR(KBr)1)(cm$^{-1}$)" should read -- IR(KBr) υ (cm$^{-1}$) --;
Line 59, "N-([4-Chloro-2-X" should read -- N-[4-Chloro-2- --;
Line 65, "(2H," should read -- (1H, --; and
Line 66, "(2H," should read -- (1H, --.

Column 119,
Line 10, "mp:" should read -- m.p.: --;
Line 41, "br)," should read -- brs), --; and
Line 55, "15" should be deleted.

Column 120,
Line 5, "991" should read -- 991. --;
Line 14, "5 7.33(1H, a, J=8.6Hz)g" should read
-- 7.33(1H, d, J=8.6Hz), --; and
Line 45, insert -- IR(KBr) υ (cm$^{-1}$):1637, 1569, 1507, 1416,
1232, 1208, 989. --.

Column 121,
Line 53, "-N-14-" should read -- -N-[4- --.

Column 122,
Line 49, "mp.:" should read -- m.p.: --; and
Line 52, "(3H. s)," should read -- (3H, s), --.

Column 124,
Line 45, "25" should be deleted.

Column 125,
Line 34, "1.0Hz)," should read -- 1.0Hz), --; and
Line 50, "J=2.0Hz)," should read -- J=2.0Hz), --.

Column 126,
Line 2, "(cml) :" should read -- (cm$^{-1}$) : --.

Column 128,
Line 54, "25" should be deleted.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 129,
Line 17, "J=3.6," should read -- J=3.6Hz, --; and
Line 29, "$^6$(ppm):" should read -- $\delta$(ppm): --.

Column 130,
Line 31, "N-14-" should read -- N-[4- --; and
Line 60, "(CDCl$_3$+DMSO-d$_6$)" should read -- (CDCl$_3$ + DMSO-d$_6$) -- .

Column 131,
Line 3, "-(4-" should read -- -[4- --; and
Line 18, "$^1$–NMR" should read -- $^1$H-NMR --.

Column 132,
Line 16, "25" should be deleted and "J=6.9)." should read -- J=6.9Hz). --;
Line 40, "8.68," should read -- 868, --; and
Line 63, "-N-" should read -- N- --.

Column 133,
Line 7, "10" should be deleted;
Lines 43 and 62, "QC" should read -- °C. --; and Column 134,
Line 39, "CDCl$_{3+}$" should read -- (CDCl$_3$+ --; and
Line 43, "GAB-" should read -- FAB- --.

Column 135,
Line 50, "hloroformate" should read -- chloroformate --;
Line 52, "ater" should read -- water --; and
Line 53, "ere" should read -- were --.

Column 138,
Line 50, "15" should be deleted; and
Line 67, "3.8614 3.83(4H, m)," should read -- 3.86-3.83 (4H, m), --.

Column 139,
Line 10, insert -- ¶ m. p.: 191-192°C. ¶ --;
Line 11, "7.24(1H, s)," should read -- 7.25(1H, s), -- and "5.06(1H8" should read -- 5.06(1H, --;
Line 12, "4.98(mH, brd, Js6.6Hz)9," should read -- 4.98(1H, brd, J=6.6Hz), --; and
Line 39, "$^1$NMR" should read -- $^1$H-NMR --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 140,
Line 22, "ut)." should read -- m). --;
Line 29, "4-4" should read -- 4- --;
Line 35, "7.09(3H, s)," should read -- 7.09(1H, s), -- and "6.27(4H," should read -- 6.27 (1H, --; and
Line 45, "1-" should read -- -1- --.

Column 142,
Lines 7 and 10, "S)," should read -- s), --;
Line 26, "3.45(H, m)6," should read -- 3.45(1H, m), --;
Line 27, "1.62(2H, m)." should read -- 1.62(1H, m). --;
Line 34, "4-4" should read -- 4- --;
Line 49, "--1-" should read -- -1- --;
Line 51, "307%" should read -- 30% --;
Line 52, "218-2186°C." should read -- 218-186°C. --;
Lines 55 and 56, "(3H," should read -- (1H, --; and
Line 57, "3.97 3.90" should read -- 3.97-3.90 --.

Column 143,
Line 7, "1) (cm$^{-1}$) :" should read -- $\upsilon$(cm$^{-1}$): --;
Line 16, " (CDC$_3$)" should read -- (CDCl$_3$) --; and
Line 17, "(5H," should read -- (1H, -- and "7.08(CH," should read -- 7.08(1H, --.

Column 144,
Line 24, "$^3$-isopropylaniline" should read -- 3-isopropylaniline --; and
Line 36, "7.2714" should read -- 7.27- --.

Column 145,
Line 1, "$^6$(ppm):" should read -- $\delta$(ppm): --; and
Line 49, "(6,,7-" should read -- (6,7- --; and "guinazolinyl)" should read -- quinazolinyl) --.

Column 146,
Line 17, "1H-NMR" should read -- $^1$H-NMR --;
Line 20, "10" should be deleted;
Line 51, "4-isopropylbenzylamine" should read -- 4-isopropylbenzylamine, --; and
Line 64, "(4-Dif luoromethoxyphenyl)" should read -- (4-Difluoromethoxyphenyl) --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 147,
Line 6, "7.J8(Hz, s)," should read -- 7.11(1H, s), -- and "s," should read -- d, --; and
Line 7, "6.46(3H, t, J=7.4Hz),, " should read -- 6.46(1H, t, J=7.4Hz), --.

Column 148,
Line 32, "m.p." should read -- m.p.: --;
Line 33, "8.67(4H, s)₁" should read -- 8.67(4H, s), --;
Line 36, "(4H5m)," should read -- (4H, m), --;
Line 44, "piperaziinecarboxamide" should read -- piperazinecarboxamide --;
Line 47, "diphenyiphospho-" should read -- diphenylphospho --;
Line 50, "piperazinyiquinazoline" should read -- piperazinylquinazoline --; and
Line 51, "6706512" should read -- 67 06512 --.

Column 149,
Line 2, "(cm$^{-1}$)1619," should read -- (cm$^{-1}$):1619, --;
Lines 42 and 63, "-N-[4-" should read -- -N-{4- --;
Line 53, "10" should be deleted;
Line 54, "4,45" should read -- 4.45 --; and Column 150,
Line 24, "10" should be deleted.

Column 151,
Line 7, "4.03(3H, s).," should read -- 4.03(3H, s), --; and
Line 55, "6" should read -- δ --.

Column 152,
Line 2, "d(ppm):" should read -- δ (ppm): --; and
Line 46, "10" should be deleted.

Column 153,
Line 11, "490(M+3)," should read -- 490(M$^+$+3), --;

Column 154,
Line 50, "6" should read -- δ --.

Column 155,
Line 24, "472(MW+1)" should read -- 472(M$^+$+1) --;
Line 50, "25" should be deleted; and
Line 61, "35" should be deleted.

UNITED STATES PATENT AND TRADEMARK OFFICE
CERTIFICATE OF CORRECTION

PATENT NO.   : 6,207,667 B1
DATED         : March 27, 2001
INVENTOR(S)  : Kenji Matsuno et al.

It is certified that error appears in the above-identified patent and that said Letters Patent is hereby corrected as shown below:

Column 156,
Line 2, "N-(4-B) romo-3-" should read -- N-(4-Bromo-3- --;
Line 8, "86 (ppm): 9.07(H, brs)," should read -- δ (ppm): 9.07(1H, brs), --;
Line 9, "(dH, s)," should read -- (1H, s), --;
Line 28, "m)," should read -- s), --;
Line 59, "7.29(2H," should read -- 7.29(1H, --;
Line 60, "7.27(6H," should read -- 7.27(1H, --; and
Line 61, "5.73(2H," should read -- 5.73(1H, -- and "4.8(2H," should read -- 4.87(2H, --.

Column 157,
Line 12, "7.09(6H,)" should read -- 7.09(1H, --;
Line 13, "a," should read -- d, -- and "4.03(3111" should read -- 4.03(3H, --;
Line 14, "in)," should read -- m), --;
Line 15, "in)." should read -- m). --;
Line 51, "(2H, d,.)" should read -- (2H, d, -- and close up right margin;
Line 53, "4.04(23H," should read -- 4.04(2H, --; and
Line 54, "Hz)8, 4.02(31," should read -- Hz), 4.02 (3H, --.

Column 158,
Line 67, "35" should be deleted

Column 159,
Line 17, "($cm^{-1}$):516" should read -- ($cm^{-1}$):1516 --.

Column 160,
Line 4, "n)," should read -- m), --;
Line 5, "s)4" should read -- s), --;
Line 7, "1($cm^{-1}$):" should read -- υ($cm^{-1}$): --; and
Line 36, "30" should be deleted.

Column 161,
Line 12, "35" should be deleted;
Line 50, "guinazolinyl)" should read -- quinazolinyl) --; and
Line 67, "15" should be deleted.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 162,
Line 18, "(M++1)" should read -- $(M^++1)$ --;
Line 20, "916," should read -- 916. --;
Line 34, "7.35(bH," should read -- 7.35(1H, --;
Line 35, "7.26(2H," should read -- 7.26(1H -- and "7d12(H," should read -- 7.12 (1H, -- and "6.97(sH," should read -- 6.97(1H, --;
Line 39, "151," should be deleted;
Line 53, "8.55((H," should read -- 8.55(1H, --;
Line 54, "a," should read -- d, --; and
Line 55, "m)," should read -- s), --.

Column 163,
Line 25, "25" should be deleted;
Line 49, "1H-" should read -- $^1$H- --; and
Line 50, "6.65(211," should read -- 6.65(2H, --.

Column 164,
Line 22, "10" should be deleted;
Line 61, "10" should be deleted and "7.12(5H," should read -- 7.12(1H, -- and "J=9.1" should read -- J=9.0 --;
Line 62, "6.22(mH," should read -- 6.22(1H, --; and
Line 63, "1.13(6.(," should read -- 1.13(6H, --.

Column 165,
Line 13, "7.90(2H," should read -- 7.90(1H, -- and "7.56(H$_7$" should read -- 7.56 (1H, -- and "7.25(sH," should read -- 7.25(1H, -- and "7.19(2H," should read -- 7.19 (1H, --;
Line 14, "(11z," should read -- (1H, -- and "7.09(bs," should read -- 7.09(1H, -- and "6.97(11," should read -- 6.97(1H, --;
Line 15, "2.10(3z," should read -- 2.10(3H, --;
Line 32, "10" should be deleted;
Line 48, "C" should be deleted; and
Line 62, "229) Substantially" should read -- 229 ¶ Substantially --.

Column 166,
Line 39, "V" should read -- υ --;
Line 65, "d(ppm):" should read -- δ(ppm): --; and
Line 66, "30" should be deleted.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 167,
Line 25, "$^1$-NMR" should read -- $^1$H-NMR --.

Column 168,
Line 42, "1)(cm$^{-1}$):" should read -- $\upsilon$(cm$^{-1}$): --; and
Line 51, "(PPM) :" should read -- $\delta$(ppm): --.

Column 169,
Line 43, "15" should be deleted; and
Line 65, "1(cm$^{-1}$):" should read -- $\upsilon$(cm$^{-1}$): --.

Column 170,
Line 19, "F" should be deleted;
Line 20, "$^6$(ppm):" should read -- $\delta$(ppm): --; and
Line 60, "(cm$^{-1}$):" should read -- $\upsilon$(cm$^{-1}$): --.

Column 171,
Lines 16 and 37, "6(ppm):" should read -- $\delta$(ppm): --;and
Line 42, "20" should be deleted.

Column 173,
Line 30, "35" should be deleted; and
Line 58, "44-" should read -- 4- --.

Column 177,
Line 37, "409(M$^+$+1)," should read -- 409(M$^+$+1) --;
Line 52, "1)(cm$^{-1}$)" should read -- $\upsilon$(cm$^{-1}$): --; and
Line 60, "1H-" should read -- $^1$H- --.

Column 178,
Line 11, "8(ppm):" should read -- $\delta$(ppm): --;
Line 14, "467(M++5)," should read -- 467(M$^+$+5), --; and
Line 29, "30" should be deleted.

Column 179,
Lines 20, 39 and 58, "$\sigma$" should read -- $\upsilon$ --; and
Line 31, "to give" should read -- , to give --.

Column 180,
Lines 10, 31 and 52, "$\sigma$" should read -- $\upsilon$ --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 181,
Lines 23, 37 and 58, "σ" should read -- υ --.

Column 182,
Line 6, "σ($cm^{-1}$)" should read -- υ($cm^{-1}$): --; and
Line 53, "σ" should read -- υ --.

Column 183,
Lines 7, 22, and 48, "σ" should read -- υ --; and
Line 30, "46%." should read -- 46% --;

Column 184,
Lines 2, 16, 32 and 48, "σ" should read -- υ --.

Column 185,
Lines 2, 16, 31 and 50, "σ" should read -- υ --.

Column 186,
Lines 5, 19 and 53, "σ" should read -- υ --; and
Line 28, "8,27" should read -- 8.27 --;

Column 187,
Lines 1, 16, 31 and 50, "σ" should read -- υ --.

Column 188,
Lines 4, 17, 30 and 46, "σ" should read -- υ --.

Column 189,
Lines 6, and 28, "σ" should read -- υ --.

Column 190,
Line 23, "σ" should read -- υ --.

Column 191,
Lines 10, 30, 45 and 58, "σ" should read -- υ --.

Column 192,
Lines 22, 40 and 56, "σ" should read -- υ --; and
Line 35, "H-" should read -- $^{1}$H- --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 193,
Lines 8 and 44, "σ" should read -- υ --; and
Line 29, "σ(cm$^{-1}$)" should read -- υ(cm$^{-1}$): --.

Column 194,
Lines 2, 16, 31 and 48"σ" should read -- υ --.

Column 195,
Lines 2 and 58, "σ" should read -- υ --;
Line 34, "C.°C." should read -- C. --;
Line 39, "Hz)" should read -- Hz). --; and
Line 40, "σ(cm$^{-1}$)" should read -- υ(cm$^{-1}$) --.

Column 197,
Lines 11, 35, 51 and 65, "σ" should read -- υ --.

Column 198,
Lines 15, 39 and 54, "σ" should read -- υ --.

Column 199,
Lines 7, 22, 38 and 58, "σ" should read -- υ --; and
Line 16, "H-" should read -- $^{1}$H- --.

Column 200,
Lines 38 and 52, "σ" should read -- υ --.

Column 202,
Lines 18, 32, 47 and 63, "σ" should read -- υ --.

Column 203,
Lines 15, 30, 45 and 58, "σ" should read -- υ --.

Column 204,
Lines 8, 31 and 46, "σ" should read -- υ --;
Line 50, "-4- ($^{6}$,$^{7}$-" should read -- -4-(6,7- --; and
Line 59, "σ(cm$^{-1}$)" should read -- υ(cm$^{-1}$): --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

Page 13 of 16

It is certified that error appears in the above-identified patent and that said Letters Patent is hereby corrected as shown below:

Column 205,
Line 2, "H, ddd," should read -- (1H, ddd, --;
Lines 8, 30, 46 and 61, "σ" should read -- υ --;
Line 20, "-N-" should read -- -1- --;
Line 28, "(3H," should read -- (1H, --; and
Line 41, "(2H," should read -- (1H, --.

Column 206,
Line 14, "3.73-371" should read -- 3.73-3.71 --;
Lines 16, 33 and 55, "σ" should read -- υ --;
Line 50, "S)," should read -- s), --;
Line 51, "(7H," should read -- (1H, --;
Line 53, "(3Hz s)," should read -- (3H, s), --
Line 64, "((H," should read -- (1H, --;
Line 66, "(9H," should read -- (1H, --; and
Line 67, "(mH," should read -- (1H, -- and "(5H," should read -- (1H, --.

Column 207,
Lines 4, 26, 40 and 58, "σ" should read -- υ --;
Line 7, "I" should read -- 1 --; and
Line 20, "(]H," should read -- (1H, --.

Column 208,
Lines 11, 37 and 54, "σ" should read -- υ --.

Column 209,
Lines 8, 30 and 49, "σ" should read -- υ--.

Column 210,
Lines 15, 35 and 58, "σ" should read -- υ --.

Column 211,
Lines 7, 26 and 50, "σ" should read -- υ--; and
Line 23, "J=5.,3" should read -- J=5.3 --.

Column 212,
Lines 4, 25, 40, 56 and 58, "σ" should read -- υ --.

Column 213,
Lines 7, and 28 "σ" should read -- υ --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 214,
Lines 4, 23 and 46, "σ" should read -- υ --;
Line 34, close up right margin; and
Line 35, close up left margin.

Column 215,
Lines 5, 20, 39 and 59, "σ" should read -- υ --; and
Line 36, "(-3H," should read -- (3H, --.

Column 216,
Lines 10, 33 and 55, "σ" should read -- υ --.

Column 217,
Lines 22 and 52, "σ" should read -- υ --.

Column 218,
Line 8, "σ" should read -- υ --.

Column 219,
Lines 2, 22, 44 and 58 "σ" should read -- υ --.

Column 220,
Lines 8, 31 and 48, "σ" should read -- υ --; and
Line 65, "3.67" should read -- 8.67 --.

Column 221,
Lines 5, 21, 40 and 58, "σ" should read -- υ --;
Line 16, "(11H," should read -- (1H, --; and
Line 17, "(11H," (both occurrences) should read -- (1H, --.

Column 222,
Line 9, "(2H,d.," should read -- (2H, d, --; and
Lines 15, 31 and 48, "σ" should read -- υ --.

Column 223,
Lines 6, 22 and 41, "σ" should read -- υ --;
Line 17, "4.00-4.05" should read -- 4.09-4.05 --; and
Line 36, "Drt," should read -- brt, --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 224,
Line 22, "J=3.9H,)," should read -- J=3.9Hz), --.

Column 225,
Line 19, "((H," should read -- (1H, -- and "(4H," should read -- (1H, --;
Line 24, "N-[4-" should read -- N-[1- --;
Line 25, "quinazolinyl)-" should read -- quinzaolinyl)-1- --;
Line 41, "(2H," should read -- (1H, --.

Column 225 (continued),
Line 42, "(3H," should read -- (1H, -- and "(2H," should read -- (1H, --; and
Line 64, "-1-1-" should read -- -1- --.

Column 226,
Line 2, "Hz).," should read -- Hz), --; and
Line 43, "(4H, m)" should read -- (4H, m). --.

Column 227,
Line 7, "-{4-( [1-" should read -- -{4-[1- --;
Line 13, "(2H," should read -- (1H, -- and "s)." should read -- s), --;
Line 14, "(4H," should read -- (1H, -- and "(3H," should read -- (1H, --;
Line 15, "6), 3.88-3.09" should read -- s), 3.88-3.89 --;
Line 44, "was;" should read -- was --; and
Line 47, "(ppm.):" should read -- (ppm): --.

Column 228,
Line 5, "(ppm):; 3.69" should read -- (ppm): 8.69 --; and
Line 52, "mi)," should read -- m), --.

Column 229,
Line 24, "crystals;" should read -- crystals --;
Line 55, "(911," should read -- (9H, --; and
Line 62, "ethyl amino" should read -- ethylamino --.

Column 233,
Line 66, "609," should read -- 60% --.

Column 234,
Line 46, "dime(thylformamide" should read -- dimethylformamide --.

UNITED STATES PATENT AND TRADEMARK OFFICE
CERTIFICATE OF CORRECTION

PATENT NO. : 6,207,667 B1
DATED : March 27, 2001
INVENTOR(S) : Kenji Matsuno et al.

It is certified that error appears in the above-identified patent and that said Letters Patent is hereby corrected as shown below:

Column 235,
Line 67, "crystals;" should read -- crystals --

Column 236,
Line 25, "(1L)-(6)" should read -- (1)-(6) --;
Line 26, "isovanillic(," should read -- isovanillic --;
Line 38, "was;" should read -- was --; and
Line 47, "Acid" should read -- acid -- and "Ester" should read -- ester --.

Column 237,
Line 7, "-dimiothoxy-" should read -- -dimethoxy- --; and
Line 41, "compound" should read -- compound (10%). --.

Column 238,
Line 39, "4-7g" should read -- 47g --; and
Lines 61 and 65, "procedure(" should read -- procedure --.

Column 239,
Line 29, "EXAMPLE" should read -- EXAMPLE 2 --.

Column 241,
Line 29, "the adjoining nitrogen atom to represent a" should be deleted; and
Lines 30-34, should be deleted.

Column 242,
Line 10, "wherein" should read -- (wherein --;
Line 29, close up right margin; and
Line 61, "claims 2-8 or 1" should read -- claims 1-8 --.

Signed and Sealed this

Twenty-third Day of April, 2002

Attest:

JAMES E. ROGAN
Attesting Officer        Director of the United States Patent and Trademark Office